(12) United States Patent
Yum et al.

(10) Patent No.: US 12,274,794 B2
(45) Date of Patent: Apr. 15, 2025

(54) ORAL DOSAGE FORM WITH DRUG COMPOSITION, BARRIER LAYER AND DRUG LAYER

(71) Applicant: ORIENT PHARMA CO., LTD., Taipei (TW)

(72) Inventors: Su Il Yum, Los Altos, CA (US);
Wendy Chao, San Jose, CA (US);
Huey-Ching Su, San Jose, CA (US);
Yen-Fei Chen, Taichung (TW);
Chin-Chih Chiang, West Covina, CA (US)

(73) Assignee: Orient Pharma Co., Ltd., Taipei (TW)

( * ) Notice: Subject to any disclaimer, the term of this patent is extended or adjusted under 35 U.S.C. 154(b) by 194 days.

(21) Appl. No.: 16/309,436

(22) PCT Filed: Jul. 5, 2017

(86) PCT No.: PCT/US2017/040750
§ 371 (c)(1),
(2) Date: Dec. 12, 2018

(87) PCT Pub. No.: WO2018/009566
PCT Pub. Date: Jan. 11, 2018

(65) Prior Publication Data
US 2020/0197315 A1  Jun. 25, 2020

Related U.S. Application Data

(60) Provisional application No. 62/359,111, filed on Jul. 6, 2016.

(51) Int. Cl.
*A61P 25/26* (2006.01)
*A61K 9/48* (2006.01)
*A61K 31/4458* (2006.01)

(52) U.S. Cl.
CPC .......... *A61K 9/4891* (2013.01); *A61K 9/4816* (2013.01); *A61K 9/4858* (2013.01); *A61K 31/4458* (2013.01); *A61P 25/26* (2018.01)

(58) Field of Classification Search
CPC ... A61K 9/4891; A61K 9/4816; A61K 9/4808
See application file for complete search history.

(56) References Cited

U.S. PATENT DOCUMENTS

| | | |
|---|---|---|
| 2,799,241 A | 7/1957 | Wurster |
| 2,931,802 A | 4/1960 | Toney et al. |
| 3,339,546 A | 9/1967 | Chen |
| 3,743,398 A | 7/1973 | Johnson et al. |
| 3,845,770 A | 11/1974 | Theeuwes et al. |
| 3,853,837 A | 12/1974 | Fujino et al. |
| 3,916,889 A | 11/1975 | Russell |
| 3,916,899 A | 11/1975 | Theeuwes et al. |
| 3,952,741 A | 4/1976 | Baker |
| 3,992,365 A | 11/1976 | Beddell et al. |
| 3,995,631 A | 12/1976 | Higuchi et al. |
| 4,008,719 A | 2/1977 | Theeuwes et al. |
| 4,014,334 A | 3/1977 | Theeuwes et al. |
| 4,016,880 A | 4/1977 | Theeuwes et al. |
| 4,024,248 A | 5/1977 | Konig et al. |
| 4,063,064 A | 12/1977 | Saunders et al. |
| 4,088,864 A | 5/1978 | Theeuwes et al. |
| 4,100,274 A | 7/1978 | Dutta et al. |
| 4,111,202 A | 9/1978 | Theeuwes |
| 4,160,020 A | 7/1979 | Ayer et al. |
| 4,327,725 A | 5/1982 | Cortese et al. |
| 4,360,019 A | 11/1982 | Portner et al. |
| 4,395,405 A | 7/1983 | Noda et al. |
| 4,395,495 A | 7/1983 | Cummings |
| 4,411,890 A | 10/1983 | Momany |
| 4,487,603 A | 12/1984 | Harris |
| 4,530,840 A | 7/1985 | Tice et al. |
| 4,578,075 A | 3/1986 | Urquhart et al. |
| 4,622,219 A | 11/1986 | Haynes |

(Continued)

FOREIGN PATENT DOCUMENTS

| | | |
|---|---|---|
| AU | 8374575 | 8/1975 |
| CA | 2222567 | 1/2002 |

(Continued)

OTHER PUBLICATIONS

"New Drugs/Programs"; *Current Drug Discovery*; Nov. 2004; pp. 7-10.
"Ritalin product monograph"; *CPS Compendium of Pharmaceuticals and Specialties*, 34th ed.; Gillis, M., Ed. Canadian Pharmacists Association: Ottawa, (1999); pp. 1573-1574.
3M, "3M DDS Announces Development of New HFA-Compatible Excipients: Novel Oligomeric Acids as MDI Suspension Aid and Solubilizers" 3M Delivery Newsletter, vol. 15, *3M Drug Delivery Systems*; Jun. 2000, pp. 9-11.
Abdul-Fattah, Ahmad M., et al; "Preparation and In Vitro Evaluation of Solid Dispersions of Halofantrine."; *International Journal of Pharmaceutics 235*; (2002); pp. 17-33.
Adams, Edgar G, et al.; "A comparison of the abuse liability of tramadol, NSAIDS, and hydrocodone in patients with chronic pain"; *Journal of Pain and Symptom Management*. 31(5); (2006); pp. 465-476.

(Continued)

Primary Examiner — Alton N Pryor

(57) ABSTRACT

The present disclosure provides dosage forms designed to deliver active pharmaceutical ingredients (APIs) in a controlled release manner. For instance, the present disclosure includes dosage forms with adequate time of onset of action and reduced lag times in the fed state. Such dosage forms find use in a variety of conditions where a rapid onset of action is desired followed by an extended release phase for the active agent, for example in the treatment of ADHD, pain or anxiety. In some cases, the dosage form includes a drug composition including a pharmacologically active agent, a barrier layer covering at least a portion of the drug composition, and a drug layer covering at least a portion of the barrier layer, wherein the drug layer includes the pharmacologically active agent. Related methods of making and administering the disclosed dosage forms are also provided.

12 Claims, 24 Drawing Sheets

(56) References Cited

U.S. PATENT DOCUMENTS

| | | |
|---|---|---|
| 4,681,583 A | 7/1987 | Urquhart et al. |
| 4,681,765 A | 7/1987 | Guley |
| 4,689,222 A | 8/1987 | McMichael |
| 4,692,147 A | 9/1987 | Duggan |
| 4,725,442 A | 2/1988 | Haynes |
| 4,725,852 A | 2/1988 | Gamblin et al. |
| 4,767,628 A | 8/1988 | Hutchinson |
| 4,769,372 A | 9/1988 | Kreek |
| 4,795,641 A | 1/1989 | Kashdan |
| 4,834,984 A | 5/1989 | Goldie et al. |
| 4,844,909 A | 7/1989 | Goldie et al. |
| 4,861,598 A | 8/1989 | Oshlack |
| 4,891,225 A | 1/1990 | Langer et al. |
| 4,906,474 A | 3/1990 | Langer et al. |
| 4,931,285 A | 6/1990 | Edgren et al. |
| 4,938,763 A | 7/1990 | Dunn et al. |
| 4,957,681 A | 9/1990 | Klimesch et al. |
| 4,957,744 A | 9/1990 | della Valle et al. |
| 4,961,932 A | 10/1990 | Theeuwes |
| 4,970,075 A | 11/1990 | Oshlack |
| 4,990,341 A | 2/1991 | Goldie et al. |
| 5,006,346 A | 4/1991 | Edgren et al. |
| 5,019,397 A | 5/1991 | Wong et al. |
| 5,024,842 A | 6/1991 | Edgren et al. |
| 5,149,543 A | 9/1992 | Cohen et al. |
| 5,156,850 A | 10/1992 | Wong et al. |
| 5,160,743 A | 11/1992 | Edgren et al. |
| 5,188,837 A | 2/1993 | Domb |
| 5,190,765 A | 3/1993 | Jao et al. |
| 5,252,338 A | 10/1993 | Jao et al. |
| 5,266,331 A | 11/1993 | Oshlack et al. |
| 5,273,760 A | 12/1993 | Oshlack et al. |
| 5,278,201 A | 1/1994 | Dunn et al. |
| 5,278,202 A | 1/1994 | Dunn et al. |
| 5,286,493 A | 2/1994 | Oshlack et al. |
| 5,286,496 A | 2/1994 | Stapler et al. |
| 5,324,351 A | 6/1994 | Oshlack et al. |
| 5,324,519 A | 6/1994 | Dunn et al. |
| 5,324,520 A | 6/1994 | Dunn et al. |
| 5,330,835 A | 7/1994 | Kikuchi et al. |
| 5,340,572 A | 8/1994 | Patel et al. |
| 5,340,849 A | 8/1994 | Dunn et al. |
| 5,350,741 A | 9/1994 | Takada |
| 5,352,662 A | 10/1994 | Brooks et al. |
| 5,356,467 A | 10/1994 | Oshlack et al. |
| 5,356,635 A | 10/1994 | Raman et al. |
| 5,366,738 A | 11/1994 | Rork et al. |
| 5,382,424 A | 1/1995 | Stapler et al. |
| 5,391,381 A | 2/1995 | Wong et al. |
| 5,399,363 A | 3/1995 | Liversidge et al. |
| 5,472,712 A | 12/1995 | Oshlack et al. |
| 5,478,577 A | 12/1995 | Sackler et al. |
| 5,487,898 A | 1/1996 | Lu et al. |
| 5,508,042 A | 4/1996 | Oshlack et al. |
| 5,540,912 A | 7/1996 | Roorda et al. |
| 5,545,408 A | 8/1996 | Trigg et al. |
| 5,549,912 A | 8/1996 | Oshlack et al. |
| 5,569,450 A | 10/1996 | Duan et al. |
| 5,580,578 A | 12/1996 | Oshlack et al. |
| 5,599,552 A | 2/1997 | Dunn et al. |
| 5,620,705 A | 4/1997 | Dong et al. |
| 5,633,000 A | 5/1997 | Grossman et al. |
| 5,633,011 A | 5/1997 | Dong et al. |
| 5,639,476 A | 6/1997 | Oshlack et al. |
| 5,656,295 A | 8/1997 | Oshlack et al. |
| 5,672,360 A | 9/1997 | Sackler et al. |
| 5,681,585 A | 10/1997 | Oshlack et al. |
| 5,702,716 A | 12/1997 | Dunn et al. |
| 5,725,841 A | 3/1998 | Duan et al. |
| 5,728,396 A | 3/1998 | Peery et al. |
| 5,733,950 A | 3/1998 | Dunn et al. |
| 5,736,152 A | 4/1998 | Dunn |
| 5,739,176 A | 4/1998 | Dunn et al. |
| 5,743,947 A * | 4/1998 | Jordan ............... A61K 9/2866 106/162.7 |
| 5,744,280 A | 4/1998 | Mooney, III et al. |
| 5,747,051 A | 5/1998 | Granger et al. |
| 5,747,058 A | 5/1998 | Tipton et al. |
| 5,750,100 A | 5/1998 | Yamagata et al. |
| 5,759,563 A | 6/1998 | Yewey et al. |
| 5,777,124 A | 7/1998 | Zavareh et al. |
| 5,780,044 A | 7/1998 | Yewey et al. |
| 5,786,484 A | 7/1998 | Dyer et al. |
| 5,837,284 A | 11/1998 | Mehta et al. |
| 5,840,329 A | 11/1998 | Bai |
| 5,840,731 A | 11/1998 | Mayer et al. |
| 5,879,705 A | 3/1999 | Haefield et al. |
| 5,908,850 A | 6/1999 | Zeitlin et al. |
| 5,919,473 A | 7/1999 | Elkhoury |
| 5,932,597 A | 8/1999 | Brown et al. |
| 5,942,241 A | 8/1999 | Chasin et al. |
| 5,958,446 A | 9/1999 | Miranda et al. |
| 5,958,452 A | 9/1999 | Oshlack et al. |
| 5,965,161 A | 10/1999 | Oshlack et al. |
| 5,968,542 A | 10/1999 | Tipton |
| 5,985,305 A | 11/1999 | Peery et al. |
| 5,994,548 A | 11/1999 | Langston et al. |
| 6,008,355 A | 12/1999 | Huang et al. |
| 6,042,811 A | 3/2000 | Duan et al. |
| 6,051,558 A | 4/2000 | Burns et al. |
| 6,093,419 A | 7/2000 | Rolf |
| 6,126,919 A | 10/2000 | Stefely et al. |
| 6,143,322 A | 11/2000 | Sackler et al. |
| 6,171,618 B1 | 1/2001 | Johnson et al. |
| 6,190,680 B1 | 2/2001 | Sakurada et al. |
| 6,203,813 B1 | 3/2001 | Gooberman et al. |
| 6,210,705 B1 | 4/2001 | Mantelle et al. |
| 6,228,398 B1 | 5/2001 | Devane et al. |
| 6,245,351 B1 | 6/2001 | Nara et al. |
| 6,291,013 B1 | 9/2001 | Gibson et al. |
| 6,294,195 B1 | 9/2001 | Oshlack et al. |
| 6,312,717 B1 | 11/2001 | Molinoff et al. |
| 6,344,215 B1 | 2/2002 | Bettman et al. |
| 6,348,211 B1 | 2/2002 | Mantelle et al. |
| 6,355,656 B1 | 3/2002 | Zeitlin et al. |
| 6,375,957 B1 | 4/2002 | Kaiko et al. |
| 6,384,227 B2 | 5/2002 | Dyer et al. |
| 6,403,609 B1 | 6/2002 | Asgharian et al. |
| 6,413,356 B1 | 7/2002 | Chokshi et al. |
| 6,413,536 B1 | 7/2002 | Gibson et al. |
| 6,419,952 B2 * | 7/2002 | Wong ............... A61K 9/0004 424/463 |
| 6,419,960 B1 | 7/2002 | Krishnamurthy |
| 6,426,339 B1 | 7/2002 | Berde et al. |
| 6,440,493 B1 | 8/2002 | Gibson et al. |
| 6,479,074 B2 | 11/2002 | Murdock et al. |
| 6,486,138 B1 | 11/2002 | Asgharian et al. |
| 6,498,153 B1 | 12/2002 | Cady et al. |
| 6,512,009 B1 | 1/2003 | Daoust et al. |
| 6,514,516 B1 | 2/2003 | Chasin et al. |
| 6,521,259 B1 | 2/2003 | Chasin et al. |
| 6,524,607 B1 | 2/2003 | Goldenheim et al. |
| 6,528,530 B2 | 3/2003 | Zeitlin et al. |
| 6,552,031 B1 | 4/2003 | Burch et al. |
| 6,635,284 B2 | 10/2003 | Mehta et al. |
| 6,699,908 B2 | 3/2004 | Sackler et al. |
| 6,730,325 B2 | 5/2004 | Devane et al. |
| 6,733,783 B2 | 5/2004 | Oshlack et al. |
| 6,919,373 B1 | 7/2005 | Lam et al. |
| 6,921,541 B2 | 7/2005 | Chasin et al. |
| 6,930,129 B2 | 8/2005 | Lam et al. |
| 6,992,065 B2 | 1/2006 | Okumu et al. |
| 7,053,209 B1 | 5/2006 | Gibson et al. |
| 7,431,944 B2 | 10/2008 | Mehta et al. |
| 7,691,880 B2 | 4/2010 | Herman |
| 7,833,543 B2 | 11/2010 | Gibson et al. |
| 7,838,522 B2 | 11/2010 | Esposito et al. |
| 8,088,786 B2 | 1/2012 | McKinney et al. |
| 8,124,123 B2 | 2/2012 | Pillai et al. |
| 8,133,507 B2 | 3/2012 | Yum et al. |
| 8,147,870 B2 | 4/2012 | Yum et al. |
| 8,153,152 B2 | 4/2012 | Yum et al. |
| 8,163,798 B2 | 4/2012 | Gupta et al. |
| 8,168,217 B2 | 5/2012 | Yum et al. |

(56) References Cited

U.S. PATENT DOCUMENTS

| | | | |
|---|---|---|---|
| 8,354,124 B2 | 1/2013 | Yum et al. | |
| 8,415,401 B2 | 4/2013 | Yum et al. | |
| 8,420,120 B2 | 4/2013 | Yum et al. | |
| 8,926,783 B2 | 1/2015 | Akhtar et al. | |
| 8,945,614 B2 | 2/2015 | Yum et al. | |
| 8,951,556 B2 | 2/2015 | Yum et al. | |
| 8,974,821 B2 | 3/2015 | Yum et al. | |
| 9,233,160 B2 | 1/2016 | Yum et al. | |
| 9,517,271 B2 | 12/2016 | Yum et al. | |
| 9,572,885 B2 | 2/2017 | Yum et al. | |
| 9,592,204 B2 | 3/2017 | Yum et al. | |
| 9,616,055 B2 | 4/2017 | Scicinski et al. | |
| 9,655,861 B2 | 5/2017 | Yum et al. | |
| 10,328,068 B2 | 6/2019 | Scicinski et al. | |
| 2001/0000522 A1 | 4/2001 | Dyer et al. | |
| 2001/0029257 A1 | 10/2001 | Murdock et al. | |
| 2001/0036472 A1* | 11/2001 | Wong | A61K 9/0004 424/456 |
| 2001/0047005 A1 | 11/2001 | Farrar et al. | |
| 2001/0055613 A1 | 12/2001 | Burnside et al. | |
| 2002/0086878 A1 | 7/2002 | Dobrozsi et al. | |
| 2002/0114835 A1 | 8/2002 | Sackler et al. | |
| 2002/0143065 A1 | 10/2002 | Liu et al. | |
| 2002/0155154 A1 | 10/2002 | Wong et al. | |
| 2002/0164371 A1 | 11/2002 | Ting et al. | |
| 2003/0004177 A1 | 1/2003 | Kao et al. | |
| 2003/0035839 A1* | 2/2003 | Hirsh | A61K 9/4808 424/471 |
| 2003/0045454 A1 | 3/2003 | Okumu et al. | |
| 2003/0152637 A1 | 8/2003 | Chasin et al. | |
| 2003/0157168 A1 | 8/2003 | Breder et al. | |
| 2003/0165562 A1 | 9/2003 | Gutierrez-Rocca et al. | |
| 2003/0185873 A1 | 10/2003 | Chasin et al. | |
| 2003/0191147 A1 | 10/2003 | Sherman et al. | |
| 2004/0001889 A1 | 1/2004 | Chen et al. | |
| 2004/0024021 A1 | 2/2004 | Sudo et al. | |
| 2004/0052336 A1 | 3/2004 | Langlet et al. | |
| 2004/0101557 A1 | 5/2004 | Gibson et al. | |
| 2004/0109893 A1 | 6/2004 | Chen et al. | |
| 2004/0138237 A1 | 7/2004 | Shah | |
| 2004/0146562 A1 | 7/2004 | Shah | |
| 2004/0156896 A1 | 8/2004 | Manesh et al. | |
| 2004/0161382 A1* | 8/2004 | Yum | A61P 43/00 514/960 |
| 2004/0224020 A1 | 11/2004 | Schoenhard | |
| 2004/0224903 A1 | 11/2004 | Berry et al. | |
| 2005/0042194 A1 | 2/2005 | Ng et al. | |
| 2005/0106304 A1 | 5/2005 | Cook et al. | |
| 2005/0158382 A1 | 7/2005 | Cruz et al. | |
| 2005/0171052 A1 | 8/2005 | Cook et al. | |
| 2005/0208132 A1 | 9/2005 | Sathyan et al. | |
| 2005/0232876 A1 | 10/2005 | Minga et al. | |
| 2005/0244489 A1 | 11/2005 | Paris | |
| 2005/0260264 A1 | 11/2005 | Edgren et al. | |
| 2005/0266087 A1 | 12/2005 | Junnarkar et al. | |
| 2006/0034926 A1 | 2/2006 | Fraatz et al. | |
| 2006/0058401 A1 | 3/2006 | Ishikawa et al. | |
| 2006/0104909 A1 | 5/2006 | Vaghefi et al. | |
| 2006/0115527 A1 | 6/2006 | Hassan et al. | |
| 2006/0165800 A1 | 7/2006 | Chen et al. | |
| 2006/0210599 A1 | 9/2006 | Gibson et al. | |
| 2007/0027105 A1 | 2/2007 | Junnarkar et al. | |
| 2007/0031502 A1 | 2/2007 | Pettersson et al. | |
| 2007/0104763 A1 | 5/2007 | Jobdevairakkam et al. | |
| 2007/0212411 A1 | 9/2007 | Fawzy et al. | |
| 2007/0259033 A1 | 11/2007 | Cruz | |
| 2008/0023261 A1 | 1/2008 | Kaneko et al. | |
| 2008/0026052 A1 | 1/2008 | Schoenhard | |
| 2008/0145419 A1 | 6/2008 | Gibson et al. | |
| 2008/0152708 A1 | 6/2008 | Gibson et al. | |
| 2008/0206321 A1 | 8/2008 | Yum et al. | |
| 2009/0023689 A1 | 1/2009 | Yum et al. | |
| 2009/0023690 A1 | 1/2009 | Yum et al. | |
| 2009/0164240 A1 | 6/2009 | Friedmann et al. | |
| 2009/0165578 A1 | 7/2009 | Zamloot et al. | |
| 2009/0169631 A1 | 7/2009 | Zamloot et al. | |
| 2009/0215808 A1 | 8/2009 | Yum et al. | |
| 2009/0298862 A1 | 12/2009 | Yum et al. | |
| 2010/0260844 A1 | 10/2010 | Scicinski et al. | |
| 2011/0287093 A1 | 11/2011 | Schoenhard | |
| 2012/0135072 A1 | 5/2012 | Yum et al. | |
| 2012/0135073 A1 | 5/2012 | Yum et al. | |
| 2012/0165358 A1 | 6/2012 | Cruz et al. | |
| 2012/0189695 A1 | 7/2012 | Kramer et al. | |
| 2013/0022678 A1 | 1/2013 | Dixit et al. | |
| 2013/0281480 A1 | 10/2013 | Yum et al. | |
| 2013/0287845 A1 | 10/2013 | Yum et al. | |
| 2013/0295168 A1 | 11/2013 | Yum et al. | |
| 2013/0309176 A1 | 11/2013 | Port et al. | |
| 2013/0317049 A1 | 11/2013 | Yum et al. | |
| 2013/0337059 A1 | 12/2013 | Yum et al. | |
| 2013/0337060 A1 | 12/2013 | Yum et al. | |
| 2014/0004189 A1 | 1/2014 | Roy et al. | |
| 2014/0011842 A1* | 1/2014 | Scicinski | A61K 9/4858 514/317 |
| 2014/0275147 A1 | 9/2014 | Yum et al. | |
| 2015/0196644 A1 | 7/2015 | Yum et al. | |
| 2016/0038479 A1 | 2/2016 | Zamloot et al. | |
| 2016/0038592 A1 | 2/2016 | Yum et al. | |
| 2016/0058746 A1 | 3/2016 | Scicinski et al. | |
| 2016/0106683 A1 | 4/2016 | Venkatesh | |
| 2016/0136102 A1 | 5/2016 | Yum et al. | |
| 2016/0193345 A1 | 7/2016 | Yum et al. | |
| 2017/0165255 A1 | 6/2017 | Yum et al. | |
| 2017/0196978 A1 | 7/2017 | Yum et al. | |
| 2017/0209581 A1 | 7/2017 | Yum et al. | |
| 2017/0319501 A1 | 11/2017 | Yum et al. | |

FOREIGN PATENT DOCUMENTS

| | | |
|---|---|---|
| DE | 1569231 | 8/1969 |
| DE | 2213717 | 11/1972 |
| DE | 2321174 | 4/1973 |
| DE | 2438352 | 2/1976 |
| DE | 2720245 | 11/1977 |
| DE | 19714765 | 10/1998 |
| EP | 0244118 | 11/1987 |
| EP | 0535899 | 4/1993 |
| EP | 0539559 | 5/1993 |
| EP | 0539751 | 5/1993 |
| EP | 0544612 | 6/1993 |
| EP | 0621042 | 10/1994 |
| EP | 0290983 | 1/1995 |
| EP | 0640336 | 3/1995 |
| EP | 0773604 | 5/1997 |
| EP | 0778768 | 6/1997 |
| EP | 0537559 | 1/1998 |
| EP | 0711548 | 1/1998 |
| EP | 0635531 | 6/2001 |
| EP | 0782569 | 3/2002 |
| EP | 1010436 | 10/2002 |
| EP | 0804417 | 6/2003 |
| EP | 0788480 | 7/2003 |
| EP | 0788481 | 8/2003 |
| EP | 0999825 | 10/2003 |
| EP | 1348427 | 10/2003 |
| EP | 1032390 | 11/2003 |
| EP | 1548093 | 6/2005 |
| EP | 2510924 | 10/2012 |
| GB | 1088992 | 10/1967 |
| GB | 2238478 | 6/1991 |
| JP | 59210024 | 11/1984 |
| JP | 62000419 | 1/1987 |
| JP | 2096516 | 4/1990 |
| JP | 5194273 | 8/1993 |
| JP | 7053356 | 2/1995 |
| JP | 7112940 | 5/1995 |
| JP | 7115901 | 5/1995 |
| JP | 7124196 | 5/1995 |
| JP | 9502181 | 3/1997 |
| JP | 2003508449 | 3/2003 |
| WO | WO 1990003768 | 4/1990 |
| WO | WO 1990003809 | 4/1990 |
| WO | WO 1991018016 | 11/1991 |

(56) References Cited

FOREIGN PATENT DOCUMENTS

| | | |
|---|---|---|
| WO | WO 199214466 | 3/1992 |
| WO | WO 1992017900 | 10/1992 |
| WO | WO 1993003751 | 3/1993 |
| WO | WO 1993007833 | 4/1993 |
| WO | WO 1994005265 | 3/1994 |
| WO | WO 1994015587 | 7/1994 |
| WO | WO 1995009613 | 4/1995 |
| WO | WO 1995017901 | 7/1995 |
| WO | WO 1996009290 | 3/1996 |
| WO | WO 1996012699 | 5/1996 |
| WO | WO 1996012700 | 5/1996 |
| WO | WO 1996022281 | 7/1996 |
| WO | WO 1996039995 | 12/1996 |
| WO | WO 1996041616 | 12/1996 |
| WO | WO 1997015285 | 5/1997 |
| WO | WO 1997027840 | 8/1997 |
| WO | WO 1997049391 | 12/1997 |
| WO | WO 1998027962 | 7/1998 |
| WO | WO 1998027963 | 7/1998 |
| WO | WO 1998034596 | 8/1998 |
| WO | WO 1998044903 | 10/1998 |
| WO | WO 1998051246 | 11/1998 |
| WO | WO 1998053837 | 12/1998 |
| WO | WO 1999006023 | 2/1999 |
| WO | WO 1999013913 | 3/1999 |
| WO | WO 1999025349 | 5/1999 |
| WO | WO 2000000120 | 1/2000 |
| WO | WO 200016750 | 3/2000 |
| WO | WO 2000078335 | 12/2000 |
| WO | WO 2001008661 | 2/2001 |
| WO | WO 2001015734 | 3/2001 |
| WO | WO 2001037808 | 5/2001 |
| WO | WO 2001051024 | 7/2001 |
| WO | WO 2001076599 | 10/2001 |
| WO | WO 2002010436 | 2/2002 |
| WO | WO 2002053187 | 7/2002 |
| WO | WO 2002087512 | 11/2002 |
| WO | WO 2003000282 | 1/2003 |
| WO | WO 2003013476 | 2/2003 |
| WO | WO 2003055475 | 7/2003 |
| WO | WO 2003086368 | 10/2003 |
| WO | WO 2003101358 | 12/2003 |
| WO | WO 2004026262 | 4/2004 |
| WO | WO 2004037224 | 5/2004 |
| WO | WO 2004037289 | 5/2004 |
| WO | WO 2004052336 | 6/2004 |
| WO | WO 2004056337 | 7/2004 |
| WO | WO 2004056338 | 7/2004 |
| WO | WO 2004082658 | 9/2004 |
| WO | WO 2004101557 | 11/2004 |
| WO | WO 2005009408 | 2/2005 |
| WO | WO 2005048744 | 6/2005 |
| WO | WO 2005105031 | 11/2005 |
| WO | WO 2005105050 | 11/2005 |
| WO | WO 2005112896 | 12/2005 |
| WO | WO 2005115333 | 12/2005 |
| WO | WO 2006008141 | 1/2006 |
| WO | WO 2006069293 | 6/2006 |
| WO | WO 2006084139 | 8/2006 |
| WO | WO 2006134018 | 12/2006 |
| WO | WO 2007058923 | 5/2007 |
| WO | WO 2007070632 | 6/2007 |
| WO | WO 2007135193 | 11/2007 |
| WO | WO 2008023261 | 2/2008 |
| WO | WO 2009076227 | 6/2009 |
| WO | WO 2009076231 | 6/2009 |
| WO | WO 2009076236 | 6/2009 |
| WO | WO 2009088414 | 7/2009 |
| WO | WO 2013142279 | 9/2013 |
| WO | WO 2014144984 | 3/2014 |
| WO | WO 2004054542 | 7/2014 |
| WO | WO 2014144975 | 9/2014 |

OTHER PUBLICATIONS

Ajayaghosh, A., et al., "Solid-Phase Synthesis of N-Methyl- and N-Ethylamides of Peptides Using Photolytically Detachable ((3-Nitro-4-((alkylamino)methyl)benzamido)methyl)polystyrene Resin"; *J. Org. Chem.* 55; (1990); pp. 2826-2829.

Allahham Allahham, et al; "Flow and injection characteristics of pharmaceutical parenteral formulations using a micro-capillary rheometer"; *International Journal of Pharmaceutics*. 270; (2004); pp. 139-148.

Ansel, H.C. et al.; *Pharmaceutical Dosage Forms and Drug Delivery System, sixth ed.*, (1995); 20 pages.

ASH Michael and ASH Irene; "Handbook of Pharmaceutical Additives: An International Guide to More Than 6000 Products by Trade Name, Chemical, Function, and Manufacturer"; *Gower* (1995); 3 pages.

Aungst, B.J., et al; "Improved Oral Bioavailability Of An HIV Protease Inhibitor Using Gelucire 44/14 and Labrasol Vehicles"; *Bulletin Technique Gattefosse*, No. 87,(1994); pp. 49-54.

Aungst, B.J et al; "Amphiphilic vehicles improve the oral bioavailability of a poorly soluble HIV Protease inhibitor at high doses."; *International Journal of Pharmaceutics*, vol. 156; (1997); pp. 79-88.

Bansal, Tripta, et al; "Solid Self Nanoemulsifying Delivery Systems as a Platform Technology for Formulation of Poorly Soluble Drugs"; *Critical Reviews™ in Therapeutic Drug Carrier Systems*, 25(1); (2008); pp. 63-116.

Barakat, N S.; "Etodolac-Liquid-Filled Dispersion into Hard Gelatin Capsules: An Approach to Improve Dissolution and Stability of Etodolac Formulation."; Drug Pev. Pharm. 32[7]; (2006); pp. 865-876.

Barb, R., et al.; "Evaluation of the SABER Delivery System for the Controlled Release of Deslorelin: Effect of Dose in Estrogen Primed Ovarectomized Gilts"; *Proceed. Int'l, Symp. Control. Rel. Bioact. Mater.*; (1999) Controlled Release Society, Inc.; pp. 1170-1171.

Barker, S.A., et al; "An investigation into the structure and bioavailability of α-tocopherol dispersions in Gelucire 44/14"; *Journal of Controlled Release 91*; (2003); pp. 477-488.

Becker & Johnson "Effects of Gonadotropin-Releasing Hormone Infused in a Pulsatile or Continuous Fashion Serum Gonadotropin Concentrations and Ovulation in the Mare"; *J. Anim. Sci.* vol. 70; (1992); pp. 1208-1215.

Bekersky I, et al.; "Effect of low- and high-fat meals on tacrolimus absorption following 5 mg single oral doses to healthy human subjects"; *J Clin Pharmacol*; 41; (2001); pp. 176-182.

Berge et al. "Pharmaceutical salts" *J Pharm. Sci.* 66(1); Jan. 1977; pp. 1-19.

Betschart, R., et al.; "Evaluation of the SABER™M Delivery System for the Controlled Release of the GnRH Analogue Deslorelin for Advancing Ovulation in Mares: Effect of Gamma Radiation"; *Proceed. Int'l. Symp. Control. Rel. Bioact. Mater.*, 25, Controlled Release Society, Inc.; (1998); pp. 655-656.

Blachez, P., et al; "Development of immediate release pellets of poorly soluble compounds using Gelucire 44/14 using melt pelletization"; Poster, Oct. 26, 2003. Conference "*AAPS Annual Meeting & Exposition*", Salt Lake City, Utah, United States.X.

Blažková, A. et al, "Viscosity properties of aqueous solutions of hydroxyethylcellulose"; *Chem Papers 44* (3); (1990) pp. 289-301.

Brevard J, et al. "Pain and opioid abuse in a population of substance abuse patients: data from the NAVIPPRO™ system." *Conference paper presented at the 42nd American Pain Society (APS) Annual Scientific Meeting*, Washington D.C.; (2007); 1 page.

Bühler, K.; GnRH Agonists and Safety, In GnRH Analagoues The State of the Art 1993, A Summary of the 3rd International Symposium on GnRH Analogues in Cancer and Human Reproduction, Geneva, Feb. 1993; pp. 139-146.

Burns, P et al.; "Pharmacodynamic Evaluation of the Saber™ Delivery System for the Controlled Release of the GnRH Analogue Deslorelin Acetate for Advancing Ovulation in Cyclic Mares"; *Proceed. Int'l. Symp. Control. Rel. Bioact. Mater.*, 24; Controlled Release Society, Inc. (1997); 4 pages.

(56) References Cited

OTHER PUBLICATIONS

"CAB-O-SIL®, Untreated Fumed Silica: Properties & Functions"; Cabot Corporation, *Cab-O-Sil Division*; (1993); pp. 1-34.

Carraway, et al.; "Drug Delivery From a Controlled Release Aerosol: Effects of Formulation Variables"; *AAPS J Abstract*. Southern BioSystems, Inc., Birmingham AL, USA; (2000); 1 page.

Carraway, et al.; "Drug Release from a Novel Controlled Release Aerosol Based on Sucrose Acetate Isobutyrate" *AAPS Midwest Regional Meeting* Chicago, IL; May 22, 2000; 2 pages.

Cellulose Acetate Butyrate. In: European pharmacopoeia. 4 edn. Strasbourg Cedex, France: Council of Europe; 2001; p. 853-4.

Chambin, O., et al; "Interest of Multifunctional Lipid Excipients: Case of Gelucire® 44/14"; *Drug Development and Industrial Pharmacy*, 31; (2005); pp. 527-534.

Chambin, O., et al; "Influence of drug polarity upon the solid-state structure and release properties of self-emulsifying drug delivery systems in relation with water affinity"; *Colloids and Surfaces B: Biointerfaces* 71 (2009) pp. 73-78.

Chauhan Bhaskar, et al; "Preparation and Characterization of Etoricoxib Solid Dispersions Using Lipid Carriers by Spray Drying Technique"; *AAPS PharmSciTech 6* (3), *Article* 50; (2005); pp. E405-E412; (http://www.aapspharmscitech.org).

Chauhan, B., et al; "Preparation and evaluation of glibenclamide-polyglycolized glycerides solid dispersions with silicon dioxide by spray drying technique"; *European J. Pharm . . . Scl*. 26[2]; (2005); pp. 219-230.

Chen, X. Q., et al; "Evaluation of Lipid-based Formulations in Dogs and Monkeys for a Highly Lipophilic Compound"; (2007); *Conference "Annual Meeting of AAPS"*, San Diego, CA. poster pages.

Coy, et al.; "Solid Phase Synthesis of Lutenizing Hormone-Releasing Hormone and Its Analogs"; *Methods Enzymol*. 37; (1975); pp. 416-424.

Cuine, Jean F., et al; "Evaluation of the Impact of Surfactant Digestion on the Bioavailability of Danazol after Oral Administration of Lipidic Self-Emulsifying Formulations to Dogs"; *Journal of Pharmaceutical Sciences*, vol. 97, No. 2; Feb. 2008; pp. 995-1012; article first published online Dec. 6, 2007.

Damian, Festo, et al; "Physicochemical characterization of solid dispersions of the antiviral agent UC-781 with polyethylene glycol 6000 and Gelucire 44/14"; European Journal of Pharmaceutical Sciences 10; (2000); pp. 311-322.

Darling, et al. (2000) "Extended Release of Human Growth Hormone Suspended in SABER™ Formulation Design and in Vitro Assessment" Genentech, Inc., South San Francisco, CA USA and Southern BioSystems, Inc. Birmingham AL, USA. Poster; 1 page.

DataBase WPI Section Ch, Week 198532 Derwent Publications Ltd., London GB; Class B07, AN 1985-193549 XP002284488 & JP 60120811 A (Sealer, R P Kk) Jun. 28, 1985 (Abstract).

Desai et al.; "Surface Modification of Polymeric Biomaterials for Reduced Thrombogenicity"; *Polym. Mater. Sci. Eng.*, 62; Jun. 1990; pp. 731-735.

Dodson, K.M., et al. "Oral Controlled Release of Antiretrovirals Using the SABER Delivery System Incorporated into Soft Gelatin Capsules", *AAPS Meeting*, (1999), New Orleans, LA.; 2 pages.

Dordunoo, S.K., et al; "Preformulation Studies on Solid Dispersions Containing Triamterene or Temazepam in Polyethylene Glycols or Gelucire® 44/14 for Liquid Filling of Hard Gelatin Capsules."; *Drug Development and Industrial Pharmacy*, vol. 17, No. 12; (1991); pp. 1685-1713.

Dordunoo, S.K., et al; "Solidification studies of polyethylene glycols, Gelucire® 44/14 or their dispersions with Triamterene or Temazepam."; *Journal of Pharm. Pharmacology*, vol. 101; (1996); pp. 782-789.

Duan, D.C. et al.; "Novel Dispersing Aids for Hydrofluoroalkane-Based Metered Dose Inhalers"; *1998 Conference of the American Association of Pharmaceutical Scientists*, San Francisco, California; Nov. 1998; 1 page.

Duan, D.C. et al., "Oligomeric Lactic Acids as Solubilizing Aids for HFA-Based Metered Dose Inhalers"; *1998 Conference of the American Association of Pharmaceutical Scientists*, San Francisco, California; Nov. 1998; 1 page.

Dunbar SA, Katz NP; "Chronic opioid therapy for nonmalignant pain in patients with a history of substance abuse: report of 20 cases." *Journal of Pain and Symptom Management*. 11(3); (1996) pp. 163-171.

Edimo, A., et al; "Capacity of Lipophilic Auxiliary Substances to Give Spheres By Extrusion—Spheronization"; *Drug Development And Industrial Pharmacy*, 19(7); (1993); pp. 827-842.

Eliasen, Helle; et al; "Effects of binder rheology on melt agglomeration in a high shear mixer"; *International Journal of Pharmaceutics* 176; (1998) pp. 73-83.

Fernandez, Sylvie, et al; "Lipolysis of the semi-solid self-emulsifying excipient Gelucire® 44/14 by digestive lipases"; *Biochimica et Biophysica Acta* 1781; (2008); pp. 367-375.

Fitzgerald, B. P., et al., "Effect of Constant Administration of a Gonadotropin-Releasing Hormone Agonist on Reproductive Activity in Mares: Preliminary Evidence on Suppression of Ovulation During the Breeding Season"; *Am. J. Vet. Res.*, vol. 54, No. 10; Oct. 1993; pp. 1746-1751.

Fleury, J., et al. (1998) "Evaluation of the SABER Delivery System for the Controlled Release of Deslorelin for Advancing Ovulation in the Mare: Effects of Formulation & Dose"; Proceed. Int'l. Symp. Control. Rel. Bioact. Mater., 25 Controlled Release Society, Inc.; pp. 657-658.

Friedmann N, Klutzaritz V, Webster L; "Efficacy and safety of an extended-release oxycodone (Remoxy) formulation in patients with moderate to severe osteoarthritic pain"; *J Opioid Manag*. 7(3); (2011); pp. 193-202.

Friedmann N, Klutzaritz V, Webster L.; "Long-term safety of Remoxy(R) (extended-release oxycodone) in patients with moderate to severe chronic osteoarthritis or low back pain"; *Pain Med.*, 12(5); (2011); pp. 755-760.

Gad, Shayne C., et al; "Nonclinical Vehicle Use in Studies by Multiple Routes in Multiple Species"; *International Journal of Toxicology*, 25; Sep. 20, 2006; pp. 1-23.

Gattefossé Corporation (1989); "To Help With Your Impossible Formulations: A Guide to Gattefossé Liquid Excipients"; 6 pages.

Gattefossé (1998); "Oral Route Excipients" 8 pages.

Gelucire 44-14 brochure (1999); "Immediate Release and Enhanced Bioavailability"; pp. 1-16.

Gelucire Technical Dossier (1996); "Answering The Need for Enhanced Bioavailability"; pp. 1-16.

Gelucire®, (1996); "Answering The Need for Enhanced Bioavailability"; 5 pages.

"General Characteristics of Polymers"; *Museum of Fine Arts*, Boston; (2007); pp. 1-4.

Gibson, et al.; "Effects of Formulation Variables on Controlled Release of Paclitaxel and other Chemotherapeutic Agents from a Novel Delivery System" *AAPS* New Orleans, LA; (1999); Southern BioSystems, Inc. Birmingham AL, USA; 2 pages.

Gibson, et al.; "In Vitro and In Vivo Evaluation of a Novel In Situ-Forming Pareteral Delivery System"; *Meeting of Recent Advances in Drug Delivery Systems*, Salt Lake City, UT; (1999); Southern BioSystems, Inc. Birmingham AL, USA; 2 pages.

Gilderman L., et al; "Remoxy™: A New Opioid Drug With Effective Analgesia and Abuse-Resistance." *American Pain Society Annual Meeting*, San Antonio, TX, May 2006; 1 page.

Ginther, O.J, "Follicles", Ultrasonic Imaging and Reproductive Events in the Mare. EquiServices, Chapter 4: 43-72, Cross Plains, WI, 1986.

Ginther, O.J., "Effect of a Synthetic Gonadotropin-Releasing Hormone on Plasma Concentrations of Luteinizing Hormone in Ponies", *Am. J. Vet. Res.*, 1 vol. 35, No. x; Jan. 1974; pp. 79-8.

Ginther, O.J., "Reproductive Efficiency", *Reproductive Biology of the Mare Basic and Applied Aspects*, Second Ed., Chapter 12; (1992); pp. 499-509.

Glajchen, M. (2001) "Chronic Pain: Treatment Barriers and Strategies for Clinical Practice"; *J AM Board Fam Pract*. 14(3): 178-183.

González et al; "Methylphenidate bioavailability from two extended-release formulations"; *International Journal of Clinical Pharmacology Therapeutics*, vol. 40, No. 4; (2002) pp. 175-184.

Gould Phillip; "Salt selection for basic drugs"; *International Journal of Pharmaceutics*, 33 (1986), pp. 201-217.

(56) References Cited

OTHER PUBLICATIONS

Greydanus, D. E.; "Psychopharmacology for ADHD in Adolescents: Quo Vadis?"; *Psychiatric Times* vol. 20, No. 5; May 5, 2003; pp. 1-7.
Handbook of Pharmaceutical Excipients: Sixth Edition; "Medium-chain Triglycerides"; *Pharmaceutical Press and American Pharmacists Association 2009*; pp. 429-431.
Harrison, L.A., et al.; "Comaprison of HCG, Buserelin and Luprostiol for Induction of Ovulation in Cycling Mares"; *Equine Veterinary Science*, vol. 11, No. 3; (1991); pp. 163-166.
Hatakeyama et al.; "Synthesis and physical properties of polyurethanes from saccharide-based polycaprolactones"; *Macromolecular Symposia*, vol. 130; (1998); pp. 127-138.
Hauss, D.J., et al; "Lipid-Based Delivery Systems for Improving the Bioavailability and Lymphatic Transport of a Poorly Water-Soluble LTB4 Inhibitor."; *Journal of Pharmaceutical Sciences*, vol. 87, No. 2; (1998) pp. 164-169.
Hays Lon R. (2004) "A profile of OxyContin addiction"; *Journal of Addictive Diseases* 23(4); pp. 1-9.
He, Y., et al; "Oral Formulation of a Novel Antiviral Agent, PG301029, in a Mixture of Gelucire 44/14 and DMA (2:1, wt/wt)"; *AAPS Pharm. Sci. Tech.* 6(1); (2005); pp. E1-E5.
Henry, C.; "Sucrose Acetate Isobutyrate Special Grade for Beverage Applications" *International Food Ingred*; (1995); pp. 47-49.
Hoskin PJ, et al; "The bioavailability and pharmacokinetics of morphine after intravenous, oral and buccal administration in healthy volunteers."; *Br J Clin Pharmacol*; 27 (4); (1989); pp. 499-505.
Hülsmann, S., et al; "Melt extrusion—an alternative method for enhancing the dissolution rate of 17β-estradiol hemihydrate"; *European Journal of Pharmaceutics and Biopharmaceutics* 49; (2000); pp. 237-242.
Hyland, J.H., et al.; "Infusion of Gonadotrophin-releasing hormone (GnRH) Induces Ovulation and Fertile Oestrus in Mares During Seasonal Anoestrus"; *J. Reprod. Fert., Suppl.* 35 (1987); pp. 211-220.
Inciardi James A, et al; "Mechanisms of prescription drug diversion among drug-involved club- and street-based populations"; *Pain Medicine.* 8(2), (2007); pp. 171-183.
Irvine, D.S., et al; "Duration of Oestrus and Time of Ovulation in Mares Treated with Synthetic GnRH (Ay24,031)"; *J. Reprod. Fert. Supp.* 23; (1975); pp. 279-283.
Irvine; "GnRH Clinical Application"; *In Equine Reproduction, (eds) McKinon, A.O. and Voss, J.L., Chapter 36, Lea & Febiger*; (1993); pp. 41-45.
Ishida T, Oguri K, et al.; "Isolation and identification of urinary metabolites of oxycodone in rabbits"; *Drug Metab Dispos*; 7(3); (1979); pp. 162-165.
Ishida T, Oguri K, Yoshimura H.; "Determination of oxycodone metabolites in urines and feces of several mammalian species"; *J Pharmacobiodyn*; 5(7); (1982); pp. 521-525.
Itoh, K., et al; "Improvement of physiochemical properties of N-4472 part I formulation design by using self-microemulsifying system"; *Int .J. Pharm.*, 238[1-2]; (2002); pp. 153-160.
Iwanaga, Kazunori, et al; "Disposition of Lipid-Based Formulation in the Intestinal Tract Affects the Absorption of Poorly Water-Soluble Drugs"; *Biol. Pharm. Bull.* vol. 29, No. 3; (2006); pp. 508-512; published online Dec. 5, 2005.
Iyakuhin Tenkabutsu Kenkyykai Ed.; "Jitsuyo Iyakuhin Tenkabutsu (Practical Medical Additives)"; *pub. Kagaku Kogyo-sha*; Mar. 5, 1974; Tokyo; 6 pages.
Jannin, V., et al; "Systemes auto-émulsionnables et émulsions séches"; *STP Pharma Pratiques*, vol. 15, No. 3; May/Jun. 2005; pp. 246-255.
Jannin, V., et al; "Approaches for the development of solid and semi-solid lipid-based formulations"; *Advanced Drug Delivery Reviews* 60; (2008); pp. 734-746; available online Nov. 4, 2007.
Japanese Office Action for Japanese Application No. 2010-537128, mailed Jun. 5, 2013.
Jöchle, W., et al.; "Control of Ovulation in the Mare with Ovuplant a Short-Term Release Implant (STI) Containing the GnRH Analogue Deslorelin Acetate: Studies from 1990 to 1994"; *Journal of Equine Veterinary Science*, vol. 14m No. 12; (1994); pp. 632-644.
Johnson, et al; "Biodegradable Delivery Systems for Estradiol: Comparison Between Poly(DL-Lactide) Microspheres and the Saber Delivery System"; *Proceed. Int'l Symp. Control. Rel. Bioact. Mater.*, 26; Controlled Release Society, Inc.; (1999); 1 page.
Johnson, R.M., et al; "Applications of Continuous Site-Directed Drug Delivery"; *Proc. West Pharmacol Soc.* vol. 45; (2002); pp. 219-222.
Johnston Lloyd D, et al; "Monitoring the future. National results on adolescent drug use: overview of key findings"; (NIH Publication No. 05-5726). Bethesda, MD: *National Institute on Drug Abuse*; (2004); pp. 1-66.
Kaiko (2005) "Pharmacology of Tablets of Oxycontin the Development Process Thereof" *Palliative Care Research* 7(1):3-13.
Kale, A., et al; "Design and Evaluation of Self-Emulsifying Drug Delivery Systems (SEDDS) of Nimodipine"; *AAPS Pharm. Sci. Tech.*, 9(1); (2008); pp. 191-196.
Kamel S., et al; "Pharmaceutical significance of cellulose: A review"; *eXPRESS Polymer Letters* vol. 2, No. 11; (2008); pp. 758-778.
Kane, Anil, et al; "A Statistical Mixture Design Approach Fo Formulating Poorly Soluble Compounds In Liquid Filled Hard Shell Capsules"; *Bulletin Technique Gattefosse* No. 99; (2006); pp. 43-49.
Karatas, A., et al; "Improved solubility and dissolution rate of piroxicam using gelicore 44/14 and labrasol"; *II Farmaco* 60(9); (2005); pp. 777-782.
Katz NP, et al.; "Behavioral monitoring and urine toxicology testing in patients receiving long-term opioid therapy" *Anesth Analg.* 97(4); (2003); pp. 1097-1102.
Katz NP, et al; "Development and preliminary experience with an ease of extractability rating system for prescription opioids"; *Drug Development and Industrial Pharmacy.* 32(6); (2006); pp. 727-746.
Katz NP, et al; "Prescription monitoring of medical and non-medical Schedule II opioid abuse in Massachusetts: 1996-2005"; *Conference paper presented at the 69th College on Problems of Drug Dependence (CPDD)*, Quebec, Canada; (2007); 1 page.
Katz NP, et al; "Challenges in the development of prescription opioid abuse-deterrent formulations"; *Clin J Pain*, 23(8); (2007); pp. 648-660.
King; "Tablets, Capsules, and Pills" *Remington's Pharmaceutical Sciences, Ed. Arthur Osol, Chapter 89*, (1980); pp. 1553-1584.
Koga, Kenjiro, et al; "In vitro and in situ evidence for the contribution of Labrasol® and Gelucire 44/14 on transport of cephalexin and cefoperazone by rat intestine"; *European Journal of Pharmaceutics and Biopharmaceutics* 54; (2002); pp. 311-318.
Kulkarni, et al., "Polyactic Acid for Surgical Implants," *Arch. Surg.* vol. 93; (1966); pp. 839-843.
Lacoste, D., et al.; "Reversible Inhibition of Testicular Androgen Secretion by 3- , 5- and 6-Month Controlled-Release Microsphere Formulations of the LH-RH Agonist [D-Trp.sup.6, des-Gly-NH.sub.2]LH-RH Ethylamide in the Dog"; *J. Seroid Biochem.* vol. 33, No. 5; (1989); pp. 1007-1011.
Laforet, Jean-Pierre, et al; "The Right Mix"; *Gattefosse*, vol. 7, No. 1; (1995); pp. 1-10.
Lalovic Bojan, et al; "Pharmacokinetics and pharmacodynamics of oral oxycodone in healthy human subjects: role of circulating active metabolites"; *Clin Pharmacol Ther* 79(5); (2006); pp. 461-479.
Larsen, A., et al; "In vitro evaluation of Pharmaceutical surfactants fate during lipolysis and its effects on solubilization of a poorly soluble model compound: Danazol"; *Conference on When Poor Solubility Becomes an Issue: From Early Stage to Proof of Principles*; (2006); Verona (Italy); 2 pages.
Larsen, Anne, et al; "Pharmaceutical Surfactants In Biorelevant Media: Impact On Lipolysis and Solubility of a Poorly Soluble Compound; Danazol"; *Conference, 5th World Meeting on Pharmaceutics Biopharmaceutics and Pharmaceutical Technology*, Geneva, Switzerland; (2006); 2 pages.
Lopez et al.; "Comparative efficacy of two once daily methylphenidate formulations (Ritalin LA and Concerta) and placebo in children with attention deficit hyperactivity disorder across the school day"; *Pediatr Drugs* 5(8); (2003); pp. 545-555.

(56) References Cited

OTHER PUBLICATIONS

Lowden, K.; "Filling hard gelatin capsules: experience in a new environment"; *Pharmaceutical Manufacturing Review*, vol. 10, No. 5; (1998); pp. 27 29.

Loy, R.G., et al., "The Effects of Human Chorionic Gonadotrophin on Ovulation, Length of Estrus, and Fertility in the Mare"; University of California, Davis, California, Jan. 30, 1965, pp. 41-50.

Malhotra et al. "The pharmacokinetics of oxycodone and its metabolites following single oral doses of Remoxy®, an abuse-deterrent formulation of extended-release oxycodone, in patients with hepatic or renal impairment," Journal of Opioid Mgmt 11(2):157-169 (Mar./Apr. 2015).

Markowitz et al; "Advances in the pharmacotherapy of attention-deficit-hyperactivity disorder: focus on methylphenidate formulations"; *Pharmacotherapy* 23(10); (2003); pp. 1281-1299.

Markowitz et al; "Pharmacokinetics of methylphenidate after oral administration of two modified-release formulations in healthy adults"; *Clin Pharmacokinet* 42(4); (2003); pp. 393-401.

Material Safety Data Sheet "Eastman: Cellulose Acetate Butyrate CAB-381-2 BP CAB381-20 BP: Coating Chemicals" Eastman Chemical Company, Publication E-296B, Aug. 1994.

Material Safety Data Sheet "Eastman: Cellulose Esters for Pharmaceutical Drug Delivery" Eastman Chemical Company, Publication PCI-105B, Jun. 2004.

Material Safety Data Sheet of Eastman Chemical Products, "SAIB" Sucrose Acetate Isobutyrate, pp. 1-24. Publication GN-311F (Jun. 2004).

Material Safety Data Sheet of Eastman Fine Chemical Pharmaceutical Ingredients, Sucrose Acetate Isobutyrate Special Grade (SAIB-SG), Publication No. EFC-211, (May 1991).

Material Safety Data Sheet of Eastman Products for the Food Industry, "Sucrose Acetate Isbutyrate (SAIB-SB) for Use in Fruit-Flavored Beverages," Publication No. ZM-90, (Sep. 1989); pp. 2-7.

McCabe SE, et al; "Motives, diversion and routes of administration associated with nonmedical use of prescription opioids"; *Addictive Behaviors*. 32; (2007); pp. 562-575.

McCarthy, P.F., et al.; "Management of Stallions on Large Breeding Farms"; *Veterinary Clinics of North America: Equine Practice*, vol. 8, No. 1; Apr. 1992; pp. 219-235.

McKinnon, A.O., et al.; "Effect of GnRH Analogue (Ovuplant), hCG and Dexamethasone on Time to Ovulation in Cycling Mares"; *World Equine Veterinary Review*, vol. 2: No. 3; (1997); pp. 16-18.

McKinnon, A.O., et al.; "Repeated Use of a GnRH Analogue Deslorelin (Ovuplant) for Hastening Ovulation in the Transitional Mare"; *Equine Veterinary Journal* 29 (2); (1996); pp. 153-155.

McLellan AT, et al; An improved diagnostic instrument for substance abuse patients—The Addiction Severity Index: *The Journal of Nervous and Mental Disease*. vol. 168, No. 1; (1980); pp. 26-33.

Mearns, D.; "Changing Seasons"; *The Blood-Horse*; Sep. 28, 1996; pp. 4794-4765.

Meehan, E., et al; "Monitoring the stability of excipients used in lipid matrix formulations"; (Poster Abstract), Conference "*33rd Annual Meeting of the Controlled Release Society*", Vienna, Austria. Jul. 22, 2006; 2 pages.

Mehuys, E., et al.; "Human bioavailability of propranolol from a matrix-in-cylinder system with a HPMC-Gelucire® core"; *Journal of Controlled Release* 107; (2005); pp. 523-536; available online Aug. 1, 2005.

Merrifield, Bruce; "Solid Phase Synthesis"; *Science*, vol. 232; Apr. 18, 1986; pp. 341-347.

Meyer RJ, Hussain AS. Awareness topic: mitigating the risk of ethanol induced dose dumping from oral sustained/controlled release dosage forms. In: FDA's Advisory Committee for Pharmaceutical Science Meeting, Oct. 2005.

Montovan, S.M., et al; "The Effect of a Potent GnRH Agonist on Gonadal and Sexual Activity in the Horse"; *Theriogenology*, vol. 33 No. 6; Jun. 1990; pp. 1305-1321.

Mumford, E.L.; "Use of Deslorelin Short-Term Implants to Induce Ovulation in Cycling Mares During Three Consecutive Estrous Cycles"; *Animal Reproduction Science*, vol. 39; (1995); pp. 129-140.

Murray Sally, et al; "Alcohol-associated rapid release of a long-acting opioid"; *CMAJ*; 173(7); Sep. 27, 2005; pp. 756.

Nabors, et al; "Controlled Release of Diclofenac-Na from Cellulose Ester Microspheres"; *PDD Presentation 7481 at the 1994 Ninth Annual AAPS Meeting* in San Diego, CA; Nov. 6-10, 1994; 2 pages.

Nakagaki, Arita; "Seizai Butsuri Kagaku (Physical Chemistry of Medical Preparations)", *pub. Asakura Shoten*; Nov. 5, 1968; Tokyo; 6 pages.

Nally, J., et al.; "Induction of Mucosal IgA Specific for SeMF3 for *Streptococcus equi* with Intranasal Vaccination Using a Sucrose Acetate Isobutyrate Based Delivery System", *Proceed. Int'l. Symp. Control. Rel. Bioact. Mater.*, 26; (1999); Controlled Release Society, Inc. 2 pages.

"NATROSOL® Hydroxyethylcellulose A Nonionic Water-Soluble Polymer"; Hercules Incorporated, Aqualon Division; (1999); pp. 1-24.

Nett, T.M., et al.; "Further Studies on the Radioimmunoassay of Gonadotropin-releasing Hormone: Effect of Radioiodination, Antiserum and Unextracted Serum on Levels of Immunoreactivity in Serum"; *Endocrinology* vol. 101, No. 4, (1977); pp. 1135-1144.

O'Driscoll, Caitriona M.; "Lipid-based formulations for intestinal lymphatic delivery"; *European Journal of Pharmaceutical Sciences* 15; (2002); pp. 405-415.

Okumu, et al; "Evaluation of SABER™ as a Local Delivery System for rhVEGF-Formulation Design and In Vitro Assessment" Genentech, Inc., South San Francisco, CA USA and Southern BioSystems, Inc. Birmingham AL, USA; (2000); 1 page.

Okumu, et al; "Evaluation of SABER™ as a Local Delivery System for rhVEGF-Formulation Design and In Vitro Assessment" Genentech, Inc., South San Francisco, CA USA and Southern BioSystems, Inc. Birmingham AL, USA. Poster; (2001); 1 page.

Patel Pranav, et al; "Preparation, Evaluation and Comparison Of Lipid Based Drug Delivery Systems Of Tacrolimus"; *International Journal of Pharmacy and Pharmaceutical Sciences*, vol. 6 Suppl 2; (2014); pp. 588-591.

Patrick et al; "New methylphenidate formulations for the treatment of attention-deficit/hyperactivity disorder" *Expert Opin Drug Deliv* 2(1); (2005); pp. 121-143.

Pelham et al; "Once-a-day Concerta methylphenidate versus three-times-daily methylphenidate in laboratory and natural settings"; *Pediatrics* vol. 107, No. 6; Jun. 6, 2001; pp. 1-15.

Perissutti, B, et al.; "Solid dispersions of carbamazepine with Gelucire 44/14 and 50/13"; *S.T.P. Pharma Sciences* 10 (6); (2000); pp. 479-484.

Pozzi, Franco, et al; "Formulations of Ubidecarenone with Improved Bioavailability"; *Eur. J. Pharm. Biopharm*, vol. 37, No. 4; (1991); pp. 243-246.

Pulido et al.; "Enzymatic Regioselective Acylation of Hexoses and Pentoses Using Oxime Esters"; *J. Chem. Soc. Perkin Trans.* 1, (21); (1992); pp. 2891-2898.

Rabb et al.; "Effects of Active Immunication Against GnRH on LH, FSH and Prolactin Storage, Sectretion and Response to Their Secretagogues in Pony Geldings"; *J. Anim. Sci.*, 68; (1990); pp. 3322-3329.

Ren, Shan, et al; "In Vitro Metabolic Stability of Moisture-Sensitive Rabeprazole in Human Liver Microsomes and Its Modulation by Pharmaceutical Excipients"; *Arch Pharm Res* vol. 31, No. 3; (2008); pp. 406-413; published online Apr. 13, 2008.

Reynolds, R.C. et al.; "Sucrose acetate isobutyrate (SAIB): historical aspects of its use in beverages and a review of toxicity studies prior to 1988"; *Food Chem. Toxicol*.36(2), (1998); pp. 81-93.

Reynolds, R.C.; "Metabolism and pharmacokinetics of sucrose acetate isobutyrate (SAIB) and sucrose octaisobutyrate (SOIB) in rats, dogs, monkeys or humans: a review"; *Food Chem. Toxicol.*, 36(2); (1998); pp. 95-99.

Robinson; "Coating of Pharmaceutical Dosage Forms" *Remington's Pharmaceutical Sciences, Ed. Arthur Osol. Chapter 90*; (1980); pp. 1585-1593.

(56) References Cited

OTHER PUBLICATIONS

Roser, J.J., et al.; "The Development of Antibodies to Human Chorionic Gonadotrpins Following its Repeated Injection in the Cyclic Mare"; *J. Reprod. Fert Suppl.*, (1979); pp. 173-179.

Roussin, P. et al; "Gelucire® 44/14: A High-Performance System To Enhance Bioavailability of Poorly Water Soluble Drugs"; *Bulletin Technique Gattefosse*; (1997); pp. 51-58.

Sachs-Barrable, K., et al; "Lipid Excipients Peceol and Gelucire 44/14 decrease p. glycoprotein mediated efflux of Rhodamine 123 partially due to modifying P-glycoprotein expression within Caco-2 Cells."; *J. Pharm. Pharm. Sci.*, 10[3], (2007); pp. 319-331.

Saeio, Kiattisak, et al; "Factors Influencing Drug Dissolution Characteristic From Hydrophilic Polymer Matrix Tablet"; *Scientia Pharmaceutica (Sci. Pharm.)* 75; (2007); pp. 147-163.

Saeki (2005) "Progress of Orally Opiate Analgesics and Non-Steroidal Anti-Flammatory Agent" *Drug Deliv Syst* 20(5):521-529.

Santus et al.; "Osmotic Drug Delivery: A Review of the Patent Liter" *J Control Release* 35(1); (1995); pp. 1-21.

Schamp Karen, et al; "Development of an in vitro/in vivo correlation for lipid formulations of EMD 50733, a poorly soluble, lipophilic drug substance"; *European Journal of Pharmaceutics and Biopharmaceutics* 62; (2006); pp. 227-234.

Serajuddin, A.T.M., et al.; "Effect of vehicle amphiphilicity on the dissolution and bioavailability of a poorly water-soluble drug from solid dispersions."; *Journal of Pharmaceutical Sciences*, vol. 77, No. 5, (1988); pp. 414-417.

Serajuddin, A.T.M., et al; "Water Migration from Soft Gelatin Capsule Shell to Fill Material and Its Effect on Drug Solubility"; *Journal of Pharmaceutical Sciences*, vol. 75, No. 1; (1986); pp. 62-64.

Selimovic, Seila, and Hu Yue; "Aging Effects in Suspensions of Silica Particles"; Mat. Res. Soc. Symp. Proc., vol. 790 *Materials Research Society*; (2004) pp. P7.11.1-P7.11.6.

Sethia Sundeep, et al; "Physicochemical Characterization of Solid Dispersions of Carbamazepine Formulated by Supercritical Carbon Dioxide and Conventional Solvent Evaporation Method"; *Journal of Pharmaceutical Sciences*, vol. 91, No. 9; Sep. 2002; pp. 1948-1957.

Sethia Sundeep, et al; "In Vitro-In Vivo Evaluation of Supercritical Processed Solid Dispersions: Permeability and Viability Assessment in Caco-2 Cells"; *Journal of Pharmaceutical Sciences*, vol. 93, No. 12; Dec. 2004; pp. 2985-2993.

Setnik B, et al.; (2011) "The abuse potential of Remoxy®, an extended-release formulation of oxycodone, compared with immediate- and extended-release oxycodone"; *Pain Med.* 12(4):618-631.

Shah N. H; et al; "Self-Emulsifying Drug Delivery Systems (SEDDS) For Improving In Vitro Dissolution and Oral Absorption of Lipophilic Drugs"; *Bulletin Technique. Gattefossé Report* No. 85; (1992/93); pp. 45-54.

Sheen, P.C., et al; "Bioavallabiltty of a poorly water soluble drug from tablet and solid dispersion in humans."; *Journal of Pharmaceutical Sciences*, vol. 80, No. 7, (1991); pp. 712-714.

Shimpi Shyam, et al; "Preparation and Evaluation of Diltiazem Hydrochloride-Gelucire 43/01 Floating Granules Prepared by Melt Granulation"; *AAPS PharmSciTech* 5(3), Article 43; (2004); pp. 1-6; (http://www.aapspharmscitech.org).

Smith & Tipton (1996) "A Novel Parental Delivery System" *AAPS Presentation PDD* 7270, Seattle, WA; (1996) Annual Meeting; 2 pages.

Soliman M. S., et al; "Preparation and in vitro characterization of a semi-solid dispersion of flurbiprofen with Gelucire 44/14 and Labrasol"; *Pharmazie* 60(4); (2005); pp. 288-293.

Srinivas et al.; "Enantioselective pharmacokinetics and pharmacodynamics of dl-threo-methylphenidate in children with attention deficit hyperactivity disorder"; *Clin Pharmacal Ther* 52(5); (1992); pp. 561-568.

Stegemann. S., et al; "When Poor Solubility Becomes an Issue: From Early Stage to Proof of Concept"; *European Journal of Pharmaceutical Sciences* 31; (2007); pp. 249-261.

Strickley, Robert G; "An Overview of Lipid Excipients Currently Available: Strengths, Weaknesses and Opportunity Gaps: The Options for the Formulator"; *Bulletin Technique Gattefosse*, No. 100; (2007); pp. 31-37.

Strickley, Robert G.; "Solubilizing Excipients in Oral and Injectable Formulations"; *Pharmaceutical Research*, vol. 21, No. 2; Feb. 2004; pp. 201-230.

Subramanian, Ramaswamy, et al; "Effect of Lipid Excipients on In Vitro Pancreatic Lipase Activity"; *Drug Development and Industrial Pharmacy*, vol. 29, No. 8; (2003); pp. 885-890.

Sucrose Acetate Isobutyrate, 21 CFR 172.831 (1999).

Sullivan, et al.; "Delivery of Taxol® and other Antineoplastic Agents from a Novel System Based on Sucrose Acetate Isobutyrate" *AAPS* Boston, MA. Southern BioSystems, Inc. Birmingham AL, USA (1997); 2 pages.

Sullivan, et al; "Sustained Release of Orally Administered Active Using SABER Delivery System Incorporated into Soft Gelatin Capsules"; *Proceed. Int'l. Control. Rei. Bioact. Mater. Controlled Release Society*. vol. 25; Jun. 1998 Las Vegas NV; pp. 918-919.

Sullivan, et al; "Sustained Release of Progesterone and Estradiol from the SABER™ Delivery System: In Vitro and In Vivo Release Rates" *CRS* Las Vegas, NV. Southern BioSystems, Inc. Birmingham AL, USA; (1998); 2 pages.

Sullivan, et al; "Sustained Release of Lysozyme from the SABER™ Delivery System" *AAPS*, New Orleans, LA. Southern BioSystems, Inc. Birmingham AL, USA; (1999); 2 pages.

Sullivan, et al. (1998) "Sustained Release of Bupivacaine from the SABER TM Delivery System" AAPS, San Francisco, CA. Southern BioSystems, Inc. Birmingham AL, USA.

Sullivan, et al; "Incorporation of Polymer Microparticles Into Sucrose Acetate Isobutyrate Reduces Burst and Extends Release" *Proceed. Int'l Symp. Control. Rel. Bioact. Mater.*, 27, Controlled Release Society, Inc. Paris, France; Jul. 7-13, 2000.

Sullivan, J. J., et al.; "Duration of Estrus and Ovulation Time in Nonlactating Mares Given Human Chorionic Gonadotropin During Three Successive Estrous Periods"; *J.A.V.M.A.*, vol. 162, No. x; May 15, 1973; pp. 895-898.

Svensson, A., et al; "Hydration of an amphiphilic excipient Gelucire® 44/14"; *Int. J. Pharm.* 281(1-2); (2004); pp. 107-118.

Swanson et al; "Objective and subjective measures of the pharmacodynamic effects of Adderall in the treatment of children with ADHD in a controlled laboratory classroom setting"; *Psychopharmacol Bull* 34(1); (1998); pp. 55-60.

Swanson et al; "Acute tolerance to methylphenidate in the treatment of attention deficit hyperactivity disorder in children" *Clin Pharmacal Ther* 66(3); (1999); pp. 295-305.

Swanson et al. Ritalin: Theory and Practice. 2nd Edition, Greenhill & Osman Ed., Mary Ann Liebert, Larchmont, NY; (1999) pp. 405-430.

Swanson et al; "Efficacy of a new pattern of delivery of methylphenidate for the treatment of ADHD: effects on activity level in the classroom and on the playground" *J Am Acad Child Adolesc Psychiatry* 41(11); (2002); pp. 1306-1314.

Swanson et al; "Pharmacokinetic and pharmacodynamic properties of stimulants: implications for the design of new treatments for ADHD"; *Behav Brain Res* 130(1-2); (2002); pp. 73-78.

Swanson et al; "Development of a new once-a-day formulation of methylphenidate for the treatment of attention-deficit/hyperactivity disorder: proof-of-concept and proof-of-product studies"; *Arch Gen Psychiatry* 60(2); (2003); pp. 204-211.

Swanson et al; "Serum and brain concentrations of methylphenidate: implications for use and abuse"; *Neurosci Biobehav Rev* 27(7); (2003); pp. 615-621.

Swanson et al; "A comparison of once-daily extended-release methylphenidate formulations in children with attention-deficit/hyperactivity disorder in the laboratory school (the Comacs Study)"; *Pediatrics* 113(3 Pt. 1); (2004); pp. e206-e216.

Swiderski et al.; "Application of 14C Isotope in Studies on the Lability of Sugar Substituents" *Nukleonika, Supl.*, vol. 10; (1966); pp. 347-352.

Tashtoush, Bassam M., et al; "In Vitro and In Vivo Evaluation of Glibenclamide in Solid Dispersion Systems"; *Drug Development and Industrial Pharmacy*, vol. 30, No. 6; (2004); pp. 601-607.

(56) References Cited

OTHER PUBLICATIONS

Thompson, D. L., et al., "Effects of Melatonin and Thyrotropin Releasing Hormone on Mares During the Nonbreeding Season", Journal of Animal Science, vol. 56, No. 3, (1983), pp. 668-677.

Thompson, D. L., et al., "Testosterone Effects on Mares During Synchronization with Altrenogest: FHS, LH, Estrous Duration and Pregnancy Rate"; *Journal of Animal Science*, vol. 56, No. 3; (1983); pp. 678-686.

Tipton; "Peptide Delivery from an In Situ Gelling System Based Ion Sucrose Acetate Isobutyrate" *AAPS J Abstract*. Southern BioSystems, Inc. Birmingham AL, USA; (1999); 1 page.

Tipton, "In Situ Gelling Systems"; Sustained-Release Injectable Products, Ed. Senior & Radomsky, Interpharm Press, Denver, CO; (2000); pp. 258-259.

Tipton, et al; "Local Delivery from a Novel Biodegradable in Situ Delivery System"; *Sixth World Biomaterials Congress*, Kamuela, HI,. Southern BioSystems, Inc. Birmingham AL, USA, May 15-20, 2000; 1 page.

Tran Thao Truong-Dinh; et al; "Dissolution-modulating mechanism of alkalizers and polymers in a nanoemulsifying solid dispersion containing ionizable and poorly water-soluble drug"; *European Journal of Pharmaceutics and Biopharmaceutics* 72; (2009); pp. 83-90.

Trescot AM, et al; "Opioid Guidelines in the Management of Chronic Non-Cancer Pain." *Pain Physician*, vol. 9; (2006), pp. 1-40.

U.S. Department of Health and Human Services "Guidance for Industry: Food-Effect Bioavailability and Fed Bioequivalence Studies" FDA, Center for Drug Evaluation and Research (CDER), Dec. 2002.

U.S. Appl. No. 12/754,486, filed Apr. 5, 2010, 103 pages; with Preliminary Amendment filed Nov. 23, 2010, 13 pages.

U.S. Appl. No. 60/434,839, filed Dec. 18, 2002, 111 pages.

Vega-Rios Aracelly, et al; "Acid-catalyzed hydrolysis of triacylglycerols obeys monoexponential kinetics."; *International Journal of Chemical Kinetics*, vol. 24; (1992); pp. 887-894.

Venkatesan, N. et al; "Gelucire® 44/14 and Labrasol® in Enhancing Oral Absorption of Poorly Absorbable Drugs"; *Bulletin Technique Gattefosse*, No. 99; (2006); pp. 79-88.

Vila, Jato J.L., et al; "Influence of melting point and HLB on the release of amoxicillin from granulates containing Geludre® as excipients"; *S.T.P. Pharma*, vol. 6, No. 5 (1990); pp. 287-292.

Voss, J.L., et al., "The Effect of HCG on Duration of Oestrus, Ovulation Time and Fertility in Mares", Journal of Reprod. Fert., Suppl. 23 (1975), 297-301.

Volkow et al; "Relationship between psychostimulant-induced "high" and dopamine transporter occupancy"; *Proc Natl Acad Sci USA* 93(19); (1996); pp. 10388-10392.

Volkow et al. "Temporal relationships between the pharmacokinetics of methylphenidate in the human brain and its behavioral and cardiovascular effects"; *Psychopharmacology* 123; (1996) pp. 26-33.

Volkow et al; "Methylphenidate and cocaine have a similar in vivo potency to block dopamine transporters in the human brain"; *Life Sciences* vol. 65, No. 1; (1999); p. L7-p. L12.

Volkow et al; "Relationship between blockade of dopamine transporters by oral methylphenidate and the increases in extracellular dopamine: therapeutic implications"; *Synapse* 43(3); (2002); pp. 181-187.

Volkow, et al; "Dopamine transporter occupancies in the human brain induced by therapeutic doses of oral methylphenidate"; *Am J Psychiatry* 155(10); (1998); pp. 1325-1331.

Wigal et al; "Reliability and validity of the SKAMP rating scale in a laboratory school setting" *Psychopharmacol Bulletin*, vol. 34, No. 1; (1998); pp. 47-53.

Wigal et al; "Selection of the Optimal Dose Ratio for a Controlled-Delivery Formulation of Methylphenidate"; *The Journal of Applied Research* 3; (2003); pp. 46-63.

Wightman et al; "Transient changes in mesolimbic dopamine and their association with 'reward'"; *Journal of Neurochemistry* 82(4); (2002); pp. 721-735.

Wolraich et al; "Randomized, controlled trial of oros methylphenidate once a day in children with attention-deficit/hyperactivity disorder"; *Pediatrics* 108(4); (2001); pp. 883-892.

Yüksel, Nilüfer, et al; "Enhanced bioavailability of piroxicam using Gelucire 44/14 and Labrasol: in vitro and in vivo evaluation"; *European Journal of Pharmaceutics and Biopharmaceutics* 56; (2003); pp. 453-459.

Webster LR. PTI-821: sustained-release oxycodone using gel-cap technology. Expert Opin Investig Drugs. 2007; 16(3):359-366.

Zamloot M, et al.; "Remoxy®: a novel formulation of extended-release oxycodone developed using the ORADUR® technology"; *J Appl Res*. 10(3) (2010); pp. 88-96.

Australian application No. AU2017292791 Examination Report No. 1 dated Jun. 15, 2022.

Australian application No. AU2017292791—ExaminationReport No. 2 dated Dec. 19, 2022.

Australian application No. AU2017292791—ExaminationReport No. 3 dated Mar. 30, 2023.

EP publication No. EP3481381 extended European Search Report dated Dec. 12, 2019.

EP publication No. EP3481381 Office action with search report dated Feb. 4, 2021.

Singapore application No. 11201811760V Examination Report dated Aug. 6, 2021.

\* cited by examiner

FIGURE 5(A)
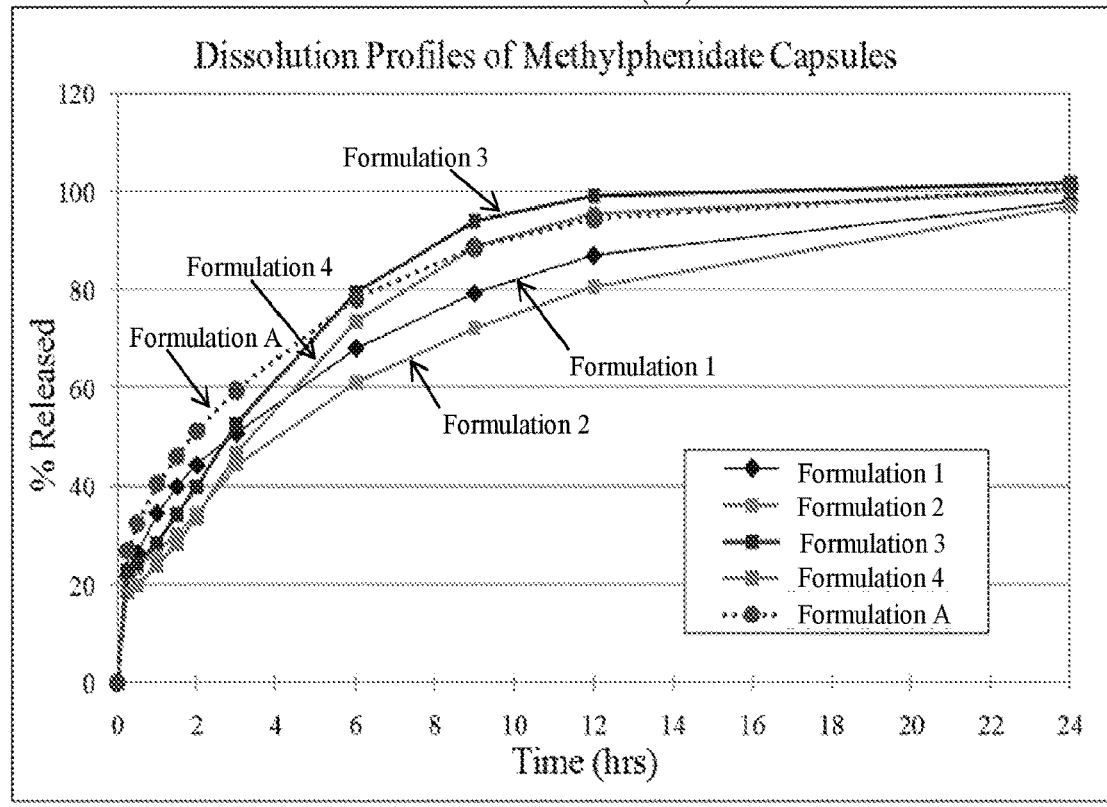
FIGURE 5(B) (Expanded 0-2 hrs)
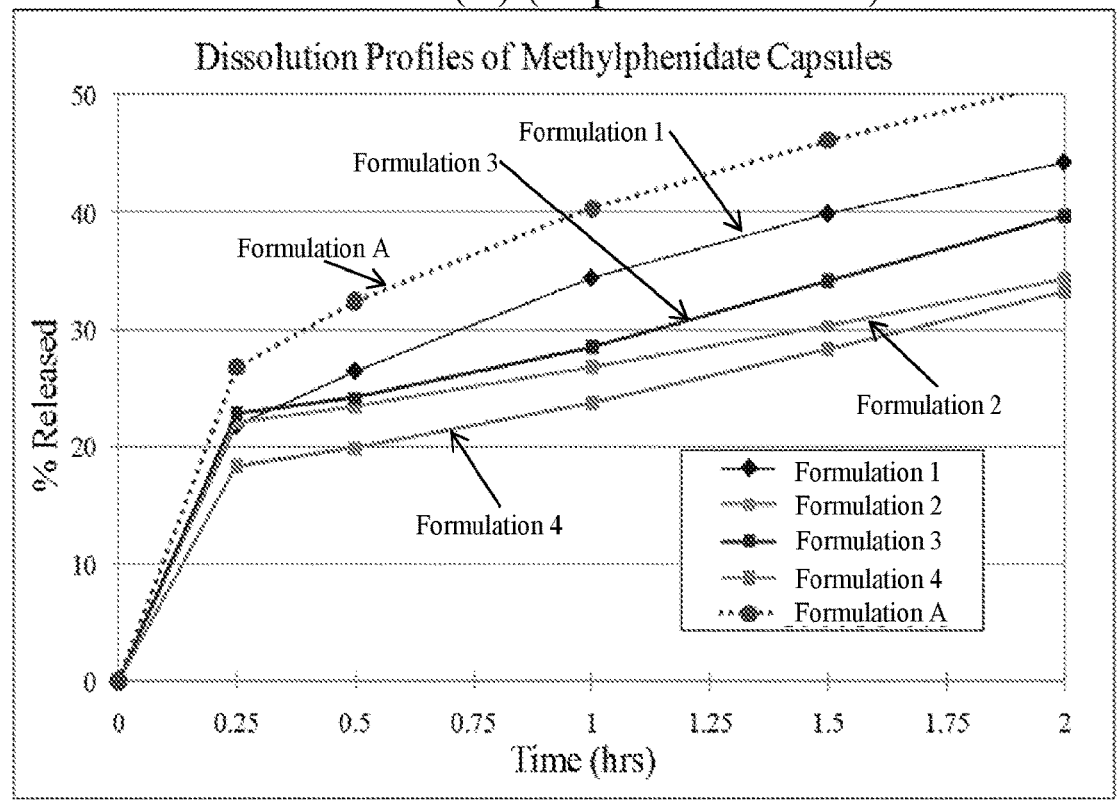

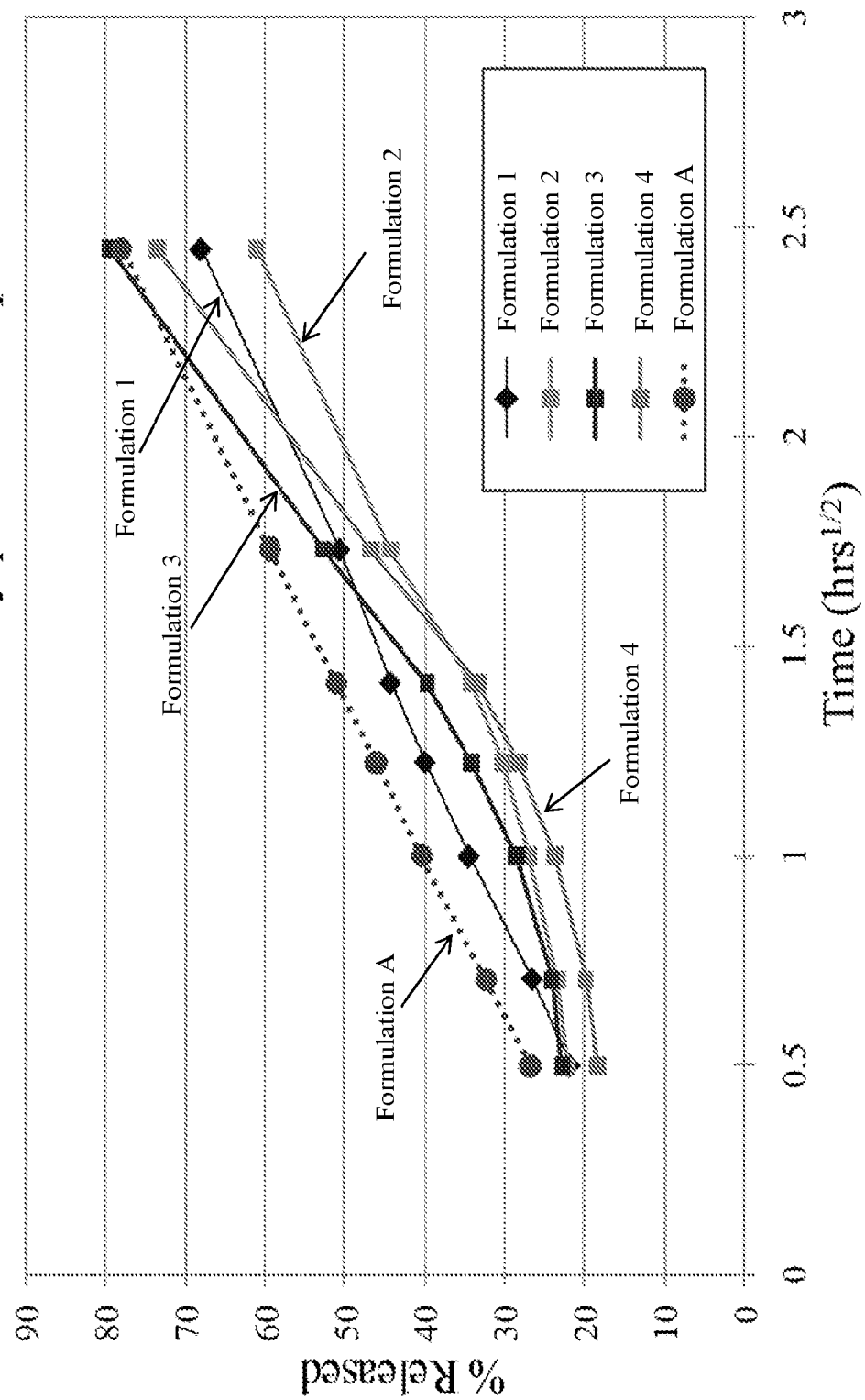
FIGURE 5(C) (Higuchi-Plot)

FIGURE 19A
22 mg MPH capsules

| Lot No. | Packaging Material/ Stability Conditions | Time Point (Months) | Water Content | % Cumulative Drug Released | | | | Organic Impurities | | | | Assay (%LC) | Microbial Limit Tests | | |
|---|---|---|---|---|---|---|---|---|---|---|---|---|---|---|---|
| | | | | 1 HR | 3 HR | 9 HR | 24 HR | MPH Related Compound A (LOQ=0.05%) | Erythro Isomer (LOQ=0.06%) | Other Degradation Product (LOQ=0.10%) | Total Impurity | | TAMC (cfu/g) | TYMC (cfu/g) | E. Coli |
| A | 120cc HDPE Bottle 25°C/60%RH | 0 | 3.70 | 29 | 62 | 102 | 105 | ND | ND | ND | <LOQ | 103.7 | <10 | <10 | Negative |
| | | 3 | 1.71 | 29 | 61 | 101 | 105 | ND | ND | ND | <LOQ | 103.2 | - | - | - |
| | | 6 | 2.34 | 28 | 61 | 100 | 104 | 0.11 | ND | ND | 0.11 | 103.8 | - | - | - |
| | | 9 | 2.90 | 28 | 58 | 99 | 103 | 0.16 | ND | ND | 0.16 | 104.5 | - | - | - |
| | | 12 | 2.18 | 29 | 65 | 97 | 101 | 0.20 | ND | ND | 0.20 | 102.8 | <10 | <10 | Negative |
| | | 18 | 2.2 | 30 | 56 | 96 | 103 | 0.32 | ND | ND | 0.32 | 102.5 | - | - | - |
| | | 24 | 2.3 | 29 | 56 | 93 | 103 | 0.43 | ND | ND | 0.43 | 104.3 | <10 | <10 | Negative |
| | 120cc HDPE Bottle 30°C/75%RH | 0 | 3.7 | 29 | 62 | 102 | 105 | ND | ND | ND | <LOQ | 103.7 | <10 | <10 | Negative |
| | | 3 | 3.4 | 27 | 59 | 100 | 104 | 0.16 | ND | ND | 0.16 | 105.5 | - | - | - |
| | | 6 | 2.6 | 29 | 58 | 98 | 103 | 0.24 | ND | ND | 0.24 | 103.2 | - | - | - |
| | | 9 | 2.6 | 29 | 62 | 98 | 103 | 0.39 | ND | ND | 0.39 | 103.3 | - | - | - |
| | | 12 | 2.6 | 27 | 55 | 96 | 102 | 0.52 | ND | ND | 0.52 | 102.6 | <10 | <10 | Negative |
| | | 18 | 2.9 | 30 | 57 | 92 | 103 | 0.81 | ND | ND | 0.81 | 101.3 | - | - | - |
| | | 24 | 3.0 | 28 | 55 | 90 | 103 | 1.04 | 0.068 | ND | 1.11 | 103.0 | <10 | <10 | Negative |
| | 120cc HDPE Bottle 40°C/75%RH | 0 | 3.7 | 29 | 62 | 102 | 105 | ND | ND | ND | <LOQ | 103.7 | <10 | <10 | Negative |
| | | 1 | 2.3 | 28 | 62 | 103 | 106 | 0.20 | ND | ND | 0.20 | 103.6 | - | - | - |
| | | 3 | 2.5 | 28 | 62 | 100 | 102 | 0.56 | ND | ND | 0.60 | 104.4 | - | - | - |
| | | 6 | 2.8 | 29 | 60 | 99 | 103 | 0.83 | 0.06 | ND | 0.90 | 102.4 | - | - | - |

ND = Not Detected, LOQ = Limit of Quantification, TAMC = Total Aerobic Microbial Count, TYMC = Total Combined Yeast/Molds Count FIGURE 19B
22 mg MPH capsules

| Lot No. | Packaging Material/ Stability Conditions | Time Point (Month) | Water Content | % Cumulative Drug Released | | | | Organic Impurities | | | | Microbial Limit Tests | | |
|---|---|---|---|---|---|---|---|---|---|---|---|---|---|---|
| | | | | 1 HR | 3 HR | 9 HR | 24 HR | MPH Related Compound A (LOQ=0.02%) | Erythro Isomer (LOQ=0.06%) | Other Degradation Product (LOQ=0.10%) | Total Impurity | Assay (%LC) | TAMC (cfu/g) | TYMC (cfu/g) | E. Coli |
| B | Blister-PVC/PVDC 40g with aluminum bag 25°C/60%RH | 0 | 1.1 | 31 | 48 | 74 | 90 | 0.10 | ND | ND | 0.10 | 102.9 | 690 | 10 | Negative |
| | | 3 | 1.9 | 32 | 48 | 74 | 88 | 0.15 | ND | ND | 0.15 | 104.3 | - | - | - |
| | | 6 | 1.5 | 33 | 50 | 76 | 88 | 0.18 | ND | ND | 0.18 | 104.6 | - | - | - |
| | | 9 | 1.0 | 33 | 50 | 72 | 82 | 0.2 | ND | ND | 0.2 | 104.2 | - | - | - |
| | | 13 | 1.6 | 31 | 49 | 78 | 92 | 0.2 | ND | ND | 0.2 | 105.3 | 700 | <10 | Negative |

ND = Not Detected, TAMC = Total Aerobic Microbial Count, TYMC = Total Combined Yeast/Molds Count

FIGURE 20A
33 mg MPH capsules

| Lot No. | Packaging Material Stability Condition | Time Point (Month) | Water Content | % Cumulative Drug Released ||||| Organic Impurities |||| Assay (%LC) | Microbial Limit Tests |||
|---|---|---|---|---|---|---|---|---|---|---|---|---|---|---|---|
| | | | | 1 HR | 1 HR | 1 HR | 9 HR | 24 HR | MPH Related Compound A (LOQ=0.13%) | Erythro Isomer (LOQ=0.08%) | Other Degradation Product (LOQ=0.13%) | Total Impurity | | TAMC (cfu/g) | TYMC (cfu/g) | E. Coli |
| C | 120cc HDPE Bottle 25°C/60%RH | 0 | 4.0 | 24 | 46 | 90 | 103 | <LOQ | ND | ND | <LOQ | 103.5 | <10 | <10 | Negative |
| | | 3 | 1.7 | 24 | 49 | 89 | 101 | <LOQ | ND | ND | <LOQ | 102.1 | - | - | - |
| | | 6 | 1.8 | 24 | 47 | 86 | 101 | <LOQ | ND | ND | <LOQ | 100.8 | - | - | - |
| | | 9 | 2.0 | 26 | 52 | 90 | 102 | 0.16 | ND | ND | 0.16 | 101.3 | - | - | - |
| | | 12 | 2.0 | 23 | 44 | 83 | 100 | 0.21 | ND | ND | 0.21 | 101.1 | <10 | <10 | Negative |
| | | 18 | 2.7 | 24 | 48 | 86 | 101 | 0.35 | ND | ND | 0.35 | 100.3 | - | - | - |
| | | 24 | 2.2 | 24 | 47 | 84 | 103 | 0.49 | ND | ND | 0.49 | 102.1 | <10 | <10 | Negative |
| | 120cc HDPE Bottle 30°C/75%RH | 0 | 4.0 | 24 | 46 | 90 | 103 | <LOQ | ND | ND | <LOQ | 103.5 | <10 | <10 | Negative |
| | | 3 | 2.0 | 25 | 50 | 86 | 100 | 0.16 | ND | ND | 0.16 | 102.2 | - | - | - |
| | | 6 | 2.4 | 24 | 49 | 91 | 101 | 0.25 | ND | ND | 0.25 | 101.4 | - | - | - |
| | | 9 | 2.5 | 25 | 51 | 89 | 102 | 0.42 | ND | ND | 0.42 | 100.1 | <10 | <10 | Negative |
| | | 12 | 2.7 | 24 | 48 | 85 | 102 | 0.55 | ND | ND | 0.55 | 100.4 | - | - | - |
| | | 18 | 2.8 | 24 | 46 | 86 | 102 | 0.85 | ND | ND | 0.85 | 99.2 | <10 | <10 | Negative |
| | | 24 | 3.1 | 25 | 46 | 81 | 105 | 1.11 | ND | ND | 1.11 | 99.3 | <10 | <10 | Negative |
| | 120cc HDPE Bottle 40°C/75%RH | 0 | 4.01 | 24 | 46 | 90 | 103 | <LOQ | <LOD | <LOD | <LOQ | 103.5 | <10 | <10 | Negative |
| | | 1 | 1.49 | 25 | 49 | 92 | 104 | 0.20 | <LOD | <LOD | 0.20 | 101.5 | - | - | - |
| | | 3 | 2.13 | 25 | 50 | 90 | 102 | 0.58 | <LOD | <LOD | 0.60 | 102.0 | - | - | - |
| | | 6 | 2.52 | 27 | 55 | 96 | 103 | 0.91 | <LOD | <LOD | 0.91 | 100.5 | - | - | - |

ND = Not Detected, LOD = Limit of Detection, LOQ = Limit of Quantification, TAMC = Total Aerobic Microbial Count, TYMC = Total Combined Yeast/Molds Count FIGURE 20B
33 mg MPH capsules

| Lot No. | Packaging Material/ Stability Conditions | Time Point (Months) | Water Content | % Cumulative Drug Released | | | | Organic Impurities | | | | Assay (%LC) | Microbial Limit Tests | | |
|---|---|---|---|---|---|---|---|---|---|---|---|---|---|---|---|
| | | | | 1 HR | 3 HR | 9 HR | 24 HR | MPH Related Compound A (LOQ=0.13%) | Erythro Isomer (LOQ=0.18%) | Other Degradation Product (LOQ=0.13%) | Total Impurity | | TAMC (cfu/g) | TYMC (cfu/g) | E. Coli |
| D | Blister-PVC/PVDC 40g with aluminum bag 25°C/60%RH | 0 | 1.4 | 24 | 51 | 86 | 99 | <LOQ | ND | ND | <LOQ | 100.5 | 140 | <10 | Negative |
| | | 3 | 2.1 | 28 | 53 | 86 | 102 | 0.14 | ND | ND | 0.14 | 102.8 | - | - | - |
| | | 6 | 1.3 | 27 | 52 | 85 | 100 | 0.16 | ND | ND | 0.16 | 101.8 | - | - | - |
| | | 9 | 0.9 | 26 | 54 | 86 | 98 | 0.20 | ND | ND | 0.20 | 102.3 | - | - | - |
| | | 13 | 2.0 | 26 | 51 | 84 | 100 | 0.40 | ND | ND | 0.40 | 101.1 | 170 | <10 | Negative |

ND = Not Detected, LOQ = Limit of Quantification, TAMC = Total Aerobic Microbial Count, TYMC = Total Combined Yeast/Molds Count FIGURE 21A
44 mg MPH capsules

| Lot No. | Packaging Material/ Stability Conditions | Time Point (Month) | Water Content | % Cumulative Drug Released | | | | Organic Impurities | | | Total Impurities | Assay (%LC) | Microbial Limit Tests | | |
|---|---|---|---|---|---|---|---|---|---|---|---|---|---|---|---|
| | | | | 1 HR | 3 HR | 9 HR | 24 HR | MPH Related Compound A (LOQ=0.06%) | Erythro Isomer (LOQ=0.05%) | Other Degradation Product (LOQ=0.10%) | | | TAMC (cfu/g) | TYMC (cfu/g) | E. Coli |
| E | 120cc HDPE Bottle 25°C/60%RH | 0 | 3.9 | 22 | 43 | 85 | 101 | <LOQ | ND | ND | <LOQ | 101.0 | <10 | <10 | Negative |
| | | 3 | 1.5 | 22 | 42 | 84 | 102 | <LOQ | ND | ND | <LOQ | 100.4 | - | - | - |
| | | 6 | 1.6 | 23 | 42 | 81 | 101 | 0.10 | ND | ND | 0.10 | 99.8 | - | - | - |
| | | 9 | 2.0 | 22 | 43 | 84 | 97 | 0.15 | ND | ND | 0.15 | 100.2 | - | - | - |
| | | 12 | 1.7 | 22 | 45 | 86 | 100 | 0.20 | ND | ND | 0.20 | 100.0 | <10 | <10 | Negative |
| | | 18 | 2.9 | 22 | 43 | 83 | 99 | 0.35 | ND | ND | 0.35 | 97.9 | - | - | - |
| | | 24 | 2.0 | 22 | 44 | 82 | 100 | 0.48 | ND | ND | 0.48 | 101.4 | <10 | <10 | Negative |
| | 120cc HDPE Bottle 30°C/75%RH | 0 | 3.9 | 22 | 43 | 85 | 101 | <LOQ | ND | ND | <LOQ | 101.0 | <10 | <10 | Negative |
| | | 3 | 2.0 | 22 | 47 | 87 | 102 | 0.14 | ND | ND | 0.14 | 99.5 | - | - | - |
| | | 6 | 2.2 | 23 | 46 | 86 | 99 | 0.24 | ND | ND | 0.24 | 99.8 | - | - | - |
| | | 9 | 2.3 | 23 | 45 | 84 | 101 | 0.40 | ND | ND | 0.40 | 99.4 | <10 | <10 | Negative |
| | | 12 | 2.1 | 23 | 46 | 88 | 102 | 0.56 | ND | ND | 0.56 | 99.7 | - | - | - |
| | | 18 | 2.7 | 23 | 44 | 82 | 101 | 0.90 | ND | ND | 0.90 | 98.0 | <10 | <10 | Negative |
| | | 24 | 2.8 | 24 | 45 | 82 | 101 | 1.07 | <LOD | ND | 1.07 | 98.7 | <10 | <10 | Negative |
| | 120cc HDPE Bottle 40°C/75%RH | 0 | 3.85 | 22 | 43 | 85 | 101 | <LOQ | <LOD | <LOD | <LOQ | 101.0 | <10 | <10 | Negative |
| | | 1 | 1.40 | 25 | 50 | 90 | 102 | 0.19 | <LOD | <LOD | 0.20 | 100.1 | - | - | - |
| | | 3 | 1.80 | 24 | 49 | 88 | 101 | 0.56 | <LOD | <LOD | 0.60 | 96.7 | - | - | - |
| | | 6 | 2.30 | 24 | 47 | 86 | 101 | 0.89 | <LOD | <LOD | 0.89 | 98.7 | - | - | - |

ND = Not Detected, LOD = Limit of Detection, LOQ = Limit of Quantification, TAMC = Total Aerobic Microbial Count, TYMC = Total Combined Yeast/Molds Count FIGURE 21B
44 mg MPH capsules

| Lot No. | Packaging Material/ Stability Conditions | Time Point (Months) | Water Content | % Cumulative Drug Released | | | | Organic Impurities | | | Assay (%LC) | Microbial Limit Tests | | |
|---|---|---|---|---|---|---|---|---|---|---|---|---|---|---|
| | | | | 1 HR | 3 HR | 9 HR | 24 HR | MPH Related Compound A (LOQ=0.10%) | Erythro Isomer (LOQ=0.06%) | Other Degradation Product (LOQ=0.10%) | Total Impurities | | TAMC | TYMC | E. Coli |
| F | Blister-PVC/PVDC 40g with aluminum bag 25°C/60%RH | 0 | 1.9 | 22 | 47 | 89 | 102 | <LOQ | ND | ND | <LOQ | 100.1 | 230 | <10 | Negative |
| | | 3 | 1.5 | 24 | 47 | 83 | 101 | 0.13 | ND | ND | 0.13 | 103.1 | - | - | - |
| | | 6 | 1.2 | 23 | 48 | 90 | 104 | 0.16 | ND | ND | 0.16 | 102.9 | - | - | - |
| | | 9 | 0.8 | 23 | 48 | 88 | 102 | 0.2 | ND | ND | 0.20 | 100.6 | - | - | - |
| | | 13 | 1.3 | 23 | 46 | 83 | 103 | 0.2 | ND | ND | 0.20 | 102.2 | 210 | <10 | Negative |

ND = Not Detected, LOQ = Limit of Quantification, TAMC = Total Aerobic Microbial Count, TYMC = Total Combined Yeast/Molds Count

ORAL DOSAGE FORM WITH DRUG COMPOSITION, BARRIER LAYER AND DRUG LAYER

This application claims the benefit of U.S. Provisional Patent Application No. 62/359,111 filed Jul. 6, 2016, which application is incorporated herein by reference in its entirety.

INTRODUCTION

In general, there are two significant differences in the pharmacokinetic profiles of immediate release drug formulations relative to controlled release drug formulations. First, the time to achieve the Cmax in the plasma is often longer in the controlled release versus the immediate release formulations. In controlled release formulations, a later Tmax may be undesirable for patients in need of urgent treatment and/or where it is necessary to maintain minimum effective concentration (MEC) levels. A second difference in the pharmacokinetic profiles of controlled release drug formulations relative to immediate release drug formulations is that the duration of sustained plasma levels is longer in the controlled release formulations. The longer duration of such sustained plasma levels may be advantageous, for example, where the goal is to prolong the desired biological effect. Therefore, although a controlled release formulation may facilitate the maintenance of plasma levels of drug or active metabolite(s) for a substantially longer period of time, it generally suffers from the drawback of requiring longer periods of time to achieve the Cmax, when compared to immediate release formulations. Thus, there remains a need for improved controlled release formulations, including dosage formulations that have one or more desirable characteristics of both immediate release and controlled release formulations.

Many controlled release dosage forms exhibit significant lag times (Tlag) depending on whether the subject to whom they are administered is in a fed or fasted state. For example, Focalin XR® Capsules, Ritalin LA® Capsules, and Metadate CD® each exhibit a significant lag time for subjects in the fed state relative to the fasted state.

Extended release pharmaceutical compositions may include various pharmaceutically inactive components which contribute to the desired pharmacokinetic parameters of the active agent in the composition. Such compositions may also include pharmaceutically inactive components which contribute to one or more abuse-deterrent characteristics of the composition.

The present disclosure addresses these issues and provides related advantages.

SUMMARY

Dosage forms of the present disclosure are designed to deliver pharmacologically active agents in a controlled release manner. For instance, the present disclosure includes dosage forms with adequate time of onset of action and reduced lag times in the fed state. Such dosage forms find use in the treatment of a variety of conditions where a rapid onset of action is desired followed by an extended release phase for the pharmacologically active agent, for example in the treatment of attention deficit hyperactivity disorder (ADHD), pain or anxiety. In some embodiments, the present disclosure provides a dosage form including a drug composition including a pharmacologically active agent, a barrier layer covering at least a portion of the drug composition, and a drug layer covering at least a portion of the barrier layer, wherein the drug layer comprises the pharmacologically active agent. Related methods are also provided.

BRIEF DESCRIPTION OF THE DRAWINGS

The present invention is further described in the description of invention that follows, in reference to the noted plurality of non-limiting drawings, wherein:

FIG. 5(A) provides a graph showing the in vitro dissolution profiles for Formulations A and 1-4 in connection with Example 4.

FIG. 5(B) provides a graph showing an expanded portion of the graph of FIG. 5(A) for the 0-2 hr time period.

FIG. 5(C) provides a Higuchi-Plot of the dissolution profiles of Formulations A and 1-4 in connection with Example 4.

FIGS. 19A and 19B provide tables showing the results of a stability study for Formulation 10.

FIGS. 20A and 20B provide tables showing the results of a stability study for Formulation 11.

FIGS. 21A and 21B provide tables showing the results of a stability study for Formulation 4.

DEFINITIONS

Figure 1A:
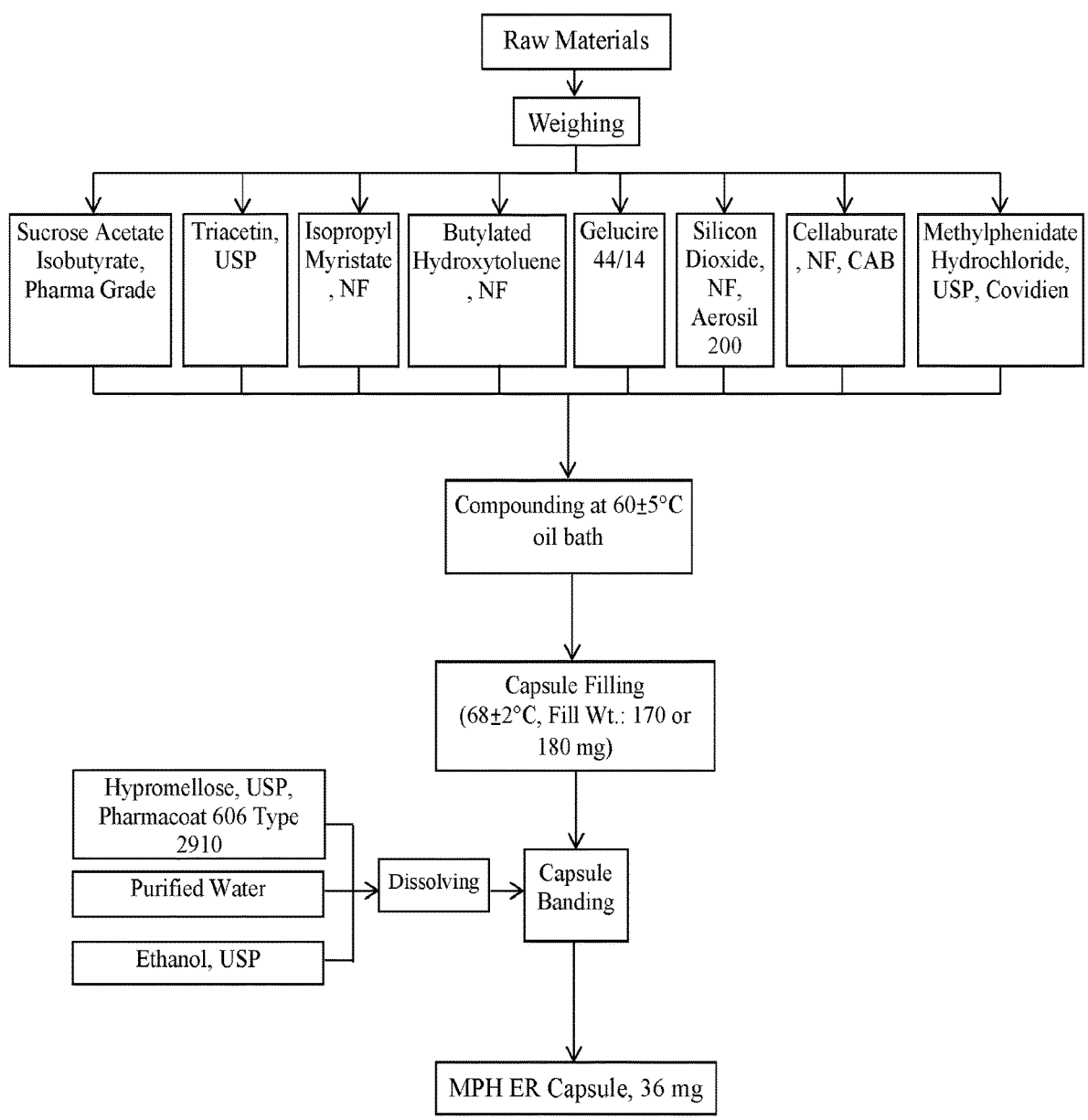
FIG. 1A provides a flow diagram showing the steps of an exemplary method of preparing an extended release (ER) composition in connection with preparation of exemplary dosage forms described herein.

As used interchangeably herein, the terms "active agent", "pharmacologically active agent" and "beneficial agent" refer to any substance intended for use in the diagnosis, cure, mitigation, treatment, or prevention of any disease, disorder, or condition or intended to affect the structure or function of the body, other than food. It can include any beneficial agent or substance that is biologically active or meant to alter animal physiology.

As used herein, the term "$T_{lag}$" or "lag time" refers to the finite time taken for a pharmacologically active agent to appear in systemic circulation following extravascular administration. $T_{lag}$ may be calculated, e.g., as the time from administration to first quantifiable plasma concentration.

As used herein, the term "high viscosity liquid carrier material (HVLCM)" refers to a non-polymeric, non-water soluble liquid material having a viscosity of at least 5000 cP at 37° C. that does not crystallize neat at 25° C. and 1 atmosphere.

As used herein, the term "rheology modifier" refers to a substance that possesses both a hydrophobic and a hydrophilic moiety. Rheology modifiers suitable for use in the disclosed dosage forms and methods generally have a logarithm of octanol-water partition coefficient ("Log P") of between about −7 and +15, e.g., between −5 and +10, e.g., between −1 and +7.

As used herein, the term "network former" refers to a material or compound that forms a network structure when introduced into a liquid medium (such as a HVLCM).

As used herein, the term "hydrophilic agent" means a compound or material having a natural affinity for aqueous systems. A material may be regarded as a hydrophilic agent for the purposes of this disclosure if the material displays a water sorption between about 10 to 100% (w/w). Hydrophilic agents will have a low Log P value, for example, a Log P of less than +1.

As used herein, the term "hydrophilic solvent" means a solvent meeting the definition of a hydrophilic agent as described above.

The term "solvent", as used herein, refers to any substance that dissolves another substance (solute).

As used herein, the term "treatment", "treat" and "treating" refers to eliminating, reducing, suppressing or ameliorating, either temporarily or permanently, either partially or completely, a clinical symptom or manifestation. In addition, or alternatively, the terms "treatment", "treat" and "treating" as used herein with respect to the methods as described refer to inhibiting, delaying, suppressing, reducing, eliminating or ameliorating, either temporarily or permanently, either partially or completely, a clinical symptom or manifestation. "Treatment," "treat," and "treating" include prophylactic treatment. In some embodiments the treating is effective to reduce a symptom, sign, and/or condition in a subject by at least about 10% (e.g., 15%, 20%, 25%, 30%, 35%, 40%, 45%, 50%, 55%, 60%, 65%, 70%, 75%, 80%, 85%, 90%, 95%, or 100%) including, as compared to a baseline measurement of the symptom, sign, and/or condition made prior to the treatment. In some embodiments, the treating is effective to improve an assessment used to diagnose a symptom or manifestation in a subject including, as compared to a baseline assessment made prior to the treatment. Such treating as provided herein need not be absolute to be useful.

The term "pharmaceutically acceptable salt," as used herein, refers to those salts that retain the biological effectiveness and properties of neutral active agents and are not otherwise unacceptable for pharmaceutical use.

As used herein, the term "viscosity enhancing agent" refers to a compound or material that can be added to an extended release composition in order to increase the viscosity of the resulting composition.

As used herein, the term "stabilizer" refers to any substance used to inhibit or reduce degradation (e.g., physical or chemical) of other substances with which the stabilizer is mixed.

As used herein, the term "soluble" refers to a level of solubility of a solute in a solvent of greater than or equal to 33.3 mg/mL at a specified temperature, e.g., at 37° C.

The terms "% by weight", "% w/w" and "w %" are used interchangeably herein to refer to percent weight per weight.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a dosage form" includes a plurality of such dosage forms and reference to "the capsule" includes reference to one or more capsules and equivalents thereof known to those skilled in the art, and so forth. It is further noted that the claims may be drafted to exclude any element, e.g., any optional element. As such, this statement is intended to serve as antecedent basis for use of such exclusive terminology as "solely," "only" and the like in connection with the recitation of claim elements, or use of a "negative" limitation.

To the extent the definition or usage of any term herein conflicts with a definition or usage of a term in an application or reference incorporated by reference herein, the instant application shall control.

The publications discussed herein are provided solely for their disclosure prior to the filing date of the present application. Nothing herein is to be construed as an admission that the present invention is not entitled to antedate such publication. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. This is intended to provide support for all such combinations.

DETAILED DESCRIPTION

Dosage forms of the present disclosure are designed to deliver pharmacologically active agents in a controlled release manner with adequate time of onset of action and reduced lag times in the fed state. In some embodiments, the present disclosure provides a dosage form including a drug composition (or extended release (ER) composition) including a pharmacologically active agent, a barrier layer covering at least a portion of the drug composition, and a drug layer covering at least a portion of the barrier layer, wherein the drug layer comprises the pharmacologically active agent. In some embodiments, the dosage forms of the present disclosure may be characterized by an initial increasing release rate and plasma concentration of API within 2 hours following dosing and a second non-ascending release rate to provide sustained plasma concentration between 2-6 hours, followed by a plasma concentration effective to maintain a therapeutic effect through about 10-12 hours post administration.

Drug Composition

The drug composition (or ER composition) of the dosage forms of the present disclosure includes a pharmacologically active agent. The drug composition may comprise a drug core, or the drug composition may be coated onto other material(s). The drug composition may also include one or more components which alone or in combination facilitate controlled release of the pharmacologically active agent from the dosage form and/or provide for abuse deterrence characteristics. Such components include, e.g., a High Viscosity Liquid Carrier Material (HVLCM), such as sucrose acetate isobutyrate (SAB), an organic solvent, a rheology modifier, a network former, a viscosity enhancing agent, and a polyoxylglyceride. Each of these components is described in greater detail below.

Pharmacologically Active Agent

The pharmacologically active agents that may be included in the dosage forms of the present disclosure may include any type of biologically active compound or composition of matter which, when administered to an organism (human or animal subject) induces a desired pharmacologic and/or physiologic effect by local and/or systemic action.

Examples of such biologically active compounds or compositions of matter useful in the disclosed dosage forms include, but are not limited to, opioids, CNS depressants, and CNS stimulants.

Opioids are a class of potent narcotics that includes, for example, morphine, codeine, oxycodone and fentanyl and related drugs. Morphine is often used to alleviate severe pain. Codeine is used for milder pain. Other examples of opioids that can be prescribed to alleviate pain include oxycodone (e.g. OxyContin®—an oral, controlled release form of the drug); propoxyphene (e.g. Darvon™); hydrocodone (e.g. Vicodin™); hydromorphone (e.g. Dilaudid™); and meperidine (e.g. Demerol™).

In addition to relieving pain, opioids can also produce a sensation of euphoria, and when taken in large doses, can cause severe respiratory depression which can be fatal.

CNS depressants slow down normal brain function by increasing GABA activity, thereby producing a drowsy or calming effect. In higher doses, some CNS depressants can become general anesthetics, and in very high doses may cause respiratory failure and death. CNS depressants are frequently abused, and often the abuse of CNS depressants occurs in conjunction with the abuse of another substance or drug, such as alcohol or cocaine. Many deaths occur yearly through such drug abuse. CNS depressants can be divided into two groups, based on their chemistry and pharmacology: (1) Barbiturates, such as mephobarbital (e.g. Mebaral™) and pentobarbital sodium (e.g. Nembutal™), which are used to treat anxiety, tension, and sleep disorders; and (2) Benzodiazepines, such as diazepam (e.g. Valium™), chlordiazepoxide HCl (e.g. Librium™), and alprazolam (e.g. Xanax™), which can be prescribed to treat anxiety, acute stress reactions, and panic attacks. Benzodiazepines that have a more sedating effect, such as triazolam (e.g. Halcion™) and estazolam (e.g. ProSom™) can be prescribed for short-term treatment of sleep disorders.

Stimulants are a class of drugs that enhance brain activity—they cause an increase in alertness, attention, and energy that is accompanied by increases in blood pressure, heart rate, and respiration. Stimulants are frequently prescribed for treating narcolepsy, attention-deficit hyperactivity disorder (ADHD), and depression. Stimulants may also be used for short-term treatment of obesity, and for patients with asthma. Stimulants such as dextroamphetamine (Dexedrine™) and methylphenidate (Ritalin™) have chemical structures that are similar to key brain neurotransmitters called monoamines, which include norepinephrine and dopamine. Stimulants increase the levels of these chemicals in the brain and body. This, in turn, increases blood pressure and heart rate, constricts blood vessels, increases blood glucose, and opens up the pathways of the respiratory system. In addition, the increase in dopamine is associated with a sense of euphoria that can accompany the use of these drugs.

Taking high doses of a stimulant can result in an irregular heartbeat, dangerously high body temperatures, and/or the potential for cardiovascular failure or lethal seizures. Taking high doses of some stimulants repeatedly over a short period of time can lead to hostility or feelings of paranoia in some individuals.

One class of biologically active compounds that may be included in the dosage forms of the present disclosure is the opioids class, which includes alfentanil, allylprodine, alphaprodine, anileridine, apomorphine, apocodeine, benzylmorphine, bezitramide, buprenorphine, butorphanol, clonitazene, codeine, cyclazocine, cyclorphen, cyprenorphine, desomorphine, dextromoramide, dextromethorphan, dezocine, diampromide, dihydrocodeine, dihydromorphine, dimenoxadol, dimepheptanol, dimethylthiambutene, dioxyaphetyl butyrate, dipipanone, eptazocine, ethoheptazine, ethylmethylthiambutene, ethylmorphine, etonitazene, fentanyl, heroin, hydrocodone, hydroxymethylmorphinan, hydromorphone, hydroxypethidine, isomethadone, ketobemidone, levallorphan, levorphanol, levophenacylmorphan, levomethorphan, lofentanil, meperidine, meptazinol, metazocine, methadone, methylmorphine, metopon, morphine, myrophine, nalbuphine, narceine, nicomorphine, norlevorphanol, normethadone, nalorphine, normorphine, norpipanone, ohmefentanyl, opium, oxycodone, oxymorphone, papaveretum, pentazocine, phenadoxone, phenomorphan, phenazocine, phenoperidine, pholcodine, piminodine, piritramide, prophepzazine, promedol, profadol, properidine, propiram, propoxyphene, remifentanyl, sufentanyl, tramadol, tilidine, naltrexone, naloxone, nalmefene, methylnaltrexone, naloxone methiodide, nalorphine, naloxonazine, nalide, nalmexone, nalbuphine, nalorphine dinicotinate, naltrindole (NTI), naltrindole isothiocyanate (NTII), naltriben (NTB), nor-binaltorphimine (nor-BNI), tapentadol, beta-funaltrexamine (b-FNA), 7-Benzylidenenaltrexone (BNTX), cyprodime, N,N-diallyl-Tyr-Aib-Aib-Phe-Leu (ICI-174,864), 3-[1-(3-hydroxy-3-phenylpropyl)-3,4-dimethylpiperidin-4-yl]phenol (LY117413), [(−)-(1R,5R,9R)-5, 9-diethyl-2-(3-furylmethyl)-2'-hydroxy-6,7-benzomorphan] (MR2266), etorphine, [D-Ala$^2$, NMe-Phe$^4$, Gly-ol$^5$]-enkephalin (DAMGO), CTOP (CAS No:103429-31-8), diprenorphine, naloxone benzoylhydrazone, bremazocine, ethylketocyclazocine, (U50,488), (U69,593), spiradoline, [D-Pen$^{2,5}$]Enkephalin (DPDPE), [D-Ala2,Glu4] deltorphin, [D-Ser$^2$, Leu$^5$, Thr$^6$]-enkephalin (DSLET), Met-enkephalin, Leu-enkephalin, ß-endorphin, dynorphin A, dynorphin B, a-neoendorphin, or an opioid having the same pentacyclic nucleus as nalmefene, naltrexone, buprenorphine, levorphanol, meptazinol, pentazocine, dezocine, or their pharmacologically effective esters or salts.

In some embodiments, opioids for use in the dosage forms of the present disclosure are selected from morphine, hydrocodone, oxycodone, codeine, fentanyl (and its relatives), hydromorphone, meperidine, methadone, oxymorphone, propoxyphene or tramadol, or mixtures thereof. In some embodiments, opioids for use in the dosage forms of the present disclosure are selected from oxycodone, oxymorphone, hydrocodone and hydromorphone. In some embodiments, the opioids for use in the dosage forms of the present disclosure may be micronized. With respect to the opioid oxycodone, it may be beneficial to provide dosage forms that have a reduced level of peroxide degradation products such as alpha beta unsaturated ketones (ABUK). In such cases, the dosage forms of the present disclosure can be subjected to peroxide contaminant reduction and/or removal techniques in accordance with known methods.

Other pharmacologically active compounds or compositions of matter useful in the disclosed dosage forms include prochlorperazine edisylate, ferrous sulfate, aminocaproic acid, potassium chloride, mecamylamine, procainamide, amphetamine (all forms including dexamphetamine, dextroamphetamine, d-S-amphetamine, and levoamphetamine), benzphetamine, isoproternol, methamphetamine, dexmethamphetamine, phenmetrazine, bethanechol, metacholine, pilocarpine, atropine, methascopolamine, isopropamide, tridihexethyl, phenformin, methylphenidate (all forms including dexmethylphenidate, d-threo methylphenidate, and dl-threo methylphenidate), oxprenolol, metroprolol, cimetidine, diphenidol, meclizine, prochlorperazine, phenoxybenzamine, thiethylperazine, anisindone, diphenadione erythrityl, digoxin, isofurophate, reserpine, acetazolamide, methazolamide, bendroflumethiazide, chlorpropamide, tolazamide, chlormadinone, phenaglycodol, allopurinol, aluminum aspirin, methotrexate, acetyl sulfisoxazole, erythromycin, progestins, estrogenic progrestational, corticosteroids, hydrocortisone, hydrocorticosterone acetate, cortisone acetate, triamcinolone, methyltestosterone, 17 beta-estradiol, ethinyl estradiol, ethinyl estradiol 3-methyl ether, prednisolone, 17-hydroxyprogesterone acetate, 19-nor-progesterone, norgestrel, orethindone, norethiderone, progesterone, norgestrone, norethynodrel, aspirin, indomethacin, naproxen, fenoprofen, sulindac, diclofenac, indoprofen, nitroglycerin, propranolol, metroprolol, sodium valproate, valproic acid, taxanes such as paclitaxel, camptothecins such as 9-aminocamptothecin, oxprenolol, timolol, atenolol, alprenolol, cimetidine, clonidine, imipramine, levodopa, chloropropmazine, resperine, methyldopa, dihydroxyphenylalanine, pivaloyloxyethyl ester of α-methyldopa hydrochloride, theophylline, calcium gluconate ferrous lactate, ketoprofen, ibuprofen, cephalexin, haloperiodol, zomepirac, vincamine, diazepam, phenoxybenzamine, β-blocking agents, calcium-channel blocking drugs such as nifedipine, diltiazen, verapamil, lisinopril, captopril, ramipril, fosimopril, benazepril, libenzapril, cilazapril cilazaprilat, perindopril, zofenopril, enalapril, indalapril, qumapril, and the like. Pharmacologically active compounds or compositions of matter useful in the disclosed dosage forms may include a mixture of two or more of the above pharmacologically active compounds or compositions.

The active agent can be present in the dosage forms of the present disclosure in a variety of forms, e.g., neutral form, free base form, or in the form of a pharmaceutically acceptable salt. Pharmaceutically acceptable salts include salts of acidic or basic groups, which groups may be present in the active agents. Those active agents that are basic in nature are capable of forming a wide variety of salts with various inorganic and organic acids. Pharmaceutically acceptable acid addition salts of basic active agents suitable for use herein include those that form acid addition salts, i.e., salts including pharmacologically acceptable anions, such as the hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Active agents that include an amino moiety may form pharmaceutically acceptable salts with various amino acids, in addition to the acids mentioned above. Suitable base salts can be formed from bases which form non-toxic salts, for example, aluminium, calcium, lithium, magnesium, potassium, sodium, zinc and diethanolamine salts. See, e.g., Berge et al. (1977) *J. Pharm. Sci.* 66:1-19, the disclosure of which is incorporated by reference herein.

In the dosage forms of the present disclosure, the pharmacologically active agent will be dissolved (fully or partially) in one or more components of the dosage form or dispersed within one or more components of the dosage form. The phrase "dissolved or dispersed" is intended to encompass all means of establishing a presence of the pharmacologically active agent in the subject dosage forms and includes dissolution, dispersion, partial dissolution and dispersion, and/or suspension and the like. In addition, in certain embodiments of the present disclosure wherein the pharmacologically active agent is in a solid particulate form suspended within one or more other components of the dosage form, the pharmacologically active agent particulate may be pre-treated with a micronization process such as those described in U.S. Application Publication No. 2009/0215808, the disclosure of which is incorporated by reference herein, to provide a particle population having a substantially homogeneous particle size the bulk of which fall within the micron (μm) range. For instance, the present disclosure provides dosage forms comprising stabilized micronized particles, including preparations of such particles with a Dv90 particle distribution of less than or equal to 20 μm or less than or equal to 10 μm.

The pharmacologically active agent, which can include one or more suitable pharmacologically active agents, may be present in the disclosed dosage forms in an amount of from about 90 to about 0.1 percent by weight relative to the total weight of the dosage form (wt %), e.g., in an amount of from about 80 to about 0.1 wt %, in an amount of from about 70 to about 0.1 wt %, in an amount of from about 60 to about 0.1 wt %, in an amount of from about 50 to about 0.1 wt %, in an amount of from about 40 to about 0.1 wt %, in an amount of from about 30 to about 0.1 wt %, in an amount of from about 20 to about 0.1 wt %, in an amount of from about 10 to about 0.1 wt %, in an amount of from about 9 to about 0.1 wt %, in an amount of from about 8 to about 0.1 wt %, in an amount of from about 7 to about 0.1 wt %, in an amount of from about 6 to about 0.1 wt %, in an amount of from about 5 to about 0.1 wt %, in an amount of from about 4 to about 0.1 wt %, in an amount of from about 3 to about 0.1 wt %, in an amount of from about 2 to about 0.1 wt %, or in an amount of from about 1 to about 0.1 wt %, depending upon the identity of the active agent, the desired dose required for the dosage form, and the intended use thereof.

In some embodiments, the pharmacologically active agent may be present in the disclosed dosage forms in an amount from about 0.1 to about 5 w %, in an amount from about 5 to about 10 w %, in an amount from about 10 to about 20 w %, in an amount from about 20 to about 30 w %, in an amount from about 30 to about 40 w %, in an amount from about 40 to about 50 w %, in an amount from about 50 to about 60 w %, in an amount from about 60 to about 70 w %, in an amount from about 70 to about 80 w %, or in an amount from about 80 to about 90 w %, depending upon the identity of the pharmacologically active agent, the desired dose required for the dosage form, and the intended use thereof.

In some embodiments, the pharmacologically active agent is loaded into a suitable dosage form to provide single dosages ranging from about 0.01 mg to about 1000 mg, or from about 0.1 mg to about 500 mg, or from about 2 mg to about 250 mg, or from about 2 mg to about 200 mg, or from about 2 mg to about 150 mg, or from about 5 mg to about 100 mg, or from about 5 mg to about 80 mg. In some embodiments, the pharmacologically active agent is present in the dosage form in an amount of from about 1 wt % to about 10 wt %, from about 2 wt % to about 9 wt %, from about 3 wt % to about 8 wt %, from about 4 wt % to about 7 wt %, or from about 5 wt % to about 6 wt %. In some embodiments, the pharmacologically active agent is present in the dosage form in an amount of about 1 wt %, about 2 wt %, about 3 wt %, about 4 wt %, about 5 wt %, about 6 wt %, about 7 wt %, about 8 wt %, about 9 wt %, or about 10 wt %.

In some embodiments, methylphenidate is present in the disclosed dosage forms in an amount of from about 90 to about 0.1 percent by weight relative to the total weight of the dosage form (wt %), e.g., in an amount of from about 80 to about 0.1 wt %, in an amount of from about 70 to about 0.1 wt %, in an amount of from about 60 to about 0.1 wt %, in an amount of from about 50 to about 0.1 wt %, in an amount of from about 40 to about 0.1 wt %, in an amount of from about 30 to about 0.1 wt %, in an amount of from about 20 to about 0.1 wt %, in an amount of from about 10 to about 0.1 wt %, in an amount of from about 9 to about 0.1 wt %, in an amount of from about 8 to about 0.1 wt %, in an amount of from about 7 to about 0.1 wt %, in an amount of from about 6 to about 0.1 wt %, in an amount of from about 5 to about 0.1 wt %, in an amount of from about 4 to about 0.1 wt %, in an amount of from about 3 to about 0.1 wt %, in an amount of from about 2 to about 0.1 wt %, or in an amount of from about 1 to about 0.1 wt %, depending upon the desired dose required for the dosage form, and the intended use thereof.

In some embodiments, methylphenidate is present in the disclosed dosage forms in an amount from about 0.1 to about 5 w %, in an amount from about 5 to about 10 w %, in an amount from about 10 to about 20 w %, in an amount from about 20 to about 30 w %, in an amount from about 30 to about 40 w %, in an amount from about 40 to about 50 w %, in an amount from about 50 to about 60 w %, in an amount from about 60 to about 70 w %, in an amount from about 70 to about 80 w %, or in an amount from about 80 to about 90 w %, depending upon the desired dose required for the dosage form, and the intended use thereof.

In some embodiments, methylphenidate is loaded into a suitable dosage form to provide single dosages ranging from about 0.01 mg to about 1000 mg, or from about 0.1 mg to about 500 mg, or from about 2 mg to about 250 mg, or from about 2 mg to about 200 mg, or from about 2 mg to about 150 mg, or from about 5 mg to about 100 mg, or from about 5 mg to about 80 mg. In some embodiments, methylphenidate is present in the dosage form in an amount of from about 1 wt % to about 10 wt %, from about 2 wt % to about 9 wt %, from about 3 wt % to about 8 wt %, from about 4 wt % to about 7 wt %, or from about 5 wt % to about 6 wt %. In some embodiments, methylphenidate is present in the dosage form in an amount of about 1 wt %, about 2 wt %, about 3 wt %, about 4 wt %, about 5 wt %, about 6 wt %, about 7 wt %, about 8 wt %, about 9 wt %, or about 10 wt %.

For some embodiments that include an opioid pharmacologically active agent, exemplary single dosages include, but are not limited to, about 1, about 2, about 3, about 4, about 5, about 10, about 15, about 20, about 25, about 30, about 35, about 40, about 45, about 50, about 55, about 60, about 65, about 70, about 75, about 80, about 85, about 90, about 95, about 100, about 110, about 120, about 130, about 140, about 150 and about 160 mg.

In other embodiments that include a CNS depressant or CNS stimulant as the pharmacologically active agent, exemplary single dosages include, but are not limited to, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, and about 100 mg.

The pharmacologically active agent may be present in the drug composition (or ER composition) of the dosage forms described herein at from about 10% to about 50% w/w relative to the total weight of the drug composition (or ER composition), e.g., from about 10% to about 40%, from about 10% to about 30%, or from about 10% to about 20% w/w relative to the total weight of the drug composition (or ER composition). In some embodiments, the pharmacologically active agent may be present in the drug composition (or ER composition) of the dosage forms described herein at about 10% w/w, about 15% w/w, about 20% w/w, about 25% w/w, about 30% w/w, about 35% w/w, about 40% w/w, about 45% w/w, or about 50% w/w relative to the total weight of the drug composition (or ER composition).

The precise amount of pharmacologically active agent desired can be determined by known methods, and will depend on the type of agent, and the pharmacokinetics and pharmacodynamics of that agent.

High Viscosity Liquid Carrier Material (HVLCM)

The drug composition (or ER composition) of the dosage forms of present disclosure may include a High Viscosity Liquid Carrier Material (HVLCM) (e.g., sucrose acetate isobutyrate (SAB). An HVLCM is a non-polymeric, non-water soluble liquid material having a viscosity of at least 5000 cP at 37° C. that does not crystallize neat at 25° C. and 1 atmosphere. The term "non-water soluble" refers to a material that is soluble in water to a degree of less than one percent by weight at 25° C. and 1 atmosphere. The term "non-polymeric" refers to esters or mixed esters having essentially no repeating units in the acid moiety of the ester, as well as esters or mixed esters having acid moieties wherein functional units in the acid moiety are repeated a small number of times (i.e., oligomers). Generally, materials having more than five identical and adjacent repeating units or mers in the acid moiety of the ester are excluded by the term "non-polymeric" as used herein, but materials containing dimers, trimers, tetramers, or pentamers are included within the scope of this term. When the ester is formed from hydroxy-containing carboxylic acid moieties that can further esterify, such as lactic acid or glycolic acid, the number of repeat units is calculated based upon the number of lactide or glycolide moieties, rather than upon the number of lactic acid or glycolic acid moieties, where a lactide repeat unit contains two lactic acid moieties esterified by their respective hydroxy and carboxy moieties, and where a glycolide repeat unit contains two glycolic acid moieties esterified by their respective hydroxy and carboxy moieties. Esters having 1 to about 20 etherified polyols in the alcohol moiety thereof, or 1 to about 10 glycerol moieties in the alcohol moiety thereof, are considered non-polymeric as that term is used herein. HVLCMs may be carbohydrate-based, and may include one or more cyclic carbohydrates chemically combined with one or more carboxylic acids. HVLCMs also include non-polymeric esters or mixed esters of one or more carboxylic acids, having a viscosity of at least 5,000 cP at 37° C., that do not crystallize neat at 25° C. and 1 atmosphere, wherein when the ester contains an alcohol moiety (e.g., glycerol). The ester may, for example include from about 2 to about 20 hydroxy acid moieties. Various HVLCMs, which may be included in disclosed dosage forms, are described in U.S. Pat. Nos. 5,747,058; 5,968,542; and 6,413,536; the disclosures of each of which are incorporated by reference herein. The presently disclosed dosage forms may employ any HVLCM described in these patents but is not limited to any specifically described materials.

The HVLCM may be present in the drug composition (or ER composition) of the dosage forms of the present disclosure at from about 30% by weight to about 60% by weight based on total weight of the drug composition (or ER composition). For example, the HVLCM may be present in the drug composition (or ER composition) at from about 35% by weight to about 60% by weight, from about 40% by weight to about 60% by weight, from about 45% by weight to about 60% by weight, from about 50% by weight to about 60% by weight, or from about 55% by weight to about 60% by weight relative to the total weight of the drug composition (or ER composition).

In some embodiments, the HVLCM may be present in the drug composition (or ER composition) at from about 35% by weight to about 55% by weight, or from about 40% by weight to about 50% by weight relative to the total weight of the drug composition (or ER composition).

In some embodiments, the HVLCM may be present in the drug composition (or ER composition) at about 30% by weight, about 31% by weight, about 32% by weight, about 33% by weight, about 34% by weight, about 35% by weight, about 36% by weight, about 37% by weight, about 38% by weight, about 39% by weight, about 40% by weight, about 41% by weight, about 42% by weight, about 43% by weight, about 44% by weight, about 45% by weight, about 46% by weight, about 47% by weight, about 48% by weight, about 49% by weight, about 50% by weight, about 51% by weight, about 52% by weight, about 53% by weight, about 54% by weight, about 55% by weight, about 56% by weight, about 57% by weight, about 58% by weight, about 59% by weight, or about 60% by weight relative to the total weight of the drug composition (or ER composition).

In some embodiments, the amount of the HVLCM present in the drug composition (or ER composition) is provided relative to the amount of the solvent present in the drug composition (or ER composition). For example, the HVLCM and the solvent may be provided in the composition at a weight ratio of about 2:1 to about 0.8:1, e.g., about 1.9:1 to about 0.8:1, about 1.8:1 to about 0.8:1, about 1.7:1 to about 0.8:1, about 1.6:1 to about 0.8:1, about 1.5:1 to about 0.8:1, about 1.4:1 to about 0.8:1, about 1.3:1 to about 0.8:1, about 1.2:1 to about 0.8:1, about 1.1:1 to about 0.8:1, about 1:1 to about 0.8:1, or about 0.9:1 to about 0.8:1. For example, in some embodiments, the HVLCM and the solvent may be provided in the drug composition (or ER composition) at a weight ratio of about 2:1, about 1.9:1, about 1.8:1, about 1.7:1, about 1.6, about 1.5:1, about 1.4:1, about 1.3:1, about 1.2:1, about 1:1, about 0.9:1 or about 0.8:1.

In some embodiments, sucrose acetate isobutyrate ("SAB") may be included in the drug composition (or ER composition) or the HVLCM may include SAIB, e.g., at any of the above % by weight or ratios relative to solvent. SAIB is a non-polymeric highly viscous liquid at temperatures ranging from −80° C. to over 100° C., it is a fully esterified sucrose derivative, at a nominal ratio of six isobutyrates to two acetates. The chemical structure of SAIB is provided in U.S. Application Publication No. 2009/0215808, the disclosure of which is incorporated by reference herein. The SAIB material is available from a variety of commercial sources including Eastman Chemical Company, where it is available as a mixed ester that does not crystallize but exists as a very highly viscous liquid. It is a hydrophobic, non-crystalline, low molecular weight molecule that is water insoluble and has a viscosity that varies with temperature. For example, pure SAIB exhibits a viscosity of approximately 2,000,000 centipoise (cP) at ambient temperature (RT) and approximately 600 cP at 80° C. The SAIB material has unique solution-viscosity relationship in that a SAIB solution established in a number of organic solvents has a significantly lower viscosity value than the pure SAIB material, and therefore the SAB-organic solvent solutions render themselves capable of processing using conventional equipment such as mixers, liquid pumps and capsule production machines. SAIB also has applications in drug formulation and delivery, for example as described in U.S. Pat. Nos. 5,747,058; 5,968,542; 6,413,536; and 6,498,153, the disclosures of which are incorporated by reference herein.

In some embodiments, it may be beneficial to provide a SAIB containing material having a low peroxide level to avoid peroxide-based degradation of various components of the drug composition (or ER composition) and/or the pharmacologically active agent. See, e.g., U.S. Patent Application Publication Number US 2007/0027105, "Peroxide Removal From Drug Delivery Vehicle", the disclosure of which is incorporated by reference herein.

Solvents

The drug composition (or ER composition) of the dosage forms of the present disclosure may include one or more solvents. Solvents may be used in the drug composition (or ER composition) to dissolve one or more of the following constituents: HVLCMs; active agents; network formers; rheology modifiers; viscosity enhancing agents; and stabilizing agents. In some embodiments, the solvent can dissolve both the HVLCM and the network former. In some embodiments of the dosage forms of the present disclosure, the drug composition (or ER composition) may include both a hydrophilic solvent and a hydrophobic solvent. Organic solvents suitable for use in the drug composition (or ER composition) of the dosage forms of the present disclosure include, but are not limited to: substituted heterocyclic compounds such as N-methyl-2-pyrrolidone (NMP) and 2-pyrrolidone (2-pyrol); triacetin; esters of carbonic acid and alkyl alcohols such as propylene carbonate, ethylene carbonate and dimethyl carbonate; fatty acids such as acetic acid, lactic acid and heptanoic acid; alkyl esters of mono-, di-, and tricarboxylic acids such as 2-ethoxyethyl acetate, ethyl acetate, methyl acetate, ethyl lactate, ethyl butyrate, diethyl malonate, diethyl glutonate, tributyl citrate, diethyl succinate, tributyrin, dimethyl adipate, dimethyl succinate, dimethyl oxalate, dimethyl citrate, triethyl citrate, acetyl tributyl citrate, glyceryl triacetate; alkyl ketones such as acetone and methyl ethyl ketone; ether alcohols such as 2-ethoxyethanol, ethylene glycol dimethyl ether, glycofurol and glycerol formal; alcohols such as benzyl alcohol, ethanol and propanol; polyhydroxy alcohols such as propylene glycol, polyethylene glycol (PEG), glycerin (glycerol), 1,3-butyleneglycol, and isopropylidene glycol (2,2-dimethyl-1,3-dioxolone-4-methanol); solketal; dialkylamides such as dimethylformamide, dimethylacetamide; dimethylsulfoxide (DMSO) and dimethylsulfone; tetrahydrofuran; lactones such as ε-caprolactone and butyrolactone; cyclic alkyl amides such as caprolactam; aromatic amides such as N,N-dimethyl-m-toluamide, and 1-dodecylazacycloheptan-2-one; and the like; and mixtures and combinations thereof.

In some embodiments, the solvent includes or comprises at least one member selected from triacetin, N-methyl-2-pyrrolidone, 2-pyrrolidone, dimethylsulfoxide, ethyl lactate, propylene carbonate, and glycofurol. In some embodiments, the solvent is triacetin which is a hydrophilic solvent. In some embodiments, the hydrophilic triacetin solvent can be combined with a hydrophobic solvent to provide a hydrophobic/hydrophilic solvent system within the composition.

The solvent, which can include one or more suitable solvent materials, can be present in the drug composition (or ER composition) of the dosage forms of the present disclosure at from about 0.1% by weight to about 40% by weight, based on total weight of the drug composition (or ER composition). For example, the solvent may be present in the drug composition (or ER composition) at from about 1% by weight to about 45% by weight, from about 2% by weight to about 45% by weight, from about 3% by weight to about 45% by weight, from about 4% by weight to about 45% by weight, from about 5% by weight to about 45% by weight, from about 6% by weight to about 45% by weight, from about 7% by weight to about 45% by weight, from about 8% by weight to about 45% by weight, from about 9% by weight to about 45% by weight, from about 10% by weight to about 45% by weight, from about 11% by weight to about 45% by weight, from about 12% by weight to about 45% by weight, from about 13% by weight to about 45% by weight, from about 14% by weight to about 45% by weight, from about 15% by weight to about 45% by weight, from about 16% by weight to about 45% by weight, from about 17% by weight to about 45% by weight, from about 18% by weight to about 45% by weight, from about 19% by weight to about 45% by weight, from about 20% by weight to about 45% by weight, from about 21% by weight to about 45% by weight, from about 22% by weight to about 45% by weight, from about 23% by weight to about 45% by weight, from about 24% by weight to about 45% by weight, from about 25% by weight to about 45% by weight, from about 26% by weight to about 45% by weight, from about 27% by weight to about 45% by weight, from about 28% by weight to about 45% by weight, from about 29% by weight to about 45% by weight, from about 30% by weight to about 45% by weight, from about 31% by weight to about 45% by weight, from about 32% by weight to about 45% by weight, from about 33% by weight to about 45% by weight, from about 34% by weight to about 45% by weight, from about 35% by weight to about 45% by weight, from about 36% by weight to about 45% by weight, from about 37% by weight to about 45% by weight, from about 38% by weight to about 45% by weight, from about 39% by weight to about 45% by weight, from about 40% by weight to about 45% by weight, from about 41% by weight to about 45% by weight, from about 42% by weight to about 45% by weight, from about 43% by weight to about 45% by weight, or from about 44% by weight to about 45% by weight relative to the total weight of the drug composition (or ER composition).

In some embodiments, the solvent may be present in the drug composition (or ER composition) of the dosage forms of the present disclosure at from about 10% by weight to about 35% by weight, e.g., from about 15% by weight to about 30% by weight, or from about 20% by weight to about 25% by weight relative to the total weight of the drug composition (or ER composition). In some embodiments, the solvent may be present in the drug composition (or ER composition) at about 10% by weight, about 11% by weight, about 12% by weight, about 13% by weight about 14% by weight, about 15% by weight, about 16% by weight, about 17% by weight, about 18% by weight, about 19% by weight, about 20% by weight, about 21% by weight, about 22% by weight, about 23% by weight, about 24% by weight, about 25% by weight, about 26% by weight, about 27% by weight, about 28% by weight, about 29% by weight, about 30% by weight, about 31% by weight, about 32% by weight, about 33% by weight, about 34% by weight, or about 35% by weight relative to the total weight of the drug composition (or ER composition).

Rheology Modifier

The drug composition (or ER composition) of the dosage forms of the present disclosure may include one or more rheology modifiers. Rheology refers to the property of deformation and/or flow of a liquid, and rheology modifiers are used to modify viscosity and flow of a liquid composition. Rheology modifiers, which may be used in the drug composition (or ER composition) of the present disclosure include, for example, caprylic/capric triglyceride (e.g., Miglyol® 810 or Miglyol® 812), isopropyl myristate (IM or IPM), ethyl oleate, triethyl citrate, dimethyl phthalate, labrafil, labrasol, a polyglycolized glyceride, benzyl benzoate, and mixtures thereof.

In some embodiments, the rheology modifier utilized in the drug composition (or ER composition) of the dosage forms of the present disclosure is or includes IPM.

The rheology modifier, which can include one or more suitable rheology modifier materials, e.g., one or more suitable rheology modifiers listed herein, can be present in the drug composition (or ER composition) of the dosage forms of the present disclosure at from about 0.1 to about 20 percent by weight relative to the total weight of the composition (wt %), e.g., at from about 1 to about 20 wt %, from about 2 to about 20 wt %, from about 3 to about 20 wt %, from about 4 to about 20 wt %, from about 5 to about 20 wt %, from about 6 to about 20 wt %, from about 7 to about 20 wt %, from about 8 to about 20 wt %, from about 9 to about 20 wt %, from about 10 to about 20 wt %, from about 11 to about 20 wt %, from about 12 to about 20 wt %, from about 13 to about 20 wt %, from about 14 to about 20 wt %, from about 15 to about 20 wt %, from about 16 to about 20 wt %, from about 17 to about 20 wt %, from about 18 to about 20 wt %, or from about 19 to about 20 wt % relative to the total weight of the drug composition (or ER composition).

In some embodiments, the rheology modifier is present in the drug composition (or ER composition) at from about 1 to about 15 wt %, e.g., at from about 5 to about 10 wt %, relative to the total weight of the drug composition (or ER composition). For example, in some embodiments, the rheology modifier, e.g., IPM, is present in the drug composition (or ER composition) at about 1 wt %, about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, or about 15 wt % relative to the total weight of the drug composition (or ER composition).

Network Former

The drug composition (or ER composition) of the dosage forms of the present disclosure may include one or more network formers. Network formers may be added to a composition such that, upon exposure to an aqueous environment, they form a three dimensional network within the composition. While not intending to be bound by any particular theory, it is believed that the network former allows the formation of a micro-network within the composition upon exposure to an aqueous environment. This micro-network formation appears to be due, at least in part, to a phase inversion (e.g., a change in glass transition temperature, $T_g$) of the network former. The result is believed to be a skin or surface layer of precipitated network former at the interface between the composition and the aqueous environment, as well as the formation of a three-dimensional micro-network of precipitated network former within the composition. The network former is selected so as to have good solubility in the selected solvent used in the drug composition (or ER composition), for example a solubility of between about 0.1 and 20 wt %. Additionally, good network formers will typically have a Log P between about −1 and 7. Suitable network formers include, for example; cellulose acetate butyrate ("CAB"); carbohydrate polymers; organic acids of carbohydrate polymers and other polymers; hydrogels; cellulose acetate phthalate; ethyl cellulose; a triblock copolymer, e.g., Pluronic® (nonionic triblock copolymer); an acrylic polymer, e.g., Eudragit® (polymethacrylate) or Carbomer™ (polyacrylic acid); hydroxyl propyl methyl cellulose (HPMC), other cellulose acetates such as cellulose triacetate, Poly(methyl methacrylate) (PMMA), as well as any other material capable of associating, aligning or congealing to form three-dimensional networks in an aqueous environment, and mixtures thereof.

In some embodiments, the network former used in the drug composition (or ER composition) of the dosage forms of the present disclosure is or includes a CAB having a number average molecular weight ranging from about 50,000 Daltons to about 100,000 Daltons, e.g., from about 60,000 Daltons to about 100,000 Daltons, from about 70,000 Daltons to about 100,000 Daltons, from about 80,000 Daltons to about 100,000 Daltons, or from about 90,000 Daltons to about 100,000 Daltons. In some embodiments, the network former used in the drug composition (or ER composition) of the present disclosure is or includes a CAB having a number average molecular weight ranging from about 60,000 Daltons to about 90,000 Daltons, or from about 70,000 Daltons to about 80,000 Daltons. In some embodiments, the network former used in the drug composition (or ER composition) of the present disclosure is or includes a CAB having a number average molecular weight of about 50,000 Daltons, about 55,000 Daltons, about 60,000 Daltons, about 65,000 Daltons, about 70,000 Daltons, about 75,000 Daltons, about 80,000 Daltons, about 85,000 Daltons, about 90,000 Daltons, about 95,000 Daltons, or about 100,000 Daltons.

In some embodiments, the network former used in the drug composition (or ER composition) of the present disclosure is or includes a CAB having at least one feature selected from a butyryl content ranging from about 17% to about 41%, an acetyl content ranging from about 13% to about 30%, and a hydroxyl content ranging from about 0.5% to about 1.7%. In some further embodiments, the network former used in the drug composition (or ER composition) of the present disclosure is or includes a CAB comprising at least two of a butyryl content ranging from about 17% to about 41%, an acetyl content ranging from about 13% to about 30%, and a hydroxyl content ranging from about 0.5% to about 1.7%. In still further embodiments, the network former used in the drug composition (or ER composition) of the present disclosure is or includes a CAB comprising all three of a butyryl content ranging from about 17% to about 41%, an acetyl content ranging from about 13% to about 30%, and a hydroxyl content ranging from about 0.5% to about 1.7%.

Accordingly, in some embodiments, the network former used in the drug composition (or ER composition) of the present disclosure is or includes a CAB having a butyryl content ranging from about 17% to about 41%. In some embodiments, the network former used in the drug composition (or ER composition) of the present disclosure is or includes a CAB having an acetyl content ranging from about 13% to about 30%. In some embodiments, the network former used in the drug composition (or ER composition) of the present disclosure is or includes a CAB having a hydroxyl content ranging from about 0.5% to about 1.7%. In some embodiments, the network former used in the drug composition (or ER composition) of the present disclosure is or includes a CAB having a butyryl content ranging from about 17% to about 41% and an acetyl content ranging from about 13% to about 30%. In some embodiments, the network former used in the drug composition (or ER composition) of the present disclosure is or includes a CAB having a butyryl content ranging from about 17% to about 41% and a hydroxyl content ranging from about 0.5% to about 1.7%. In some embodiments, the network former used in the drug composition (or ER composition) of the present disclosure is or includes a CAB having an acetyl content ranging from about 13% to about 30% and a hydroxyl content ranging from about 0.5% to about 1.7%. In still other embodiments, the network former used in the drug composition (or ER composition) of the present disclosure is or includes a CAB having a butyryl content ranging from about 17% to about 41%, an acetyl content ranging from about 13% to about 30%, and a hydroxyl content ranging from about 0.5% to about 1.7%. In further embodiments, in addition to at least one of the above features of butyryl content, acetyl content and/or hydroxyl content, the CAB also has a number average molecular weight ranging from about 50,000 Daltons to about 100,000 Daltons, e.g., from about 60,000 Daltons to about 100,000 Daltons, from about 70,000 Daltons to about 100,000 Daltons, from about 80,000 Daltons to about 100,000 Daltons, or from about 90,000 Daltons to about 100,000 Daltons. In further embodiments, in addition to at least one of the above features of butyryl content, acetyl content and/or hydroxyl content, the CAB also has a number average molecular weight ranging from about 60,000 Daltons to about 90,000 Daltons, or from about 70,000 Daltons to about 80,000 Daltons. In further embodiments, in addition to at least one of the above features of butyryl content, acetyl content and/or hydroxyl content, the CAB also has a number average molecular weight of about 50,000 Daltons, about 55,000 Daltons, about 60,000 Daltons, about 65,000 Daltons, about 70,000 Daltons, about 75,000 Daltons, about 80,000 Daltons, about 85,000 Daltons, about 90,000 Daltons, about 95,000 Daltons, or about 100,000 Daltons.

In some embodiments, the network former used in the drug composition (or ER composition) of the present disclosure is or includes cellulose acetate butyrate grade 381-20BP ("CAB 381-20BP" available from Eastman Chemicals). In some embodiments, the network former used in the drug composition (or ER composition) of the present disclosure is or includes a CAB, wherein the CAB is a non-biodegradable polymer material that has the following chemical and physical characteristics: butyryl content of about 36 wt %, acetyl content of about 15.5 wt %, hydroxyl content of about 0.8%, a melting point of from about 185-196° C., a glass transition temperature of about 128° C., and a number average molecular weight of from about 66,000 Daltons to 83,000 Daltons, e.g., about 70,000 Daltons. In some embodiments, if a CAB material is used in the drug composition (or ER composition), it may be subjected to an ethanol washing step (and subsequent drying step) prior to addition to the drug composition (or ER composition) in order to remove potential contaminants therefrom.

In some embodiments, the network former used in the drug composition (or ER compositions) of the present disclosure specifically excludes a network former having an acetyl content of about 2.0%, a butyryl content of about 46.0%, a hydroxyl content of 4.8%, a melting point of from about 150-160° C., a glass transition temperature of about 136° C., and a number average molecular weight of about 20,000 Daltons, e.g., CAB-553-0.4 available from Eastman Chemicals.

In some embodiments, the network former used in the drug composition (or ER composition) of the present disclosure specifically excludes a network former, e.g., a CAB, which is soluble in ethanol.

The network former, which can include one or more suitable network former materials, can be present in the drug composition (or ER composition) of the dosage forms of the present disclosure at from about 0.1 to about 20 percent by weight relative to the total weight of the drug composition (or ER composition) (wt %), e.g., at from about 1 to about 20 wt %, from about 2 to about 20 wt %, from about 3 to about 20 wt %, from about 4 to about 20 wt %, from about 5 to about 20 wt %, from about 6 to about 20 wt %, from about 7 to about 20 wt %, from about 8 to about 20 wt %, from about 9 to about 20 wt %, from about 10 to about 20 wt %, from about 11 to about 20 wt %, from about 12 to about 20 wt %, from about 13 to about 20 wt %, from about 14 to about 20 wt %, from about 15 to about 20 wt %, from about 16 to about 20 wt %, from about 17 to about 20 wt %, from about 18 to about 20 wt %, or from about 19 to about 20 wt % relative to the total weight of the drug composition (or ER composition).

In some embodiments, the network former is present in the drug composition (or ER composition) at from about 2 to about 10 wt %, e.g., at from about 4 to about 8 wt %, or about 4 to about 6 wt % about relative to the total weight of the drug composition (or ER composition). For example, in some embodiments, the network former is present in the drug composition (or ER composition) at about 2 wt %, about 3 wt %, about 4 wt %, about 5 wt %, about 6 wt %, about 7 wt %, about 8 wt %, about 9 wt %, about 10 wt %, about 11 wt %, about 12 wt %, about 13 wt %, or about 15 wt % relative to the total weight of the drug composition (or ER composition).

Viscosity Enhancing Agent

The drug composition (or ER composition) of the dosage forms of the present disclosure may include one or more viscosity enhancing agents. Viscosity enhancing agents can be selected to have good hydrogen bonding capability, such as a bonding capability greater than or equal to one per molecule. In certain cases, the viscosity enhancing agent has very low to no significant solubility in the composition. If the agent is soluble, then, in some embodiments, the solubility is less than 50 wt %. For inorganic or mineral viscosity enhancing agents, it is preferable if the material has a specific surface area greater than or equal to about 100 m²/g. Suitable viscosity enhancing agents include biodegradable and non-biodegradable polymer materials. Non-limiting examples of suitable biodegradable polymers and oligomers include: poly(lactide), poly(lactide-co-glycolide), poly(glycolide), poly(caprolactone), polyamides, polyanhydrides, polyamino acids, polyorthoesters, polycyanoacrylates, poly(phosphazines), poly(phosphoesters), polyesteramides, polydioxanones, polyacetals, polyketals, polycarbonates, polyorthocarbonates, degradable polyurethanes, polyhydroxybutyrates, polyhydroxyvalerates, polyalkylene oxalates, polyalkylene succinates, poly(malic acid), chitin, chitosan, and copolymers, terpolymers, oxidized cellulose, hydroxyethyl cellulose, or combinations or mixtures of the above materials. Suitable non-biodegradable polymers include: polyacrylates, ethylene-vinyl acetate polymers, cellulose and cellulose derivatives, acyl substituted cellulose acetates and derivatives thereof including cellulose acetate butyrate (CAB), which is also used herein as a network former, non-erodible polyurethanes, polystyrenes, polyvinyl chloride, polyvinyl fluoride, polyvinyl (imidazole), chlorosulphonated polyolefins, polyethylene oxide, polyethylene, and mixtures thereof.

Other suitable viscosity enhancing materials include mineral particles such as clay compounds, including, talc, bentonite and kaolin; metal oxides including silicon dioxide, zinc oxide, magnesium oxide, titanium oxide, and calcium oxide; fumed silica, reagent grade sand, precipitated silica, amorphous silica, colloidal silicon dioxide, fused silica, silica gel, and quartz; and mixtures thereof. In some embodiments of the present disclosure, a colloidal silicon dioxide, e.g., Cab-O-Sil® M-5P (untreated fumed silica that complies with the pharmacopeia monograph "Colloidal Silicon Dioxide" in the U.S. Pharmacopeia/National Formulary), is used in the drug composition (or ER composition) as a viscosity enhancing agent.

The viscosity enhancing agent, e.g., mineral particle, which can include one or more suitable viscosity enhancing materials, can be present in the drug composition (or ER composition) of the dosage forms of the present disclosure at from about 0.01 to about 10 percent by weight relative to the total weight of the drug composition (or ER composition) (wt %), e.g., at from about 0.05 to about 1.0 wt %, from about 0.1 to about 1.0 wt %, from about 1.0 to about 1.5 wt %, from about 1.5 to about 2.0 wt %, from about 2.0 to about 2.5 wt %, from about 2.5 to about 3.0 wt %, from about 3.0 to about 3.5 wt %, from about 3.5 to about 4.0 wt %, from about 4.0 to about 4.5 wt %, from about 4.5 to about 5.0 wt %, from about 5.0 to about 5.5 wt %, from about 5.5 to about 6.0 wt %, from about 6.0 to about 6.5 wt %, from about 6.5 to about 7.0 wt %, from about 7.0 to about 7.5 wt %, from about 7.5 to about 8.0 wt %, from about 8.0 to about 8.5 wt %, from about 8.5 to about 9.0 wt %, from about 9.0 to about 9.5 wt %, or from about 9.5 to about 10.0 wt % relative to the total weight of the drug composition (or ER composition).

In some embodiments, a drug composition (or ER composition) according to the present disclosure includes a viscosity enhancing agent, e.g., mineral particle, at from about 0.5 wt % to about 1.5 wt %, e.g., from about 0.6 wt % to about 1.4 wt %, from about 0.7 wt % to about 1.3 wt %, from about 0.8 wt % to about 1.2 wt %, or from about 0.9 wt % to about 1.0 wt % relative to the total weight of the drug composition (or ER composition).

In some embodiments, a drug composition (or ER composition) according to the present disclosure includes a viscosity enhancing agent, e.g., mineral particle (e.g., silicon dioxide) at about 0.1 wt %, about 0.2 wt %, about 0.3 wt %, about 0.4 wt %, about 0.5 wt %, about 0.6 wt %, about 0.7 wt %, about 0.8 wt %, about 0.9 wt %, or about 1.0 wt % relative to the total weight of the drug composition (or ER composition).

Stabilizing Agent

Materials that can be used as stabilizing agents in the drug composition (or ER composition) of the dosage forms of the present disclosure include any material or substance that can inhibit or reduce degradation (e.g., by chemical reactions) of other substances or substances in the composition with which the stabilizer is mixed. Exemplary stabilizers typically are antioxidants that prevent oxidative damage and degradation, e.g., sodium citrate, ascorbyl palmitate, vitamin A, propyl gallate, reducing agents, and mixtures thereof. Other examples include ascorbic acid, vitamin E, sodium bisulfite, butylhydroxyl toluene (BHT), BHA, acetylcysteine, monothioglycerol, phenyl-alpha-nathylamine, lecithin, EDTA, and mixtures thereof. These stabilizing materials, which can include one or more of such suitable materials, can be present in the drug composition (or ER composition) at from about 0.001 to about 2 percent by weight relative to the total weight of the composition (wt %), e.g., at from about 0.01 to about 0.1 wt %, or at from about 0.01 to about 0.02 wt %. In some embodiments, the drug composition (or ER composition) of the present disclosure specifically excludes a stabilizing agent, such as those listed above.

Surfactants

In some embodiments, a drug composition (or ER composition) of a dosage form according to the present disclosure may include one or more surfactants. Materials that can be used as surfactants in the practice of the present disclosure include neutral and/or anionic/cationic excipients. Accordingly, suitable charged lipids include, without limitation, phosphatidylcholines (lecithin), and the like. Detergents will typically be a nonionic, anionic, cationic or amphoteric surfactant. Examples of suitable surfactants include, for example, Tergitol® and Triton® surfactants (Union Carbide Chemicals and Plastics); polyoxyethylenesorbitans, e.g., TWEEN® surfactants (Atlas Chemical Industries); polysorbates; polyoxyethylene ethers, e.g. Brij; pharmaceutically acceptable fatty acid esters, e.g., lauryl sulfate and salts thereof, amphiphilic surfactants (glycerides, etc.); polyoxyglycerides, e.g., caprylocaproyl polyoxylglycerides, lauroyl polyoxylglycerides, linoleoyl polyoxylglycerides, oleoyl poloxylglycerides, stearoyl polyoxylglycerides, and Gelucire®s (saturated polyglycolized glyceride (e.g., Gattefosse brand)); like materials; and mixtures thereof. Surfactants, which can include one or more suitable surfactant material, can be present in the drug composition (or ER composition) of the present disclosure at from about 0.01 to about 5 percent by weight relative to the total weight of the drug composition (or ER composition) (wt %), e.g., at from about 0.1 to about 5 wt %, from about 0.1 to about 4 wt %, from about 0.1 to about 3 wt %, from about 0.1 to about 2 wt %, or from about 0.1 to about 1 wt %. In some embodiments, a surfactant is present in the drug composition (or ER composition) of the present disclosure at about 0.1 wt %, about 0.5 wt %, about 1 wt %, about 2 wt %, about 3 wt %, about 4 wt %, or about 5 wt % relative to the total weight of the drug composition (or ER composition).

In some embodiments, a suitable surfactant for incorporation into the drug composition (or ER composition) of the dosage forms of the present disclosure includes one or more Gelucire®s (saturated polyglycolized glycerides). Suitable Gelucire®s include, e.g., Gelucire® 44/14 (lauroyl polyoxylglycerides), Gelucire® 43/01 (hard fat EP/NF/JPE), Gelucire® 39/01 (glycerol esters of fatty acids, e.g., glycerol esters of saturated C12-C18 fatty acids), Gelucire® 48/16 (Polyoxyl stearate (Type I) NF), and Gelucire® 50/13 (stearoyl polyoxylglycerides). Accordingly, in some embodiments, a Gelucire®, e.g., Gelucire® 44/14, Gelucire® 43/01, Gelucire® 39/01, Gelucire® 48/16, Gelucire® 50/13, or a combination thereof, is present the compositions of the present disclosure at from about 0.01 to about 5 percent by weight relative to the total weight of the drug composition (or ER composition) (wt %), e.g., from about 0.1 to about 5 wt %, from about 0.1 to about 4 wt %, from about 0.1 to about 3 wt %, from about 0.1 to about 2 wt %, or from about 0.1 to about 1 wt %. In some embodiments, a Gelucire®, e.g., Gelucire® 44/14, Gelucire® 43/01, Gelucire® 39/01, Gelucire® 48/16, Gelucire® 50/13, or a combination thereof, is present in the drug composition (or ER composition) of the present disclosure at about 0.1 wt %, about 0.5 wt %, about 1 wt %, about 2 wt %, about 3 wt %, about 4 wt %, or about 5 wt % relative to the total weight of the drug composition (or ER composition).

Each Gelucire is designated by two numbers separated by a slash, the first number (two-digit number) indicating its melting point and the second, the HLB (hydrophilic-lipophilic balance).

In some embodiments, a suitable surfactant for incorporation into the drug composition (or ER composition) of the dosage forms of the present disclosure includes a saturated polyglycolized glyceride having a melting point of from about 39° C. to about 50° C. (e.g., about 40° C., about 41° C., about 42° C., about 43° C., about 44° C., about 45° C., about 46° C., about 47° C., about 48° C., or about 49° C.) and an HLB of from about 1 to about 16 (e.g., about 2, about 3, about 4, about 5, about 6, about 7, about 8, about 9, about 10, about 11, about 12, about 13, about 14, or about 15). Accordingly, in some embodiments, a saturated polyglycolized glyceride having a melting point of from about 38° C. to about 50° C. (e.g., about 39° C., about 40° C., about 41° C., about 42° C., about 43° C., about 44° C., about 45° C., about 46° C., about 47° C., about 48° C., or about 49° C.) and an HLB of from about 1 to about 16 (e.g., about 2, about 3, about 4, about 5, about 6, about 7, about 8, about 9, about 10, about 11, about 12, about 13, about 14, or about 15) is present the compositions of the present disclosure at from about 0.01 to about 5 percent by weight relative to the total weight of the drug composition (or ER composition) (wt %), e.g., from about 0.1 to about 5 wt %, from about 0.1 to about 4 wt %, from about 0.1 to about 3 wt %, from about 0.1 to about 2 wt %, or from about 0.1 to about 1 wt %. In some embodiments, a saturated polyglycolized glyceride having a melting point of from about 38° C. to about 50° C. (e.g., about 39° C., about 40° C., about 41° C., about 42° C., about 43° C., about 44° C., about 45° C., about 46° C., about 47° C., about 48° C., or about 49° C.) and an HLB of from about 1 to about 16 (e.g., about 2, about 3, about 4, about 5, about 6, about 7, about 8, about 9, about 10, about 11, about 12, about 13, about 14, or about 15) is present in the drug composition (or ER composition) of the present disclosure at about 0.1 wt %, about 0.5 wt %, about 1 wt %, about 2 wt %, about 3 wt %, about 4 wt %, or about 5 wt % relative to the total weight of the drug composition (or ER composition).

Fill Weight of Drug Composition

The drug composition (or ER composition) of the dosage forms of the present disclosure may have a fill weight of, e.g., from about 50 mg to about 800 mg, e.g., from about 100 mg to about 700 mg, from about 100 mg to about 600 mg, from about 100 mg to about 500 mg, from about 100 mg to about 400 mg, from about 100 mg to about 300 mg, or from about 100 mg to about 200 mg. In some embodiments, the drug composition (or ER composition) of the dosage forms of the present disclosure may have a fill weight of about 100 mg, about 120 mg, about 140 mg, about 160 mg, about 180 mg, about 200 mg, about 300 mg, about 400 mg, about 500 mg, about 600 mg, about 700 mg, or about 800 mg. In some embodiments, the drug composition (or ER composition) of the dosage forms of the present disclosure may have a fill weight of 50 mg, 55 mg, 60 mg, 65 mg, 70 mg, 75 mg, 80 mg, 85 mg, 90 mg, 95 mg, 100 mg, 105 mg, 110 mg, 115 mg, 120 mg, 125 mg, 130 mg, 135 mg, 140 mg, 145 mg, 150 mg, 155 mg, 160 mg, 165 mg, 170 mg, 175 mg, 180 mg, 185 mg, 190 mg, 195 mg, or 200 mg.

Barrier Layer

The barrier layer (or first layer) of the dosage forms of the present disclosure is a layer which covers at least a portion of the drug composition (or ER composition) of the present disclosure. In some embodiments, the barrier layer does not include the pharmacologically active agent. Where the dosage form includes a capsule in which the drug composition (or ER composition) of the present disclosure is encapsulated, the barrier layer (or first layer) may cover at least a portion of such capsule. For example, in some embodiments, the barrier layer (or first layer) may cover at least a portion of an outer surface of such capsule. In some embodiments, the barrier layer (or first layer) functions as a delay layer which is sufficient to delay release of the pharmacologically active agent from the drug composition (or ER composition) of the present disclosure relative to a dosage form lacking such a barrier layer (or first layer), e.g., for an amount of time sufficient to allow for complete dissolution of a drug layer coated on the barrier layer. In some embodiments, the barrier layer (or first layer) functions to control the dissolution characteristics of an encapsulated drug composition (or ER composition) as described herein.

In some embodiments, the barrier layer (or first layer) includes one or more of cellulose acetate phthalate, HPMC phthalate, HPMC acetate succinate, polyvinyl acetate phthalate, cellulose acetate trimelitate, methyacrylic acid copolymer, shellac, and zein. In some embodiments, in addition or alternatively, the barrier layer (or first layer) includes one or more of a hydrophobic cellulose, a polyalcohol, magnesium stearate, and silicon dioxide.

In some embodiments, the barrier layer (or first layer) includes an acrylic coating system, e.g., an acrylic coating system including a methacrylic acid copolymer containing composition, such as Acryl-EZE® White (93018509), and a moisture barrier coating system, e.g., a moisture barrier coating system including a polyvinyl alcohol containing composition, such as Opadry® AMB White (80W68912). The methacrylic acid copolymer containing composition may be present in the barrier layer (or first layer) at from about 60% to about 90% w/w relative to the total weight of the barrier layer (or first layer). For example, the methacrylic acid copolymer containing composition may be present in the barrier layer (or first layer) at from about 70% to about 80% w/w, e.g., about 75% w/w, relative to the total weight of the barrier layer (or first layer). In some embodiments, the methacrylic acid copolymer containing composition may be present in the barrier layer (or first layer) at about 60% w/w, about 61% w/w, about 62% w/w, about 63% w/w, about 64% w/w, about 65% w/w, about 66% w/w, about 67% w/w, about 68% w/w, about 69% w/w, about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, or about 90% w/w relative to the total weight of the barrier layer (or first layer).

The polyvinyl alcohol containing composition may be present in the barrier layer (or first layer) at from about 10% to about 40% w/w relative to the total weight of the barrier layer (or first layer). For example, the polyvinyl alcohol containing composition may be present in the barrier layer (or first layer) at from about 20% to about 30% w/w, e.g., about 25% w/w, relative to the total weight of the barrier layer (or first layer). In some embodiments, the polyvinyl alcohol containing composition may be present in the barrier layer (or first layer) at about 10% w/w, about 11% w/w, about 12% w/w, about 13% w/w, about 14% w/w, about 15% w/w, about 16% w/w, about 17% w/w, about 18% w/w, about 19% w/w, about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, or about 40% w/w, relative to the total weight of the barrier layer (or first layer).

In some embodiments, the barrier layer (or first layer) includes an acrylic coating system, e.g., an acrylic coating system including a methacrylic acid copolymer containing composition, such as Acryl-EZE® White (93018509), and a moisture barrier coating system, e.g., a moisture barrier coating system including a polyvinyl alcohol containing composition, such as Opadry® AMB White (80W68912) in a ratio of from about 2:1 to about 10:1, e.g., from about 3:1 to about 9:1, from about 4:1 to about 8:1, from about 5:1 to about 7:1, or about 6:1. In some embodiments, the weight of such a barrier layer (or first layer) is from about 20 mg to about 40 mg, e.g., from about 25 mg to about 35 mg, or about 30 mg. In some embodiments, the weight of such a barrier layer (or first layer) is about, 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, or about 40 mg.

In some embodiments, the barrier layer (or first layer) includes an acrylic coating system, e.g., an acrylic coating system including a methacrylic acid copolymer containing composition, such as Acryl-EZE® White (93018509), and a moisture barrier coating system, e.g., a moisture barrier coating system including a polyvinyl alcohol containing composition, such as Opadry® AMB White (80W68912) in a ratio of about 2:1, about 3:1, about 4:1, about 5:1, about 6:1, about 7:1, about 8:1, about 9:1 or about 10:1. In some embodiments, the weight of the barrier layer (or first layer) is from about 20 mg to about 40 mg, e.g., from about 25 mg to about 35 mg, or about 30 mg. In some embodiments, the weight of the barrier layer (or first layer) is about, 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, or about 40 mg.

The barrier layer (or first layer) may have a finished product coating weight of from about 0.5 mg to about 50 mg, e.g., from about 5 mg to about 40 mg, or from about 10 mg to about 30 mg. In some embodiments, the barrier layer (or first layer) has a finished product coating weight from about 0.5 mg to about 1 mg, from about 1 mg to about 5 mg, from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg, or from about 45 mg to about 50 mg. In some embodiments, the barrier layer (or first layer) has a finished product coating weight of about 0.5 mg, about 1 mg, about 5 mg, about 10 mg, about 11 mg, about 12 mg, about 13 mg, about 14 mg, about 15 mg, about 16 mg, about 17 mg, about 18 mg, about 19 mg, about 20 mg, about 21 mg, about 22 mg, about 23 mg, about 24 mg, about 25 mg, about 26 mg, about 27 mg, about 28 mg, about 29 mg, about 30 mg, about 31 mg, about 32 mg, about 33 mg, about 34 mg, about 35 mg, about 36 mg, about 37 mg, about 38 mg, about 39 mg, about 40 mg, about 41 mg, about 42 mg, about 43 mg, about 44 mg, about 45 mg, about 46 mg, about 47 mg, about 48 mg, about 49 mg, or about 50 mg.

In some embodiments, the barrier layer (or first layer) specifically excludes a gelling agent. For example, the barrier layer (or first layer) may specifically exclude one or more of the following gelling agents: acacia, alginic acid, bentonite, Carbopols® (also known as carbomers), carboxymethylcellulose. ethylcellulose, gelatin, hydroxyethylcellulose, hydroxypropyl cellulose, magnesium aluminum silicate (Veegum®), methylcellulose, poloxamers (Pluronics®), polyvinyl alcohol, sodium alginate, tragacanth, and xanthan gum.

Other examples of materials which may be used in the barrier layer include Opadry® Enteric coating system, Nutrateric® coating system, and Sureteric® coating system.

In some embodiments, the barrier layer (or first layer) is soluble at a pH of about 1.0 to about 4.0, e.g., a pH of about 1.5 to about 3.5, or a pH of about 2.0 to about 3.0, in aqueous HCl at a temperature of about 25° C. or about 37° C. In some embodiments the barrier layer (or first layer) dissolves when exposed to aqueous HCl at a pH of about 1.0 to about 4.0, e.g., a pH of about 1.5 to about 3.5, or a pH of about 2.0 to about 3.0, at a temperature of about 25° C. or about 37° C., in a time period of about 5 minutes to about 10 minutes, about 10 minutes to about 20 minutes, or about 20 minutes to about 30 minutes.

Accordingly, in some embodiments, the barrier layer (or first layer) dissolves when exposed to the acidic environment of the stomach. In some embodiments, the barrier layer (or first layer) does not preferentially dissolve at a pH of 5.0 or above.

In some embodiments, the barrier layer (or first layer) includes a first material which is soluble in 0.1N HCl at 37° C. and a second material which is insoluble in 0.1N HCl at 37° C. (e.g., at 1 atm). For example, in some embodiments, the barrier layer (or first layer) includes a first material which is soluble in 0.1N HCl at 37° C., which material includes a hydrophilic cellulose (e.g., HPMC, hydroxypropyl cellulose (HPC), or HEC) and/or a hydrophilic polymer (e.g., PEG or polyvinyl alcohol (PVA)); and a second material which is insoluble in 0.1N HCl at 37° C., which material includes one or more of cellulose acetate phthalate, HPMC phthalate, HPMC acetate succinate, polyvinyl acetate phthalate, cellulose acetate trimelitate, methacrylic acid copolymer, shellac, and zein.

In some embodiments, a third material may be substituted for the first material or used in combination with the first material where the third material is not soluble in 0.1N HCl at 37° C., but nevertheless possesses properties of high water uptake and/or high water permeability. Such materials include, e.g., polyvinylpyrrolidone (PVP), starch, ethyl cellulose (EC), carboxyl methylcellulose (CMC), microcrystalline cellulose, and silicon dioxide.

In some embodiments, the first material, the third material, or a combination thereof, is present in the barrier layer (or first layer) at from about 10% to about 40% w/w relative to the total weight of the barrier layer (or first layer). For example, the first material, the third material, or a combination thereof, may be present in the barrier layer (or first layer) at from about 30% to about 40% w/w, e.g., about 35% w/w, relative to the total weight of the barrier layer (or first layer). In some embodiments, the first material, the third material, or a combination thereof may be present in the barrier layer (or first layer) at about 10% w/w, at about 20% w/w, about 21% w/w, about 22% w/w, about 23% w/w, about 24% w/w, about 25% w/w, about 26% w/w, about 27% w/w, about 28% w/w, about 29% w/w, about 30% w/w, about 31% w/w, about 32% w/w, about 33% w/w, about 34% w/w, about 35% w/w, about 36% w/w, about 37% w/w, about 38% w/w, about 39% w/w, or about 40% w/w, relative to the total weight of the barrier layer (or first layer).

In some embodiments, the second material is present in the barrier layer (or first layer) at from about 60% to about 90% w/w relative to the total weight of the barrier layer (or first layer). For example, the second material may be present in the barrier layer (or first layer) at from about 70% to about 80% w/w, e.g., about 75% w/w, relative to the total weight of the barrier layer (or first layer). In some embodiments, the second material may be present in the barrier layer (or first layer) at about 60% w/w, about 61% w/w, about 62% w/w, about 63% w/w, about 64% w/w, about 65% w/w, about 66% w/w, about 67% w/w, about 68% w/w, about 69% w/w, about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, or about 90% w/w relative to the total weight of the barrier layer (or first layer).

In some embodiments, the ratio of the first material, the third material, or a combination thereof, to the second material in the barrier layer (or first layer) is from 0.2:1 to 0.8:1, e.g., 0.3:1 to 0.7:1, 0.4:1 to 0.6:1, or 0.5:1.

In some embodiments, the barrier layer (or first layer) includes a first material which includes a water soluble inorganic salt, a water soluble organic salt or a sugar; and a second material which is insoluble in 0.1N HCl at 37° C. (e.g., at 1 atm), e.g., at a ratio of 0.2:1 to 0.8:1, e.g., 0.3:1 to 0.7:1, 0.4:1 to 0.6:1, or 0.5:1.

Drug Layer

The drug layer (or second layer) of the dosage forms of the present disclosure is a layer which covers at least a portion of the barrier layer (or first layer) and includes a pharmacologically active agent. In some embodiments, the pharmacologically active agent included in the drug layer (or second layer) is the same as the pharmacologically active agent present in the drug composition (or ER composition) of the present disclosure. In other embodiments, the pharmacologically active agent included in the drug layer (or second layer) is different from the pharmacologically active agent present in the drug composition (or ER composition) of the present disclosure. In still other embodiments, the drug layer (or second layer) includes a first pharmacologically active agent which is the same as the pharmacologically active agent present in the drug composition (or ER composition) of the present disclosure and at least a second pharmacologically active agent which is different from the pharmacologically active agent present in the drug composition (or ER composition) of the present disclosure.

The pharmacologically active agent, e.g., a pharmacologically active agent as described herein, may be present in the drug layer (or second layer) of the dosage forms described herein at from about 1% w/w to about 50% w/w relative to the total weight of the drug layer (or second layer), e.g., from about 5% w/w to about 40% w/w, from about 10% w/w to about 30% w/w, or from about 10% w/w to about 20% w/w relative to the total weight of the drug layer (or second layer). In some embodiments, the pharmacologically active agent may be present in the drug layer (or second layer) of the dosage forms described herein at about 1% w/w, about 5% w/w, about 10% w/w, about 15% w/w, about 20% w/w, about 25% w/w, about 30% w/w, about 35% w/w, about 40% w/w, about 45% w/w, or about 50% w/w relative to the total weight of the drug layer (or second layer).

In some embodiments, the amount of the pharmacologically active agent present in the drug layer is from about 5% to about 40% of the total amount of the pharmacologically active agent in the dosage form, e.g., from about 15% to about 30% or from about 20% to 25% of the total amount of the pharmacologically active agent in the dosage form. In some embodiments, the amount of the pharmacologically active agent present in the drug layer is about 5%, about 10%, about 15%, about 16%, about 17%, about 18%, about 19%, about 20%, about 21%, about 22%, about 23%, about 24%, about 25%, about 26%, about 27%, about 28%, about 29%, about 30%, about 31%, about 32%, about 33%, about 34%, about 35%, about 36%, about 37%, about 38%, about 39% or about 40% of the total amount of the pharmacologically active agent in the dosage form.

In addition to the pharmacologically active agent the drug layer (or second layer) may include, e.g., a bulking agent, such as a hydroxypropyl methylcellulose (HPMC), mannitol, lactose, sucrose, dextrose, starch, cellulose, and mixtures thereof. The bulking agent may be present in the drug layer (or second layer) at from about 60% to about 95% w/w relative to the total weight of the drug layer (or second layer), e.g., about 60% w/w, about 65% w/w, about 66% w/w, about 67% w/w, about 68% w/w, about 69% w/w, about 70% w/w, about 71% w/w, about 72% w/w, about 73% w/w, about 74% w/w, about 75% w/w, about 76% w/w, about 77% w/w, about 78% w/w, about 79% w/w, about 80% w/w, about 81% w/w, about 82% w/w, about 83% w/w, about 84% w/w, about 85% w/w, about 86% w/w, about 87% w/w, about 88% w/w, about 89% w/w, about 90% w/w, about 91% w/w, about 92% w/w, about 93% w/w, about 94% w/w, or about 95% w/w relative to the total weight of the drug layer (or second layer). The drug layer (or second layer) may have a finished product coating weight of from about 5 mg to about 70 mg, e.g., about 10 mg to about 65 mg, about 15 mg to about 60 mg, about 20 mg to about 55 mg, about 25 mg to about 50 mg, or about 30 mg to about 45 mg. In some embodiments, the drug layer (or second layer) has a finished product coating weight of from about 5 mg to about 10 mg, from about 10 mg to about 15 mg, from about 15 mg to about 20 mg, from about 20 mg to about 25 mg, from about 25 mg to about 30 mg, from about 30 mg to about 35 mg, from about 35 mg to about 40 mg, from about 40 mg to about 45 mg, or from about 45 mg to about 50 mg. In some embodiments, the drug layer (or second layer) has a finished product coating weight of 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, or 65 mg.

The drug layer (or second layer) may include, e.g., a film former, a plasticizer, a colorant, a solvent, other additives, and mixtures thereof. Examples of film formers include, but are not limited to, hydroxypropyl methylcellulose (HPMC), methylcellulose (MC), hydroxypropyl cellulose (HC), hydroxyl ethylcellulose (HEC), carboxyl methylcellulose (CMC), polyvinylpyrrolidone (PVP), and modified food starch. Examples of plasticizers include, but are not limited to, polyethylene glycol (PEG), propylene glycol (PG), tributyl citrate (TBC), acetylated monoglyceride (AMG), dibutyl sebacate (DBS), triacetin, oleic acid, and castor oil. In one embodiment, the drug layer (or second layer) includes a polyvinyl alcohol containing composition, such as Opadry® II (85F18422) which is believed to contain polyvinyl alcohol, polyethylene glycol, talc, and $TiO_2$. Other materials for the drug layer include Opadry® coating system, Opadry® 200 coating system, Opadry® amb coating system, Opadry® Fx™ coating system, and Opalux® coating system.

In some embodiments, the drug layer (or second layer) specifically excludes a gelling agent. For example, the drug layer (or second layer) may specifically exclude one or more of the following gelling agents: acacia, alginic acid, bentonite, Carbopols® (also known as carbomers), carboxymethylcellulose. ethylcellulose, gelatin, hydroxyethylcellulose, hydroxypropyl cellulose, magnesium aluminum silicate (Veegum®), methylcellulose, poloxamers (Pluronics®), polyvinyl alcohol, sodium alginate, tragacanth, and xanthan gum.

Film Coating Layer

In some embodiments, in addition to a drug composition (or extended release (ER) composition) including a pharmacologically active agent, a barrier layer (or first layer) covering at least a portion of the drug composition, and a drug layer (or second layer) covering at least a portion of the barrier layer (or first layer), wherein the drug layer (or second layer) comprises a pharmacologically active agent (e.g., the same pharmacologically active agent present in the drug composition (or extended release (ER) composition), the dosage forms of the present disclosure include a film coating layer (or third layer), which covers at least a portion of the drug layer (or second layer). The film coating layer (or third layer) may include, e.g., a film former, a plasticizer, a colorant, a solvent, other additives, and mixtures thereof. Examples of film formers include, but are not limited to, hydroxypropyl methylcellulose (HPMC), methylcellulose (MC), hydroxypropyl cellulose (HC), hydroxyl ethylcellulose (HEC), carboxyl methylcellulose (CMC), polyvinylpyrrolidone (PVP), and modified food starch. Examples of plasticizers include, but are not limited to, polyethylene glycol (PEG), propylene glycol (PG), tributyl citrate (TBC), acetylated monoglyceride (AMG), dibutyl sebacate (DBS), triacetin, oleic acid, and castor oil. In one embodiment, the film coating layer (or third layer) includes a polyvinyl alcohol containing composition, such as Opadry® II (e.g., 85F18422, 85F12398, and/or 85F17644) which is believed to contain polyvinyl alcohol, polyethylene glycol, talc, and $TiO_2$. Other materials for the film coating layer include Opadry® coating system, Opadry® 200 coating system, Opadry® amb coating system, Opadry® Fx™ coating system, and Opalux® coating system.

In some embodiments, the film coating layer (or third layer) has a finished product coating weight of from about 5 mg to about 10 mg, e.g., from about 6 mg to about 9 mg, or from about 7 mg to about 8 mg. In some embodiments, the coating layer (or third layer) has a finished product coating weight of about 5 mg, about 6 mg, about 7 mg, about 8 mg, about 9 mg, or about 10 mg.

In some embodiments, the combined thickness of the barrier layer, the drug layer (or second layer) and the film coating layer (or third layer) is from about 0.1 mm to about 1 mm, e.g., about 0.2 mm to about 0.5 mm or about 0.3 mm to about 0.4 mm.

Methods of Making, Encapsulating and Administering

Once components have been selected to produce a drug composition (or ER composition) in accordance with the present disclosure, a liquid pharmaceutical composition can be prepared by simply mixing, for example a HVLCM, a rheology modifier, a network former, a pharmacologically active agent, a solvent and any additional additives. The drug composition (or ER compositions) of the present disclosure may be produced as liquid mixtures, having a number of excipient ingredients that are in solution, suspension, or in partial solution within the final composition.

Suitable methods for compounding or manufacturing the drug composition (or ER compositions) make use of typical pharmaceutical/chemical mixing and handling apparatus and techniques. Since the liquid mixtures of the present disclosure are formed from a number of highly viscous liquids and solids, they may have high final viscosities. Accordingly, the specific equipment and techniques employed in the manufacture of such compositions may be selected so as to accommodate such material demands. In particular, various excipients, such as network formers, may be added to the composition mixture in the solid or semi-solid state, and as such they may be screened or otherwise size-reduced prior to addition to a composition mixing apparatus.

Other solid excipients may require melting prior to addition to the liquid mixture. The HVLCM materials are very high viscosity liquid materials, however they tend to exhibit a dramatic reduction in viscosity with increases in heat, and as such the mixing apparatus may be heated to accommodate the addition of the HVLCM material or other similar materials. However, the mixing and processing conditions should take into account the final integrity of the composition and accordingly the mixing conditions may be selected so as to have a low-shear effect on the composition, and/or to avoid any extended or pronounced excursions into high or low heat conditions.

Once the composition has been properly combined, an appropriate amount of the resulting liquid mixture can be placed into a suitable capsule, such as a gelatin or HPMC capsule to provide an encapsulated form of the drug composition (or ER composition). Alternative liquid compositions may include emulsifying the mixture in water, and introducing this emulsion into a capsule.

In some embodiments, an oral dosage form is provided which includes the drug composition (or ER composition) within an enclosure or capsule, e.g., a biodegradable enclosure or capsule, such as a capsule or a gelatin capsule ("gelcap"), wherein the capsule is made of a substance that degrades or otherwise dissociates when exposed to conditions present in the gastro-intestinal tract of a mammal. Capsules and gelcaps are well known in drug delivery technology and one of skill could select such a capsule as appropriate for delivery of a particular active agent.

Suitable capsules which may be utilized in connection with the disclosed compositions include, but are not limited to hard-shelled capsules, soft-shelled capsules, and interlocking capsules. Suitable capsules sizes range from size 5 capsules to size 00 capsules, including e.g., size 5, size 4, size 3, size 2, size 1, size 0 and size 00.

In some embodiments, a suitable capsule includes gelatin or synthetic polymers such as hydroxyl ethyl cellulose and/or hydroxy propylmethyl cellulose. Gelcaps can be of the hard or soft variety, including, for example, polysaccharide or hypromellose acetate succinate based caps (e.g., Vegicaps brand, available from Catalent). The capsule can also be coated with an enteric coating material such as AQIAT (Shin-Etsu) to delay release of the pharmacologically active agent.

An exemplary method for formulating a drug composition (or ER composition) according to the present disclosure is depicted in FIG. 1A, wherein the components of the drug composition (or ER composition) are weighed to the desired component weight, compounded, e.g., at 60±5° C. in an oil bath, filled into a suitable capsule at a desired fill weight. Following capsule filling, the capsule may be banded, e.g., using a solution of HPMC in ethanol and water.

Once the drug composition (or ER composition) has been formed and/or encapsulated as described herein, one or more of the additional coating layers described herein may be progressively added, e.g., with a curing step between the application of one or more progressive coating layers, e.g., as described in the Examples.

In some embodiments, it may be desirable to reduce the amount of water available to the drug composition (or ER composition) of the present disclosure. For example, by utilizing HPMC capsules (~2-6% w/w water, e.g., 4-6% w/w water) instead of gelatin capsules (~13-16% w/w water) the amount of water available to the drug composition (or ER composition) may be reduced. Accordingly, in some embodiments, the drug composition (or ER composition) of the present disclosure is specifically encapsulated within capsules having lower water content than gelatin capsules, e.g., water content of less than about 15% w/w, less than about 14% w/w, less than about 13% w/w, less than about 12% w/w, less than about 11% w/w, less than 10% w/w, less than about 9% w/w, less than about 8% w/w, less than about 7% w/w, less than about 6% w/w, less than about 5% w/w, less than about 4% w/w, less than about 3% w/w, less than about 2% w/w, or less than about 1% w/w. In some embodiments, the drug composition (or ER composition) of the present disclosure is encapsulated within capsules having a water content of from about 1% w/w to about 10% w/w, e.g., from about 1% w/w to about 9% w/w, from about 1% w/w to about 8% w/w, from about 1% w/w to about 7% w/w, from about 1% w/w to about 6% w/w, from about 1% w/w to about 5% w/w, from about 1% w/w to about 4% w/w, from about 1% w/w to about 3% w/w, or from about 1% w/w to about 2% w/w. In some embodiments, the drug composition (or ER composition) of the present disclosure is encapsulated in capsules having a water content less than about 1% w/w including, for example, from about 0.1% w/w to about 1% w/w, from about 0.2% w/w to about 0.8% w/w, from about 0.4% w/w to about 0.8% w/w, or from about 0.6% w/w to about 0.8% w/w. Suitable HPMC capsules may include, for example, V-caps™, V-caps Plus™, Quali-V™, VegiCaps™, Embo Caps-Vg™, and HMPC capsules provided by Baotou Capstech Co., Ltd, and Zhejiang LinFeng Capsules Co. Ltd.

The water content of a capsule, composition, or composition in combination with a capsule, when provided within a capsule as described in the present disclosure, may be determined by Karl Fischer titration method as set forth in USP <921> Method 1C. In some embodiments, an AquaStar C3000 Karl Fischer Coulometric Titrator may be used in connection with the disclosed titration method.

In some embodiments, a drug composition (or ER composition) according to the present disclosure is one which has relatively low water content. For example, in some embodiments, a drug composition (or ER composition) according to the present disclosure does not include more than about 5% water by weight, based on total weight of the composition. For example, the drug composition (or ER composition) may include water at less than about 5% by weight, less than about 4% by weight, less than about 3% by weight, or less than about 2% by weight, based on the total weight of the drug composition (or ER composition). In some embodiments, a drug composition (or ER composition) according to the present disclosure includes water at from about 1.0 to about 5.0% by weight, based on total weight of the drug composition (or ER composition), e.g., at from about 1.0 to about 4.5% by weight, at from about 1.0 to about 3.0% by weight, at from about 1.0 to about 2.5% by weight, at from about 1.0 to about 2.0% by weight, or at from about 1.0 to about 1.5% by weight, based on total weight of the drug composition (or ER composition). In some embodiments, a drug composition (or ER composition) according to the present disclosure includes water at about 1.0% by weight, about 1.5% by weight, about 2% by weight, about 2.5% by weight, about 3% by weight, about 3.5% by weight, about 4% by weight, about 4.5% by weight, or about 5% by weight, based on the total weight of the drug composition (or ER composition). In the above embodiments, each of the above drug composition (or ER compositions) may be a drug composition (or ER composition) which has been encapsulated within a capsule having a water content of less than about 15% w/w (e.g., less than about 10% w/w or less than about 5% w/w), e.g., an HPMC capsule, and stored for a period of time, e.g., 1, 2, 3, 4, 5, 6, 7, 8, 9, 10, 11 or 12 months, at 25° C. and 60% relative humidity (RH), 30° C. and 65% RH, or 40° C. and 75% RH.

The water content of a drug composition (or ER composition) as described in the present disclosure may be determined by Karl Fischer titration method as set forth in USP <921> Method 1C. In some embodiments, an AquaStar C3000 Karl Fischer Coulometric Titrator may be used in connection with the disclosed titration method.

In some embodiments, the water content of the drug composition (or ER composition) and the capsule combined is less than about 5% by weight based on the total weight of the drug composition (or ER composition) and the capsule combined, e.g., less than about 4% by weight, less than about 3% by weight, or less than about 2% by weight based on the total weight of the drug composition (or ER composition) and the capsule combined. In some embodiments, the water content of the drug composition (or ER composition) and the capsule combined is from about 5% by weight to about 4% by weight, from about 4% by weight to about 3% by weight, from about 3% by weight to about 2% by weight, or from about 2% by weight to about 1% by weight based on the total weight of the drug composition (or ER composition) and the capsule combined. In some embodiments, the water content of the drug composition (or ER composition) and the capsule combined is about 1.0% by weight, about 1.5% by weight, about 2% by weight, about 2.5% by weight, about 3% by weight, about 3.5% by weight, about 4% by weight, about 4.5% by weight, or about 5% by weight, based on the total weight of the drug composition (or ER composition) and the capsule combined. The water content of a drug composition (or ER composition) and capsule combined as described in the present disclosure may be determined by Karl Fischer titration method as set forth in USP <921> Method 1C. In some embodiments, an AquaStar C3000 Karl Fischer Coulometric Titrator may be used in connection with the disclosed titration method.

Dosage regimens for a particular pharmacologically active agent of interest may be determined by a physician in accordance with standard practices. Once per day (QD) or twice per day (BID) dosing may be used to maintain a sufficient clinical effect, e.g., to relieve the symptoms of ADHD. In some embodiments, the dosage forms of the present disclosure are administered orally, e.g., QD or BID.

In some embodiments, the present disclosure provides a method of treating Attention Deficit Disorder (ADD) or Attention Deficit Hyperactivity Disorder (ADHD) in a subject, the method comprising administering, e.g., orally administering, a dosage form as described herein, wherein the pharmacologically active agent is methylphenidate.

In Vitro Dissolution and Pharmacokinetics

The dosage forms of the present disclosure may be characterized by a desirable in vitro dissolution profile. For example, in some embodiments the % cumulative release of the pharmacologically active agent from an oral dosage form according to the present disclosure is from 5% to 40%, e.g., 10% to 30%, at T=1 hr when assayed by USP Apparatus II using 750 mL of 1-stage 0.1 N HCl dissolution medium, a paddle speed of 50 rpm, a dissolution medium temperature of 37° C., and a sampling volume of 1 mL.

In some embodiments, the in vitro % cumulative release of the pharmacologically active agent from an oral dosage form according to the present disclosure is at least 80% at T=12 hr when assayed by USP Apparatus II using a 2-stage dissolution protocol, a paddle speed of 50 rpm, a dissolution medium temperature of 37° C., and a sampling volume of 1 mL, wherein the 2-stage dissolution protocol includes exposing the oral dosage form to 750 mL of 0.1 N HCl for T=0 to T=2 hrs, adding 200 mL of 0.19 M phosphate buffer to obtain a final dissolution medium volume of 950 mL, and exposing the oral dosage form to the final dissolution medium volume from T=2 hrs to T=24 hr.

In some embodiments, a dosage form of the present disclosure is constituted such that initial release from the dosage form, of a pharmacologically active agent comprised by the drug composition (or ER composition), occurs at a time of 5 minutes to 120 minutes when assayed by USP Apparatus II using 750 mL of 0.1 N HCl dissolution medium, a paddle speed of 50 rpm, and a dissolution medium temperature of 37° C. For example, in some embodiments, a dosage form of the present disclosure is constituted such that initial release from the dosage form, of a pharmacologically active agent comprised by the drug composition (or ER composition), occurs at a time of 10 minutes to 120 minutes, 15 minutes to 120 minutes, 20 minutes to 120 minutes, 25 minutes to 120 minutes, 30 minutes to 120 minutes, 35 minutes to 120 minutes, 40 minutes to 120 minutes, 45 minutes to 120 minutes, 50 minutes to 120 minutes, 55 minutes to 120 minutes, 60 minutes to 120 minutes, 65 minutes to 120 minutes, 70 minutes to 120 minutes, 75 minutes to 120 minutes, 80 minutes to 120 minutes, 85 minutes to 120 minutes, 90 minutes to 120 minutes, 95 minutes to 120 minutes, 100 minutes to 120 minutes, 105 minutes to 120 minutes, 110 minutes to 120 minutes, or 115 minutes to 120 minutes, when assayed by USP Apparatus II using 750 mL of 0.1 N HCl dissolution medium, a paddle speed of 50 rpm, and a dissolution medium temperature of 37° C.

In some embodiments, a dosage form of the present disclosure is constituted such that initial release from the dosage form, of a pharmacologically active agent comprised by the drug composition (or ER composition), occurs at a time of 5 minutes to 10 minutes, 10 minutes to 20 minutes, 20 minutes to 30 minutes, 30 minutes to 40 minutes, 40 minutes to 50 minutes, 50 minutes to 60 minutes, 60 minutes to 70 minutes, 70 minutes to 80 minutes, 80 minutes to 90 minutes, 90 minutes to 100 minutes, 100 minutes to 110 minutes, or 110 minutes to 120 minutes, when assayed by USP Apparatus II using 750 mL of 0.1 N HCl dissolution medium, a paddle speed of 50 rpm, and a dissolution medium temperature of 37° C.

In some embodiments, a dosage form of the present disclosure is constituted such that initial release from the dosage form, of a pharmacologically active agent comprised by the drug composition (or ER composition), occurs at a time of 10 minutes to 110 minutes, 20 minutes to 100 minutes, 30 minutes to 90 minutes, 40 minutes to 80 minutes, or 50 minutes to 70 minutes, when assayed by USP Apparatus II using 750 mL of 0.1 N HCl dissolution medium, a paddle speed of 50 rpm, and a dissolution medium temperature of 37° C.

Where the pharmacologically active agent of a drug composition (first pharmacologically active agent) as described herein is the same as the pharmacologically active agent (second pharmacologically active agent) of a drug layer as described herein, the initial release of the first pharmacologically active agent from a dosage form as described herein, e.g., as discussed above, can be determined by determining the time at which cumulative release of the first and second pharmacologically active agents from the dosage form exceeds the amount of the second pharmacologically active agent in the drug layer.

In some embodiments, a dosage form of the present disclosure is constituted such that initial release from the dosage form, of a pharmacologically active agent comprised by the drug composition (or ER composition), occurs at a time of 5 minutes to 120 minutes when assayed by USP Apparatus II using 750 mL of 0.1 N HCl dissolution medium, a paddle speed of 50 rpm, and a dissolution medium temperature of 37° C., wherein the initial release of the pharmacologically active agent from the dosage form is determined in the absence of the drug layer. For example, in some embodiments, a dosage form of the present disclosure is constituted such that initial release from the dosage form, of a pharmacologically active agent comprised by the drug composition (or ER composition), occurs at a time of 10 minutes to 120 minutes, 15 minutes to 120 minutes, 20 minutes to 120 minutes, 25 minutes to 120 minutes, 30 minutes to 120 minutes, 35 minutes to 120 minutes, 40 minutes to 120 minutes, 45 minutes to 120 minutes, 50 minutes to 120 minutes, 55 minutes to 120 minutes, 60 minutes to 120 minutes, 65 minutes to 120 minutes, 70 minutes to 120 minutes, 75 minutes to 120 minutes, 80 minutes to 120 minutes, 85 minutes to 120 minutes, 90 minutes to 120 minutes, 95 minutes to 120 minutes, 100 minutes to 120 minutes, 105 minutes to 120 minutes, 110 minutes to 120 minutes, or 115 minutes to 120 minutes, when assayed by USP Apparatus II using 750 mL of 0.1 N HCl dissolution medium, a paddle speed of 50 rpm, and a dissolution medium temperature of 37° C., wherein the initial release of the pharmacologically active agent from the dosage form is determined in the absence of the drug layer.

In some embodiments, a dosage form of the present disclosure is constituted such that initial release from the dosage form, of a pharmacologically active agent comprised by the drug composition (or ER composition), occurs at a time of 5 minutes to 10 minutes, 10 minutes to 20 minutes, 20 minutes to 30 minutes, 30 minutes to 40 minutes, 40 minutes to 50 minutes, 50 minutes to 60 minutes, 60 minutes to 70 minutes, 70 minutes to 80 minutes, 80 minutes to 90 minutes, 90 minutes to 100 minutes, 100 minutes to 110 minutes, or 110 minutes to 120 minutes, when assayed by USP Apparatus II using 750 mL of 0.1 N HCl dissolution medium, a paddle speed of 50 rpm, and a dissolution medium temperature of 37° C., wherein the initial release of the pharmacologically active agent from the dosage form is determined in the absence of the drug layer.

In some embodiments, a dosage form of the present disclosure is constituted such that initial release from the dosage form, of a pharmacologically active agent comprised by the drug composition (or ER composition), occurs at a time of 10 minutes to 110 minutes, 20 minutes to 100 minutes, 30 minutes to 90 minutes, 40 minutes to 80 minutes, or 50 minutes to 70 minutes, when assayed by USP Apparatus II using 750 mL of 0.1 N HCl dissolution medium, a paddle speed of 50 rpm, and a dissolution medium temperature of 37° C., wherein the initial release of the pharmacologically active agent from the dosage form is determined in the absence of the drug layer.

In some embodiments, a dosage form of the present disclosure is constituted so as to delay release from the dosage form, of a pharmacologically active agent comprised by the drug composition (or ER composition), such that not more than 15%, e.g., not more than 10%, e.g., not more than 5%, or not more than 2% of the pharmacologically active agent is released from the dosage form at 60 min, when assayed by USP Apparatus II using 750 mL of 0.1 N HCl dissolution medium, a paddle speed of 50 rpm, and a dissolution medium temperature of 37° C.

In some embodiments, a dosage form of the present disclosure is constituted so as to delay release from the dosage form, of a pharmacologically active agent comprised by the drug composition (or ER composition), such that from 0% to 15%, e.g., from 0% to 10%, from 0% to 5%, or from 0% to 2% of the pharmacologically active agent is released from the dosage form at 60 min, when assayed by USP Apparatus II using 750 mL of 0.1 N HCl dissolution medium, a paddle speed of 50 rpm, and a dissolution medium temperature of 37° C.

In some embodiments, a dosage form of the present disclosure is constituted so as to delay release from the dosage form, of a pharmacologically active agent comprised by the drug composition (or ER composition), such that about 1%, about 2%, about 3%, about 4%, about 5%, about 6%, about 7%, about 8%, about 9%, about 10%, about 11%, about 12%, about 13%, or about 14% of the pharmacologically active agent is released from the dosage form at 60 min, when assayed by USP Apparatus II using 750 mL of 0.1 N HCl dissolution medium, a paddle speed of 50 rpm, and a dissolution medium temperature of 37° C.

In some embodiments, a dosage form of the present disclosure is constituted so as to delay release from the dosage form, of a pharmacologically active agent comprised by the drug composition (or ER composition), such that not more than 25%, not more than 25%, not more than 15%, not more than 10%, not more than 5%, or not more than 2% of the pharmacologically active agent is released from the dosage form at 90 min, when assayed by USP Apparatus II using 750 mL of 0.1 N HCl dissolution medium, a paddle speed of 50 rpm, and a dissolution medium temperature of 37° C.

In some embodiments, a dosage form of the present disclosure is constituted so as to delay release from the dosage form, of a pharmacologically active agent comprised by the drug composition (or ER composition), such that from 0% to 25%, e.g., from 0% to 20%, from 0% to 15%, from 0% to 10%, from 0% to 5%, or 0% to 2% of the pharmacologically active agent is released from the dosage form at 90 min, when assayed by USP Apparatus II using 750 mL of 0.1 N HCl dissolution medium, a paddle speed of 50 rpm, and a dissolution medium temperature of 37° C.

In some embodiments, a dosage form of the present disclosure is constituted so as to delay release from the dosage form, of a pharmacologically active agent comprised by the drug composition (or ER composition), such that 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, or about 24% of the pharmacologically active agent is released from the dosage form at 90 min, when assayed by USP Apparatus II using 750 mL of 0.1 N HCl dissolution medium, a paddle speed of 50 rpm, and a dissolution medium temperature of 37° C.

In some embodiments, a dosage form of the present disclosure is constituted such that a cumulative release of 5% or more, e.g., 10% or more, 15% or more or 20% or more, of a pharmacologically active agent comprised by the drug composition (or ER composition) occurs at a time of 120 minutes when assayed by USP Apparatus II using 750 mL of 0.1 N HCl dissolution medium, a paddle speed of 50 rpm, and a dissolution medium temperature of 37° C. For example, in some embodiments, a dosage form of the present disclosure is constituted such that a cumulative release of between 10% and 20% of a pharmacologically active agent comprised by the drug composition (or ER composition) occurs at a time of 120 minutes when assayed by USP Apparatus II using 750 mL of 0.1 N HCl dissolution medium, a paddle speed of 50 rpm, and a dissolution medium temperature of 37° C.

In some embodiments, a dosage form of the present disclosure is constituted such that a cumulative release of 5% or more, e.g., 10% or more, 15% or more or 20% or more of a pharmacologically active agent comprised by the drug composition (or ER composition) occurs at a time of 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, or 120 minutes, when assayed by USP Apparatus II using 750 mL of 0.1 N HCl dissolution medium, a paddle speed of 50 rpm, and a dissolution medium temperature of 37° C.

For example, in some embodiments, a dosage form of the present disclosure is constituted such that a cumulative release of between 5% and 20% of a pharmacologically active agent comprised by the drug composition (or ER composition) occurs at a time of 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, or 120 minutes, when assayed by USP Apparatus II using 750 mL of 0.1 N HCl dissolution medium, a paddle speed of 50 rpm, and a dissolution medium temperature of 37° C.

Where the pharmacologically active agent of a drug composition (first pharmacologically active agent) as described herein is the same as the pharmacologically active agent (second pharmacologically active agent) of a drug layer as described herein, the % release of the first pharmacologically active agent from a dosage form as described herein at a particular time point, e.g., as discussed above, can be determined by determining the % cumulative release of the first and second pharmacologically active agents from the dosage form that exceeds the amount of the second pharmacologically active agent in the drug layer at the particular time point.

In some embodiments, a dosage form of the present disclosure is constituted so as to delay release from the dosage form, of a pharmacologically active agent comprised by the drug composition (or ER composition), such that not more than 15%, e.g., not more than 10%, e.g., not more than 5%, or not more than 2% of the pharmacologically active agent is released from the dosage form at 60 min, when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer.

In some embodiments, a dosage form of the present disclosure is constituted so as to delay release from the dosage form, of a pharmacologically active agent comprised by the drug composition (or ER composition), such that from 0% to 15%, e.g., from 0% to 10%, from 0% to 5%, or from 0% to 2% of the pharmacologically active agent is released from the dosage form at 60 min, when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer.

In some embodiments, a dosage form of the present disclosure is constituted so as to delay release from the dosage form, of a pharmacologically active agent comprised by the drug composition (or ER composition), such that about 1%, about 2%, about 3%, about 4%, about 5%, about 6%, about 7%, about 8%, about 9%, about 10%, about 11%, about 12%, about 13%, or about 14% of the pharmacologically active agent is released from the dosage form at 60 min, when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer.

In some embodiments, a dosage form of the present disclosure is constituted so as to delay release from the dosage form, of a pharmacologically active agent comprised by the drug composition (or ER composition), such that not more than 25%, not more than 25%, not more than 15%, not more than 10%, not more than 5%, or not more than 2% of the pharmacologically active agent is released from the dosage form at 90 min, when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer.

In some embodiments, a dosage form of the present disclosure is constituted so as to delay release from the dosage form, of a pharmacologically active agent comprised by the drug composition (or ER composition), such that from 0% to 25%, e.g., from 0% to 20%, from 0% to 15%, from 0% to 10%, from 0% to 5%, or 0% to 2% of the pharmacologically active agent is released from the dosage form at 90 min, when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer.

In some embodiments, a dosage form of the present disclosure is constituted so as to delay release from the dosage form, of a pharmacologically active agent comprised by the drug composition (or ER composition), such that 1%, about 2%, about 3%, about 4%, about 5%, about 6%, about 7%, about 8%, about 9%, about 10%, about 11%, about 12%, about 13%, about 14%, about 15%, about 16%, about 17%, about 18%, about 19%, about 20%, about 21%, about 22%, about 23%, or about 24% of the pharmacologically active agent is released from the dosage form at 90 min, when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer.

In some embodiments, a dosage form of the present disclosure is constituted such that a cumulative release of 5% or more, e.g., 10% or more, 15% or more or 20% or more, of a pharmacologically active agent comprised by the drug composition (or ER composition) occurs at a time of 120 minutes when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer. For example, in some embodiments, a dosage form of the present disclosure is constituted such that a cumulative release of between 10% and 20% of a pharmacologically active agent comprised by the drug composition (or ER composition) occurs at a time of 120 minutes when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer.

In some embodiments, a dosage form of the present disclosure is constituted such that a cumulative release of 5% or more, e.g., 10% or more, 15% or more or 20% or more of a pharmacologically active agent comprised by the drug composition (or ER composition) occurs at a time of 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, or 120 minutes, when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer.

For example, in some embodiments, a dosage form of the present disclosure is constituted such that a cumulative release of between 5% and 20% of a pharmacologically active agent comprised by the drug composition (or ER composition) occurs at a time of 10 minutes, 15 minutes, 20 minutes, 25 minutes, 30 minutes, 35 minutes, 40 minutes, 45 minutes, 50 minutes, 55 minutes, 60 minutes, 65 minutes, 70 minutes, 75 minutes, 80 minutes, 85 minutes, 90 minutes, 95 minutes, 100 minutes, 105 minutes, 110 minutes, 115 minutes, or 120 minutes, when assayed by USP Apparatus II using 750 mL of 0.1 N HCl dissolution medium, a paddle speed of 50 rpm, and a dissolution medium temperature of 37° C., wherein the % release of the pharmacologically active agent is determined in the absence of the drug layer.

In certain embodiments, the dosage forms of the present disclosure may be formulated so as to produce particular controlled plasma levels of a pharmacologically active agent over a particular period, e.g., to maintain a plasma level within an appropriate therapeutic range following administration to a subject. An appropriate therapeutic range will vary depending on the pharmacologically active agent, but can range from femtogram/mL levels up to above microgram/mL levels for a desired period of time. For example, administration of a single dosage form described herein may result in maintenance of plasma levels of greater than 5 ng/mL for a period of greater than 8 hours. In other embodiments, the plasma level achieved using a single dose may be greater than about 5 ng/mL for a period of greater than about 10 hours, greater than about 12 hours, greater than about 14 hours, greater than about 16 hours, greater than about 18 hours, or greater than about 20 hours. In yet other embodiments, the plasma level achieved using a single dose may be greater than about 5 ng/mL, greater than about 10 ng/mL, greater than about 15 ng/mL, greater than about 20 ng/mL, greater than about 30 ng/mL, greater than about 40 ng/mL, or greater than about 50 ng/mL for a period of about 4, about 8, about 10, about 12, about 14, about 16, about 18, about 20 or about 24 hours. The maximum plasma concentration of a pharmacologically active agent may be reached at a time following administration from between about 0.1 hr to about 24 hr, or from about 0.25 hr to about 10 hr, or from about 0.25 hr to about 8 hr, or from about 0.5 hr to about 6 hr, or from about 0.5 hr to about 4 hr, or from about 0.5 hr to about 2 hr, or from about 0.5 hr to about 1 hr. The time to maximum plasma concentration may be adjusted by adjusting various components of the dosage forms as taught herein.

In some embodiments, a dosage form according to the present disclosure is sufficient to provide an in vivo Tmax of from about 3 hrs to about 6 hrs, e.g., from about 4 hrs to about 5 hrs, following oral administration to a subject.

In some embodiments, a dosage form according to the present disclosure is sufficient to provide an in vivo Cmax of from about 5 ng/mL to about 18 ng/mL, e.g., from about 6 ng/mL to about 17 ng/mL, from about 7 ng/mL to about 16 ng/mL, from about 8 ng/mL to about 15 ng/mL, from about 9 ng/mL to about 14 ng/mL, from about 10 ng/mL to about 13 ng/mL, or from about 11 ng/mL to about 12 ng/mL following oral administration to a subject. In some embodiments, a dosage form according to the present disclosure is sufficient to provide an in vivo Cmax of about 5 ng/mL, about 6 ng/mL, about 7 ng/mL, about 8 ng/mL, about 9 ng/mL, about 10 ng/mL, about 11 ng/mL, about 12 ng/mL, about 13 ng/mL, about 14 ng/mL, about 15 ng/mL, about 16 ng/mL, about 17 ng/mL, or about 18 ng/mL following oral administration to a subject.

The plasma levels obtained may be adjusted by adjusting the dose of the pharmacologically active agent, and/or by adjusting the components of the dosage forms, and desirable plasma levels will depend on the therapeutic range or its index for any particular pharmacologically active agent. It is readily within the skill of one in the art to determine the desired therapeutic index.

The rate of pharmacologically active agent release from the composition may be varied depending on the agent used and the dosage required. Release rates may be different in different parts of the GI tract, and release rates may be averaged over the time of transit through the GI tract (approximately 8-24 hrs). Typical average release rates may vary substantially. For many active agents, they may range from about 0.01 to about 500 mg/hr, e.g., from about 0.5 to about 250 mg/hr, from about 0.75 to about 100 mg/hr, from about 1 to about 100 mg/hr, from about 2 to about 100 mg/hr, from about 5 to about 100 mg/hr, from about 10 to about 100 mg/hr, from about 10 to about 80 mg/hr, from about 20 to about 50 mg/hr, or from about 20 to about 40 mg/hr.

Exemplary Non-Limiting Aspects of the Disclosure

Aspects, including embodiments, of the present subject matter described above may be beneficial alone or in combination, with one or more other aspects or embodiments. Without limiting the foregoing description, certain non-limiting aspects of the disclosure numbered 1-442 are provided below. As will be apparent to those of skill in the art upon reading this disclosure, each of the individually numbered aspects may be used or combined with any of the preceding or following individually numbered aspects. This is intended to provide support for all such combinations of aspects and is not limited to combinations of aspects explicitly provided below.

1. A dosage form, comprising:
    a drug composition comprising a first pharmacologically active agent;
    a barrier layer covering at least a portion of the drug composition; and
    a drug layer covering at least a portion of the barrier layer, wherein the drug layer comprises a second pharmacologically active agent, and
    wherein initial release of the first pharmacologically active agent from the dosage form occurs at a time of 5 minutes to 120 minutes when assayed by USP Apparatus II using 750 mL of 0.1 N HCl dissolution medium, a paddle speed of 50 rpm, and a dissolution medium temperature of 37° C.
2. The dosage form of 1, wherein the first pharmacologically active agent and the second pharmacologically active agents are the same, and wherein the initial release of the first pharmacologically active agent is determined by determining the time at which cumulative release of the first and second pharmacologically active agents exceeds the amount of the second pharmacologically active agent in the drug layer.
3. The dosage form of 1, wherein the barrier layer is soluble in 0.1 N HCl at 37° C.
4. The dosage form of 1, wherein the barrier layer comprises a first material which is soluble in 0.1 N HCl at 37° C. and a second material which is insoluble in 0.1 N HCl at 37° C.
5. The dosage form of any one of 1-4, wherein the first pharmacologically active agent and the second pharmacologically active agent are the same.
6. The dosage form of any one of 1-5, wherein the first pharmacologically active agent is present in the drug composition at from about 10% to about 50% w/w relative to the total weight of the drug composition.
7. The dosage form of any one of 1-6, wherein the drug composition is encapsulated in a capsule and the barrier layer covers at least a portion of the capsule.
8. The dosage form of 7, wherein the capsule comprises an outer surface and an inner surface, and wherein the barrier layer covers at least a portion of the outer surface of the capsule.
9. The dosage form of 7, wherein the capsule comprises at least one of hydroxypropyl methylcellulose (HPMC) and gelatin.
10. The dosage form of any one of 1-9, wherein the drug composition comprises a High Viscosity Liquid Carrier Material (HVLCM).
11. The dosage form of 10, wherein the HVLCM is present at about 30% to about 60% w/w relative to the total weight of the drug composition.

12. The dosage form of 11, wherein the HVLCM is present at about 35% to about 45% w/w relative to the total weight of the drug composition.
13. The dosage form of any one of 10-12, wherein the HVLCM is sucrose acetate isobutyrate (SAB).
14. The dosage form of any one of 1-13, wherein the drug composition comprises an organic solvent.
15. The dosage form of 14, wherein the organic solvent is present at about 0.1% to about 45% w/w relative to the total weight of the drug composition.
16. The dosage form of 14 or 15, wherein the organic solvent is present at about 10% to about 35% w/w relative to the total weight of the drug composition.
17. The dosage form of any one of 14-16, wherein the organic solvent is present at about 20% to about 35% w/w relative to the total weight of the drug composition.
18. The dosage form of any one of 14-17, wherein the organic solvent comprises at least one member selected from triacetin, N-methyl-2-pyrrolidone, 2-pyrrolidone, dimethylsulfoxide, ethyl lactate, propylene carbonate, and glycofurol.
19. The dosage form of any one of 14-18, wherein the organic solvent comprises triacetin.
20. The dosage form of any one of 1-19, wherein the drug composition comprises a rheology modifier.
21. The dosage form of 20, wherein the rheology modifier is present at about 0.1% to about 20% w/w relative to the total weight of the drug composition.
22. The dosage form of 20 or 21, wherein the rheology modifier is present at about 2% to about 15% w/w relative to the total weight of the drug composition.
23. The dosage form of any one of 20-22, wherein the rheology modifier is present at about 5% to about 7% w/w relative to the total weight of the drug composition.
24. The dosage form of any one of 20-23, wherein the rheology modifier comprises at least one member selected from a caprylic/capric triglyceride, isopropyl myristate, ethyl oleate, triethyl citrate, dimethyl phthalate, labrafil, labrasol, a polyglycolized glyceride, and benzyl benzoate.
25. The dosage form of any one of 20-24, wherein the rheology modifier comprises isopropyl myristate.
26. The dosage form of any one of 1-25, wherein the drug composition comprises a network former.
27. The dosage form of 26, wherein the network former is present at about 0.1% to about 20% w/w relative to the total weight of the drug composition.
28. The dosage form of 26 or 27, wherein the network former is present at about 2% to about 10% w/w relative to the total weight of the drug composition.
29. The dosage form of any one of 26-28, wherein the network former is present at about 4% to about 6% w/w relative to the total weight of the drug composition.
30. The dosage form of any one of 26-29, wherein the network former comprises at least one member selected from a cellulose acetate butyrate, a carbohydrate polymer, an organic acid of a carbohydrate polymer, a hydrogel, a cellulose acetate phthalate, an ethyl cellulose, a triblock copolymer, an acrylic polymer, hydroxyl propyl methyl cellulose, cellulose triacetate, and poly(methyl methacrylate).
31. The dosage form of any one of 26-30, wherein the network former comprises a cellulose acetate butyrate.
32. The dosage form of any one of 1-31, wherein the drug composition comprises a viscosity enhancing agent.
33. The dosage form of 32, wherein the viscosity enhancing agent is present at about 0.01% to about 10% w/w relative to the total weight of the drug composition.
34. The dosage form of 32 or 33, wherein the viscosity enhancing agent is present at about 0.1% to about 6% w/w relative to the total weight of the drug composition.
35. The dosage form of any one of 32-34, wherein the viscosity enhancing agent is present at about 0.5% to about 1.5% w/w relative to the total weight of the drug composition.
36. The dosage form of any one of 32-35, wherein the viscosity enhancing agent comprises silicon dioxide.
37. The dosage form of any one of 1-36, wherein the drug composition comprises a polyoxylglyceride.
38. The dosage form of 37, wherein the polyoxylglyceride is present at about 0.1% to about 5% w/w relative to the total weight of the drug composition.
39. The dosage form of 37 or 38, wherein the polyoxylglyceride is present at about 0.5% to about 1.5% w/w relative to the total weight of the drug composition.
40. The dosage form of any one of 1-39, wherein the fill weight of the drug composition is from about 100 mg to about 800 mg.
41. The dosage form of any one of 1-40, wherein the fill weight of the drug composition is from about 150 mg to about 200 mg.
42. The dosage form of any one of 1-41, wherein the barrier layer comprises at least one member selected from cellulose acetate phthalate, HPMC phthalate, HPMC acetate succinate, polyvinyl acetate phthalate, cellulose acetate trimelitate, methyacrylic acid copolymer, shellac, and zein.
43. The dosage form of any one of 1-41, wherein the barrier layer comprises at least one member selected from a hydrophobic cellulose, a polyalcohol, magnesium stearate, and silicon dioxide.
44. The dosage form of any one of 1-41, wherein the barrier layer comprises a methacrylic acid copolymer and a polyvinyl alcohol.
45. The dosage form of 44, wherein the methacrylic acid copolymer and the polyvinyl alcohol are present in the barrier layer in a ratio of about 2:1 to about 10:1.
46. The dosage form of 45, wherein the methacrylic acid copolymer and the polyvinyl alcohol are present in the barrier layer in a ratio of about 4:1 to about 8:1.
47. The dosage form of 44, wherein the methacrylic acid copolymer is present at about 60% to about 90% w/w relative to the total weight of the barrier layer.
48. The dosage form of 44 or 47, wherein the polyvinyl alcohol is present at about 10% to about 40% w/w relative to the total weight of the barrier layer.
49. The dosage form of any one of 1-48, wherein the barrier layer has a finished product coating weight of from about 5 mg to about 40 mg.
50. The dosage form of any one of 1-49, wherein the drug layer comprises about 15% to about 40% w/w of the second pharmacologically active agent relative to the total weight of the drug layer.
51. The dosage form of any one of 1-50, wherein the drug layer comprises a bulking agent.
52. The dosage form of 51, wherein the bulking agent comprises hydroxypropyl methylcellulose (HPMC).
53. The dosage form of 51 or 52, wherein the bulking agent is present at about 60% to about 75% w/w relative to the total weight of the drug layer.

54. The dosage form of any one of 1-53, wherein the drug layer has a finished product coating weight of from about 20 mg to about 35 mg.
55. The dosage form of any one of 1-54, wherein the dosage form comprises a coating layer covering at least a portion of the drug layer.
56. The dosage form of 55, wherein the coating layer comprises a polyvinyl alcohol.
57. The dosage form of 55 or 56, wherein the coating layer has a finished product coating weight of from about 5 mg to about 10 mg.
58. The dosage form of any one of 55-57, wherein the combined thickness of the barrier layer, the drug layer and the coating layer is from about 0.2 mm to about 0.5 mm.
59. The dosage form of any one of 1-58, wherein the amount of the second pharmacologically active agent present in the drug layer is from about 15% to about 30% of the total amount of the first and second pharmacologically active agent in the dosage form.
60. The dosage form of any one of 1-59, wherein the amount of the second pharmacologically active agent present in the drug layer is from about 20% to about 25% of the total amount of the first and second pharmacologically active agent in the dosage form.
61. The dosage form of any one of 1-60, wherein the first and second pharmacologically active agent is methylphenidate.
62. The dosage form of any one of 1-61, wherein the combined % cumulative release of the first and second pharmacologically active agent from the oral dosage form is from 5% to 40% at T=1 hr when assayed by USP Apparatus II using 750 mL of 0.1 N HCl dissolution medium, a paddle speed of 50 rpm, and a dissolution medium temperature of 37° C.
63. The dosage form of any one of 1-62, wherein the combined % cumulative release of the first and second pharmacologically active agent from the oral dosage form is from 10% to 30% at T=1 hr when assayed by USP Apparatus II using 750 mL of 0.1 N HCl dissolution medium, a paddle speed of 50 rpm, and a dissolution medium temperature of 37° C.
64. The dosage form of any one of 1-63, wherein the combined % cumulative release of the first and second pharmacologically active agent from the oral dosage form is at least 80% at T=12 hrs when assayed by USP Apparatus II using a 2-stage dissolution protocol, a paddle speed of 50 rpm, a dissolution medium temperature of 37° C., a sampling volume of 1 mL, and sampling time points of 0.3 hrs, 0.5 hrs, 1 hr, 1.5 hrs, 2 hrs, 3 hrs, 6 hrs, 9 hrs, 12 hrs and 24 hrs, and wherein the 2-stage dissolution protocol comprises exposing the oral dosage form to 750 mL of 0.1 N HCl for T=0 to T=2 hrs, adding 200 mL of 0.19 M phosphate buffer to obtain a final dissolution medium volume of 950 mL, and exposing the oral dosage form to the final dissolution medium volume from T=2 hrs to T=24 hrs.
65. The dosage form of any one of 1-64, wherein the dosage form is sufficient to provide an in vivo Tmax of from about 3 hrs to about 6 hrs following oral administration to an adult human subject.
66. The dosage form of any one of 1-65, wherein the dosage form is sufficient to provide an in vivo Tmax of from about 4 hrs to about 5 hrs following oral administration to an adult human subject.
67. The dosage form of any one of 1-66, wherein the dosage form is sufficient to provide an in vivo Cmax of from about 5 ng/mL to about 18 ng/mL following oral administration to an adult human subject.
68. The dosage form of any one of 1-67, wherein the dosage form is sufficient to provide an in vivo Cmax of from about 9 ng/mL to about 13 ng/mL following oral administration to an adult human subject.
69. The dosage form of any one of 1-68, wherein the dosage form is sufficient to provide an in vivo Cmax of from about 10 ng/mL to about 12 ng/mL following oral administration to an adult human subject.
70. A dosage form, comprising:
a drug composition comprising a first pharmacologically active agent;
a first layer covering at least a portion of the drug composition, wherein the first layer comprises a first material which is soluble in 0.1N HCl at 37° C. and a second material selected from cellulose acetate phthalate, HPMC phthalate, HPMC acetate succinate, polyvinyl acetate phthalate, cellulose acetate trimelitate, methyacrylic acid copolymer, shellac, and zein; and
a second layer covering at least a portion of the first layer, wherein the second layer comprises a second pharmacologically active agent.
71. The dosage form of 70, wherein the first pharmacologically active agent and the second pharmacologically active agent are the same.
72. The dosage form of any one of 70-71, wherein the first pharmacologically active agent is present in the drug composition at from about 10% to about 50% w/w relative to the total weight of the drug composition.
73. The dosage form of any one of 70-72, wherein the drug composition is encapsulated in a capsule and the first layer covers at least a portion of the capsule.
74. The dosage form of 73, wherein the capsule comprises an outer surface and an inner surface, and wherein the barrier layer covers at least a portion of the outer surface of the capsule.
75. The dosage form of 73, wherein the capsule comprises at least one of hydroxypropyl methylcellulose (HPMC) and gelatin.
76. The dosage form of any one of 70-75, wherein the drug composition comprises a High Viscosity Liquid Carrier Material (HVLCM).
77. The dosage form of 76, wherein the HVLCM is present at about 30% to about 60% w/w relative to the total weight of the drug composition.
78. The dosage form of 77, wherein the HVLCM is present at about 35% to about 45% w/w relative to the total weight of the drug composition.
79. The dosage form of any one of 76-78, wherein the HVLCM is sucrose acetate isobutyrate (SAB).
80. The dosage form of any one of 70-79, wherein the drug composition comprises an organic solvent.
81. The dosage form of 80, wherein the organic solvent is present at about 0.1% to about 45% w/w relative to the total weight of the drug composition.
82. The dosage form of 80 or 81, wherein the organic solvent is present at about 10% to about 35% w/w relative to the total weight of the drug composition.
83. The dosage form of any one of 80-82, wherein the organic solvent is present at about 20% to about 35% w/w relative to the total weight of the drug composition.
84. The dosage form of any one of 80-83, wherein the organic solvent comprises at least one member selected from triacetin, N-methyl-2-pyrrolidone, 2-pyrrolidone, dimethylsulfoxide, ethyl lactate, propylene carbonate, and glycofurol.
85. The dosage form of any one of 80-84, wherein the organic solvent comprises triacetin.
86. The dosage form of any one of 70-85, wherein the drug composition comprises a rheology modifier.
87. The dosage form of 86, wherein the rheology modifier is present at about 0.1% to about 20% w/w relative to the total weight of the drug composition.
88. The dosage form of 86 or 87, wherein the rheology modifier is present at about 2% to about 15% w/w relative to the total weight of the drug composition.
89. The dosage form of any one of 86-88, wherein the rheology modifier is present at about 5% to about 7% w/w relative to the total weight of the drug composition.
90. The dosage form of any one of 86-89, wherein the rheology modifier comprises at least one member selected from a caprylic/capric triglyceride, isopropyl myristate, ethyl oleate, triethyl citrate, dimethyl phthalate, labrafil, labrasol, a polyglycolized glyceride, and benzyl benzoate.
91. The dosage form of any one of 86-90, wherein the rheology modifier comprises isopropyl myristate.
92. The dosage form of any one of 70-91, wherein the drug composition comprises a network former.
93. The dosage form of 92, wherein the network former is present at about 0.1% to about 20% w/w relative to the total weight of the drug composition.
94. The dosage form of 92 or 93, wherein the network former is present at about 2% to about 10% w/w relative to the total weight of the drug composition.
95. The dosage form of any one of 92-94, wherein the network former is present at about 4% to about 6% w/w relative to the total weight of the drug composition.
96. The dosage form of any one of 92-95, wherein the network former comprises at least one member selected from a cellulose acetate butyrate, a carbohydrate polymer, an organic acid of a carbohydrate polymer, a hydrogel, a cellulose acetate phthalate, an ethyl cellulose, a triblock copolymer, an acrylic polymer, hydroxyl propyl methyl cellulose, cellulose triacetate, and poly(methyl methacrylate).
97. The dosage form of any one of 92-96, wherein the network former comprises a cellulose acetate butyrate.
98. The dosage form of any one of 70-97, wherein the drug composition comprises a viscosity enhancing agent.
99. The dosage form of 98, wherein the viscosity enhancing agent is present at about 0.01% to about 10% w/w relative to the total weight of the drug composition.
100. The dosage form of 98 or 99, wherein the viscosity enhancing agent is present at about 0.1% to about 6% w/w relative to the total weight of the drug composition.
101. The dosage form of any one of 98-100, wherein the viscosity enhancing agent is present at about 0.5% to about 1.5% w/w relative to the total weight of the drug composition.
102. The dosage form of any one of 98-101, wherein the viscosity enhancing agent comprises silicon dioxide.
103. The dosage form of any one of 70-102, wherein the drug composition comprises a polyoxylglyceride.
104. The dosage form of 103, wherein the polyoxylglyceride is present at about 0.1% to about 5% w/w relative to the total weight of the drug composition.
105. The dosage form of 103 or 104, wherein the polyoxylglyceride is present at about 0.5% to about 1.5% w/w relative to the total weight of the drug composition.
106. The dosage form of any one of 70-105, wherein the fill weight of the drug composition is from about 100 mg to about 800 mg.
107. The dosage form of any one of 70-106, wherein the fill weight of the drug composition is from about 150 mg to about 200 mg.
108. The dosage form of any one of 70-107, wherein the first layer comprises at least one member selected from a hydrophobic cellulose, a polyalcohol, magnesium stearate, and silicon dioxide.
109. The dosage form of any one of 70-108, wherein the first layer comprises a methacrylic acid copolymer and a polyvinyl alcohol.
110. The dosage form of 109, wherein the methacrylic acid copolymer is present at about 60% to about 90% w/w relative to the total weight of the first layer.
111. The dosage form of 109 or 110, wherein the polyvinyl alcohol is present at about 10% to about 40% w/w relative to the total weight of the first layer.
112. The dosage form of any one of 70-111, wherein the first layer has a finished product coating weight of from about 10 mg to about 40 mg.
113. The dosage form of any one of 70-112, wherein the second layer comprises about 25% to about 40% w/w of the second pharmacologically active agent relative to the total weight of the second layer.
114. The dosage form of any one of 70-113, wherein second layer comprises a bulking agent.
115. The dosage form of 114, wherein the bulking agent comprises hydroxypropyl methylcellulose (HPMC).
116. The dosage form of 114 or 115, wherein the bulking agent is present at about 60% to about 75% w/w relative to the total weight of the second layer.
117. The dosage form of any one of 70-116, wherein the second layer has a finished product coating weight of from about 20 mg to about 35 mg.
118. The dosage form of any one of 70-117, wherein the dosage form comprises a third layer covering at least a portion of the second layer.
119. The dosage form of 118, wherein the third layer comprises a polyvinyl alcohol.
120. The dosage form of 118 or 119, wherein the third layer has a finished product coating weight of from about 5 mg to about 10 mg.
121. The dosage form of any one of 118-120, wherein the combined thickness of the first layer, the second layer and the third layer is from about 0.2 mm to about 0.5 mm.
122. The dosage form of any one of 70-121, wherein the amount of the second pharmacologically active agent present in the second layer is from about 15% to about 30% of the total amount of the first and second pharmacologically active agent in the dosage form.
123. The dosage form of any one of 70-122, wherein the amount of the second pharmacologically active agent present in the second layer is from about 20% to about 25% of the total amount of the first and second pharmacologically active agent in the dosage form.
124. The dosage form of any one of 70-123, wherein the first and second pharmacologically active agent is methylphenidate.
125. The dosage form of any one of 70-124, wherein the combined % cumulative release of the first and second pharmacologically active agent from the oral dosage form is from 5% to 40% at T=1 hr when assayed by USP Apparatus II using 750 mL of 0.1 N HCl dissolution medium, a paddle speed of 50 rpm, and a dissolution medium temperature of 37° C.

126. The dosage form of any one of 70-125, wherein the combined % cumulative release of the first and second pharmacologically active agent from the oral dosage form is from 10% to 30% at T=1 hr when assayed by USP Apparatus II using 750 mL of 0.1 N HCl dissolution medium, a paddle speed of 50 rpm, and a dissolution medium temperature of 37° C.

127. The dosage form of any one of 70-126, wherein the combined % cumulative release of the first and second pharmacologically active agent from the oral dosage form is at least 80% at T=12 hrs when assayed by USP Apparatus II using a 2-stage dissolution protocol, a paddle speed of 50 rpm, a dissolution medium temperature of 37° C., a sampling volume of 1 mL, and sampling time points of 0.3 hrs, 0.5 hrs, 1 hr, 1.5 hrs, 2 hrs, 3 hrs, 6 hrs, 9 hrs, 12 hrs and 24 hrs, and wherein the 2-stage dissolution protocol comprises exposing the oral dosage form to 750 mL of 0.1 N HCl for T=0 to T=2 hrs, adding 200 mL of 0.19 M phosphate buffer to obtain a final dissolution medium volume of 950 mL, and exposing the oral dosage form to the final dissolution medium volume from T=2 hrs to T=24 hrs.

128. The dosage form of any one of 70-127, wherein the dosage form is sufficient to provide an in vivo Tmax of from about 3 hrs to about 6 hrs following oral administration to an adult human subject.

129. The dosage form of any one of 70-128, wherein the dosage form is sufficient to provide an in vivo Tmax of from about 4 hrs to about 5 hrs following oral administration to an adult human subject.

130. The dosage form of any one of 70-129, wherein the dosage form is sufficient to provide an in vivo Cmax of from about 5 ng/mL to about 18 ng/mL following oral administration to an adult human subject.

131. The dosage form of any one of 70-130, wherein the dosage form is sufficient to provide an in vivo Cmax of from about 9 ng/mL to about 13 ng/mL following oral administration to an adult human subject.

132. The dosage form of any one of 70-131, wherein the dosage form is sufficient to provide an in vivo Cmax of from about 10 ng/mL to about 12 ng/mL following oral administration to an adult human subject.

133. A dosage form, comprising:
    a drug composition comprising a first pharmacologically active agent;
    a first layer covering at least a portion of the drug composition, wherein the first layer comprises at least one member selected from hydrophobic cellulose, a polyalcohol, magnesium stearate, and silicon dioxide; and
    a second layer covering at least a portion of the first layer, wherein the second layer comprises a second pharmacologically active agent.

134. The dosage form of 133, wherein the first pharmacologically active agent and the second pharmacologically active agent are the same.

135. The dosage form of 133 or 134, wherein first pharmacologically active agent is present in the drug composition at from about 10% to about 50% w/w relative to the total weight of the drug composition.

136. The dosage form of any one of 133-135, wherein the drug composition is encapsulated in a capsule and the first layer covers at least a portion of the capsule.

137. The dosage form of 136, wherein the capsule comprises an outer surface and an inner surface, and wherein the barrier layer covers at least a portion of the outer surface of the capsule.

138. The dosage form of 136, wherein the capsule comprises hydroxypropyl methylcellulose (HPMC).

139. The dosage form of any one of 133-138, wherein the drug composition comprises a High Viscosity Liquid Carrier Material (HVLCM).

140. The dosage form of 139, wherein the HVLCM is present at about 30% to about 60% w/w relative to the total weight of the drug composition.

141. The dosage form of 140, wherein the HVLCM is present at about 35% to about 45% w/w relative to the total weight of the drug composition.

142. The dosage form of any one of 139-141, wherein the HVLCM is sucrose acetate isobutyrate (SAIB).

143. The dosage form of any one of 133-142, wherein the drug composition comprises an organic solvent.

144. The dosage form of 143, wherein the organic solvent is present at about 0.1% to about 45% w/w relative to the total weight of the drug composition.

145. The dosage form of 143 or 144, wherein the organic solvent is present at about 10% to about 35% w/w relative to the total weight of the drug composition.

146. The dosage form of any one of 143-145, wherein the organic solvent is present at about 20% to about 35% w/w relative to the total weight of the drug composition.

147. The dosage form of any one of 143-146, wherein the organic solvent comprises at least one member selected from triacetin, N-methyl-2-pyrrolidone, 2-pyrrolidone, dimethylsulfoxide, ethyl lactate, propylene carbonate, and glycofurol.

148. The dosage form of any one of 143-147, wherein the organic solvent comprises triacetin.

149. The dosage form of any one of 133-148, wherein the drug composition comprises a rheology modifier.

150. The dosage form of 149, wherein the rheology modifier is present at about 0.1% to about 20% w/w relative to the total weight of the drug composition.

151. The dosage form of 149 or 150, wherein the rheology modifier is present at about 2% to about 15% w/w relative to the total weight of the drug composition.

152. The dosage form of any one of 149-151, wherein the rheology modifier is present at about 5% to about 7% w/w relative to the total weight of the drug composition.

153. The dosage form of any one of 149-152, wherein the rheology modifier comprises at least one member selected from a caprylic/capric triglyceride, isopropyl myristate, ethyl oleate, triethyl citrate, dimethyl phthalate, labrafil, labrasol, a polyglycolized glyceride, and benzyl benzoate.

154. The dosage form of any one of 149-153, wherein the rheology modifier comprises isopropyl myristate.

155. The dosage form of any one of 149-154, wherein the drug composition comprises a network former.

156. The dosage form of 155, wherein the network former is present at about 0.1% to about 20% w/w relative to the total weight of the drug composition.

157. The dosage form of 155 or 156, wherein the network former is present at about 2% to about 10% w/w relative to the total weight of the drug composition.

158. The dosage form of any one of 155-157, wherein the network former is present at about 4% to about 6% w/w relative to the total weight of the drug composition.
159. The dosage form of any one of 155-158, wherein the network former comprises at least one member selected from a cellulose acetate butyrate, a carbohydrate polymer, an organic acid of a carbohydrate polymer, a hydrogel, a cellulose acetate phthalate, an ethyl cellulose, a triblock copolymer, an acrylic polymer, hydroxyl propyl methyl cellulose, cellulose triacetate, and poly(methyl methacrylate).
160. The dosage form of any one of 155-159, wherein the network former comprises a cellulose acetate butyrate.
161. The dosage form of any one of 133-160, wherein the drug composition comprises a viscosity enhancing agent.
162. The dosage form of 161, wherein the viscosity enhancing agent is present at about 0.01% to about 10% w/w relative to the total weight of the drug composition.
163. The dosage form of 161 or 162, wherein the viscosity enhancing agent is present at about 0.1% to about 6% w/w relative to the total weight of the drug composition.
164. The dosage form of any one of 161-163, wherein the viscosity enhancing agent is present at about 0.5% to about 1.5% w/w relative to the total weight of the drug composition.
165. The dosage form of any one of 161-164, wherein the viscosity enhancing agent comprises silicon dioxide.
166. The dosage form of any one of 133-165, wherein the drug composition comprises a polyoxylglyceride.
167. The dosage form of 166, wherein the polyoxylglyceride is present at about 0.1% to about 5% w/w relative to the total weight of the drug composition.
168. The dosage form of 166 or 167, wherein the polyoxylglyceride is present at about 0.5% to about 1.5% w/w relative to the total weight of the drug composition.
169. The dosage form of any one of 133-168, wherein the fill weight of the drug composition is from about 100 mg to about 800 mg.
170. The dosage form of any one of 133-169, wherein the fill weight of the drug composition is from about 150 mg to about 200 mg.
171. The dosage form of any one of 133-170, wherein the first layer comprises a methacrylic acid copolymer and a polyvinyl alcohol.
172. The dosage form of 171, wherein the methacrylic acid copolymer is present at about 60% to about 90% w/w relative to the total weight of the first layer.
173. The dosage form of 171 or 172, wherein the polyvinyl alcohol is present at about 10% to about 40% w/w relative to the total weight of the first layer.
174. The dosage form of any one of 133-173, wherein the first layer has a finished product coating weight of from about 10 mg to about 40 mg.
175. The dosage form of any one of 133-174, wherein the second layer comprises about 25% to about 40% w/w of the second pharmacologically active agent relative to the total weight of the second layer.
176. The dosage form of any one of 133-175, wherein second layer comprises a bulking agent.
177. The dosage form of 176, wherein the bulking agent comprises hydroxypropyl methylcellulose (HPMC).
178. The dosage form of 176 or 177, wherein the bulking agent is present at about 60% to about 75% w/w relative to the total weight of the second layer.
179. The dosage form of any one of 133-178, wherein the second layer has a finished product coating weight of from about 20 mg to about 35 mg.
180. The dosage form of any one of 133-179, wherein the dosage form comprises a third layer covering at least a portion of the second layer.
181. The dosage form of 180, wherein the third layer comprises a polyvinyl alcohol.
182. The dosage form of 180 or 181, wherein the third layer has a finished product coating weight of from about 5 mg to about 10 mg.
183. The dosage form of any one of 180-182, wherein the combined thickness of the first layer, the second layer and the third layer is from about 0.2 mm to about 0.5 mm.
184. The dosage form of any one of 133-183, wherein the amount of the second pharmacologically active agent present in the second layer is from about 15% to about 30% of the total amount of the first and second pharmacologically active agent in the dosage form.
185. The dosage form of any one of 133-184, wherein the amount of the second pharmacologically active agent present in the second layer is from about 20% to about 25% of the total amount of the first and second pharmacologically active agent in the dosage form.
186. The dosage form of any one of 133-185, wherein the first and second pharmacologically active agent is methylphenidate.
187. The dosage form of any one of 133-186, wherein the combined % cumulative release of the first and second pharmacologically active agent from the dosage form is from 5% to 40% at T=1 hr when assayed by USP Apparatus II using 750 mL of 0.1 N HCl dissolution medium, a paddle speed of 50 rpm, and a dissolution medium temperature of 37° C.
188. The dosage form of any one of 133-187, wherein the combined % cumulative release of the first and second pharmacologically active agent from the dosage form is from 10% to 30% at T=1 hr when assayed by USP Apparatus II using 750 mL of 0.1 N HCl dissolution medium, a paddle speed of 50 rpm, and a dissolution medium temperature of 37° C.
189. The dosage form of any one of 133-188, wherein the combined % cumulative release of the first and second pharmacologically active agent from the dosage form is at least 80% at T=12 hrs when assayed by USP Apparatus II using a 2-stage dissolution protocol, a paddle speed of 50 rpm, a dissolution medium temperature of 37° C., a sampling volume of 1 mL, and sampling time points of 0.3 hrs, 0.5 hrs, 1 hr, 1.5 hrs, 2 hrs, 3 hrs, 6 hrs, 9 hrs, 12 hrs and 24 hrs, and wherein the 2-stage dissolution protocol comprises exposing the dosage form to 750 mL of 0.1 N HCl for T=0 to T=2 hrs, adding 200 mL of 0.19 M phosphate buffer to obtain a final dissolution medium volume of 950 mL, and exposing the dosage form to the final dissolution medium volume from T=2 hrs to T=24 hrs.
190. The dosage form of any one of 133-189, wherein the dosage form is sufficient to provide an in vivo Tmax of from about 3 hrs to about 6 hrs following oral administration to an adult human subject.
191. The dosage form of any one of 133-190, wherein the dosage form is sufficient to provide an in vivo Tmax of from about 4 hrs to about 5 hrs following oral administration to an adult human subject.

192. The dosage form of any one of 133-191, wherein the dosage form is sufficient to provide an in vivo Cmax of from about 5 ng/mL to about 18 ng/mL following oral administration to an adult human subject.

193. The dosage form of any one of 133-192, wherein the dosage form is sufficient to provide an in vivo Cmax of from about 9 ng/mL to about 13 ng/mL following oral administration to an adult human subject.

194. The dosage form of any one of 133-193, wherein the dosage form is sufficient to provide an in vivo Cmax of from about 10 ng/mL to about 12 ng/mL following oral administration to an adult human subject.

195. A dosage form, comprising:
- a drug composition comprising a first pharmacologically active agent;
- a first layer covering at least a portion of the drug composition, wherein the first layer comprises a methacrylic acid copolymer and a polyvinyl alcohol; and
- a second layer covering at least a portion of the first layer, wherein the second layer comprises a second pharmacologically active agent.

196. The dosage form of 195, wherein initial release of the first pharmacologically active agent from the dosage form occurs at a time of 5 minutes to 120 minutes when assayed by USP Apparatus II using 750 mL of 0.1 N HCl dissolution medium, a paddle speed of 50 rpm, and a dissolution medium temperature of 37° C.

197. The dosage form of 196, wherein the first pharmacologically active agent and the second pharmacologically active agents are the same, and wherein the initial release of the first pharmacologically active agent is determined by determining the time at which cumulative release of the first and second pharmacologically active agents exceeds the amount of the second pharmacologically active agent in the drug layer.

198. The dosage form of 195 or 196, wherein the first pharmacologically active agent and the second pharmacologically active agent are the same.

199. The dosage form of any one of 195-198, wherein the first pharmacologically active agent is present in the drug composition at from about 10% to about 50% w/w relative to the total weight of the drug composition.

200. The dosage form of any one of 195-199, wherein the drug composition is encapsulated in a capsule and the first layer covers at least a portion of the capsule.

201. The dosage form of 200, wherein the capsule comprises an outer surface and an inner surface, and wherein the barrier layer covers at least a portion of the outer surface of the capsule.

202. The dosage form of 200, wherein the capsule comprises hydroxypropyl methylcellulose (HPMC).

203. The dosage form of any one of 195-202, wherein the drug composition comprises a High Viscosity Liquid Carrier Material (HVLCM).

204. The dosage form of 203, wherein the HVLCM is present at about 30% to about 60% w/w relative to the total weight of the drug composition.

205. The dosage form of 204, wherein the HVLCM is present at about 35% to about 45% w/w relative to the total weight of the drug composition.

206. The dosage form of any one of 203-205, wherein the HVLCM is sucrose acetate isobutyrate (SAIB).

207. The dosage form of any one of 195-206, wherein the drug composition comprises an organic solvent.

208. The dosage form of 207, wherein the organic solvent is present at about 0.1% to about 45% w/w relative to the total weight of the drug composition.

209. The dosage form of 207 or 208, wherein the organic solvent is present at about 10% to about 35% w/w relative to the total weight of the drug composition.

210. The dosage form of any one of 207-209, wherein the organic solvent is present at about 20% to about 35% w/w relative to the total weight of the drug composition.

211. The dosage form of any one of 207-210, wherein the organic solvent comprises at least one member selected from triacetin, N-methyl-2-pyrrolidone, 2-pyrrolidone, dimethylsulfoxide, ethyl lactate, propylene carbonate, and glycofurol.

212. The dosage form of any one of 207-211, wherein the organic solvent comprises triacetin.

213. The dosage form of any one of 195-212, wherein the drug composition comprises a rheology modifier.

214. The dosage form of 213, wherein the rheology modifier is present at about 0.1% to about 20% w/w relative to the total weight of the drug composition.

215. The dosage form of 213 or 214, wherein the rheology modifier is present at about 2% to about 15% w/w relative to the total weight of the drug composition.

216. The dosage form of any one of 213-215, wherein the rheology modifier is present at about 5% to about 7% w/w relative to the total weight of the drug composition.

217. The dosage form of any one of 213-216, wherein the rheology modifier comprises at least one member selected from a caprylic/capric triglyceride, isopropyl myristate, ethyl oleate, triethyl citrate, dimethyl phthalate, labrafil, labrasol, a polyglycolized glyceride, and benzyl benzoate.

218. The dosage form of any one of 213-217, wherein the rheology modifier comprises isopropyl myristate.

219. The dosage form of any one of 195-218, wherein the drug composition comprises a network former.

220. The dosage form of 219, wherein the network former is present at about 0.1% to about 20% w/w relative to the total weight of the drug composition.

221. The dosage form of 219 or 220, wherein the network former is present at about 2% to about 10% w/w relative to the total weight of the drug composition.

222. The dosage form of any one of 219-221, wherein the network former is present at about 4% to about 6% w/w relative to the total weight of the drug composition.

223. The dosage form of any one of 219-222, wherein the network former comprises at least one member selected from a cellulose acetate butyrate, a carbohydrate polymer, an organic acid of a carbohydrate polymer, a hydrogel, a cellulose acetate phthalate, an ethyl cellulose, a triblock copolymer, an acrylic polymer, hydroxyl propyl methyl cellulose, cellulose triacetate, and poly(methyl methacrylate).

224. The dosage form of any one of 219-223, wherein the network former comprises a cellulose acetate butyrate.

225. The dosage form of any one of 195-224, wherein the drug composition comprises a viscosity enhancing agent.

226. The dosage form of 225, wherein the viscosity enhancing agent is present at about 0.01% to about 10% w/w relative to the total weight of the drug composition.

227. The dosage form of 225 or 226, wherein the viscosity enhancing agent is present at about 0.1% to about 6% w/w relative to the total weight of the drug composition.
228. The dosage form of any one of 225-227, wherein the viscosity enhancing agent is present at about 0.5% to about 1.5% w/w relative to the total weight of the drug composition.
229. The dosage form of any one of 225-228, wherein the viscosity enhancing agent comprises silicon dioxide.
230. The dosage form of any one of 195-229, wherein the drug composition comprises a polyoxylglyceride.
231. The dosage form of 230, wherein the polyoxylglyceride is present at about 0.1% to about 5% w/w relative to the total weight of the drug composition.
232. The dosage form of 230 or 231, wherein the polyoxylglyceride is present at about 0.5% to about 1.5% w/w relative to the total weight of the drug composition.
233. The dosage form of any one of 195-232, wherein the fill weight of the drug composition is from about 100 mg to about 800 mg.
234. The dosage form of any one of 195-233, wherein the fill weight of the drug composition is from about 150 mg to about 200 mg.
235. The dosage form of any one of 195-234, wherein the methacrylic acid copolymer is present at about 60% to about 90% w/w relative to the total weight of the first layer.
236. The dosage form of any one of 195-235, wherein the polyvinyl alcohol is present at about 10% to about 40% w/w relative to the total weight of the first layer.
237. The dosage form of any one of 195-236, wherein the first layer has a finished product coating weight of from about 10 mg to about 40 mg.
238. The dosage form of any one of 195-237, wherein the second layer comprises about 25% to about 35% w/w of the second pharmacologically active agent relative to the total weight of the second layer.
239. The dosage form of any one of 195-238, wherein second layer comprises a bulking agent.
240. The dosage form of 239, wherein the bulking agent comprises hydroxypropyl methylcellulose (HPMC).
241. The dosage form of 239 or 240, wherein the bulking agent is present at about 60% to about 75% w/w relative to the total weight of the second layer.
242. The dosage form of any one of 195-241, wherein the second layer has a finished product coating weight of from about 20 mg to about 35 mg.
243. The dosage form of any one of 195-242, wherein the dosage form comprises a third layer covering at least a portion of the second layer.
244. The dosage form of 243, wherein the third layer comprises a polyvinyl alcohol.
245. The dosage form of 243 or 244, wherein the third layer has a finished product coating weight of from about 5 mg to about 10 mg.
246. The dosage form of any one of 243-245, wherein the combined thickness of the first layer, the second layer and the third layer is from about 0.2 mm to about 0.5 mm.
247. The dosage form of any one of 195-246, wherein the amount of the second pharmacologically active agent present in the second layer is from about 15% to about 30% of the total amount of the first and second pharmacologically active agent in the dosage form.
248. The dosage form of any one of 195-247, wherein the amount of the second pharmacologically active agent present in the second layer is from about 20% to about 25% of the total amount of the first and second pharmacologically active agent in the dosage form.
249. The dosage form of any one of 195-248, wherein the first and second pharmacologically active agent is methylphenidate.
250. The dosage form of any one of 195-249, wherein the combined % cumulative release of the first and second pharmacologically active agent from the dosage form is from 5% to 40% at T=1 hr when assayed by USP Apparatus II using 750 mL of 0.1 N HCl dissolution medium, a paddle speed of 50 rpm, and a dissolution medium temperature of 37° C.
251. The dosage form of any one of 195-250, wherein the combined % cumulative release of the first and second pharmacologically active agent from the dosage form is from 10% to 30% at T=1 hr when assayed by USP Apparatus II using 750 mL of 0.1 N HCl dissolution medium, a paddle speed of 50 rpm, and a dissolution medium temperature of 37° C.
252. The dosage form of any one of 195-251, wherein the combined % cumulative release of the first and second pharmacologically active agent from the dosage form is at least 80% at T=12 hr when assayed by USP Apparatus II using a 2-stage dissolution protocol, a paddle speed of 50 rpm, a dissolution medium temperature of 37° C., a sampling volume of 1 mL, and sampling time points of 0.3 hrs, 0.5 hrs, 1 hr, 1.5 hrs, 2 hrs, 3 hrs, 6 hrs, 9 hrs, 12 hrs and 24 hrs, and wherein the 2-stage dissolution protocol comprises exposing the dosage form to 750 mL of 0.1 N HCl for T=0 to T=2 hrs, adding 200 mL of 0.19 M phosphate buffer to obtain a final dissolution medium volume of 950 mL, and exposing the dosage form to the final dissolution medium volume from T=2 hrs to T=24 hrs.
253. The dosage form of any one of 195-252, wherein the dosage form is sufficient to provide an in vivo Tmax of from about 3 hrs to about 6 hrs following oral administration to an adult human subject.
254. The dosage form of any one of 195-253, wherein the dosage form is sufficient to provide an in vivo Tmax of from about 4 hrs to about 5 hrs following oral administration to an adult human subject.
255. The dosage form of any one of 195-254, wherein the dosage form is sufficient to provide an in vivo Cmax of from about 5 ng/mL to about 18 ng/mL following oral administration to an adult human subject.
256. The dosage form of any one of 195-255, wherein the dosage form is sufficient to provide an in vivo Cmax of from about 9 ng/mL to about 13 ng/mL following oral administration to an adult human subject.
257. The dosage form of any one of 195-256, wherein the dosage form is sufficient to provide an in vivo Cmax of from about 10 ng/mL to about 12 ng/mL following oral administration to an adult human subject.
258. A dosage form, comprising:
a capsule comprising
an extended release (ER) composition encapsulated therein, the ER composition comprising methylphenidate (MPH) at about 15% to about 25% w/w relative to the total weight of the ER composition, a High Viscosity Liquid Carrier Material (HVLCM) at about 35% to about 45% w/w relative to the total weight of the ER composition, an organic solvent at about 20% to about 35% w/w relative to the total weight of the ER composition, a first layer covering at least a portion of the capsule, the first layer comprising a methacrylic acid copolymer at about 60% to about 90% w/w relative to the total weight of the first layer, and a polyvinyl alcohol at about 40% to about 10% w/w relative to the total weight of the first layer;

a second layer covering at least a portion of the first layer, the second layer comprising MPH at about 25% to about 40% w/w relative to the total weight of the second layer, and a bulking agent at about 75% to about 60% w/w relative to the total weight of the second layer.

259. The dosage form of 258, wherein the capsule comprises hydroxypropyl methylcellulose (HPMC).

260. The dosage form of 258 or 259, wherein the HVLCM is sucrose acetate isobutyrate (SAB).

261. The dosage form of any one of 258-260, wherein the organic solvent comprises triacetin.

262. The dosage form of any one of 258-261, wherein the ER composition comprises a rheology modifier.

263. The dosage form of 262, wherein the rheology modifier is present at about 5% to about 7% w/w relative to the total weight of the ER composition.

264. The dosage form of 262 or 263, wherein the rheology modifier comprises isopropyl myristate (IPM).

265. The dosage form of any one of 258-264, wherein the ER composition comprises a network former.

266. The dosage form of 265, wherein the network former is present at about 4% to about 6% w/w relative to the total weight of the ER composition.

267. The dosage form of 265 or 266, wherein the network former comprises cellulose acetate butyrate (CAB).

268. The dosage form of any one of 258-267, wherein the ER composition comprises a viscosity enhancing agent.

269. The dosage form of 268, wherein the viscosity enhancing agent is present at about 0.5% to about 1.5% w/w relative to the total weight of the ER composition.

270. The dosage form of 268 or 269, wherein the viscosity enhancing agent comprises silicon dioxide.

271. The dosage form of any one of 258-270, wherein the ER composition comprises a polyoxylglyceride.

272. The dosage form of 271, wherein the polyoxylglyceride is present at about 0.5% to about 1.5% w/w relative to the total weight of the ER composition.

273. The dosage form of any one of 258-272, wherein the ER composition comprises an antioxidant.

274. The dosage form of 273, wherein the antioxidant is butylated hydroxytoluene (BHT).

275. The dosage form of 274, wherein the BHT is present in the ER composition at about 0.01% to 0.05% w/w relative to the total weight of the ER composition.

276. The dosage form of any one of 258-275, wherein the fill weight of the ER composition is from about 150 mg to about 200 mg.

277. The dosage form of any one of 258-276, wherein the first layer has a finished product coating weight of from about 10 mg to about 40 mg.

278. The dosage form of any one of 258-277, wherein the bulking agent comprises hydroxypropyl methylcellulose (HPMC).

279. The dosage form of any one of 258-278, wherein the second layer has a finished product coating weight of from about 20 mg to about 35 mg.

280. The dosage form of any one of 258-279, wherein the dosage form comprises a third layer covering at least a portion of the second layer.

281. The dosage form of 280, wherein the third layer comprises a polyvinyl alcohol.

282. The dosage form of 280 or 281, wherein the third layer has a finished product coating weight of from about 5 mg to about 10 mg.

283. The dosage form of any one of 280-282, wherein the combined thickness of the first layer, the second layer and the third layer is from about 0.2 mm to about 0.5 mm.

284. The dosage form of any one of 258-283, wherein the amount of MPH present in the second layer is from about 15% to about 30% of the total amount of the MPH in the dosage form.

285. The dosage form of any one of 258-284, wherein the amount of MPH present in the second layer is from about 20% to about 25% of the total amount of the MPH in the dosage form.

286. The dosage form of any one of 258-285, wherein the % cumulative release of the MPH from the dosage form is from 5% to 40% at T=1 hr when assayed by USP Apparatus II using 750 mL of 0.1 N HCl dissolution medium, a paddle speed of 50 rpm, and a dissolution medium temperature of 37° C.

287. The dosage form of any one of 258-286, wherein the % cumulative release of the MPH from the dosage form is from 10% to 30% at T=1 hr when assayed by USP Apparatus II using 750 mL of 0.1 N HCl dissolution medium, a paddle speed of 50 rpm, and a dissolution medium temperature of 37° C.

288. The dosage form of any one of 258-287, wherein the % cumulative release of the MPH from the dosage form is at least 80% at T=12 hrs when assayed by USP Apparatus II using a 2-stage dissolution protocol, a paddle speed of 50 rpm, a dissolution medium temperature of 37° C., a sampling volume of 1 mL, and sampling time points of 0.3 hrs, 0.5 hrs, 1 hr, 1.5 hrs, 2 hrs, 3 hrs, 6 hrs, 9 hrs, 12 hrs and 24 hrs, and wherein the 2-stage dissolution protocol comprises exposing the dosage form to 750 mL of 0.1 N HCl for T=0 to T=2 hrs, adding 200 mL of 0.19 M phosphate buffer to obtain a final dissolution medium volume of 950 mL, and exposing the dosage form to the final dissolution medium volume from T=2 hrs to T=24 hrs.

289. The dosage form of any one of 258-288, wherein the dosage form is sufficient to provide an in vivo Tmax of from about 3 hrs to about 6 hrs following oral administration to an adult human subject.

290. The dosage form of any one of 258-289, wherein the dosage form is sufficient to provide an in vivo Tmax of from about 4 hrs to about 5 hrs following oral administration to an adult human subject.

291. The dosage form of any one of 258-290, wherein the dosage form is sufficient to provide an in vivo Cmax of from about 5 ng/mL to about 18 ng/mL following oral administration to an adult human subject.

292. The dosage form of any one of 258-291, wherein the dosage form is sufficient to provide an in vivo Cmax of from about 9 ng/mL to about 13 ng/mL following oral administration to an adult human subject.
293. The dosage form of any one of 258-292, wherein the dosage form is sufficient to provide an in vivo Cmax of from about 10 ng/mL to about 12 ng/mL following oral administration to an adult human subject.
294. An oral dosage form, comprising:
a capsule comprising
an extended release (ER) composition encapsulated therein, the ER composition comprising
methylphenidate (MPH) at about 15% to about 25% w/w relative to the total weight of the ER composition,
sucrose acetate isobutyrate (SAB) at about 25% to about 40% w/w relative to the total weight of the ER composition,
triacetin at about 25% to about 35% w/w relative to the total weight of the ER composition,
isopropyl myristate (IPM) at about 5% to about 10% w/w relative to the total weight of the ER composition,
cellulose acetate butyrate (CAB) at about 2% to about 7% w/w relative to the total weight of the ER composition,
silicon dioxide at about 0.5% to about 1% w/w relative to the total weight of the ER composition, and
a polyoxylglyceride at about 0.5% to 2.5% w/w relative to the total weight of the ER composition; and
a first layer covering the capsule, the first layer comprising
a methacrylic acid copolymer at about 65% to about 75% w/w relative to the total weight of the first layer, and
a polyvinyl alcohol-based moisture barrier material at about 25% to about 35% w/w relative to the total weight of the first layer;
a second layer covering the first layer, the second layer comprising
MPH at about 30% to about 40% w/w relative to the total weight of the second layer, and
hydroxypropyl methylcellulose (HPMC) at about 70% to about 60% w/w relative to the total weight of the second layer; and
a third layer covering the second layer.
295. The dosage form of 294, wherein the capsule comprises hydroxypropyl methylcellulose (HPMC).
296. The dosage form of 294 or 295, wherein the ER composition comprises an antioxidant.
297. The dosage form of 296, wherein the antioxidant is butylated hydroxytoluene (BHT).
298. The dosage form of 297, wherein the BHT is present in the ER composition at about 0.02% w/w relative to the total weight of the ER composition.
299. The dosage form of any one of 294-298, wherein the fill weight of the ER composition is from about 150 mg to about 200 mg.
300. The dosage form of any one of 294-299, wherein the first layer has a finished product coating weight of from about 10 mg to about 40 mg.
301. The dosage form of any one of 294-300, wherein the second layer has a finished product coating weight of from about 20 mg to about 35 mg.
302. The dosage form of any one of 294-301, wherein the third layer comprises a polyvinyl alcohol.
303. The dosage form of any one of 294-302, wherein the third layer has a finished product coating weight of from about 5 mg to about 10 mg.
304. The dosage form of any one of 294-303, wherein the combined thickness of the first layer, the second layer and the third layer is from about 0.2 mm to about 0.5 mm.
305. The dosage form of any one of 294-304, wherein the amount of MPH present in the second layer is from about 15% to about 30% of the total amount of the MPH in the dosage form.
306. The dosage form of any one of 294-305, wherein the amount of MPH present in the second layer is from about 20% to about 25% of the total amount of the MPH in the dosage form.
307. The dosage form of any one of 294-306, wherein the % cumulative release of the MPH from the dosage form is from 5% to 40% at T=1 hr when assayed by USP Apparatus II using 750 mL of 0.1 N HCl dissolution medium, a paddle speed of 50 rpm, and a dissolution medium temperature of 37° C.
308. The dosage form of any one of 294-307, wherein the % cumulative release of the MPH from the dosage form is from 10% to 30% at T=1 hr when assayed by USP Apparatus II using 750 mL of 0.1 N HCl dissolution medium, a paddle speed of 50 rpm, and a dissolution medium temperature of 37° C.
309. The dosage form of any one of 294-308, wherein the % cumulative release of the MPH from the dosage form is at least 80% at T=12 hrs when assayed by USP Apparatus II using a 2-stage dissolution protocol, a paddle speed of 50 rpm, a dissolution medium temperature of 37° C., a sampling volume of 1 mL, and sampling time points of 0.3 hrs, 0.5 hrs, 1 hr, 1.5 hrs, 2 hrs, 3 hrs, 6 hrs, 9 hrs, 12 hrs and 24 hrs, and wherein the 2-stage dissolution protocol comprises exposing the dosage form to 750 mL of 0.1 N HCl for T=0 to T=2 hrs, adding 200 mL of 0.19 M phosphate buffer to obtain a final dissolution medium volume of 950 mL, and exposing the dosage form to the final dissolution medium volume from T=2 hrs to T=24 hrs.
310. The dosage form of any one of 294-309, wherein the dosage form is sufficient to provide an in vivo Tmax of from about 3 hrs to about 6 hrs following oral administration to an adult human subject.
311. The dosage form of any one of 294-310, wherein the dosage form is sufficient to provide an in vivo Tmax of from about 4 hrs to about 5 hrs following oral administration to an adult human subject.
312. The dosage form of any one of 294-311, wherein the dosage form is sufficient to provide an in vivo Cmax of from about 5 ng/mL to about 18 ng/mL following oral administration to an adult human subject.
313. The dosage form of any one of 294-312, wherein the dosage form is sufficient to provide an in vivo Cmax of from about 9 ng/mL to about 13 ng/mL following oral administration to an adult human subject.
314. The dosage form of any one of 294-313, wherein the dosage form is sufficient to provide an in vivo Cmax of from about 10 ng/mL to about 12 ng/mL following oral administration to an adult human subject.

315. A dosage form, comprising:
   a capsule comprising
      an extended release (ER) composition encapsulated therein, the ER composition comprising
         methylphenidate (MPH),
         sucrose acetate isobutyrate (SAB),
         an organic solvent,
         isopropyl myristate (IPM),
         cellulose acetate butyrate (CAB),
         $SiO_2$, and
         a polyoxylglyceride;
   a barrier layer covering at least a portion of the capsule;
   a drug layer covering at least a portion of the barrier layer, wherein the drug layer comprises MPH; and
   a coating layer covering at least a portion of the drug layer,
   wherein the dosage form is sufficient to provide an in vivo Cmax of MPH of from about 5 ng/mL to about 18 ng/ml and an in vivo Tmax of from about 3 to 6 hours following oral administration to an adult human subject.

316. The dosage form of 315, wherein the methylphenidate is present in the ER composition at from about 10% to about 50% w/w relative to the total weight of the ER composition.

317. The dosage form of 315 or 316, wherein the capsule comprises at least one of hydroxypropyl methylcellulose (HPMC) and gelatin.

318. The dosage form of any one of 315-317, wherein the organic solvent comprises triacetin.

319. The dosage form of any one of 315-318, wherein the ER composition comprises an antioxidant.

320. The dosage form of 319, wherein the antioxidant is butylated hydroxytoluene (BHT).

321. The dosage form of 320, wherein the BHT is present in the ER composition at about 0.02% w/w relative to the total weight of the ER composition.

322. The dosage form of any one of 315-321, wherein the fill weight of the ER composition is from about 150 mg to about 200 mg.

323. The dosage form of any one of 315-322, wherein the barrier layer comprises a methacrylic acid copolymer at about 60% to about 90% w/w relative to the total weight of the barrier layer, and a polyvinyl alcohol at about 40% to about 10% w/w relative to the total weight of the barrier layer.

324. The dosage form of any one of 315-323, wherein the barrier layer has a finished product coating weight of from about 10 mg to about 40 mg.

325. The dosage form of any one of 315-324, wherein the drug layer comprises hydroxypropyl methylcellulose (HPMC).

326. The dosage form of 325, wherein the HPMC is present in the drug layer at about 60% to about 75% w/w relative to the total weight of the drug layer.

327. The dosage form of any one of 315-326, wherein the drug layer has a finished product coating weight of from about 20 mg to about 35 mg.

328. The dosage form of any one of 315-327, wherein the coating layer comprises a polyvinyl alcohol.

329. The dosage form of any one of 315-328, wherein the coating layer has a finished product coating weight of from about 5 mg to about 10 mg.

330. The dosage form of any one of 315-329, wherein the combined thickness of the barrier layer, the drug layer and the coating layer is from about 0.2 mm to about 0.5 mm.

331. The dosage form of any one of 315-330, wherein the amount of MPH present in the drug layer is from about 15% to about 30% of the total amount of the MPH in the dosage form.

332. The dosage form of any one of 315-331, wherein the amount of MPH present in the drug layer is from about 20% to about 25% of the total amount of the MPH in the dosage form.

333. The dosage form of any one of 315-332, wherein the % cumulative release of the MPH from the dosage form is from 5% to 40% at T=1 hr when assayed by USP Apparatus II using 750 mL of 0.1 N HCl dissolution medium, a paddle speed of 50 rpm, and a dissolution medium temperature of 37° C.

334. The dosage form of any one of 315-333, wherein the % cumulative release of the MPH from the dosage form is from 10% to 30% at T=1 hr when assayed by USP Apparatus II using 750 mL of 0.1 N HCl dissolution medium, a paddle speed of 50 rpm, and a dissolution medium temperature of 37° C.

335. The dosage form of any one of 315-334, wherein the % cumulative release of the MPH from the dosage form is at least 80% at T=12 hrs when assayed by USP Apparatus II using a 2-stage dissolution protocol, a paddle speed of 50 rpm, a dissolution medium temperature of 37° C., a sampling volume of 1 mL, and sampling time points of 0.3 hrs, 0.5 hrs, 1 hr, 1.5 hrs, 2 hrs, 3 hrs, 6 hrs, 9 hrs, 12 hrs and 24 hrs, and wherein the 2-stage dissolution protocol comprises exposing the dosage form to 750 mL of 0.1 N HCl for T=0 to T=2 hrs, adding 200 mL of 0.19 M phosphate buffer to obtain a final dissolution medium volume of 950 mL, and exposing the dosage form to the final dissolution medium volume from T=2 hrs to T=24 hrs.

336. The dosage form of any one of 315-335, wherein the dosage form is sufficient to provide an in vivo Tmax of from about 4 hrs to about 5 hrs following oral administration to the subject.

337. The dosage form of any one of 315-336, wherein the dosage form is sufficient to provide an in vivo Cmax of from about 9 ng/mL to about 13 ng/mL following oral administration to the subject.

338. The dosage form of any one of 315-337, wherein the dosage form is sufficient to provide an in vivo Cmax of from about 10 ng/mL to about 12 ng/mL following oral administration to the subject.

339. A method of treating Attention Deficit Disorder (ADD) or Attention Deficit Hyperactivity Disorder (ADHD) in a subject, the method comprising administering the dosage form of any one of 1-338 orally to the subject on a once daily (QD) basis.

340. The method of 339, wherein the dosage form provides an in vivo Tmax of from about 3 hrs to about 6 hrs following the oral administration to the subject.

341. The method of 339 or 340, wherein the dosage form provides an in vivo Tmax of from about 4 hrs to about 5 hrs following the oral administration to the subject.

342. The method of any one of 339-341, wherein the dosage form provides an in vivo Cmax of from about 5 ng/mL to about 18 ng/mL following the oral administration to the subject.

343. The method of any one of 339-342, wherein the dosage form provides an in vivo Cmax of from about 9 ng/mL to about 13 ng/mL following the oral administration to a subject.

344. The method of any one of 339-343, wherein the dosage form provides an in vivo Cmax of from about 10 ng/mL to about 12 ng/mL following the oral administration to the subject.

345. A method of making a dosage form, the method comprising:
encapsulating in a capsule a drug composition comprising a first pharmacologically active agent;
covering at least a portion of the capsule with a barrier layer; and
covering at least a portion of the barrier layer with a drug layer, wherein the drug layer comprises a second pharmacologically active agent, and wherein initial release of the first pharmacologically active agent from the dosage form occurs at a time of 5 minutes to 120 minutes when assayed by USP Apparatus II using 750 mL of 0.1 N HCl dissolution medium, a paddle speed of 50 rpm, and a dissolution medium temperature of 37° C.

346. The method of 345, wherein the first pharmacologically active agent and the second pharmacologically active agents are the same, and wherein the initial release of the first pharmacologically active agent is determined by determining the time at which cumulative release of the first and second pharmacologically active agents exceeds the amount of the second pharmacologically active agent in the drug layer.

347. The method of 345, wherein the barrier layer is soluble in 0.1 N HCl at 37° C.

348. The method of 345, wherein the barrier layer comprises a first material which is soluble in 0.1 N HCl at 37° C. and a second material which is insoluble in 0.1 N HCl at 37° C.

349. The method of any one of 345-348, wherein the capsule comprises an outer surface and an inner surface, and wherein the method comprises covering at least a portion of the outer surface of the capsule with the barrier layer.

350. The method of any one of 345-349, wherein the first pharmacologically active agent and the second pharmacologically active agent are the same.

351. The method of any one of 345-350, wherein the first pharmacologically active agent is present in the drug composition at from about 10% to about 50% w/w relative to the total weight of the drug composition.

352. The method of any one of 345-351, wherein the capsule comprises at least one of hydroxypropyl methylcellulose (HPMC) and gelatin.

353. The method of any one of 345-352, wherein the drug composition comprises a High Viscosity Liquid Carrier Material (HVLCM).

354. The method of 353, wherein the HVLCM is present at about 30% to about 60% w/w relative to the total weight of the drug composition.

355. The method of 353 or 354, wherein the HVLCM is present at about 35% to about 45% w/w relative to the total weight of the drug composition.

356. The method of any one of 353-355, wherein the HVLCM is sucrose acetate isobutyrate (SAB).

357. The method of any one of 345-356, wherein the drug composition comprises an organic solvent.

358. The method of 357, wherein the organic solvent is present at about 0.1% to about 45% w/w relative to the total weight of the drug composition.

359. The method of 357 or 358, wherein the organic solvent is present at about 10% to about 35% w/w relative to the total weight of the drug composition.

360. The method of any one of 357-359, wherein the organic solvent is present at about 20% to about 35% w/w relative to the total weight of the drug composition.

361. The method of any one of 357-360, wherein the organic solvent comprises at least one member selected from triacetin, N-methyl-2-pyrrolidone, 2-pyrrolidone, dimethylsulfoxide, ethyl lactate, propylene carbonate, and glycofurol.

362. The method of any one of 357-361, wherein the organic solvent comprises triacetin.

363. The method of any one of 345-362, wherein the drug composition comprises a rheology modifier.

364. The method of 363, wherein the rheology modifier is present at about 0.1% to about 20% w/w relative to the total weight of the drug composition.

365. The method of 363 or 364, wherein the rheology modifier is present at about 2% to about 15% w/w relative to the total weight of the drug composition.

366. The method of any one of 363-365, wherein the rheology modifier is present at about 5% to about 7% w/w relative to the total weight of the drug composition.

367. The method of any one of 165-366, wherein the rheology modifier comprises at least one member selected from a caprylic/capric triglyceride, isopropyl myristate, ethyl oleate, triethyl citrate, dimethyl phthalate, labrafil, labrasol, a polyglycolized glyceride, and benzyl benzoate.

368. The method of any one of 363-367, wherein the rheology modifier comprises isopropyl myristate.

369. The method of any one of 345-368, wherein the drug composition comprises a network former.

370. The method of 369, wherein the network former is present at about 0.1% to about 20% w/w relative to the total weight of the drug composition.

371. The method of 369 or 370, wherein the network former is present at about 2% to about 10% w/w relative to the total weight of the drug composition.

372. The method of any one of 369-371, wherein the network former is present at about 4% to about 6% w/w relative to the total weight of the drug composition.

373. The method of any one of 369-372, wherein the network former comprises at least one member selected from a cellulose acetate butyrate, a carbohydrate polymer, an organic acid of a carbohydrate polymer, a hydrogel, a cellulose acetate phthalate, an ethyl cellulose, a triblock copolymer, an acrylic polymer, hydroxyl propyl methyl cellulose, cellulose triacetate, and poly(methyl methacrylate).

374. The method of any one of 369-373, wherein the network former comprises cellulose acetate butyrate.

375. The method of any one of 345-374, wherein the drug composition comprises a viscosity enhancing agent.

376. The method of 375, wherein the viscosity enhancing agent is present at about 0.01% to about 10% w/w relative to the total weight of the drug composition.

377. The method of 375 or 376, wherein the viscosity enhancing agent is present at about 0.1% to about 6% w/w relative to the total weight of the drug composition.

378. The method of any one of 375-377, wherein the viscosity enhancing agent is present at about 0.5% to about 1.5% w/w relative to the total weight of the drug composition.

379. The method of any one of 375-378, wherein the viscosity enhancing agent comprises silicon dioxide.

380. The method of any one of 345-379, wherein the drug composition comprises a polyoxylglyceride.
381. The method of 380, wherein the polyoxylglyceride is present at about 0.1% to about 5% w/w relative to the total weight of the drug composition.
382. The method of 380 or 381, wherein the polyoxylglyceride is present at about 0.5% to about 1.5% w/w relative to the total weight of the drug composition.
383. The method of any one of 345-382, wherein the fill weight of the drug composition is from about 100 mg to about 800 mg.
384. The method of any one of 345-383, wherein the fill weight of the drug composition is from about 150 mg to about 200 mg.
385. The method form of any one of 345-384, wherein the barrier layer comprises at least one member selected from cellulose acetate phthalate, HPMC phthalate, HPMC acetate succinate, polyvinyl acetate phthalate, cellulose acetate trimelitate, methyacrylic acid copolymer, shellac, and zein.
386. The method form of any one of 345-385, wherein the barrier layer comprises at least one member selected from a hydrophobic cellulose, a polyalcohol, magnesium stearate, and silicon dioxide.
387. The method of any one of 345-386, wherein the barrier layer comprises a methacrylic acid copolymer and a polyvinyl alcohol.
388. The method of 387, wherein the methacrylic acid copolymer is present at about 60% to about 90% w/w relative to the total weight of the barrier layer.
389. The method of 387 or 388, wherein the polyvinyl alcohol is present at about 10% to about 40% w/w relative to the total weight of the barrier layer.
390. The method of any one of 345-389, wherein the barrier layer has a finished product coating weight of from about 10 mg to about 40 mg.
391. The method of any one of 345-390, wherein drug layer comprises about 25% to about 35% w/w of the second pharmacologically active agent relative to the total weight of the drug layer.
392. The method of any one of 345-391, wherein drug layer comprises a bulking agent.
393. The method of 392, wherein the bulking agent comprises hydroxypropyl methylcellulose (HPMC).
394. The method of 392 or 393, wherein the bulking agent is present at about 60% to about 75% w/w relative to the total weight of the drug layer.
395. The method of any one of 345-394, wherein the drug layer has a finished product coating weight of from about 20 mg to about 35 mg.
396. The method of any one of 345-395, comprising covering at least a portion of the drug layer with a coating layer.
397. The method of 396, wherein the coating layer comprises a polyvinyl alcohol-based composition.
398. The method of 396 or 397, wherein the coating layer has a finished product coating weight of from about 5 mg to about 10 mg.
399. The method of any one of 396-398, wherein the combined thickness of the barrier layer, the drug layer and the coating layer is from about 0.2 mm to about 0.5 mm.
400. The method of any one of 345-399, wherein the amount of the second pharmacologically active agent present in the drug layer is from about 15% to about 30% of the total amount of the first and second pharmacologically active agent in the dosage form.
401. The method of any one of 345-400, wherein the amount of the second pharmacologically active agent present in the drug layer is from about 20% to about 25% of the total amount of the first and second pharmacologically active agent in the dosage form.
402. The method of any one of 345-401, wherein the first and second pharmacologically active agent is methylphenidate.
403. The method of any one of 345-402, wherein one or more of the steps of covering at least a portion of the drug composition with a barrier layer, covering at least a portion of the barrier layer with a drug layer, and covering at least a portion of the drug layer with a coating layer comprise spray coating.
404. The method of any one of 345-403, wherein the combined % cumulative release of the first and second pharmacologically active agent from the dosage form is from 5% to 40% at T=1 hr when assayed by USP Apparatus II using 750 mL of 0.1 N HCl dissolution medium, a paddle speed of 50 rpm, and a dissolution medium temperature of 37° C.
405. The method of any one of 345-404, wherein the combined % cumulative release of the first and second pharmacologically active agent from the dosage form is from 10% to 30% at T=1 hr when assayed by USP Apparatus II using 750 mL of 0.1 N HCl dissolution medium, a paddle speed of 50 rpm, and a dissolution medium temperature of 37° C.
406. The method of any one of 345-405, wherein the combined % cumulative release of the first and second pharmacologically active agent from the dosage form is at least 80% at T=12 hrs when assayed by USP Apparatus II using a 2-stage dissolution protocol, a paddle speed of 50 rpm, a dissolution medium temperature of 37° C., a sampling volume of 1 mL, and sampling time points of 0.3 hrs, 0.5 hrs, 1 hr, 1.5 hrs, 2 hrs, 3 hrs, 6 hrs, 9 hrs, 12 hrs and 24 hrs, and wherein the 2-stage dissolution protocol comprises exposing the dosage form to 750 mL of 0.1 N HCl for T=0 to T=2 hrs, adding 200 mL of 0.19 M phosphate buffer to obtain a final dissolution medium volume of 950 mL, and exposing the dosage form to the final dissolution medium volume from T=2 hrs to T=24 hrs.
407. The method of any one of 345-406, wherein the dosage form is sufficient to provide an in vivo Tmax of from about 3 hrs to about 6 hrs following oral administration to an adult human subject.
408. The method of any one of 345-407, wherein the dosage form is sufficient to provide an in vivo Tmax of from about 4 hrs to about 5 hrs following oral administration to an adult human subject.
409. The method of any one of 345-408, wherein the dosage form is sufficient to provide an in vivo Cmax of from about 5 ng/mL to about 18 ng/mL following oral administration to an adult human subject.
410. The method of any one of 345-409, wherein the dosage form is sufficient to provide an in vivo Cmax of from about 9 ng/mL to about 13 ng/mL following oral administration to an adult human subject.
411. The method of any one of 345-410, wherein the dosage form is sufficient to provide an in vivo Cmax of from about 10 ng/mL to about 12 ng/mL following oral administration to an adult human subject.
412. A method administering a dosage form to a subject, the method comprising administering a dosage form according to any one of 1-338 to the subject.

413. The method of 412, wherein the dosage form is administered on a once daily (QD) basis.

414. The method of 412 or 413, wherein the dosage form is administered orally.

415. The method of 414, wherein the dosage form provides an in vivo Tmax of from about 3 hrs to about 6 hrs following the oral administration to the subject.

416. The method of 414 or 415, wherein the dosage form provides an in vivo Tmax of from about 4 hrs to about 5 hrs following the oral administration to the subject.

417. The method of any one of 414-416, wherein the dosage form provides an in vivo Cmax of from about 5 ng/mL to about 18 ng/mL following the oral administration to the subject.

418. The method of any one of 414-417, wherein the dosage form provides an in vivo Cmax of from about 9 ng/mL to about 13 ng/mL following the oral administration to the subject.

419. The method of any one of 414-418, wherein the dosage form provides an in vivo Cmax of from about 10 ng/mL to about 12 ng/mL following the oral administration to the subject.

420. The dosage form of any one of 1 to 338, wherein the barrier layer is free of pharmacologically active agent.

421. The method of any one of 339 to 419, wherein the barrier layer is free of pharmacologically active agent.

422. The dosage form of any one of 1 to 338 and 420, wherein the drug composition comprises a drug core.

423. The method of any one of 339 to 419 and 421, wherein the drug composition comprises a drug core.

424. The dosage form of any one of 1 to 338, 420, and 422, wherein the drug composition is encapsulated in a capsule comprising hydroxypropyl methylcellulose (HPMC).

425. The method of any one of 339 to 419, 421, and 423, wherein the drug composition is encapsulated in a capsule comprising hydroxypropyl methylcellulose (HPMC).

426. The dosage form of any one of 37 to 39, 103 to 105, 166 to 168, 230 to 232, 271, 272, and 294 to 338, wherein the polyoxylglyceride comprises a saturated polyglycolized glyceride.

427. The method of any one of 380 to 382, wherein the polyoxylglyceride comprises a saturated polyglycolized glyceride.

428. A dosage form, comprising:
a drug composition comprising a first pharmacologically active agent;
a barrier layer covering at least a portion of the drug composition; and
a drug layer covering at least a portion of the barrier layer, wherein the drug layer comprises a second pharmacologically active agent,
wherein the drug composition is encapsulated in a capsule comprising an outer surface and an inner surface, and wherein the barrier layer covers at least a portion of the outer surface of the capsule.

429. A dosage form, comprising:
a drug composition comprising a first pharmacologically active agent;
a barrier layer covering at least a portion of the drug composition; and
a drug layer covering at least a portion of the barrier layer, wherein the drug layer comprises a second pharmacologically active agent, and
wherein the barrier layer comprises a first material which is soluble in 0.1 N HCl at 37° C. and a second material which is insoluble in 0.1 N HCl at 37° C.

430. A dosage form, comprising:
a drug composition comprising a first pharmacologically active agent;
a barrier layer covering at least a portion of the drug composition; and
a drug layer covering at least a portion of the barrier layer, wherein the drug layer comprises a second pharmacologically active agent, and
wherein not more than 15% of the first pharmacologically active agent is released at 60 min when assayed by USP Apparatus II using 750 mL of 0.1 N HCl dissolution medium, a paddle speed of 50 rpm, and a dissolution medium temperature of 37° C.

431. The dosage form of 430, wherein the first pharmacologically active agent and the second pharmacologically active agents are the same, and wherein the % release of the first pharmacologically active agent at 60 minutes is determined by determining the % cumulative release of the first and second pharmacologically active agents that exceeds the amount of the second pharmacologically active agent in the drug layer.

432. A dosage form, comprising:
a drug composition comprising a first pharmacologically active agent;
a barrier layer covering at least a portion of the drug composition; and
a drug layer covering at least a portion of the barrier layer, wherein the drug layer comprises a second pharmacologically active agent, and
wherein not more than 25% of the first pharmacologically active agent is released at 90 min when assayed by USP Apparatus II using 750 mL of 0.1 N HCl dissolution medium, a paddle speed of 50 rpm, and a dissolution medium temperature of 37° C.

433. The dosage form of 433, wherein the first pharmacologically active agent and the second pharmacologically active agents are the same, and wherein the % release of the first pharmacologically active agent at 90 minutes is determined by determining the % cumulative release of the first and second pharmacologically active agents that exceeds the amount of the second pharmacologically active agent in the drug layer.

434. A dosage form, comprising:
a drug composition comprising a first pharmacologically active agent;
a first layer covering at least a portion of the drug composition, wherein the first layer comprises a methacrylic acid copolymer and a polyvinyl alcohol; and
a second layer covering at least a portion of the first layer, wherein the second layer comprises a second pharmacologically active agent, wherein initial release of the first pharmacologically active agent from the dosage form occurs at a time of 5 minutes to 120 minutes when assayed by USP Apparatus II using 750 mL of 0.1 N HCl dissolution medium, a paddle speed of 50 rpm, and a dissolution medium temperature of 37° C., and wherein the initial release of the first pharmacologically active agent from the dosage form is determined in the absence of the drug layer.

435. A dosage form, comprising:
a drug composition comprising a first pharmacologically active agent;
a barrier layer covering at least a portion of the drug composition; and
a drug layer covering at least a portion of the barrier layer, wherein the drug layer comprises a second pharmacologically active agent, and
wherein initial release of the first pharmacologically active agent from the dosage form occurs at a time of 5 minutes to 120 minutes when assayed by USP Apparatus II using 750 mL of 0.1 N HCl dissolution medium, a paddle speed of 50 rpm, and a dissolution medium temperature of 37° C., wherein the initial release of the first pharmacologically active agent from the dosage form is determined in the absence of the drug layer.

436. A dosage form, comprising:
a drug composition comprising a first pharmacologically active agent;
a barrier layer covering at least a portion of the drug composition; and
a drug layer covering at least a portion of the barrier layer, wherein the drug layer comprises a second pharmacologically active agent, and
wherein not more than 15% of the first pharmacologically active agent is released at 60 min when assayed by USP Apparatus II using 750 mL of 0.1 N HCl dissolution medium, a paddle speed of 50 rpm, and a dissolution medium temperature of 37° C., wherein the % release of the first pharmacologically active agent from the dosage form is determined in the absence of the drug layer.

437. A dosage form, comprising:
a drug composition comprising a first pharmacologically active agent;
a barrier layer covering at least a portion of the drug composition; and
a drug layer covering at least a portion of the barrier layer, wherein the drug layer comprises a second pharmacologically active agent, and
wherein not more than 25% of the first pharmacologically active agent is released at 90 min when assayed by USP Apparatus II using 750 mL of 0.1 N HCl dissolution medium, a paddle speed of 50 rpm, and a dissolution medium temperature of 37° C., wherein the % release of the first pharmacologically active agent from the dosage form is determined in the absence of the drug layer.

438. An oral dosage form, comprising:
a capsule comprising
an extended release (ER) composition encapsulated therein, the ER composition comprising
methylphenidate (MPH) at about 20% w/w relative to the total weight of the ER composition,
sucrose acetate isobutyrate (SAB) at about 41% w/w relative to the total weight of the ER composition,
triacetin at about 26% w/w relative to the total weight of the ER composition,
isopropyl myristate (IPM) at about 6% w/w relative to the total weight of the ER composition,
cellulose acetate butyrate (CAB) 381-20 BP at about 5% w/w relative to the total weight of the ER composition,
silicon dioxide at about 1% w/w relative to the total weight of the ER composition, and
lauroyl polyoxylglycerides at about 1% w/w relative to the total weight of the ER composition; and
a first layer covering the capsule, the first layer comprising
hydroxypropyl methylcellulose (HPMC) at about 100% w/w relative to the total weight of the first layer;
a second layer covering the first layer, the second layer comprising
MPH at about 33% w/w relative to the total weight of the second layer, and
HPMC at about 67% w/w relative to the total weight of the second layer; and
a film coating layer comprising polyvinyl alcohol covering the second layer.

439. An oral dosage form, comprising:
a capsule comprising
an extended release (ER) composition encapsulated therein, the ER composition comprising
methylphenidate (MPH) at about 20% w/w relative to the total weight of the ER composition,
sucrose acetate isobutyrate (SAB) at about 41% w/w relative to the total weight of the ER composition,
triacetin at about 26% w/w relative to the total weight of the ER composition,
isopropyl myristate (IPM) at about 6% w/w relative to the total weight of the ER composition,
cellulose acetate butyrate (CAB) 381-20 BP at about 5% w/w relative to the total weight of the ER composition,
silicon dioxide at about 1% w/w relative to the total weight of the ER composition, and
lauroyl polyoxylglycerides at about 1% w/w relative to the total weight of the ER composition; and
a first layer covering the capsule, the first layer comprising
a methacrylic acid copolymer at about 70% w/w relative to the total weight of the first layer, and
a polyvinyl alcohol-based moisture barrier material at about 30% w/w relative to the total weight of the first layer;
a second layer covering the first layer, the second layer comprising
MPH at about 33% relative to the total weight of the second layer, and
hydroxypropyl methylcellulose (HPMC) at about 67% to about to the total weight of the second layer; and
a film coating layer comprising polyvinyl alcohol covering the second layer.

440. An oral dosage form, comprising:
a capsule comprising
an extended release (ER) composition encapsulated therein, the ER composition comprising
methylphenidate (MPH) at about 20% w/w relative to the total weight of the ER composition,
sucrose acetate isobutyrate (SAB) at about 38% w/w relative to the total weight of the ER composition,
triacetin at about 29% w/w relative to the total weight of the ER composition,
isopropyl myristate (IPM) at about 6% w/w relative to the total weight of the ER composition, cellulose acetate butyrate (CAB) 381-20 BP at about 5% w/w relative to the total weight of the ER composition,
silicon dioxide at about 1% w/w relative to the total weight of the ER composition, and
lauroyl polyoxylglycerides at about 1% w/w relative to the total weight of the ER composition; and
a first layer covering the capsule, the first layer comprising
a methacrylic acid copolymer at about 70% w/w relative to the total weight of the first layer, and
a polyvinyl alcohol-based moisture barrier material at about 30% w/w relative to the total weight of the first layer;
a second layer covering the first layer, the second layer comprising
MPH at about 33% relative to the total weight of the second layer, and
hydroxypropyl methylcellulose (HPMC) at about 67% to about to the total weight of the second layer; and
a film coating layer comprising polyvinyl alcohol covering the second layer.

441. An oral dosage form, comprising:
a capsule comprising
an extended release (ER) composition encapsulated therein, the ER composition comprising
methylphenidate (MPH) at about 20% w/w relative to the total weight of the ER composition,
sucrose acetate isobutyrate (SAB) at about 38% w/w relative to the total weight of the ER composition,
triacetin at about 29% w/w relative to the total weight of the ER composition,
isopropyl myristate (IPM) at about 6% w/w relative to the total weight of the ER composition,
cellulose acetate butyrate (CAB) 381-20 BP at about 5% w/w relative to the total weight of the ER composition,
silicon dioxide at about 1% w/w relative to the total weight of the ER composition, and
lauroyl polyoxylglycerides at about 1% w/w relative to the total weight of the ER composition; and
a first layer covering the capsule, the first layer comprising
a methacrylic acid copolymer at about 70% w/w relative to the total weight of the first layer, and
a polyvinyl alcohol-based moisture barrier material at about 30% w/w relative to the total weight of the first layer;
a second layer covering the first layer, the second layer comprising
MPH at about 33% relative to the total weight of the second layer, and
hydroxypropyl methylcellulose (HPMC) at about 67% to about to the total weight of the second layer; and
a film coating layer comprising polyvinyl alcohol covering the second layer.

442. A dosage form, comprising:
a drug composition comprising a first pharmacologically active agent;
a barrier layer covering at least a portion of the drug composition; and
a drug layer covering at least a portion of the barrier layer, wherein the drug layer comprises a second pharmacologically active agent, and
wherein the combined % cumulative release of the first and second pharmacologically active agent from the oral dosage form is from 5% to 40% at T=1 hr when assayed by USP Apparatus II using 750 mL of 0.1 N HCl dissolution medium, a paddle speed of 50 rpm, and a dissolution medium temperature of 37° C.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near one atmosphere. Standard abbreviations may be used, e.g., s or sec, second(s); min, minute(s); h or hr, hour(s); and the like.

Example 1: Preparation of Formulation A

Formulation A was prepared by filling clear HPMC (Hydroxypropyl Methylcellulose) capsules (Size 3) with a drug composition containing 30-mg Methylphenidate HCl (MPH), which capsules were then coated with first (I), second (II) and third (III) layers, wherein the second layer included 10 mg MPH. The components of the drug composition and the layers coated on the capsules are shown in the following tables. Amounts are % w/w unless otherwise noted.

TABLE 1

| | Formulation | | | | | | | | | |
|---|---|---|---|---|---|---|---|---|---|---|
| | MPH | SAIB | Triacetin | IPM | CAB | Cab-O-Sil® | Gelucire® 44/14 | BHT | Fill Wt (mg) | Capsule Size |
| Drug Composition | 20.00% | 41.22% | 25.76% | 6.40% | 4.80% | 0.80% | 1.00% | 0.02% | 150 | 3 (HPMC) |

TABLE 2

| | Layers | MPH | Pharmacoat® 606 HPMC E3 (2910) | Poloxamer® 188 | Opadry® II White 85F18422 | Coating Wt (mg) |
|---|---|---|---|---|---|---|
| Layers | (I): Protective Layer | | 100% | | | 12 |
| | (II): Drug Layer | 33.33% | 26.67% | 40.00% | | 30 |
| | (III): Film Coating Layer | | | | 100% | 9 |

Note:
Drug Layer solvent was water with phosphoric acid used for pH adjustment. Protective Layer solvents were 45/55 Ethanol/puritied water. Protective Layer was coated over the HPMC capsule shell followed by Drug Layer and then Film Coating Layer.

The drug composition of Formulation A was prepared generally as follows: Individual components from Table 1 were weighed to the desired component weight and compounded at 60±5° C. in an oil bath. The composition was then filled into a size 3 HPMC capsule at the indicated fill weight. Following capsule filling, the capsule was banded using a solution of HPMC in ethanol and water.

The protective layer for Formulation A was prepared generally as follows: Distilled water and ethanol were provided in a stainless steel beaker. Pharmacoat® 606 was then added and mixed until dissolved The procedure for application of the protective layer was generally as follows: A beaker containing the protective layer solution was placed next to a coating machine, and tubing was connected between a spray gun of the coating machine and the solution. The coating machine was a pan coater, specifically a REI HSIUNG Coater RH-Coater-5. Capsules containing the drug composition and placebo tablets of similar weight and size as the capsules were placed into the coating pan. The inlet air temperature was set at 43° C., the fan was started, and the inlet air heater was turned ON, until exhaust air temperature reaches the target range of 43±3° C.

Spraying commenced at an initial spray rate of 5 rpm using the following preset coating parameters: Inlet Air Pressure: 3.5 kg/cm²+0.3 kg/cm²; Atomizing flow rate (CAP): 35 NL/min+3 NL/min; Pattern flow rate (CYL): 20 NL/min+2 NL/min; Nozzle Size: 1.0 mm; Spraying rate: Increased by an increment of 1 rpm every 20 minutes up to 10 rpm. Maintained at 10 rpm and adjusted the outlet temp to 40±5° C.; Pan Speed: 10±2 rpm. Product temperature: Maintained at 38±3° C.

When coating was completed, the capsules were heat-treated in the coater for 30 minutes at an inlet temperature of 43° C. Capsules were then cooled at an inlet temperature of 25° C. until outlet temperature reached lower than 28° C.

The procedure for preparation of the drug layer solution was generally as follows: Distilled water and ethanol were provided in a stainless steel beaker. Methylphenidate HCl was added and mixed until dissolved. Pharmacoat® 606 was added and mixed until dissolved. Poloxamer® 188 was added and mixed until dissolved. Phosphoric acid was added to adjust the pH to 2.83 and provide the drug coating layer solution.

The procedure for application of the drug layer was generally as follows: Capsules and Placebo Tablets coated with protective coating were placed into the coating pan. The inlet air temperature was set at 45° C., the fans were started, and the inlet air heater was turned ON, until exhaust air temperature reached a target range of 45±3° C. Spraying commenced at an initial spray rate of 5 rpm using the following preset coating parameters: Inlet Air Pressure: 3.5 kg/cm²+0.3 kg/cm²; Atomizing flow rate (CAP): 35 NL/min+3 NL/min; Pattern flow rate (CYL): 20 NL/min+2 NL/min; Nozzle Size: 1.0 mm; Spraying rate: Started at 6 rpm. Increased by an increment of 1 rpm every 20 minutes up to 8 rpm. Maintained at 8 rpm.; Pan Speed: 12±2.0 rpm. Product temperature: Maintained at 37±3° C. The coating machine was the REI HSIUNG Coater RH-Coater-5.

When coating was completed, the capsules were heat-treated in the coater for 30 minutes at inlet temperature of 45° C. The capsules were then cooled at an inlet temperature of 25° C. until the product temperature reached lower than 28° C.

The procedure for preparation of the film coating solution was generally as follows: Distilled water was provided in a stainless steel beaker. Opadry® II White 85F18422 was added and mixed until homogenous to provide the film coating solution.

The procedure for application of the film coating layer was generally as follows: Capsules and Placebo Tablets coated with protective coating layer and drug layer were placed into the coating pan. The inlet air temperature was set at 50° C., the fans were started, and the inlet air heater was turned ON, until the exhaust air temperature reached a target range of 50±2° C. Spraying commenced at an initial spray rate of 5 rpm using the following preset coating parameters: Inlet Air Pressure: 3.5 kg/cm2±0.3 kg/cm2; Atomizing flow rate (CAP): 40 NL/min+3 NL/min; Pattern flow rate (CYL): 20 NL/min+2 NL/min; Nozzle Size: 1.0 mm; Spraying rate: spraying rate was adjusted according to product condition; Pan Speed: 12±2.0 rpm. Product temperature: Maintained at 43±3° C. The coating machine was the REI HSIUNG Coater RH-Coater-5. When coating was completed the capsules were heat-treated in the coater for 30 minutes at inlet temperature of 50° C. Capsules were then cooled at an inlet temperature of 25° C. until the outlet temperature reached lower than 28° C.

Example 2: Pharmacokinetic Profile of Formulation A

Formulation A was evaluated in a human PK study under fasted and fed conditions using Concerta® Extended Release Tablets 36 mg as a reference.

Materials and Methods

Study Design: A single-center, open-label, randomized, three-treatment, three-way crossover, single-dose, phase I study in healthy adult volunteers. The treatment conditions are provided below in Table 3.

TABLE 3

| | |
|---|---|
| Reference Drug (Treatment A) | Name: Concerta ® Extended Release Tablets 36 mg<br>Active ingredient: Methylphenidate HCl<br>Dosage form: Tablet<br>Strength: 36 mg/tablet<br>Dose: 36 mg (one tablet, single oral dose)<br>Treatment A: Orally administered under fed conditions |
| Test Drug (Formulation A) (Treatment B & C) | Name: ORADUR ®-Methylphenidate Capsules 40 mg<br>Active ingredient: Methylphenidate HCl<br>Dosage form: Capsule<br>Strength: 40 mg/capsule<br>Dose: 40 mg (one capsule, single oral dose)<br>Treatment B: Orally administered under fed conditions<br>Treatment C: Orally administered under fasting conditions |
| Drug Administration | One capsule of ORADUR ®-Methylphenidate Capsules 40 mg or one tablet of Concerta ® Extended Release Tablets 36 mg was orally administered with 240 mL of water in the morning in each of the three study periods. |
| Blood Sampling Schedule | −0.5 (Predose), 0.5, 1.0, 1.5, 2.0, 3.0, 4.0, 5.0, 6.0, 8.0, 10, 12, 16, 20, 24, 36 and 48 hr post dose (a total of 17 samples per subject in one period) |
| Analytical Method | Concentrations of methylphenidate in plasma were quantified using a validated LC-MS/MS method as appropriate |
| Pharmacokinetic Parameters | The following parameters of methylphenidate were determined using WinNonlin ®:<br>1. Peak concentration (Cmax)<br>2. Time to reach peak concentration (Tmax)<br>3. Truncated area under the plasma concentration-time curve from time zero to time of last quantifiable concentration (AUC0-t)<br>4. Area under the plasma concentration-time curve from time zero to infinity (AUC0-∞)<br>5. Elimination rate constant ($\lambda z$)<br>6. Terminal elimination half-life (T½) |

Results

Figure 4:
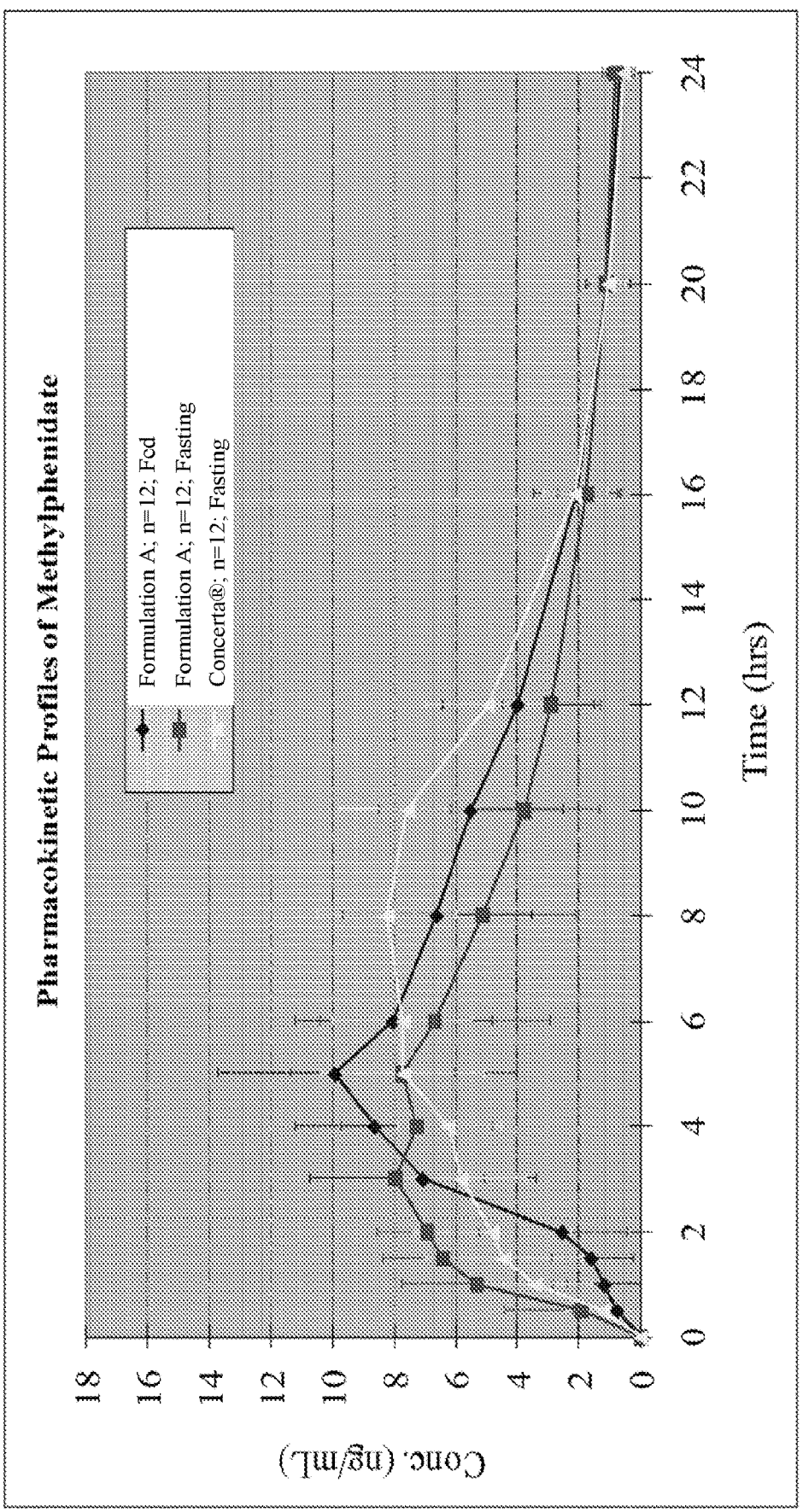
FIG. 4 provides a graph showing the pharmacokinetic profiles for Formulation A under fasting and fed conditions relative to Concerta® in connection with Example 2.

The PK results (FIG. 4) show a fast onset of action in the fasted state, however, a start-up lag time was observed in the fed condition. Formulations 1-4, as described below, were prepared in an attempt to address this start-up lag time.

Example 3: Preparation of Methylphenidate Dosage Forms

Formulation 1 was prepared by filling opaque HPMC (Hydroxypropyl Methylcellulose) capsules (Size 4) with a drug composition containing 34-mg of Methylphenidate HCl (MPH), which capsules were then coated with first (I), second (II) and third (III) layers, wherein the second layer included 10 mg MPH. The components of the drug composition and the layers coated on the capsules are shown in the following tables. Amounts are % w/w unless otherwise noted.

TABLE 4

| | MPH | SAIB | Triacetin | IPM | CAB 381-20 BP | Cab-O-Sil ® | Gelucire ® 44/14 | BHT | Fill Wt (mg) | Capsule Size |
|---|---|---|---|---|---|---|---|---|---|---|
| Drug Composition | 20.00% | 41.22% | 25.76% | 6.40% | 4.80% | 0.80% | 1.00% | 0.02% | 170 | 4 (HPMC) |

TABLE 5

| | Layers | MPH | Pharmacoat ® 606 HPMC E3 (2910) | Opadry ® II White 85F18422 | Coating Wt (mg) |
|---|---|---|---|---|---|
| Layers | (I): Protective Layer | | 100% | | 9 |
| | (II): Drug Layer | 33.33% | 66.67% | | 30 |
| | (III): Film Coating Layer | | | 100% | 7 |

Note:
Protective Layer solvents were 45/55 Ethanol/purified water. Drug Layer solvent was water with phosphoric acid for pH adjustment. Film Coating Layer solvent was purified water.

Formulation 2 was prepared by filling opaque HPMC (Hydroxypropyl Methylcellulose) capsules (Size 4) with a drug composition containing 34-mg of Methylphenidate HCl (MPH), which capsules were then coated with first (I), second (II) and third (III) layers, wherein the second layer included 10 mg MPH. The components of the drug composition and the layers coated on the capsules are shown in the following tables. Amounts are % w/w unless otherwise noted.

TABLE 6

|  | MPH | SAIB | Triacetin | IPM | CAB 381-20 BP | Cab-O-Sil ® | Gelucire ® 44/14 | BHT | Fill Wt (mg) | Capsule Size |
|---|---|---|---|---|---|---|---|---|---|---|
| Drug Composition | 20.00% | 41.22% | 25.76% | 6.40% | 4.80% | 0.80% | 1.00% | 0.02% | 170 | 4 (HPMC) |

TABLE 7

|  | Layers | MPH | Pharmacoat ® 606 HPM CE3 (2910) | Acryl-EZE ® White (93O18509) | Opadry ® AMB White (80W68912) | Opadry ® II White (85F18422) | Coating Wt (mg) |
|---|---|---|---|---|---|---|---|
| Layers | (I): Barrier Layer |  |  | 70% | 30% |  | 24 |
|  | (II): Drug Layer | 33.33% | 66.67% |  |  |  | 30 |
|  | (III): Film Coating Layer |  |  |  |  | 100% | 7 |

Note:
Barrier Layer solvent was purified water. Drug Layer solvent was purified water with phosphoric acid for pH adjustment. Film Coating Layer solvent was purified water.

Formulation 3 was prepared by filling opaque HPMC (Hydroxypropyl Methylcellulose) capsules (Size 4) with a drug composition containing 34-mg of Methylphenidate HCl (MPH) which capsules were then coated with first (I), second (II) and third (III) layers, wherein the second layer included 10 mg MPH. The components of the drug composition and the layers coated on the capsules are shown in the following tables. Amounts are % w/w unless otherwise noted.

TABLE 8

| Formulation | | | | | | | | | | |
|---|---|---|---|---|---|---|---|---|---|---|
|  | MPH | SAIB | Triacetin | IPM | CAB 381-20 BP | Cab-O-Sil ® | Gelucire ® 44/14 | BHT | Fill Wt (mg) | Capsule Size |
| Drug Composition | 20.00% | 37.86% | 29.12% | 6.40% | 4.80% | 0.80% | 1.00% | 0.02% | 170 | 4 (HPMC) |

TABLE 9

| Formulation | | | | | | | |
|---|---|---|---|---|---|---|---|
|  | Layers | MPH | Pharmacoat ® 606 HPMC E3 (2910) | Acryl-EZE ® White (93O18509) | Opadry ® AMB White (80W68912) | Opadry ® II White (85F18422) | Coating Wt (mg) |
| Layers | (I): Barrier Layer |  |  | 70% | 30% |  | 24 |
|  | (II): Drug Layer | 33.33% | 66.67% |  |  |  | 30 |
|  | (III): Film Coating Layer |  |  |  |  | 100% | 7 |

Note:
Barrier Layer solvent was purified water. Drug Layer solvent was purified water with phosphoric acid for pH adjustment. Film Coating Layer solvent was purified water.

Formulation 4 was prepared by filling opaque HPMC (Hydroxypropyl Methylcellulose) capsules (Size 4) with a drug composition containing 36-mg of Methylphenidate HCl (MPH), which capsules were then coated with first (I), second (II) and third (III) layers, wherein the second layer included 8 mg MPH. The components of the drug composition and the layers coated on the capsules are shown in the following tables. Amounts are % w/w unless otherwise noted.

TABLE 10

| | | | | | CAB 381-20 | | Gelucire ® | | Fill Wt | Capsule |
| | MPH | SAIB | Triacetin | IBM | BP | Cab-O-Sil ® | 44/14 | BHT | (mg) | Size |
|---|---|---|---|---|---|---|---|---|---|---|
| Drug Composition | 20.00% | 37.86% | 29.12% | 6.40% | 4.80% | 0.80% | 1.00% | 0.02% | 180 | 4 (HPMC) |

TABLE 11

| | Layers | MPH | Pharmacoat ® 606 HPMC E3 (2910) | Acryl-EZE ® White (93O18509) | Opadry ® AMB White (80W68912) | Opadry ® II White (85F18422) | Coating Wt (mg) |
|---|---|---|---|---|---|---|---|
| Layers | (I): Barrier Layer | | | 70% | 30% | | 24 |
| | (II): Drug Layer | 33.33% | 66.67% | | | | 24 |
| | (III): Film Coating Layer | | | | | 100% | 7 |

Note:
Barrier Layer solvent was purified water. Drug Layer solvent was purified water with phosphoric acid for pH adjustment. Film Coating Layer solvent was purified water.

Drug Composition

The drug compositions of Formulations 1, 2, 3 and 4 were prepared generally as follows and as shown in FIG. 1A: Individual components from Tables 4, 6, 8, and 10, respectively, were weighed to the desired component weight and compounded at 60±5° C. in an oil bath. The composition was then filled into a size 4 HPMC capsule at the indicated fill weight. Following capsule filling, the capsule was banded using a solution of HPMC in ethanol and water.

Barrier Layer

Figure 1B:
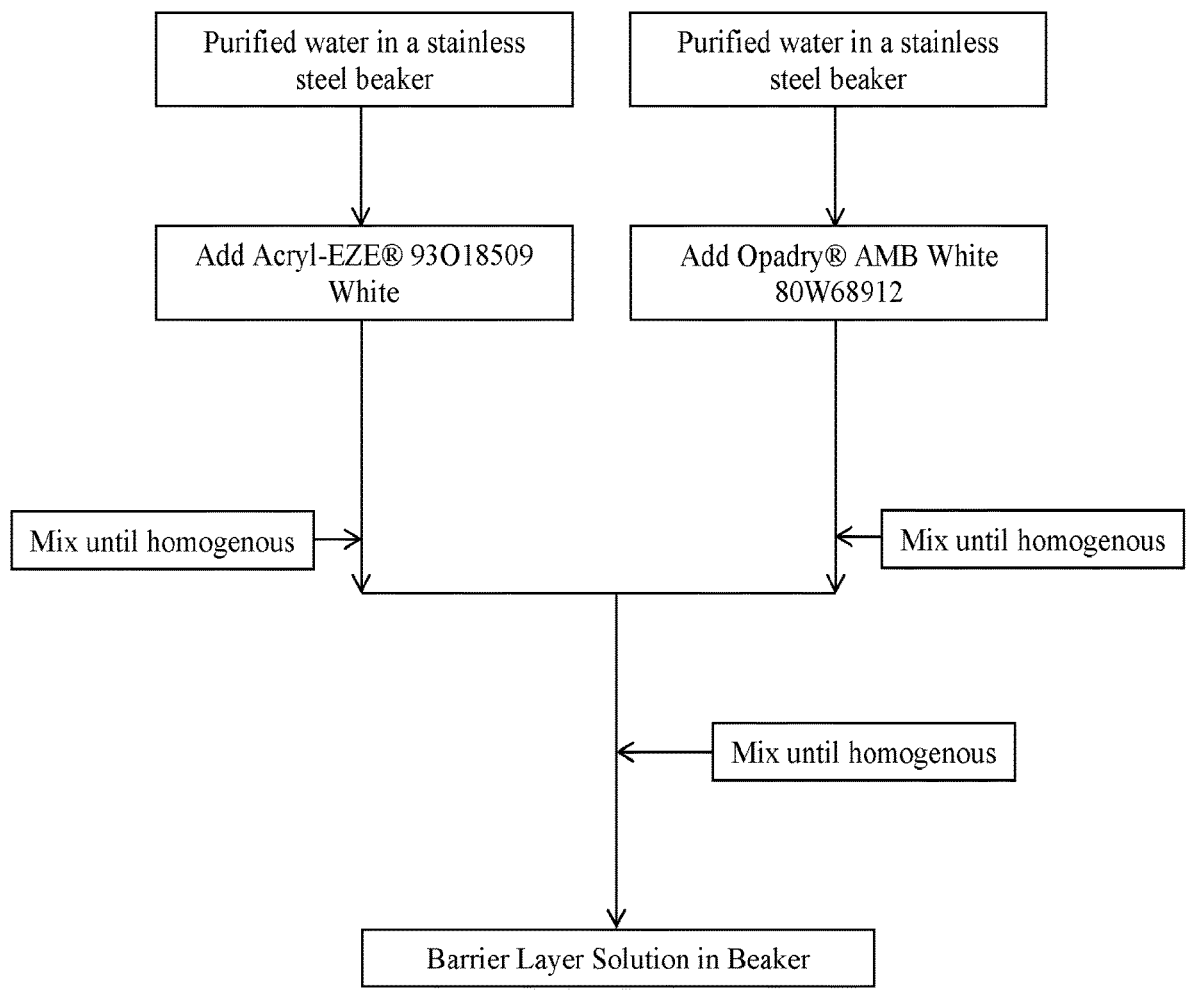
FIG. 1B provides a flow diagram showing the steps of an exemplary method of preparing a barrier coating solution utilized for the application of a barrier layer in connection with preparation of exemplary dosage forms described herein.

The barrier layer solution utilized for the application of the barrier layer for the above referenced formulations was prepared generally as set forth in FIG. 1B. Briefly, purified water was provided in two stainless steel beakers. To the first beaker, Acryl-Eze® 93018509 was added and mixed until homogenous. To the second beaker Opadry® AMB White 80W68912 was added and mixed until homogenous. The contents of the two beakers were combined and then mixed until homogenous to provide the barrier coating layer solution.

The procedure for application of the barrier layer solution was generally as follows:

A beaker containing the barrier layer coating solution was placed next to a coating machine and tubing was connected between the spray gun of the coating machine and the solution. The coating machine was a REI HSIUNG Coater RH-Coater-5. Placebo tablets (~1000 tablets, ~560 g) were placed into the coating pan as a coating process aid. The air blower of the coating machine was started and the heater turned on. The following parameters were set for the coating machine: Inlet air temperature: 45° C.; and Pan speed: 1.0±0.3 rpm. The placebo tablets were prewarmed for 30 min. Fifty placebo tablets were sampled, and weights for the individual tablets were recorded along with the average weight.

Approximately 1000 opaque HPMC capsules (Size 4) containing the drug composition were loaded into the coating pan and pre-warmed for 10 min. Fifty capsules were sampled, and weights for the individual capsules were recorded along with the average weight. The following parameters were set for the coating machine: Inlet air pressure: 3.5±0.3 kg/cm$^2$; Atomizing flow rate (CAP): 40±3 NL/min; Pattern flow rate (CYL): 20±2 NL/min; Nozzle size: 1.3 mm; Inlet air temperature: 45° C.; Spray rate: Started at 5 rpm. The spray rate was adjusted depending on the condition of the product. The product temperature was maintained at 38±3° C.; Pan speed: 11.0±2.0 rpm.

The above coating parameters were recorded every 10 min. Twenty capsules were sampled, and individual weights were recorded every 10 min. This procedure was repeated until the target coating weight was achieved. When coating was finished, the pan speed was set at 1.0±0.3 rpm, and the capsules were heat-treated for 30 min at an inlet air temperature of 45° C. The capsules were then cooled at an inlet air temperature of 25° C. until the capsules reached <28° C.

The coated placebo tablets and the coated capsules were then separated, and the total weight of all the capsules was recorded. Finally, fifty capsules were sampled, and the individual weight of each capsule was recorded along with the average weight.

Drug Layer

Figure 2:
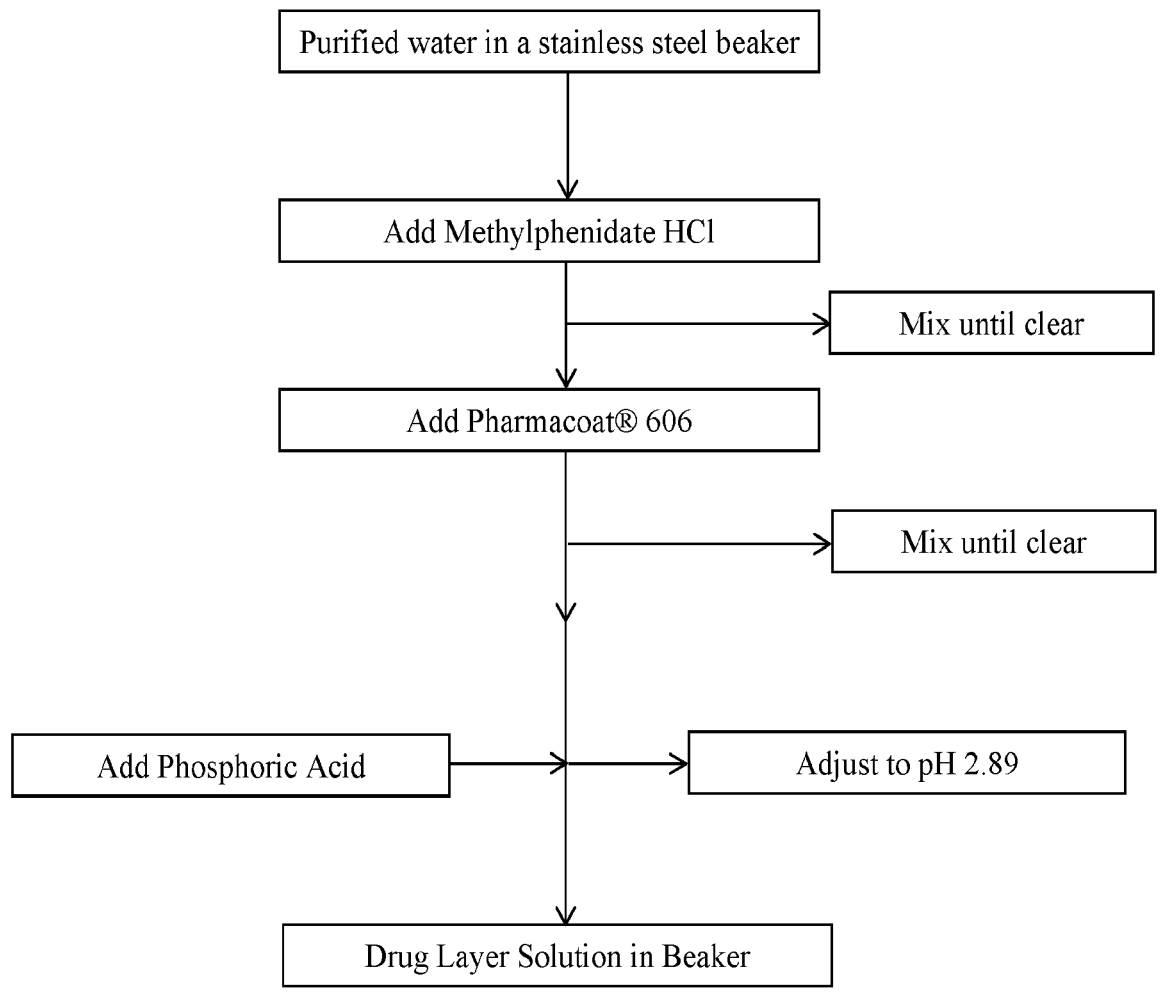
FIG. 2 provides a flow diagram showing the steps of an exemplary method of preparing a drug coating solution utilized for the application of a drug layer in connection with preparation of exemplary dosage forms described herein.

The drug layer solution utilized for the application of the drug layer for the above referenced formulations was prepared generally as set forth in FIG. 2. Briefly, purified water was provided in a stainless steel beaker to which methylphenidate HCl was added and mixed until dissolved. Pharmacoat® 606 was then added and mixed until dissolved. Finally, Phosphoric acid was added to adjust the pH to ~2.8.

The procedure for application of the drug coating layer solution was generally as follows:

A beaker containing the drug layer solution was placed next to a coating machine and tubing was connected between a spray gun of the coating machine and the solution. The coating machine was the REI HSIUNG Coater RH-Coater-5. Placebo tablets (~1000 tablets, ~560 g) were placed into the coating pan as a coating aid. The air intake blower of the coating machine was started, and the heater was turned on. The coating machine was set to the following parameters: Inlet air temperature: 45° C.; and Pan speed: 1.0±0.3 rpm. The placebo tablets were pre-warmed for 30 min. Fifty placebo tablets were sampled, and the weight for each was recorded along with the average weight.

Approximately 1000 opaque HPMC capsules (Size 4) containing the drug composition and coated with the barrier layer were loaded into the coating pan and pre-warmed for 10 min.

Fifty capsules were sampled and weights for the individual capsules were recorded along with the average weight. The following parameters were set for the coating machine: Inlet air pressure: 3.5±0.3 kg/cm$^2$; Atomizing flow rate (CAP): 35±3 NL/min; Pattern flow rate (CYL): 20±2 NL/min; Nozzle size: 1.30 mm; Inlet air temperature: 45° C.; Spray rate: Started at 6 rpm. The spray rate was adjusted depending on the condition of the product. The product temperature was maintained at 38±3° C.; Pan speed: 11.0±2.0 rpm.

Coating process parameters were recorded every 10 min. Twenty capsules were sampled, and individual weights were recorded every 20 min. This procedure was repeated until the target coating weight was achieved. When coating was finished, the pan speed was set at 1.0±0.3 rpm, and the capsules were heat-treated for 30 min at an inlet air temperature of 45° C. The capsules were then cooled at an inlet air temperature of 25° C. until the capsules reached <28° C.

The coated placebo tablets and the coated capsules were then separated, and the total weight of all the capsules was recorded. Finally, fifty capsules were sampled, and the individual weight of each capsule was recorded along with the average weight.

Film Coating Layer

Figure 3:
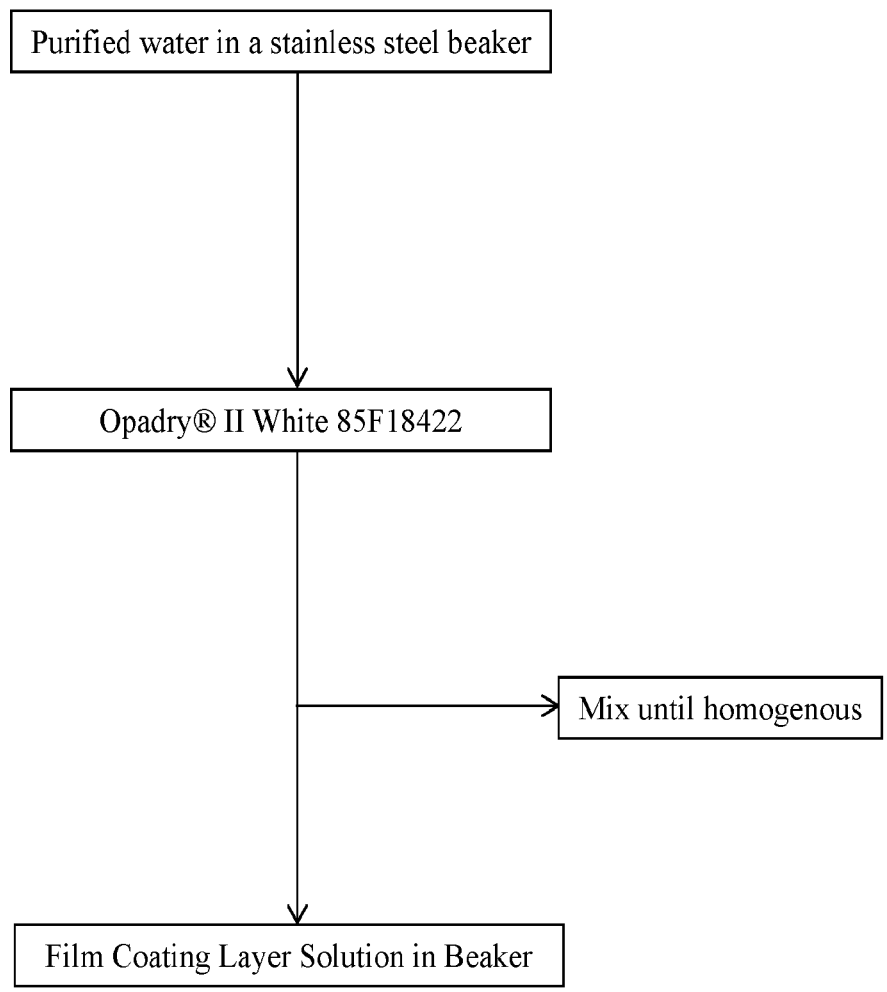
FIG. 3 provides a flow diagram showing the steps of an exemplary method of preparing a film coating solution utilized for the application of a film coating layer in connection with preparation of exemplary dosage forms described herein.

The film coating layer solution utilized for the application of the film coating layer for the above referenced formulations was prepared generally as set forth in FIG. 3. Briefly, purified water was provided in a stainless steel beaker. Opadry® II White 85F18422 was added and mixed until homogenous to provide the film coating layer solution.

The procedure for application of the film coating layer solution was generally as follows:

A beaker containing the film coating layer solution was placed next to a coating machine and tubing was connected between a spray gun of the coating machine and the solution. The coating machine was the REI HSIUNG Coater RH-Coater-5. Placebo tablets (~1000 tablets, ~560 g) were placed into the coating pan as a coating aid. The fan of the coating machine was started, and the heater was turned on. The coating machine was set to the following parameters: Inlet air temperature: 50° C.; and Pan speed: 1.0±0.3 rpm. The placebo tablets were pre-warmed for 30 min. Fifty placebo tablets were sampled, and the weight for each was recorded along with the average weight.

Approximately 1000 HMPC capsules (Size 4) containing the drug composition and coated with the barrier layer and the drug layer were loaded into the coating pan and pre-warmed for 10 min.

Fifty capsules were sampled, and weights for the individual capsules were recorded along with the average weight. The following parameters were set for the coating machine: Inlet air pressure: 3.5±0.3 kg/cm$^2$; Atomizing flow rate (CAP): 40±3 NL/min; Pattern flow rate (CYL): 20±2 NL/min; Nozzle size: 1.3 mm; Inlet air temperature: 50° C.; Spray rate: Started at 5 rpm. The spray rate was adjusted depending on the condition of the product. The product temperature was maintained at 38±3° C.; Pan speed: 11.0±2.0 rpm.

Parameters were recorded every 10 min. Twenty capsules were sampled and individual weights were recorded every 10 min. This procedure was repeated until the target coating weight was achieved. When coating was finished, the pan speed was set at 1.0±0.3 rpm, and the capsules were heat-treated for 30 min at an inlet air temperature of 50° C. The capsules were then cooled at an inlet air temperature of 25° C. until the capsules reached <28° C.

The coated placebo tablets and the coated capsules were then separated, and the total weight of all the capsules was recorded. Finally, fifty capsules were sampled and the individual weight of each capsule was recorded along with the average weight.

Example 4: In-Vitro Dissolution of Methylphenidate from Dosage Forms

Formulations 1-4 and Formulation A were tested in-vitro for dissolution characteristics using a USP Apparatus 2 as set forth below.

Materials and Methods

The dissolution testing parameters were as follows:
Dissolution Medium for Phase 1: 750 mL of 0.1 N HCl (0-2 hours);
Dissolution Medium for Phase 2: 200 mL of 0.19 M phosphate buffer;
Final Combined Dissolution Medium of 1 and 2: Volume and pH: 950 mL, pH 6.0±0.2 (2-24 hours);
Paddle Speed: 50 rpm;
Vessel Temperature: 37.0±0.5° C.;
Sampling Time Points: 0.3, 0.5, 1, 1.5, 2, 3, 6, 9, 12, and 24 hours;
Sampling Volume: 1 mL;
n=6.

Dissolution Medium for Phase 2 was equilibrated to about 37° C. before adding to the vessels in order to maintain a dissolution medium temperature of 37.0±0.5° C.

HPLC parameters were as follows: Mobile phase A: 5 mM 1-Decanesulfonic acid, sodium salt, 5 mM sodium phosphate monobasic, pH 2.5; Mobile phase B: 100% acetonitrile; Mobile phase: 71% Mobile phase A and 29% Mobile phase B;
210 nm wavelength.

Results

The results of the dissolution experiments are provided in Tables 12 and 13 below and in FIGS. 5A-5C.

TABLE 12

| Formulation | MPH in Drug Layer | MPH in Drug Composition | % Cumulative Drug Released | | | | | | | | | | |
|---|---|---|---|---|---|---|---|---|---|---|---|---|---|
| | | | 0 | 0.3 | 0.5 | 1 | 1.5 | 2 | 3 | 6 | 9 | 12 | 24 |
| 1 | 10 mg | 34 mg | 0 | 22 | 26 | 34 | 40 | 44 | 51 | 68 | 79 | 87 | 98 |
| 2 | 10 mg | 34 mg | 0 | 22 | 23 | 27 | 30 | 34 | 44 | 61 | 72 | 81 | 97 |
| 3 | 10 mg | 34 mg | 0 | 23 | 24 | 28 | 34 | 40 | 53 | 79 | 94 | 99 | 102 |

TABLE 12-continued

| Formulation | MPH in Drug Layer | MPH in Drug Composition | 0 | 0.3 | 0.5 | 1 | 1.5 | 2 | 3 | 6 | 9 | 12 | 24 |
|---|---|---|---|---|---|---|---|---|---|---|---|---|---|
| 4 | 8 mg | 36 mg | 0 | 18 | 20 | 24 | 28 | 33 | 47 | 74 | 89 | 95 | 100 |
| Formulation A | 10 mg | 30 mg | 0 | 27 | 32 | 40 | 46 | 51 | 59 | 78 | 89 | 94 | 101 |

TABLE 13

| Formulation | $t_{25\%}$ | $t_{50\%}$ | $t_{80\%}$ |
|---|---|---|---|
| 1 | 24 min | 3 hr | 9 hr |
| 2 | 45 min | 4 hr | 11.8 hr |
| 3 | 36 min | 2.75 hr | 6 hr |
| 4 | 66 min | 3.35 hr | 7.2 hr |
| Formulation A | 12 min | 1.9 hr | 6.5 hr |
| $t_{25\%}$ | Formulation A < 1 < 3 < 2 < 4 | | |
| $t_{50\%}$ | Formulation A < 3 < 1 < 4 < 2 | | |
| $t_{80\%}$ | Formulation 3 < A < 4 < 1 < 2 | | |

As shown above (Table 12) and in FIGS. 5A-5C, the drug layers dissolved within 0.3 hr (or approximately 15 min). The formulations including a first layer containing Pharmacoat® 606 HPMC E3 (2910) (Formulation 1 and Ref. Formulation A) continued the drug release while the formulations with a first layer including Acryl-EZE® White (93018509) and Opadry® AMB White (80W68912) (Formulations 2-4) exhibited a lag in drug release. By comparison of Formulation 1 vs. 2, Formulation 1 reached 44% released at 2 hours while Formulation 2 reached 44% released at 3 hours. The square root of time profiles demonstrate the effect of the first layer (FIG. 5C).

Example 5: In-Vitro Dissolution of Methylphenidate from Dosage Forms (Continued)

Figure 6:
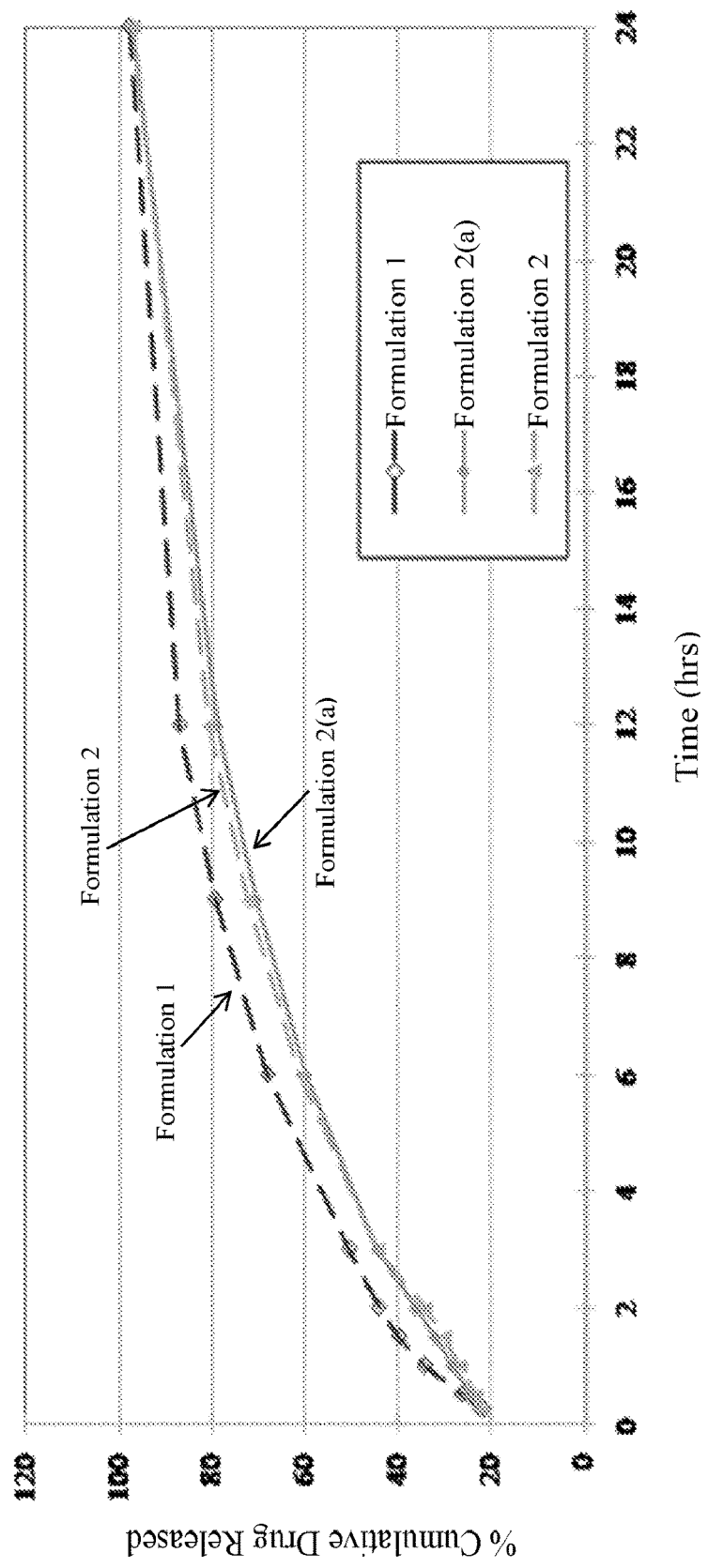
FIG. 6 provides a graph showing dissolution profiles for Formulations 1, 2 and 2(a) in connection with Example 5.
Figure 7:
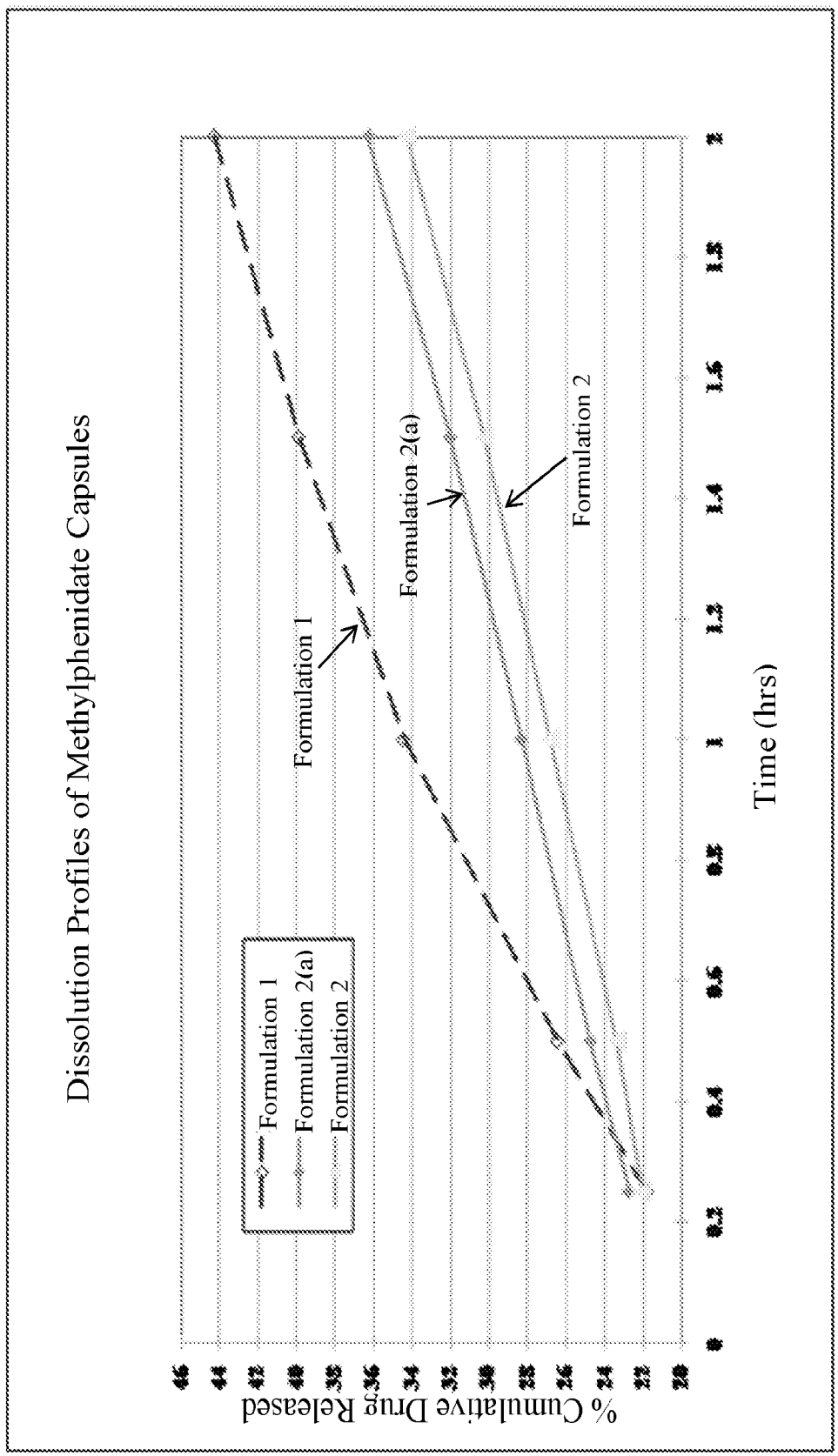
FIG. 7 provides a graph showing an expanded portion of the graph of FIG. 6 for the 0-2 hr time period.
Figure 8:
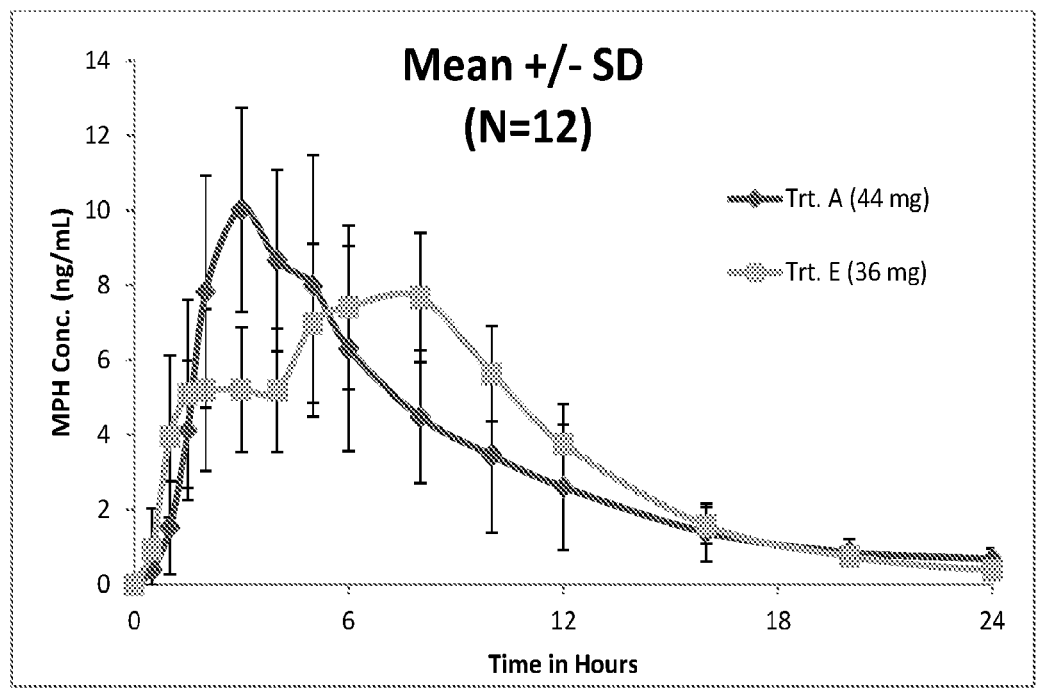
FIG. 8 provides a graph showing the mean plasma concentration of methylphenidate for Treatment A (Formulation 1) and E (Concerta®) in connection with Example 6.
Figure 9:
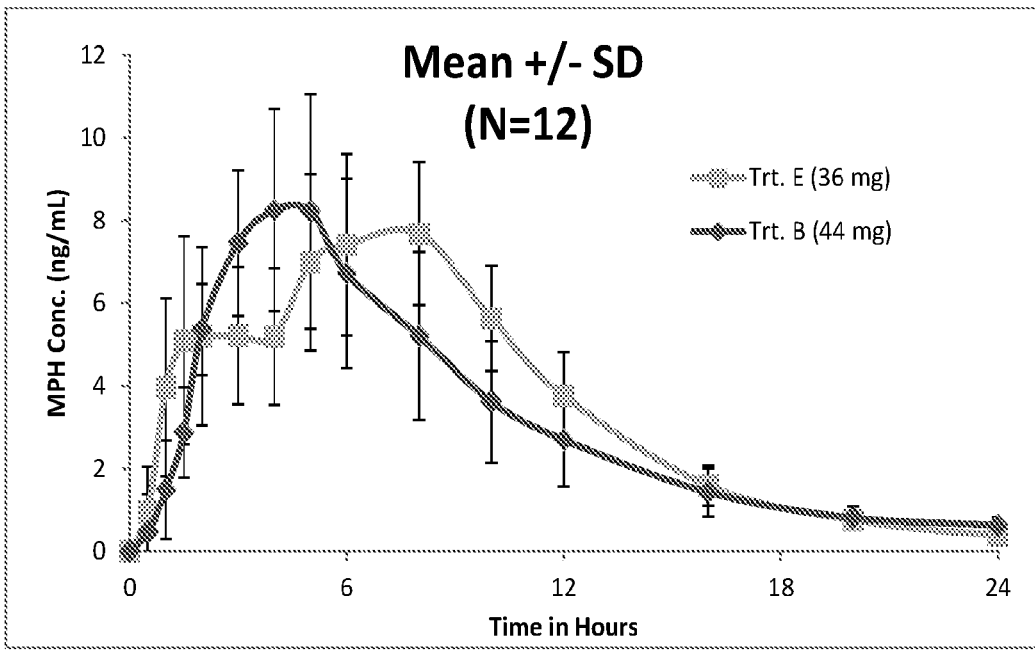
FIG. 9 provides a graph showing the mean plasma concentration of methylphenidate for Treatment B (Formulation 2) and E (Concerta®) in connection with Example 6.
Figure 10:
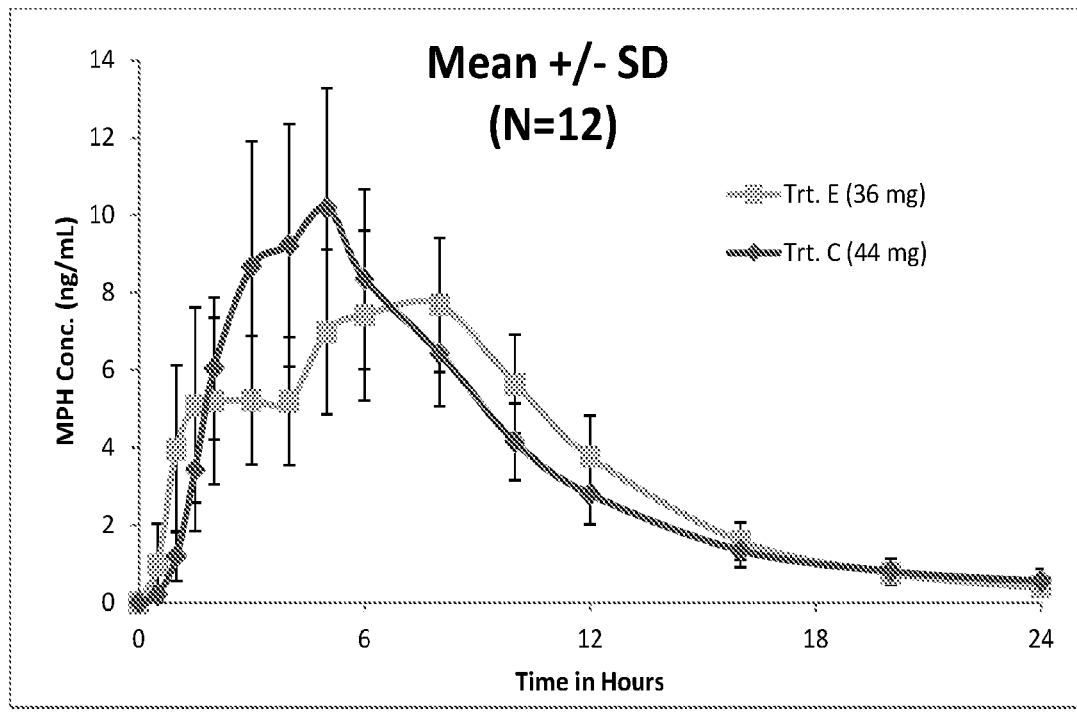
FIG. 10 provides a graph showing the mean plasma concentration of methylphenidate for Treatment C (Formulation 3) and E (Concerta®) in connection with Example 6.
Figure 11:
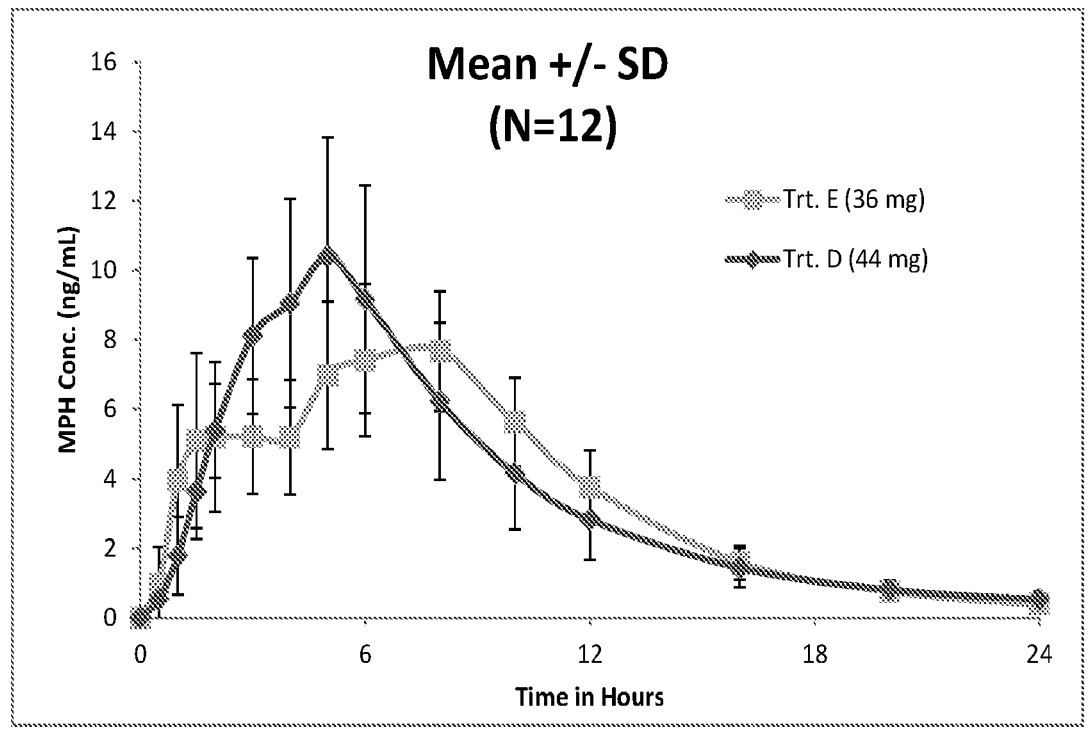
FIG. 11 provides a graph showing the mean plasma concentration of methylphenidate for Treatment D (Formulation 4) and E (Concerta®) in connection with Example 6.
Figure 12:
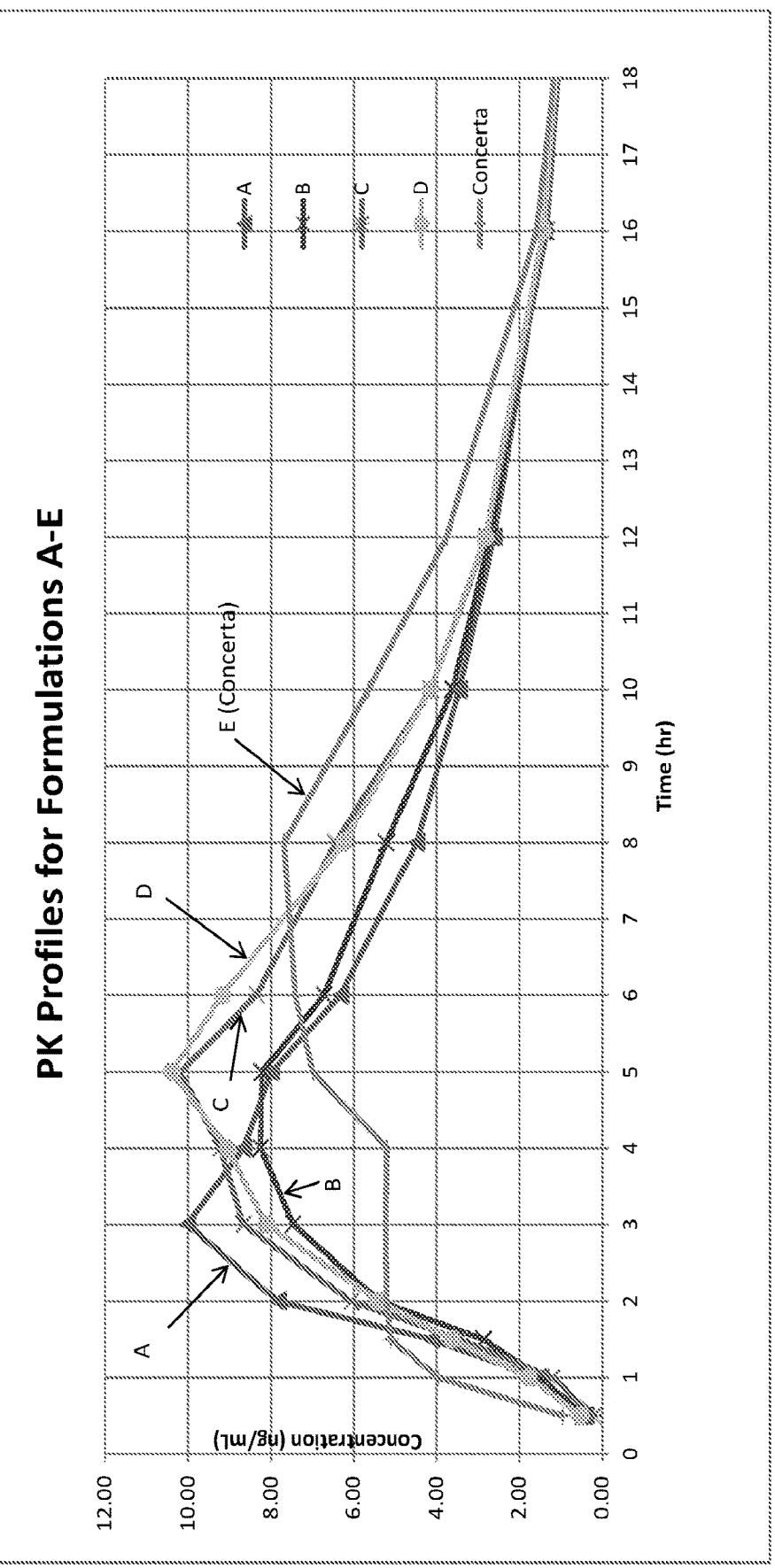
FIG. 12 provides a graph showing the mean plasma concentration for Treatments A-D (Formulations 1-4) and E (Concerta®) in connection with Example 6.
Figure 13:
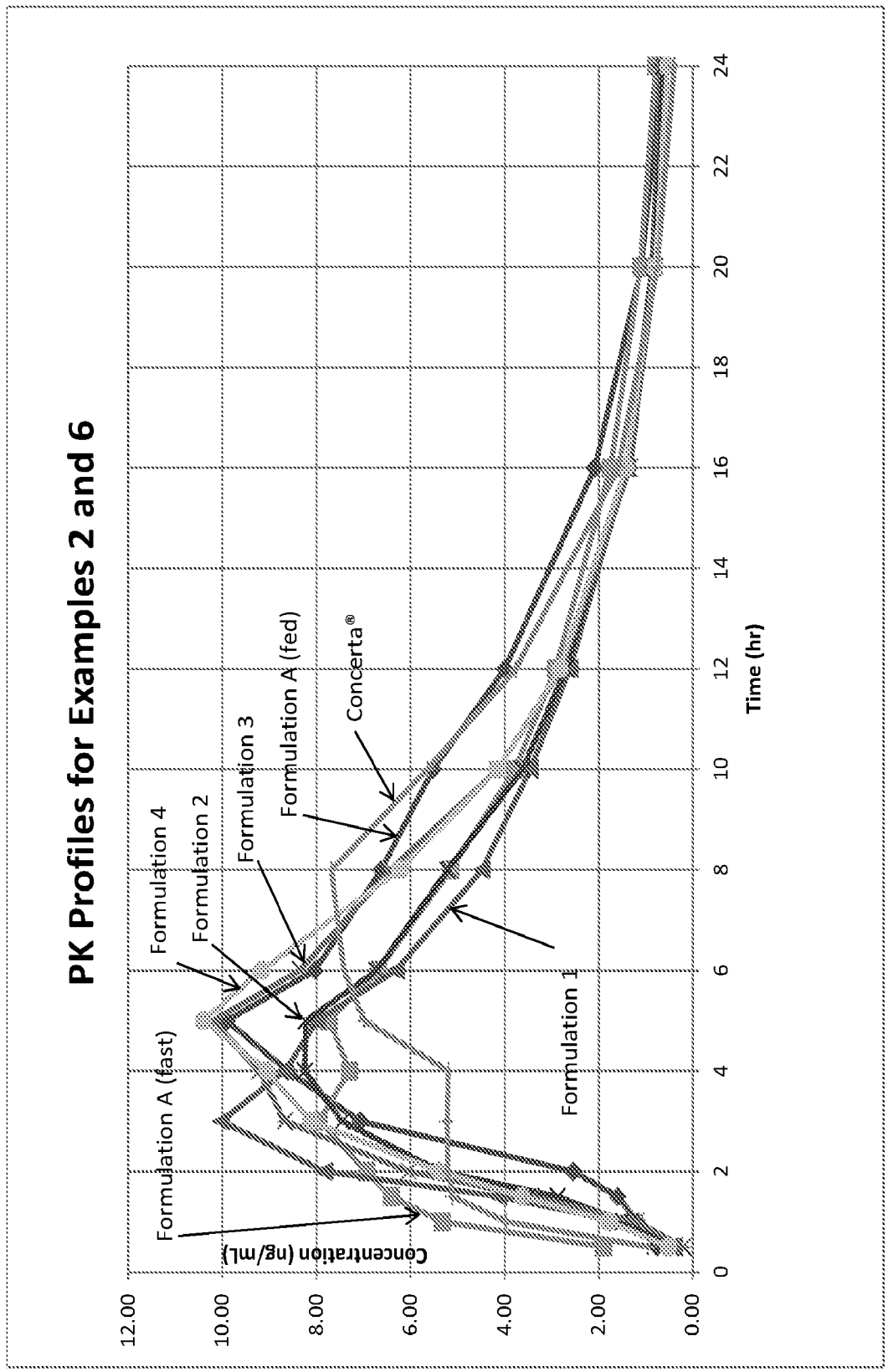
FIG. 13 provides a graph showing the mean plasma concentration for Formulation A (fasting and fed conditions), Formulations 1-4, and Concerta® in connection with Examples 2 and 6.

Formulations 1, 2 above (Example 3) and 2(a) were tested in-vitro for dissolution characteristics using a USP Apparatus 2 as set forth above in Example 2. Formulation 2(a) was prepared identically to Formulation 2 with the exception that a 12 mg coating weight was used for the barrier layer instead of a 24 mg coating weight as in Formulation 2. The results of the dissolution experiments are provided in FIGS. 6 and 7. FIG. 7 shows an expanded view of the 0 to 2 hour time frame. As shown in FIGS. 6 and 7, Formulation 2 showed delayed release of methylphenidate relative to Formulation 2(a) (with decreased coating weight of the barrier layer) and Formulation 1 without the barrier layer.

Example 6: In-Vivo Pharmacokinetic Analysis of Methylphenidate Dosage Forms

Formulations 1, 2, 3 and 4 were tested in-vivo in human subjects to determine the pharmacokinetics of methylphenidate delivered from various dosage forms. The above formulations were compared with a commercial methylphenidate product (Concerta® Extended Release Tablets 36 mg).

Materials and Methods

Study Design: A single-center, open-label, randomized, five-treatment, five-way crossover, single-dose, phase I study in 12 healthy adult volunteers under fed conditions. A total of 9 male and 3 female subjects completed the study. The treatment conditions are provided below in Table 14.

TABLE 14

| | |
|---|---|
| Formulation 1 (Treatment A) | 44 mg methylphenidate HCl; Dose: 44 mg (one capsule, single oral dose) |
| Formulation 2 (Treatment B) | 44 mg methylphenidate HCl; Dose: 44 mg (one capsule, single oral dose) |
| Formulation 3 (Treatment C) | 44 mg methylphenidate HCl; Dose: 44 mg (one capsule, single oral dose) |
| Formulation 4 (Treatment D) | 44 mg methylphenidate HCl; Dose: 44 mg (one capsule, single oral dose) |
| Concerta ® (Treatment E) | Concerta ® Extended Release Tablets 36 mg; Dose: 36 mg (one tablet, single oral dose) |
| Drug Administration | One capsule of one of Formulations 1-4 or one tablet of Concerta ® Extended Release Tablets 36 mg orally administered with 240 ml of water in the morning in each of the five study periods. |
| Blood Sampling Schedule | −0.5(predose), 0.5, 1.0, 1.5, 2.0, 3.0, 4.0, 5.0. 6.0, 8.0, 10, 12, 16, 20, 24, 36 and 48 hr post dose (a total of 17 samples per subject in one period) |
| Analytical Method | Concentrations of methylphenidate in plasma were quantified using a validated LC-MS/MS method as appropriate. |
| Pharmacokinetic Parameters | The following parameters of methylphenidate were determined using WinNolin ®: <br> 1. Peak concentration ($C_{max}$) <br> 2. Time to reach peak concentration ($T_{max}$) <br> 3. Area under the plasma concentration-time curve from time zero to time of last quantifiable concentration ($AUC_{0-t}$) <br> 4. Area under the plasma concentration-time curve from time zero to infinity ($AUC_{0-\infty}$) <br> 5. Elimination rate constant ($\lambda_z$) <br> 6. Terminal elimination half-life ($T_{1/2}$) <br> 7. Relative bioavailability |

Results

The results of the pharmacokinetic study are provided below in Tables 15-24 and in FIGS. 8-13.

TABLE 15

| Treatment A (Formulation 1) methylphenidate HCl blood plasma conc. in ng/mL | | | | | | | | | | | | | | | |
|---|---|---|---|---|---|---|---|---|---|---|---|---|---|---|---|
| Time | # 001 | #002 | # 003 | # 004 | # 005 | # 006 | # 007 | # 008 | # 009 | # 010 | # 012 | # 015 | Mean | SD | SEM |
| 0 | 0 | 0 | 0 | 0 | 0 | 0 | 0 | 0 | 0 | 0 | 0 | 0 | 0.00 | 0.00 | 0.00 |
| 0.5 | 0 | 0.104 | 0.174 | 0 | 0.79 | 0.174 | 1.207 | 0.372 | 0.742 | 0.296 | 0 | 0.832 | 0.39 | 0.40 | 0.12 |
| 1 | 0.684 | 0.226 | 0.826 | 0.124 | 1.951 | 1.879 | 2.804 | 1.357 | 1.903 | 2.044 | 0.208 | 4.369 | 1.53 | 1.25 | 0.36 |
| 1.5 | 4.216 | 0.559 | 2.861 | 3.75 | 4.552 | 6.268 | 5.423 | 5.869 | 3.292 | 3.756 | 1.93 | 7.042 | 4.13 | 1.86 | 0.54 |
| 2 | 7.826 | 2.222 | 10.04 | 8.071 | 5.914 | 8.604 | 10.61 | 13.21 | 4.211 | 5.024 | 7.735 | 10.49 | 7.83 | 3.10 | 0.89 |
| 3 | 9.728 | 12.01 | 12.65 | 9.292 | 7.96 | 7.678 | 10.93 | 16.5 | 6.531 | 8.564 | 10.32 | 8.151 | 10.03 | 2.73 | 0.79 |
| 4 | 7.117 | 13.4 | 10.16 | 8.272 | 7.845 | 6.098 | 9.887 | 12.84 | 7.083 | 7.229 | 7.761 | 6.284 | 8.66 | 2.42 | 0.70 |
| 5 | 6.812 | 18.17 | 8.892 | 7.248 | 6.957 | 5.287 | 7.828 | 9.738 | 7.486 | 5.139 | 6.883 | 5.472 | 7.99 | 3.49 | 1.01 |
| 6 | 5.454 | 14.21 | 6.939 | 5.921 | 5.028 | 3.754 | 7.479 | 7.046 | 6.231 | 4.242 | 4.846 | 4.585 | 6.31 | 2.75 | 0.79 |
| 8 | 4.274 | 9.351 | 4.646 | 4.002 | 3.534 | 2.928 | 5.919 | 4.531 | 4.818 | 2.987 | 3.827 | 2.946 | 4.48 | 1.77 | 0.51 |
| 10 | 3.55 | 9.625 | 3.022 | 3.367 | 2.785 | 2.2 | 4.387 | 2.799 | 3.219 | 2.077 | 2.492 | 1.94 | 3.46 | 2.06 | 0.60 |
| 12 | 2.975 | 7.592 | 2.008 | 2.284 | 2.015 | 1.73 | 3.457 | 2.013 | 2.534 | 1.722 | 1.592 | 1.424 | 2.61 | 1.67 | 0.48 |
| 16 | 1.386 | 3.527 | 0.777 | 1.317 | 0.914 | 1.116 | 2.194 | 1.049 | 1.554 | 0.976 | 0.998 | 0.957 | 1.40 | 0.77 | 0.22 |
| 20 | 0.909 | 1.707 | 0.328 | 0.704 | 0.661 | 0.871 | 1.373 | 0.776 | 0.914 | 0.682 | 0.672 | 0.767 | 0.86 | 0.36 | 0.10 |
| 24 | 0.804 | 1.115 | 0.175 | 0.887 | 0.525 | 0.741 | 1.108 | 0.582 | 0.79 | 0.545 | 0.416 | 0.567 | 0.69 | 0.28 | 0.08 |
| 36 | 0 | 0.267 | 0 | 0.373 | 0 | 0 | 0.357 | 0.379 | 0 | 0.374 | 0 | 0.359 | 0.18 | 0.19 | 0.05 |
| 48 | 0 | 0 | 0 | 0 | 0 | 0 | 0 | 0.2 | 0 | 0 | 0 | 0.307 | 0.04 | 0.10 | 0.03 |

TABLE 16

| Treatment B (Formulation 2) methylphenidate HCl blood plasma conc. in ng/mL | | | | | | | | | | | | | | | |
|---|---|---|---|---|---|---|---|---|---|---|---|---|---|---|---|
| Time | # 001 | #002 | # 003 | # 004 | # 005 | # 006 | # 007 | # 008 | # 009 | # 010 | # 012 | # 015 | Mean | SD | SEM |
| 0 | 0 | 0 | 0 | 0 | 0 | 0 | 0 | 0 | 0 | 0 | 0 | 0 | 0.00 | 0.00 | 0.00 |
| 0.5 | 0 | 0 | 0.884 | 0 | 0.271 | 0 | 0.227 | 3.168 | 0 | 0 | 0 | 0.932 | 0.46 | 0.92 | 0.27 |
| 1 | 0.865 | 0.654 | 2.051 | 0.319 | 2.202 | 1.24 | 1.263 | 4.747 | 0.997 | 1.6 | 0.338 | 1.541 | 1.48 | 1.19 | 0.34 |
| 1.5 | 2.132 | 2.924 | 2.761 | 1.589 | 3.436 | 1.933 | 3.058 | 5.612 | 2.391 | 3.977 | 1.932 | 2.711 | 2.87 | 1.10 | 0.32 |
| 2 | 5.613 | 6.638 | 4.838 | 5.845 | 4.021 | 3.866 | 4.899 | 7.439 | 5.075 | 6.163 | 4.061 | 5.949 | 5.37 | 1.11 | 0.32 |
| 3 | 7.173 | 8.128 | 7.747 | 8.452 | 5.866 | 4.161 | 7.893 | 11.1 | 6.318 | 8.06 | 8.738 | 5.882 | 7.46 | 1.76 | 0.51 |
| 4 | 8.139 | 14.47 | 7.815 | 9.075 | 5.156 | 5.299 | 8.3 | 9.994 | 7.193 | 8.625 | 8.568 | 6.366 | 8.25 | 2.44 | 0.71 |
| 5 | 7.34 | 16.43 | 7.124 | 8.12 | 5.314 | 7.194 | 9.438 | 8.748 | 6.832 | 8.653 | 7.599 | 5.877 | 8.22 | 2.84 | 0.82 |
| 6 | 5.627 | 12.66 | 6.768 | 7.707 | 4.342 | 5.95 | 8.618 | 6.401 | 4.829 | 7.677 | 5.261 | 4.796 | 6.72 | 2.29 | 0.66 |
| 8 | 4.899 | 8.571 | 8.115 | 5.889 | 2.928 | 4.337 | 8.13 | 3.738 | 3.643 | 5.296 | 3.573 | 3.37 | 5.21 | 2.03 | 0.59 |
| 10 | 4.24 | 5.492 | 5.014 | 4.812 | 1.966 | 3.174 | 6.235 | 2.349 | 2.453 | 3.143 | 2.252 | 2.307 | 3.62 | 1.47 | 0.42 |
| 12 | 3.427 | 3.94 | 3.102 | 4.007 | 1.67 | 2.313 | 4.852 | 1.849 | 2.182 | 2.094 | 1.454 | 1.477 | 2.70 | 1.14 | 0.33 |
| 16 | 1.702 | 2.322 | 1.581 | 1.737 | 0.767 | 1.161 | 2.512 | 1.136 | 1.432 | 1.261 | 0.646 | 0.811 | 1.42 | 0.59 | 0.17 |
| 20 | 0.929 | 1.196 | 0.77 | 1.012 | 0.553 | 0.691 | 1.258 | 0.79 | 1.027 | 0.603 | 0.382 | 0.477 | 0.81 | 0.28 | 0.08 |
| 24 | 0.652 | 0.854 | 0.427 | 0.658 | 0.472 | 0.584 | 0.932 | 0.74 | 0.849 | 0.595 | 0.277 | 0.452 | 0.62 | 0.20 | 0.06 |
| 36 | 0 | 0.124 | 0 | 0 | 0.309 | 0.217 | 0.107 | 0.267 | 0.124 | 0.402 | 0 | 0.424 | 0.16 | 0.16 | 0.05 |
| 48 | 0 | 0 | 0 | 0 | 0.129 | 0 | 0 | 0.352 | 0 | 0.229 | 0 | 0.226 | 0.08 | 0.12 | 0.04 |

TABLE 17

| Treatment C (Formulation 3) methylphenidate HCl blood plasma conc. in ng/mL | | | | | | | | | | | | | | | |
|---|---|---|---|---|---|---|---|---|---|---|---|---|---|---|---|
| Time | # 001 | #002 | # 003 | # 004 | # 005 | # 006 | # 007 | # 008 | # 009 | # 010 | # 012 | # 015 | Mean | SD | SEM |
| 0 | 0 | 0 | 0 | 0 | 0 | 0 | 0 | 0 | 0 | 0 | 0 | 0 | 0.00 | 0.00 | 0.00 |
| 0.5 | 0 | 0 | 0.291 | 0 | 0.246 | 0 | 0.209 | 0.505 | 0.395 | 0 | 0.159 | 0.585 | 0.20 | 0.21 | 0.06 |
| 1 | 0.263 | 1.696 | 1.365 | 0 | 0.641 | 0.887 | 1.415 | 1.719 | 2.219 | 1.242 | 1.6 | 1.337 | 1.20 | 0.64 | 0.19 |
| 1.5 | 3.44 | 2.594 | 2.707 | 1.358 | 3.085 | 2.717 | 4.603 | 7.537 | 3.977 | 4.021 | 3.443 | 1.73 | 3.43 | 1.59 | 0.46 |
| 2 | 6.501 | 3.896 | 6.002 | 7.319 | 3.708 | 3.791 | 8.322 | 9.232 | 4.496 | 7.445 | 6.36 | 5.523 | 6.05 | 1.84 | 0.53 |
| 3 | 8.868 | 5.877 | 6.431 | 14.32 | 6.034 | 6.567 | 11.97 | 14.52 | 7.871 | 7.199 | 8.985 | 5.395 | 8.67 | 3.23 | 0.93 |
| 4 | 10.68 | 6.029 | 7.52 | 12.11 | 7.83 | 6.549 | 10.37 | 16.67 | 10.75 | 9.379 | 6.654 | 6.175 | 9.23 | 3.13 | 0.90 |
| 5 | 12.61 | 15.09 | 8.029 | 11.26 | 7.812 | 5.864 | 10.13 | 15.35 | 10.86 | 10.48 | 6.456 | 8.338 | 10.19 | 3.08 | 0.89 |
| 6 | 9.703 | 12.95 | 7.535 | 8.908 | 6.703 | 5.002 | 8.857 | 10.89 | 8.266 | 9.228 | 4.65 | 7.555 | 8.35 | 2.33 | 0.67 |
| 8 | 7.065 | 8.475 | 7.016 | 7.373 | 4.378 | 3.73 | 6.664 | 6.46 | 5.512 | 6.603 | 7.851 | 6.059 | 6.43 | 1.36 | 0.39 |
| 10 | 4.79 | 6.159 | 4.213 | 4.363 | 2.594 | 2.593 | 5.096 | 4.183 | 3.691 | 4.247 | 4.287 | 3.575 | 4.15 | 0.99 | 0.29 |
| 12 | 3.292 | 3.756 | 2.596 | 3.92 | 1.753 | 1.718 | 3.937 | 2.634 | 2.514 | 2.82 | 2.126 | 2.442 | 2.79 | 0.78 | 0.23 |
| 16 | 1.476 | 1.908 | 1.327 | 1.745 | 0.708 | 0.919 | 2.162 | 1.204 | 1.302 | 1.255 | 0.907 | 1.139 | 1.34 | 0.43 | 0.12 |
| 20 | 0.79 | 0.861 | 0.724 | 1.124 | 0.364 | 0.66 | 1.726 | 0.726 | 0.696 | 0.726 | 0.511 | 0.692 | 0.80 | 0.34 | 0.10 |

TABLE 17-continued

Treatment C (Formulation 3) methylphenidate HCl blood plasma conc. in ng/mL

| Time | # 001 | #002 | # 003 | # 004 | # 005 | # 006 | # 007 | # 008 | # 009 | # 010 | # 012 | # 015 | Mean | SD | SEM |
|---|---|---|---|---|---|---|---|---|---|---|---|---|---|---|---|
| 24 | 0.505 | 0.565 | 0.396 | 0.908 | 0.241 | 0.403 | 1.381 | 0.573 | 0.455 | 0.504 | 0.239 | 0.422 | 0.55 | 0.31 | 0.09 |
| 36 | 0 | 0.121 | 0 | 0.193 | 0 | 0 | 0.326 | 0.313 | 0 | 0.315 | 0 | 0 | 0.11 | 0.14 | 0.04 |
| 48 | 0 | 0 | 0 | 0 | 0 | 0 | 0.26 | 0.29 | 0 | 0 | 0 | 0 | 0.05 | 0.11 | 0.03 |

TABLE 18

Treatment D (Formulation 4) methylphenidate HCl blood plasma conc. in ng/mL

| Time | # 001 | #002 | # 003 | # 004 | # 005 | # 006 | # 007 | # 008 | # 009 | # 010 | # 012 | # 015 | Mean | SD | SEM |
|---|---|---|---|---|---|---|---|---|---|---|---|---|---|---|---|
| 0 | 0 | 0 | 0 | 0 | 0 | 0 | 0 | 0 | 0 | 0 | 0 | 0 | 0.00 | 0.00 | 0.00 |
| 0.5 | 0 | 0 | 0.142 | 0 | 0.327 | 2.333 | 0.158 | 0.861 | 0.388 | 0.209 | 0.95 | 0.843 | 0.52 | 0.67 | 0.19 |
| 1 | 0.564 | 1.301 | 1.77 | 0.512 | 1.315 | 4.416 | 0.547 | 1.954 | 1.79 | 2.825 | 1.758 | 2.563 | 1.78 | 1.12 | 0.32 |
| 1.5 | 2.818 | 5.522 | 3.352 | 2.663 | 3.638 | 4.482 | 2.067 | 3.46 | 2.689 | 6.838 | 3.094 | 2.962 | 3.63 | 1.36 | 0.39 |
| 2 | 5.491 | 8.955 | 5.523 | 5.699 | 5.441 | 4.413 | 3.652 | 5.319 | 4.414 | 6.43 | 4.696 | 4.596 | 5.39 | 1.35 | 0.39 |
| 3 | 7.397 | 7.917 | 9.339 | 13.026 | 6.753 | 5.658 | 5.73 | 9.366 | 6.601 | 11.309 | 7.258 | 7.119 | 8.12 | 2.25 | 0.65 |
| 4 | 8.314 | 12.234 | 8.768 | 12.601 | 6.751 | 5.808 | 6.734 | 15.503 | 6.575 | 9.188 | 9.745 | 6.403 | 9.05 | 3.01 | 0.87 |
| 5 | 7.189 | 17.347 | 13.999 | 12.096 | 6.708 | 5.517 | 9.187 | 12.962 | 9.81 | 8.693 | 12.45 | 8.876 | 10.40 | 3.43 | 0.99 |
| 6 | 5.892 | 15.844 | 10.864 | 10.022 | 5.073 | 4.441 | 13.308 | 10.349 | 8.658 | 8.542 | 8.69 | 8.387 | 9.17 | 3.28 | 0.95 |
| 8 | 3.971 | 10.189 | 7.997 | 7.262 | 3.448 | 2.99 | 9.154 | 7.596 | 5.701 | 5.285 | 5.111 | 6.106 | 6.23 | 2.26 | 0.65 |
| 10 | 2.522 | 7.047 | 4.535 | 5.275 | 2.136 | 2.072 | 6.22 | 4.795 | 3.895 | 3.264 | 2.99 | 5.052 | 4.15 | 1.61 | 0.46 |
| 12 | 2.051 | 4.901 | 2.794 | 4.049 | 1.648 | 1.76 | 4.679 | 2.986 | 3.019 | 1.819 | 1.838 | 2.309 | 2.82 | 1.16 | 0.33 |
| 16 | 1.107 | 2.251 | 1.7 | 1.89 | 0.723 | 1.088 | 2.284 | 1.553 | 1.699 | 1 | 0.599 | 1.223 | 1.43 | 0.56 | 0.16 |
| 20 | 0.625 | 0.971 | 0.906 | 1.164 | 0.472 | 0.769 | 1.231 | 0.91 | 0.951 | 0.644 | 0.326 | 0.636 | 0.80 | 0.27 | 0.08 |
| 24 | 0.423 | 0.656 | 0.519 | 0.884 | 0.307 | 0.442 | 0.874 | 0.505 | 0.754 | 0.442 | 0.152 | 0.417 | 0.53 | 0.22 | 0.06 |
| 36 | 0.285 | 0.167 | 0.121 | 0.309 | 0 | 0 | 0.168 | 0.363 | 0 | 0.343 | 0 | 0 | 0.15 | 0.15 | 0.04 |
| 48 | 0.16 | 0 | 0 | 0.142 | 0 | 0 | 0 | 0.228 | 0 | 0.231 | 0 | 0 | 0.06 | 0.10 | 0.03 |

TABLE 19

Treatment E (Concerta ®) methylphenidate HCl blood plasma conc. in ng/mL

| Time | # 001 | #002 | # 003 | # 004 | # 005 | # 006 | # 007 | # 008 | # 009 | # 010 | # 012 | # 015 | Mean | SD | SEM |
|---|---|---|---|---|---|---|---|---|---|---|---|---|---|---|---|
| 0 | 0 | 0 | 0 | 0 | 0 | 0 | 0 | 0 | 0 | 0 | 0 | 0 | 0.00 | 0.00 | 0.00 |
| 0.5 | 0.687 | 2.583 | 0.261 | 3.05 | 0 | 0.709 | 2.456 | 0 | 0.251 | 0.554 | 0.555 | 0.408 | 0.96 | 1.08 | 0.31 |
| 1 | 3.041 | 8.856 | 1.737 | 5.571 | 1.542 | 3.375 | 5.639 | 3.604 | 2.257 | 5.531 | 1.942 | 4.504 | 3.97 | 2.16 | 0.62 |
| 1.5 | 4.28 | 7.679 | 3.28 | 6.303 | 3.472 | 3.462 | 5.558 | 11.662 | 3.039 | 5.162 | 3.043 | 4.281 | 5.10 | 2.52 | 0.73 |
| 2 | 4.508 | 6.424 | 3.69 | 6.465 | 3.725 | 3.204 | 5.693 | 11.103 | 3.483 | 4.26 | 4.719 | 5.167 | 5.20 | 2.16 | 0.62 |
| 3 | 4.91 | 6.154 | 5.555 | 5.978 | 3.753 | 2.902 | 5.399 | 9.028 | 3.314 | 4.23 | 6.589 | 4.828 | 5.22 | 1.66 | 0.48 |
| 4 | 4.832 | 7.697 | 6.415 | 6.026 | 3.103 | 2.798 | 5.686 | 7.802 | 3.69 | 4.037 | 5.678 | 4.57 | 5.19 | 1.65 | 0.48 |
| 5 | 6.727 | 10.984 | 6.313 | 7.147 | 5.37 | 3.818 | 6.797 | 10.576 | 4.762 | 6.431 | 8.423 | 6.489 | 6.99 | 2.12 | 0.61 |
| 6 | 5.942 | 11.438 | 8.406 | 7.162 | 4.462 | 3.888 | 8.894 | 9.689 | 5.922 | 7.551 | 8.929 | 6.68 | 7.41 | 2.20 | 0.63 |
| 8 | 7.595 | 10.123 | 7.863 | 8.022 | 5.403 | 4.218 | 9.941 | 9.218 | 7.259 | 7.549 | 8.445 | 6.554 | 7.68 | 1.73 | 0.50 |
| 10 | 6.886 | 7.238 | 6.8 | 6.012 | 3.58 | 3.786 | 6.758 | 6.632 | 5.384 | 4.478 | 4.652 | 5.446 | 5.64 | 1.28 | 0.37 |
| 12 | 4.203 | 4.246 | 5.591 | 4.327 | 2.207 | 3.06 | 5.385 | 3.52 | 3.962 | 2.491 | 3.031 | 3.126 | 3.76 | 1.06 | 0.31 |
| 16 | 1.788 | 1.727 | 2.292 | 1.612 | 1.02 | 1.223 | 2.584 | 1.426 | 1.726 | 0.912 | 1.336 | 1.36 | 1.58 | 0.49 | 0.14 |
| 20 | 0.919 | 0.802 | 0.86 | 0.823 | 0.601 | 0.654 | 1.298 | 0.639 | 0.754 | 0.477 | 0.587 | 0.617 | 0.75 | 0.22 | 0.06 |
| 24 | 0.512 | 0.38 | 0.433 | 0.466 | 0.315 | 0.323 | 0.75 | 0.323 | 0.478 | 0.217 | 0.227 | 0.356 | 0.40 | 0.15 | 0.04 |
| 36 | 0 | 0 | 0 | 0 | 0 | 0 | 0 | 0 | 0 | 0 | 0 | 0 | 0.00 | 0.00 | 0.00 |
| 48 | 0 | 0 | 0 | 0 | 0 | 0 | 0 | 0 | 0 | 0 | 0 | 0 | 0.00 | 0.00 | 0.00 |

TABLE 20

Treatment A (Formulation 1)

| Subject # | Trt. | Corr. | # of Pts. | Lower | Upper | half-life | Tmax | Cmax | Tlast | Clast | AUClast | AUCinf | % Extr. | AUC(0-24) | F Comp. Concerta |
|---|---|---|---|---|---|---|---|---|---|---|---|---|---|---|---|
| # 001 | A | −0.9532 | 3 | 16 | 24 | 10.2 | 3.0 | 9.7 | 24.0 | 0.8 | 75.5 | 87.3 | 13.5 | 75.5 | 79.9 |
| # 002 | A | −0.9998 | 3 | 20 | 36 | 5.9 | 5.0 | 18.2 | 36.0 | 0.3 | 159.2 | 161.5 | 1.4 | 150.9 | 113.2 |
| # 003 | A | −0.9959 | 3 | 16 | 24 | 3.7 | 3.0 | 12.6 | 24.0 | 0.2 | 77.7 | 78.6 | 1.2 | 77.7 | 65.7 |
| # 004 | A | −0.9227 | 4 | 16 | 36 | 12.3 | 3.0 | 9.3 | 36.0 | 0.4 | 80.7 | 87.3 | 7.6 | 73.1 | 73.7 |

TABLE 20-continued

Treatment A (Formulation 1)

| Subject # | Trt. | Corr. | # of Pts. | Lower | Upper | half-life | Tmax | Cmax | Tlast | Clast | AUClast | AUCinf | % Extr. | AUC(0-24) | F Comp. Concerta |
|---|---|---|---|---|---|---|---|---|---|---|---|---|---|---|---|
| # 005 | A | −0.9579 | 4 | 12 | 24 | 6.4 | 3.0 | 8.0 | 24.0 | 0.5 | 64.4 | 69.2 | 7.0 | 64.4 | 97.6 |
| # 006 | A | −0.9757 | 4 | 12 | 24 | 9.9 | 2.0 | 8.6 | 24.0 | 0.7 | 60.2 | 70.8 | 15.0 | 60.2 | 102.0 |
| # 007 | A | −0.9956 | 3 | 20 | 36 | 8.0 | 3.0 | 10.9 | 36.0 | 0.4 | 108.8 | 112.9 | 3.7 | 100.0 | 81.2 |
| # 008 | A | −0.9936 | 3 | 24 | 48 | 15.6 | 3.0 | 16.5 | 48.0 | 0.2 | 101.8 | 106.2 | 4.2 | 92.5 | 78.5 |
| # 009 | A | −0.977 | 4 | 12 | 24 | 6.9 | 5.0 | 7.5 | 24.0 | 0.8 | 71.7 | 79.5 | 9.9 | 71.7 | 84.5 |
| # 010 | A | −0.9908 | 3 | 20 | 36 | 19.2 | 3.0 | 8.6 | 36.0 | 0.4 | 62.6 | 73.0 | 14.2 | 57.1 | 81.2 |
| # 012 | A | −0.9994 | 4 | 12 | 24 | 6.3 | 3.0 | 10.3 | 24.0 | 0.4 | 64.0 | 67.8 | 5.6 | 64.0 | 65.4 |
| # 015 | A | −0.9622 | 3 | 24 | 48 | 27.1 | 2.0 | 10.5 | 48.0 | 0.3 | 72.4 | 84.4 | 14.2 | 62.9 | 88.0 |
| Mean |  |  |  |  |  | 10.96 | 3.17 | 10.89 | 32.00 | 0.44 | 83.25 | 89.89 | 8.11 | 79.17 | 84.23 |
| SD |  |  |  |  |  | 6.74 | 0.94 | 3.34 | 9.34 | 0.22 | 28.27 | 26.57 | 5.13 | 25.98 | 14.23 |
| Median |  |  |  |  |  | 8.97 | 3.00 |  | 30.00 |  |  |  |  |  |  |
| MIN |  |  |  |  |  | 3.72 | 2.00 | 7.49 | 24.00 | 0.18 | 60.18 | 67.79 | 1.19 | 57.13 | 65.37 |
| MAX |  |  |  |  |  | 27.12 | 5.00 | 18.17 | 48.00 | 0.80 | 159.19 | 161.48 | 15.00 | 150.90 | 113.20 |
| SEM |  |  |  |  |  | 1.95 | 0.27 | 0.96 | 2.70 | 0.06 | 8.16 | 7.67 | 1.48 | 7.50 | 4.11 |
| % CV |  |  |  |  |  | 61.51 | 29.60 | 30.67 | 29.19 | 50.09 | 33.96 | 29.56 | 63.26 | 32.81 | 16.89 |

TABLE 21

Treatment B (Formulation 2)

| Subject # | Trt. | Corr. | # of Pts. | Lower | Upper | half-life | Tmax | Cmax | Tlast | Clast | AUClast | AUCinf | % Extr. | AUC(0-24) | F Comp. Concerta |
|---|---|---|---|---|---|---|---|---|---|---|---|---|---|---|---|
| # 001 | B | −0.9888 | 3 | 16 | 24 | 5.8 | 4.0 | 8.1 | 24.0 | 0.7 | 77.2 | 82.6 | 6.6 | 77.2 | 75.6 |
| # 002 | B | −0.9946 | 3 | 20 | 36 | 4.7 | 5.0 | 16.4 | 36.0 | 0.1 | 126.4 | 127.2 | 0.7 | 120.5 | 89.2 |
| # 003 | B | −0.9984 | 3 | 16 | 24 | 4.2 | 8.0 | 8.1 | 24.0 | 0.4 | 85.1 | 87.7 | 3.0 | 85.1 | 73.3 |
| # 004 | B | −0.9979 | 3 | 16 | 24 | 5.7 | 4.0 | 9.1 | 24.0 | 0.7 | 88.3 | 93.7 | 5.8 | 88.3 | 79.1 |
| # 005 | B | −0.9805 | 3 | 24 | 48 | 12.8 | 3.0 | 5.9 | 48.0 | 0.1 | 57.2 | 59.5 | 4.0 | 49.8 | 83.9 |
| # 006 | B | −0.9942 | 3 | 20 | 36 | 9.3 | 5.0 | 7.2 | 36.0 | 0.2 | 65.4 | 68.3 | 4.3 | 60.6 | 98.4 |
| # 007 | B | −0.9915 | 3 | 20 | 36 | 4.3 | 5.0 | 9.4 | 36.0 | 0.1 | 111.0 | 111.6 | 0.6 | 104.7 | 80.3 |
| # 008 | B | −0.7047 | 3 | 24 | 48 | 22.4 | 3.0 | 11.1 | 48.0 | 0.4 | 88.4 | 99.8 | 11.4 | 78.7 | 73.8 |
| # 009 | B | −0.9871 | 3 | 20 | 36 | 5.0 | 4.0 | 7.2 | 36.0 | 0.1 | 69.2 | 70.1 | 1.3 | 63.4 | 74.4 |
| # 010 | B | −0.9947 | 3 | 24 | 48 | 17.4 | 5.0 | 8.7 | 48.0 | 0.2 | 85.8 | 91.6 | 6.3 | 76.1 | 101.9 |
| # 012 | B | −0.9905 | 3 | 16 | 24 | 6.5 | 3.0 | 8.7 | 24.0 | 0.3 | 57.7 | 60.3 | 4.3 | 57.7 | 58.1 |
| # 015 | B | −0.9047 | 3 | 24 | 48 | 24.0 | 4.0 | 6.4 | 48.0 | 0.2 | 63.4 | 71.2 | 11.0 | 54.2 | 74.2 |
| Mean |  |  |  |  |  | 10.19 | 4.42 | 8.86 | 36.00 | 0.29 | 81.25 | 85.31 | 4.93 | 76.36 | 80.18 |
| SD |  |  |  |  |  | 7.25 | 1.38 | 2.77 | 10.23 | 0.19 | 21.16 | 20.88 | 3.56 | 21.19 | 11.92 |
| Median |  |  |  |  |  | 6.16 | 4.00 |  | 36.00 |  |  |  |  |  |  |
| MIN |  |  |  |  |  | 4.24 | 3.00 | 5.87 | 24.00 | 0.11 | 57.16 | 59.54 | 0.60 | 49.84 | 58.12 |
| MAX |  |  |  |  |  | 24.00 | 8.00 | 16.43 | 48.00 | 0.66 | 126.38 | 127.22 | 11.39 | 120.51 | 101.86 |
| SEM |  |  |  |  |  | 2.09 | 0.40 | 0.80 | 2.95 | 0.06 | 6.11 | 6.03 | 1.03 | 6.12 | 3.44 |
| % CV |  |  |  |  |  | 71.19 | 31.22 | 31.29 | 28.43 | 66.32 | 26.05 | 24.47 | 72.26 | 27.75 | 14.87 |

TABLE 22

Treatment C (Formulation 3)

| Subject # | Trt. | Corr. | # of Pts. | Lower | Upper | half-life | Tmax | Cmax | Tlast | Clast | AUClast | AUCinf | % Extr. | AUC(0-24) | F Comp. Concerta |
|---|---|---|---|---|---|---|---|---|---|---|---|---|---|---|---|
| # 001 | C | −0.9955 | 3 | 16 | 24 | 5.2 | 5.0 | 12.6 | 24.0 | 0.5 | 97.1 | 100.9 | 3.7 | 97.1 | 92.2 |
| # 002 | C | −0.9993 | 3 | 20 | 36 | 5.6 | 5.0 | 15.1 | 36.0 | 0.1 | 108.3 | 109.3 | 0.9 | 104.2 | 76.6 |
| # 003 | C | −1.000 | 3 | 16 | 24 | 4.6 | 5.0 | 8.0 | 24.0 | 0.4 | 79.2 | 81.8 | 3.2 | 79.2 | 68.4 |
| # 004 | C | −0.9914 | 3 | 20 | 36 | 6.1 | 3.0 | 14.3 | 36.0 | 0.2 | 112.4 | 114.0 | 1.5 | 105.7 | 96.3 |
| # 005 | C | −0.9909 | 3 | 16 | 24 | 5.1 | 4.0 | 7.8 | 24.0 | 0.2 | 60.5 | 62.3 | 2.9 | 60.5 | 87.7 |
| # 006 | C | −0.9936 | 3 | 16 | 24 | 6.7 | 3.0 | 6.6 | 24.0 | 0.4 | 56.1 | 60.0 | 6.5 | 56.1 | 86.4 |
| # 007 | C | −0.9217 | 3 | 24 | 48 | 10.0 | 3.0 | 12.0 | 48.0 | 0.3 | 122.5 | 126.3 | 3.0 | 108.8 | 90.8 |
| # 008 | C | −0.9126 | 3 | 24 | 48 | 24.4 | 4.0 | 16.7 | 48.0 | 0.3 | 121.7 | 131.9 | 7.7 | 112.7 | 97.5 |
| # 009 | C | −0.9939 | 3 | 16 | 24 | 5.3 | 5.0 | 10.9 | 24.0 | 0.5 | 83.4 | 86.9 | 4.0 | 83.4 | 92.2 |
| # 010 | C | −0.9783 | 3 | 20 | 36 | 14.1 | 5.0 | 10.5 | 36.0 | 0.3 | 93.1 | 99.5 | 6.4 | 88.2 | 110.7 |
| # 012 | C | −0.9968 | 3 | 16 | 24 | 4.2 | 3.0 | 9.0 | 24.0 | 0.2 | 73.2 | 74.7 | 1.9 | 73.2 | 72.0 |
| # 015 | C | −1.000 | 3 | 16 | 24 | 5.6 | 5.0 | 8.3 | 24.0 | 0.4 | 72.0 | 75.4 | 4.5 | 72.0 | 78.6 |
| Mean |  |  |  |  |  | 8.06 | 4.17 | 10.98 | 31.00 | 0.32 | 89.95 | 93.57 | 3.86 | 86.76 | 87.45 |
| SD |  |  |  |  |  | 5.86 | 0.94 | 3.21 | 9.52 | 0.12 | 22.86 | 23.88 | 2.13 | 19.16 | 11.97 |
| Median |  |  |  |  |  | 5.59 | 4.50 |  | 24.00 |  |  |  |  |  |  |
| MIN |  |  |  |  |  | 4.16 | 3.00 | 6.57 | 24.00 | 0.12 | 56.05 | 59.96 | 0.89 | 56.05 | 68.35 |

TABLE 22-continued

Treatment C (Formulation 3)

| Subject # | Trt. | Corr. | # of Pts. | Lower | Upper | half-life | Tmax | Cmax | Tlast | Clast | AUClast | AUCinf | % Extr. | AUC(0-24) | F Comp. Concerta |
|---|---|---|---|---|---|---|---|---|---|---|---|---|---|---|---|
| MAX | | | | | | 24.43 | 5.00 | 16.67 | 48.00 | 0.51 | 122.52 | 131.88 | 7.75 | 112.73 | 110.68 |
| SEM | | | | | | 1.69 | 0.27 | 0.93 | 2.75 | 0.03 | 6.60 | 6.89 | 0.61 | 5.53 | 3.46 |
| % CV | | | | | | 72.68 | 22.50 | 29.25 | 30.70 | 36.32 | 25.41 | 25.52 | 55.17 | 22.08 | 13.69 |

TABLE 23

Treatment D (Formulation 4)

| Subject # | Trt. | Corr. | # of Pts. | Lower | Upper | half-life | Tmax | Cmax | Tlast | Clast | AUClast | AUCinf | % Extr. | AUC(0-24) | F Comp. Concerta |
|---|---|---|---|---|---|---|---|---|---|---|---|---|---|---|---|
| # 001 | D | −0.9942 | 3 | 24 | 48 | 17.1 | 4.0 | 8.3 | 48.0 | 0.2 | 71.4 | 75.3 | 5.2 | 64.5 | 68.9 |
| # 002 | D | −0.9996 | 3 | 20 | 36 | 6.2 | 5.0 | 17.3 | 36.0 | 0.2 | 139.7 | 141.2 | 1.1 | 134.8 | 99.0 |
| # 003 | D | −0.9996 | 3 | 20 | 36 | 5.6 | 5.0 | 14.0 | 36.0 | 0.1 | 103.9 | 104.9 | 0.9 | 100.1 | 87.6 |
| # 004 | D | −0.9963 | 3 | 24 | 48 | 9.1 | 3.0 | 13.0 | 48.0 | 0.1 | 119.7 | 121.6 | 1.5 | 109.8 | 102.6 |
| # 005 | D | −1.000 | 3 | 16 | 24 | 6.5 | 3.0 | 6.8 | 24.0 | 0.3 | 56.0 | 58.9 | 4.9 | 56.0 | 83.0 |
| # 006 | D | −0.9913 | 3 | 16 | 24 | 6.2 | 4.0 | 5.8 | 24.0 | 0.4 | 56.3 | 60.2 | 6.5 | 56.3 | 86.7 |
| # 007 | D | −0.9967 | 3 | 20 | 36 | 5.4 | 6.0 | 13.3 | 36.0 | 0.2 | 112.6 | 113.9 | 1.2 | 106.3 | 81.9 |
| # 008 | D | −0.9952 | 3 | 24 | 48 | 20.9 | 4.0 | 15.5 | 48.0 | 0.2 | 113.8 | 120.7 | 5.7 | 105.1 | 89.2 |
| # 009 | D | −0.9707 | 3 | 16 | 24 | 6.8 | 5.0 | 9.8 | 24.0 | 0.8 | 82.1 | 89.5 | 8.3 | 82.1 | 95.0 |
| # 010 | D | −0.9921 | 3 | 24 | 48 | 25.6 | 3.0 | 11.3 | 48.0 | 0.2 | 89.9 | 98.5 | 8.7 | 81.8 | 109.5 |
| # 012 | D | −0.9979 | 3 | 16 | 24 | 4.0 | 5.0 | 12.5 | 24.0 | 0.2 | 74.6 | 75.5 | 1.2 | 74.6 | 72.8 |
| # 015 | D | −0.9924 | 3 | 16 | 24 | 5.2 | 5.0 | 8.9 | 24.0 | 0.4 | 79.1 | 82.2 | 3.8 | 79.1 | 85.7 |
| Mean | | | | | | 9.89 | 4.33 | 11.38 | 35.00 | 0.27 | 91.60 | 95.20 | 4.08 | 87.54 | 88.50 |
| SD | | | | | | 7.17 | 0.98 | 3.54 | 10.80 | 0.18 | 26.37 | 26.01 | 2.89 | 24.02 | 11.71 |
| Median | | | | | | 6.36 | 4.50 | | 36.00 | | | | | | |
| MIN | | | | | | 4.04 | 3.00 | 5.81 | 24.00 | 0.12 | 56.05 | 58.92 | 0.92 | 56.05 | 68.89 |
| MAX | | | | | | 25.64 | 6.00 | 17.35 | 48.00 | 0.75 | 139.70 | 141.21 | 8.68 | 134.77 | 109.52 |
| SEM | | | | | | 2.07 | 0.28 | 1.02 | 3.12 | 0.05 | 7.61 | 7.51 | 0.84 | 6.93 | 3.38 |
| % CV | | | | | | 72.54 | 22.72 | 31.10 | 30.87 | 67.41 | 28.78 | 27.32 | 70.95 | 27.44 | 13.23 |

TABLE 24

Treatment E (Concerta)

| Subject # | Trt. | Corr. | # of Pts. | Lower | Upper | half-life | Tmax | Cmax | Tlast | Clast | AUClast | AUCinf | % Extr. | AUC(0-24) |
|---|---|---|---|---|---|---|---|---|---|---|---|---|---|---|
| # 001 | E | −0.9993 | 3 | 16 | 24 | 4.4 | 8.0 | 7.6 | 24.0 | 0.5 | 86.2 | 89.5 | 3.7 | 86.2 |
| # 002 | E | −1 | 3 | 16 | 24 | 3.7 | 6.0 | 11.4 | 24.0 | 0.4 | 114.7 | 116.7 | 1.7 | 114.7 |
| # 003 | E | −0.9949 | 3 | 16 | 24 | 3.3 | 6.0 | 8.4 | 24.0 | 0.4 | 95.9 | 98.0 | 2.1 | 95.9 |
| # 004 | E | −0.9988 | 3 | 16 | 24 | 4.5 | 8.0 | 8.0 | 24.0 | 0.5 | 93.9 | 96.9 | 3.1 | 93.9 |
| # 005 | E | −0.9983 | 3 | 16 | 24 | 4.7 | 8.0 | 5.4 | 24.0 | 0.3 | 55.9 | 58.1 | 3.7 | 55.9 |
| # 006 | E | −0.9994 | 3 | 16 | 24 | 4.2 | 8.0 | 4.2 | 24.0 | 0.3 | 54.9 | 56.8 | 3.4 | 54.9 |
| # 007 | E | −0.9979 | 3 | 16 | 24 | 4.5 | 8.0 | 9.9 | 24.0 | 0.8 | 108.9 | 113.8 | 4.3 | 108.9 |
| # 008 | E | −0.9981 | 4 | 12 | 24 | 3.5 | 1.5 | 11.7 | 24.0 | 0.3 | 109.1 | 110.7 | 1.5 | 109.1 |
| # 009 | E | −0.9863 | 3 | 16 | 24 | 4.3 | 8.0 | 7.3 | 24.0 | 0.5 | 74.1 | 77.1 | 3.9 | 74.1 |
| # 010 | E | −0.9984 | 3 | 16 | 24 | 3.9 | 6.0 | 7.6 | 24.0 | 0.2 | 72.4 | 73.6 | 1.6 | 72.4 |
| # 012 | E | −0.9991 | 3 | 16 | 24 | 3.1 | 6.0 | 8.9 | 24.0 | 0.2 | 83.8 | 84.9 | 1.2 | 83.8 |
| # 015 | E | −0.9947 | 3 | 16 | 24 | 4.1 | 6.0 | 6.7 | 24.0 | 0.4 | 76.4 | 78.5 | 2.7 | 76.4 |
| Mean | | | | | | 4.02 | 6.63 | 8.09 | 24.00 | 0.40 | 85.51 | 87.86 | 2.74 | 85.51 |
| SD | | | | | | 0.52 | 1.90 | 2.21 | 0.00 | 0.15 | 19.86 | 20.18 | 1.07 | 19.86 |
| Median | | | | | | 4.15 | 7.00 | | 24.00 | | | | | |
| MIN | | | | | | 3.13 | 1.50 | 4.22 | 24.00 | 0.22 | 54.87 | 56.81 | 1.21 | 54.87 |
| MAX | | | | | | 4.72 | 8.00 | 11.66 | 24.00 | 0.75 | 114.71 | 116.71 | 4.26 | 114.71 |
| SEM | | | | | | 0.15 | 0.55 | 0.64 | 0.00 | 0.04 | 5.73 | 5.83 | 0.31 | 5.73 |
| % CV | | | | | | 12.83 | 28.63 | 27.29 | 0.00 | 36.41 | 23.22 | 22.97 | 38.97 | 23.22 |

As evidenced by the above data and FIGS. 8-13, each of Formulations 1-4 exhibited a rapid onset of action, increased plasma concentration relative to Concerta during the period 2-5 hours post administration, and a similar duration relative to Concerta. In addition, Formulations 3 and 4 exhibited increased plasma concentration relative to Concerta during the period 2-6 hours post administration.

Example 7: Demonstrating the Effect of the Barrier Layer on In-Vitro Dissolution of Formulation 4

In order to demonstrate the effect of the barrier layer on dissolution in Formulation 4, Formulation 4 and Formulation 4 including only the encapsulated drug composition without the addition of the barrier layer, drug layer and film coating layer were tested in-vitro for dissolution characteristics using a USP Apparatus 2 as set forth below.

Materials and Methods

The dissolution testing parameters were as follows:
Dissolution Medium: 950 mL of 0.1 N HCl;
Paddle Speed: 50 rpm;
Vessel Temperature: 37.0±0.5° C.;
Sampling Time Points: 0.25, 0.5, 1, 1.5, 2, 3, 6, 9, 12, and 24 hours;
Sampling Volume: 1 mL;
n=12 for (a) and n=6 for (b).

Results

Figure 14:
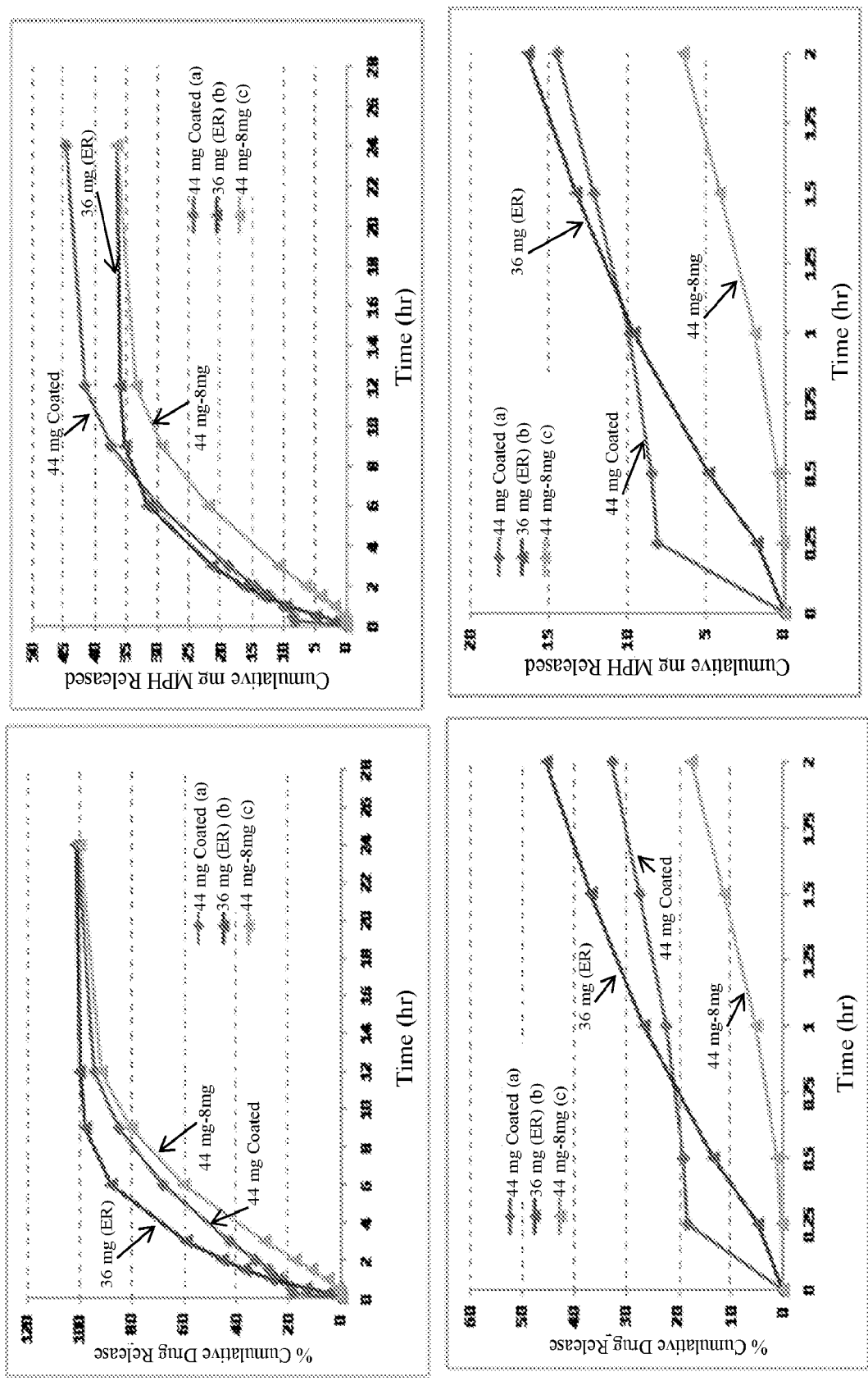
FIG. 14 provides graphs demonstrating the effect of the barrier layer on the in-vitro dissolution of Formulation 4. The two graphs on the left (top and bottom) show % cumulative release for (a) Formulation 4; (b) Formulation 4 including only the encapsulated drug composition without the addition of the barrier layer, drug layer and film coating layer; and (c) a calculated plot which represents Formulation 4 including the encapsulated drug composition with the barrier layer, but without the drug layer and film coating layer. The two graphs at the right (top and bottom) show cumulative MPH release in mg for (a) Formulation 4; (b) Formulation 4 including only the encapsulated drug composition without the addition of the barrier layer, drug layer and film coating layer; and (c) a calculated plot which represents the dissolution profile for Formulation 4 including the encapsulated drug composition and the barrier layer, but without the drug layer and film coating layer. The two bottom graphs have expanded scales for both the x- and y-axes.

The results of the dissolution experiments are presented in FIG. 14, which provides graphs demonstrating the effect of the barrier layer on the in-vitro dissolution of Formulation 4. The graphs at the top and bottom left show % cumulative release for (a) Formulation 4; (b) Formulation 4 including only the encapsulated drug composition without the addition of the barrier layer, drug layer and film coating layer; and (c) a calculated plot which represents Formulation 4 including the encapsulated drug composition with the barrier layer, but without the drug layer and film coating layer. The graphs at the top and bottom right show cumulative MPH release in mg for (a) Formulation 4; (b) Formulation 4 including only the encapsulated drug composition without the addition of the barrier layer, drug layer and film coating layer; and (c) a calculated plot which represents Formulation 4 including the encapsulated drug composition with the barrier layer, but without the drug layer and film coating layer. The top and bottom graphs differ with respect to scale of the x- and y-axes.

The values for the calculated (c) curves were obtained by subtracting 8 mg (based on a targeted drug layer coating of 8 mg) from the (a) values at each time point in the top and bottom right graphs. % cumulative drug release for the (c) curves in the graphs at the top and bottom left were calculated based on the calculated values in the graphs at top and bottom right. As shown in the graphs, release of MPH from the drug layer coating of Formulation 4 occurred within about 15 minutes, with initiation of release from the encapsulated drug composition of Formulation 4 occurring at about 30 minutes.

Example 8: Modified Formulations with Extended Release Profiles

In order to provide formulations having an extended release profile relative to Formulation 4, formulations including different barrier layers were evaluated against Formulation 4 and a formulation having the same drug composition and lacking a barrier layer.

Materials and Methods

A drug composition as set forth in Table 25 was manufactured and filled into size 4 HPMC capsules at 36 mg Methylphenidate HCl (MPH) dose strength as described above for Formulations 1-4 and in FIG. 1A.

TABLE 25

| | Formulation | | | | | | | | | |
|---|---|---|---|---|---|---|---|---|---|---|
| | MPH | SAIB | Triacetin | IPM | CAB | Cab-O-Sil® | Gelucire® 44/14 | BHT | Fill Wt (mg) | Capsule Size |
| Drug Composition | 20.00% | 37.86% | 29.12% | 6.40% | 4.80% | 0.80% | 1.00% | 0.02% | 180 | 4 (HPMC) |

The capsules were then coated with different barrier layers without a drug layer and without a film coating layer for the purpose of evaluation. Table 26 shows the composition of the barrier layer, the target coating weight and the measured weight gain.

TABLE 26

| | Composition of Barrier Layer | Batch No. | Target Wt Gain (mg) | Average Measured Wt Gain (mg) |
|---|---|---|---|---|
| 1 | No barrier layer coating | 0 | NA | NA |
| 2 | Acryl-EZE/Opadry AMB = 7:3 | a (Formulation 4)* | 24 | 23.6 |
| 3 | Acryl-EZE/Opadry AMB = 7:3 | b | 30 | 31.4 |
| 4 | Acryl-EZE/Opadry AMB = 7:3 | c | 36 | 36.9 |
| 5 | Acryl-EZE/Opadry AMB = 8:2 | d | 24 | 24.6 |
| 6 | Acryl-EZE/Opadry AMB = 8:2 | e | 30 | 30.4 |
| 7 | Acryl-EZE/Opadry AMB = 8:2 | f | 36 | 37.0 |
| 8 | Acryl-EZE/Opadry AMB = 9:1 | g | 24 | 24.3 |
| 9 | Acryl-EZE/Opadry AMB = 9:1 | h | 30 | 31.1 |
| 10 | Acryl-EZE/Opadry AMB = 9:1 | i | 36 | 34.7 |

*Formulation 4 (without drug layer and film coating layer).

The barrier layer solutions utilized for the barrier layer coatings on the capsules for the above referenced formulations were prepared and applied generally as set forth in FIG. 1B and as described in Example 3.

The coated capsules were subjected to dissolution testing for up to 2 hours in 0.1 N HCl. The dissolution parameters were as follows:
Dissolution Medium: 950 mL of 0.1 N HCl
Paddle Speed: 50 rpm
Vessel Temperature: 37.0±0.5° C.
Sampling Time Points: 5, 10, 15, 30, 45, 60, 90, 120 min
Sampling Volume: 1 mL Results The results of the dissolution experiments are provided in Tables 27-36.

TABLE 27

No Barrier Layer (0)

% cumulative release of methylphenidate Time (min)

| Sample ID | | 0 | 5 | 10 | 15 | 30 | 45 | 60 | 90 | 120 |
|---|---|---|---|---|---|---|---|---|---|---|
| 1 | (0) | 0.0 | 0.1 | 1.8 | 4.0 | 11.2 | 18.1 | 22.6 | 31.0 | 38.5 |
| 2 | (0) | 0.0 | 0.1 | 3.1 | 3.6 | 10.4 | 15.7 | 19.7 | 26.7 | 32.1 |
| 3 | (0) | 0.0 | 0.2 | 1.7 | 3.8 | 12.7 | 17.4 | 22.0 | 29.6 | 36.6 |
| 4 | (0) | 0.0 | 0.0 | 1.2 | 3.0 | 10.4 | 16.9 | 22.0 | 29.1 | 36.4 |
| | Mean (n = 4) | 0.0 | 0.1 | 1.9 | 3.6 | 11.2 | 17.0 | 21.6 | 29.1 | 35.9 |
| | SD | 0.0 | 0.1 | 0.8 | 0.4 | 1.1 | 1.0 | 1.3 | 1.8 | 2.7 |
| | Min | 0.0 | 0.0 | 1.2 | 3.0 | 10.4 | 15.7 | 19.7 | 26.7 | 32.1 |
| | Max | 0.0 | 0.2 | 3.1 | 4.0 | 12.7 | 18.1 | 22.6 | 31.0 | 38.5 |

TABLE 28

Barrier Layer (a) (Formulation 4*)

% cumulative release of methylphenidate Time (min)

| Sample ID | | 0 | 5 | 10 | 15 | 30 | 45 | 60 | 90 | 120 |
|---|---|---|---|---|---|---|---|---|---|---|
| 1 | (a) | 0.0 | 0.0 | 0.0 | 0.4 | 3.8 | 7.6 | 12.8 | 21.9 | 28.9 |
| 2 | (a) | 0.0 | 0.0 | 0.0 | 0.7 | 4.3 | 9.2 | 14.6 | 25.4 | 33.3 |
| 3 | (a) | 0.0 | 0.0 | 0.0 | 0.3 | 3.2 | 7.2 | 11.9 | 21.2 | 30.7 |
| 4 | (a) | 0.0 | 0.0 | 0.1 | 0.8 | 4.6 | 10.5 | 15.0 | 21.6 | 26.6 |
| | Mean (n = 4) | 0.0 | 0.0 | 0.0 | 0.6 | 4.0 | 8.6 | 13.6 | 22.5 | 29.9 |
| | SD | 0.0 | 0.0 | 0.1 | 0.2 | 0.6 | 1.5 | 1.5 | 2.0 | 2.9 |
| | Min | 0.0 | 0.0 | 0.0 | 0.3 | 3.2 | 7.2 | 11.9 | 21.2 | 26.6 |
| | Max | 0.0 | 0.0 | 0.1 | 0.8 | 4.6 | 10.5 | 15.0 | 25.4 | 33.3 |

*Formulation 4 (without drug layer and film coating layer).

TABLE 29

Barrier Layer (b)

% cumulative release of methylphenidate Time (min)

| Sample ID | | 0 | 5 | 10 | 15 | 30 | 45 | 60 | 90 | 120 |
|---|---|---|---|---|---|---|---|---|---|---|
| 1 | (b) | 0.0 | 0.0 | 0.0 | 1.0 | 4.5 | 8.6 | 12.5 | 20.0 | 34.2 |
| 2 | (b) | 0.0 | 0.0 | 0.0 | 0.7 | 3.1 | 6.8 | 10.7 | 19.8 | 28.9 |
| 3 | (b) | 0.0 | 0.0 | 0.0 | 0.6 | 3.7 | 10.5 | 16.8 | 23.9 | 30.5 |
| | Mean (n = 3) | 0.0 | 0.0 | 0.0 | 0.7 | 3.7 | 8.7 | 13.3 | 21.2 | 31.2 |
| | SD | 0.0 | 0.0 | 0.0 | 0.2 | 0.7 | 1.9 | 3.1 | 2.3 | 2.7 |
| | Min | 0.0 | 0.0 | 0.0 | 0.6 | 3.1 | 6.8 | 10.7 | 19.8 | 28.9 |
| | Max | 0.0 | 0.0 | 0.0 | 1.0 | 4.5 | 10.5 | 16.8 | 23.9 | 34.2 |

TABLE 30

Barrier Layer (c)

% cumulative release of methylphenidate Time (min)

| Sample ID | | 0 | 5 | 10 | 15 | 30 | 45 | 60 | 90 | 120 |
|---|---|---|---|---|---|---|---|---|---|---|
| 1 | (c) | 0.0 | 0.0 | 0.0 | 0.0 | 2.6 | 6.2 | 9.8 | 17.9 | 26.1 |
| 2 | (c) | 0.0 | 0.0 | 0.0 | 0.0 | 2.7 | 8.3 | 16.3 | 30.7 | 41.7 |
| 3 | (c) | 0.0 | 0.0 | 0.0 | 0.0 | 2.7 | 6.4 | 10.2 | 17.9 | 26.7 |
| 4 | (c) | 0.0 | 0.0 | 0.0 | 0.0 | 3.2 | 7.8 | 12.4 | 18.8 | 26.5 |
| | Mean (n = 4) | 0.0 | 0.0 | 0.0 | 0.0 | 2.8 | 7.2 | 12.2 | 21.3 | 30.2 |

TABLE 30-continued

Barrier Layer (c)

% cumulative release of methylphenidate Time (min)

| Sample ID | 0 | 5 | 10 | 15 | 30 | 45 | 60 | 90 | 120 |
|---|---|---|---|---|---|---|---|---|---|
| SD | 0.0 | 0.0 | 0.0 | 0.0 | 0.3 | 1.0 | 3.0 | 6.3 | 7.6 |
| Min | 0.0 | 0.0 | 0.0 | 0.0 | 2.6 | 6.2 | 9.8 | 17.9 | 26.1 |
| Max | 0.0 | 0.0 | 0.0 | 0.0 | 3.2 | 8.3 | 16.3 | 30.7 | 41.7 |

TABLE 31

Barrier Layer (d)

% cumulative release of methylphenidate Time (min)

| Sample ID | | 0 | 5 | 10 | 15 | 30 | 45 | 60 | 90 | 120 |
|---|---|---|---|---|---|---|---|---|---|---|
| 1 | (d) | 0.0 | 0.0 | 0.0 | 0.0 | 3.3 | 3.1 | 5.7 | 12.0 | 19.0 |
| 2 | (d) | 0.0 | 0.0 | 0.0 | 0.0 | 1.4 | 2.7 | 5.0 | 10.5 | 16.4 |
| 3 | (d) | 0.0 | 0.0 | 0.0 | 0.0 | 1.5 | 4.2 | 7.1 | 13.0 | 21.2 |
| | Mean (n = 3) | 0.0 | 0.0 | 0.0 | 0.0 | 2.0 | 3.3 | 5.9 | 11.8 | 18.9 |
| | SD | 0.0 | 0.0 | 0.0 | 0.0 | 1.1 | 0.7 | 1.1 | 1.2 | 2.4 |
| | Min | 0.0 | 0.0 | 0.0 | 0.0 | 1.4 | 2.7 | 5.0 | 10.5 | 16.4 |
| | Max | 0.0 | 0.0 | 0.0 | 0.0 | 3.3 | 4.2 | 7.1 | 13.0 | 21.2 |

TABLE 32

Barrier Layer (e)

% cumulative release of methylphenidate Time (min)

| Sample ID | | 0 | 5 | 10 | 15 | 30 | 45 | 60 | 90 | 120 |
|---|---|---|---|---|---|---|---|---|---|---|
| 1 | (e) | 0.0 | 0.0 | 0.0 | 0.0 | 1.0 | 2.6 | 4.3 | 8.6 | 13.7 |
| 2 | (e) | 0.0 | 0.0 | 0.0 | 0.0 | 0.9 | 2.8 | 5.0 | 10.6 | 17.0 |
| 3 | (e) | 0.0 | 0.0 | 0.0 | 0.0 | 1.5 | 3.4 | 5.5 | 10.2 | 14.9 |
| 4 | (e) | 0.0 | 0.0 | 0.0 | 0.0 | 1.1 | 3.3 | 5.5 | 10.8 | 17.3 |
| | Mean (n = 4) | 0.0 | 0.0 | 0.0 | 0.0 | 1.1 | 3.0 | 5.1 | 10.0 | 15.7 |
| | SD | 0.0 | 0.0 | 0.0 | 0.0 | 0.3 | 0.4 | 0.5 | 1.0 | 1.7 |
| | Min | 0.0 | 0.0 | 0.0 | 0.0 | 0.9 | 2.6 | 4.3 | 8.6 | 13.7 |
| | Max | 0.0 | 0.0 | 0.0 | 0.0 | 1.5 | 3.4 | 5.5 | 10.8 | 17.3 |

TABLE 33

Barrier Layer (f)

% cumulative release of methylphenidate Time (min)

| Sample ID | | 0 | 5 | 10 | 15 | 30 | 45 | 60 | 90 | 120 |
|---|---|---|---|---|---|---|---|---|---|---|
| 1 | (f) | 0.0 | 0.0 | 0.0 | 0.0 | 0.6 | 2.2 | 4.0 | 8.2 | 13.1 |
| 2 | (f) | 0.0 | 0.0 | 0.0 | 0.0 | 0.4 | 1.6 | 3.5 | 8.0 | 14.7 |
| 3 | (f) | 0.0 | 0.0 | 0.0 | 0.0 | 0.4 | 1.8 | 4.2 | 9.3 | 17.7 |
| | Mean (n = 3) | 0.0 | 0.0 | 0.0 | 0.0 | 0.5 | 1.9 | 3.9 | 8.5 | 15.2 |
| | SD | 0.0 | 0.0 | 0.0 | 0.0 | 0.2 | 0.3 | 0.3 | 0.7 | 2.3 |
| | Min | 0.0 | 0.0 | 0.0 | 0.0 | 0.4 | 1.6 | 3.5 | 8.0 | 13.1 |
| | Max | 0.0 | 0.0 | 0.0 | 0.0 | 0.6 | 2.2 | 4.2 | 9.3 | 17.7 |

TABLE 34

Barrier Layer (g)

| | | % cumulative release of methylphenidate Time (min) | | | | | | | |
|---|---|---|---|---|---|---|---|---|---|
| | Sample ID | 0 | 5 | 10 | 15 | 30 | 45 | 60 | 90 | 120 |
| 1 | (g) | 0.0 | 0.0 | 0.0 | 0.0 | 0.0 | 0.0 | 0.0 | 0.8 | 1.0 | 2.7 |
| 2 | (g) | 0.0 | 0.0 | 0.0 | 0.0 | 0.0 | 0.0 | 0.0 | 0.5 | 2.1 | 3.6 |
| 3 | (g) | 0.0 | 0.0 | 0.0 | 0.0 | 0.0 | 0.0 | 0.0 | 0.6 | 1.1 | 2.3 |
| | Mean (n = 3) | 0.0 | 0.0 | 0.0 | 0.0 | 0.0 | 0.0 | 0.0 | 0.6 | 1.4 | 2.9 |
| | SD | 0.0 | 0.0 | 0.0 | 0.0 | 0.0 | 0.0 | 0.0 | 0.1 | 0.6 | 0.7 |
| | Min | 0.0 | 0.0 | 0.0 | 0.0 | 0.0 | 0.0 | 0.0 | 0.5 | 1.0 | 2.3 |
| | Max | 0.0 | 0.0 | 0.0 | 0.0 | 0.0 | 0.0 | 0.0 | 0.8 | 2.1 | 3.6 |

TABLE 35

Barrier Layer (h)

| | | % cumulative release of methylphenidate Time (min) | | | | | | | |
|---|---|---|---|---|---|---|---|---|---|
| | Sample ID | 0 | 5 | 10 | 15 | 30 | 45 | 60 | 90 | 120 |
| 1 | (h) | 0.0 | 0.0 | 0.0 | 0.0 | 0.0 | 0.0 | 0.0 | 0.4 | 1.1 |
| 2 | (h) | 0.0 | 0.0 | 0.0 | 0.0 | 0.0 | 0.0 | 0.0 | 0.5 | 0.9 |
| 3 | (h) | 0.0 | 0.0 | 0.0 | 0.0 | 0.0 | 0.0 | 0.0 | 0.9 | 2.4 |
| | Mean (n = 4) | 0.0 | 0.0 | 0.0 | 0.0 | 0.0 | 0.0 | 0.0 | 0.6 | 1.5 |
| | SD | 0.0 | 0.0 | 0.0 | 0.0 | 0.0 | 0.0 | 0.0 | 0.2 | 0.8 |
| | Min | 0.0 | 0.0 | 0.0 | 0.0 | 0.0 | 0.0 | 0.0 | 0.4 | 0.9 |
| | Max | 0.0 | 0.0 | 0.0 | 0.0 | 0.0 | 0.0 | 0.0 | 0.9 | 2.4 |

TABLE 36

Barrier Layer (i)

| | | % cumulative release of methylphenidate Time (min) | | | | | | | |
|---|---|---|---|---|---|---|---|---|---|
| | Sample ID | 0 | 5 | 10 | 15 | 30 | 45 | 60 | 90 | 120 |
| 1 | (i) | 0.0 | 0.0 | 0.0 | 0.0 | 0.0 | 0.0 | 0.2 | 0.5 | 2.3 |
| 2 | (i) | 0.0 | 0.0 | 0.0 | 0.0 | 0.0 | 0.0 | 0.1 | 0.3 | 1.1 |
| 3 | (i) | 0.0 | 0.0 | 0.0 | 0.0 | 0.0 | 0.0 | 0.2 | 0.2 | 0.8 |
| 4 | (i) | 0.0 | 0.0 | 0.0 | 0.0 | 0.0 | 0.0 | 0.0 | 0.2 | 0.8 |
| | Mean (n = 4) | 0.0 | 0.0 | 0.0 | 0.0 | 0.0 | 0.0 | 0.1 | 0.3 | 1.3 |
| | SD | 0.0 | 0.0 | 0.0 | 0.0 | 0.0 | 0.0 | 0.1 | 0.1 | 0.7 |
| | Min | 0.0 | 0.0 | 0.0 | 0.0 | 0.0 | 0.0 | 0.0 | 0.2 | 0.8 |
| | Max | 0.0 | 0.0 | 0.0 | 0.0 | 0.0 | 0.0 | 0.2 | 0.5 | 2.3 |

Figure 15:
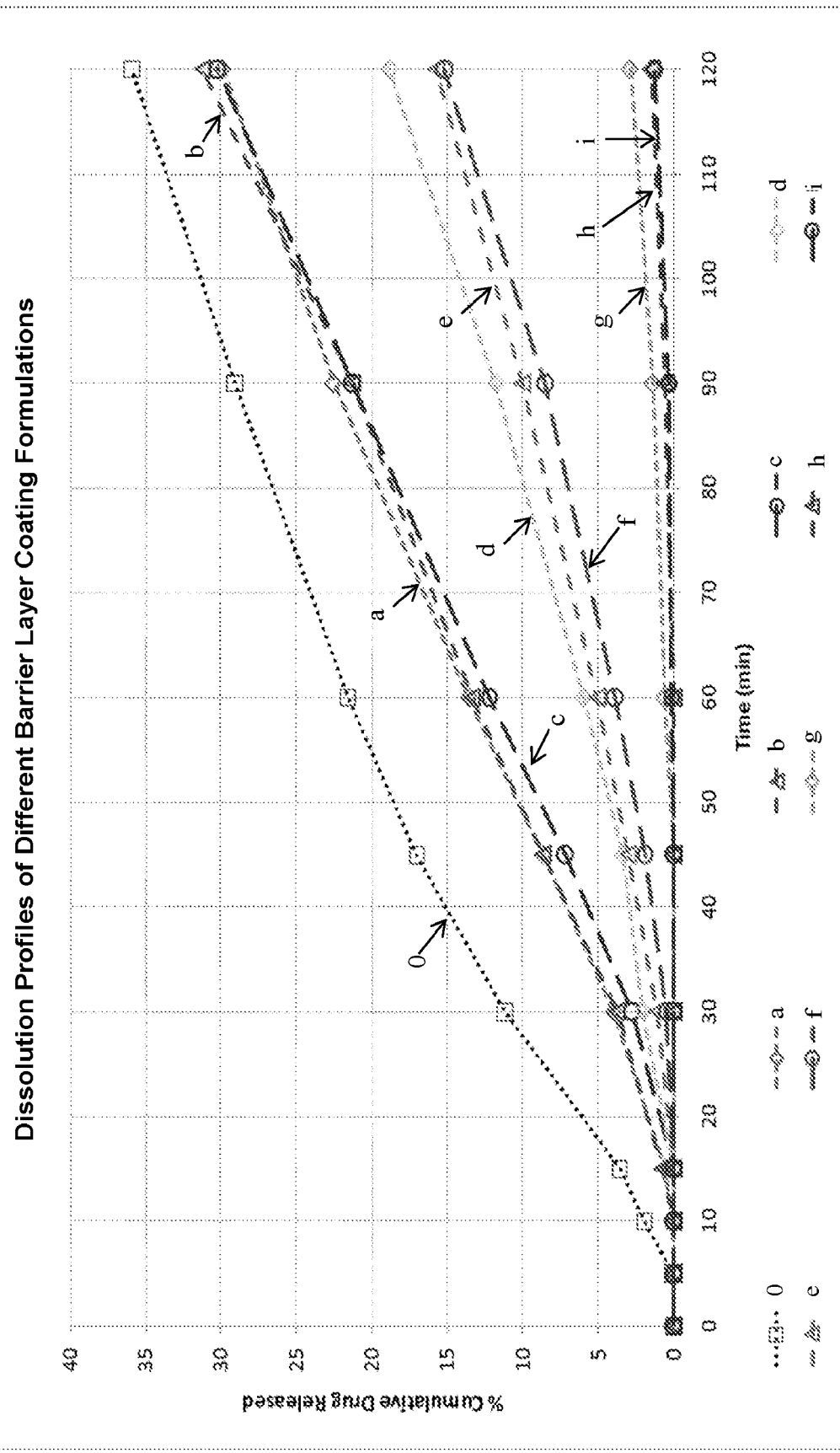
FIG. 15 provides a graph showing the dissolution profiles of different barrier layer coating formulations in connection with Example 8.

The dissolution profiles for the formulations are shown in FIG. 15. It is evident that the ratio of Acryl-EZE to Opadry AMB has an impact on the release of methylphenidate from the drug composition of the formulation, with increased ratios resulting in an increase in the delay of release.

Figure 16:
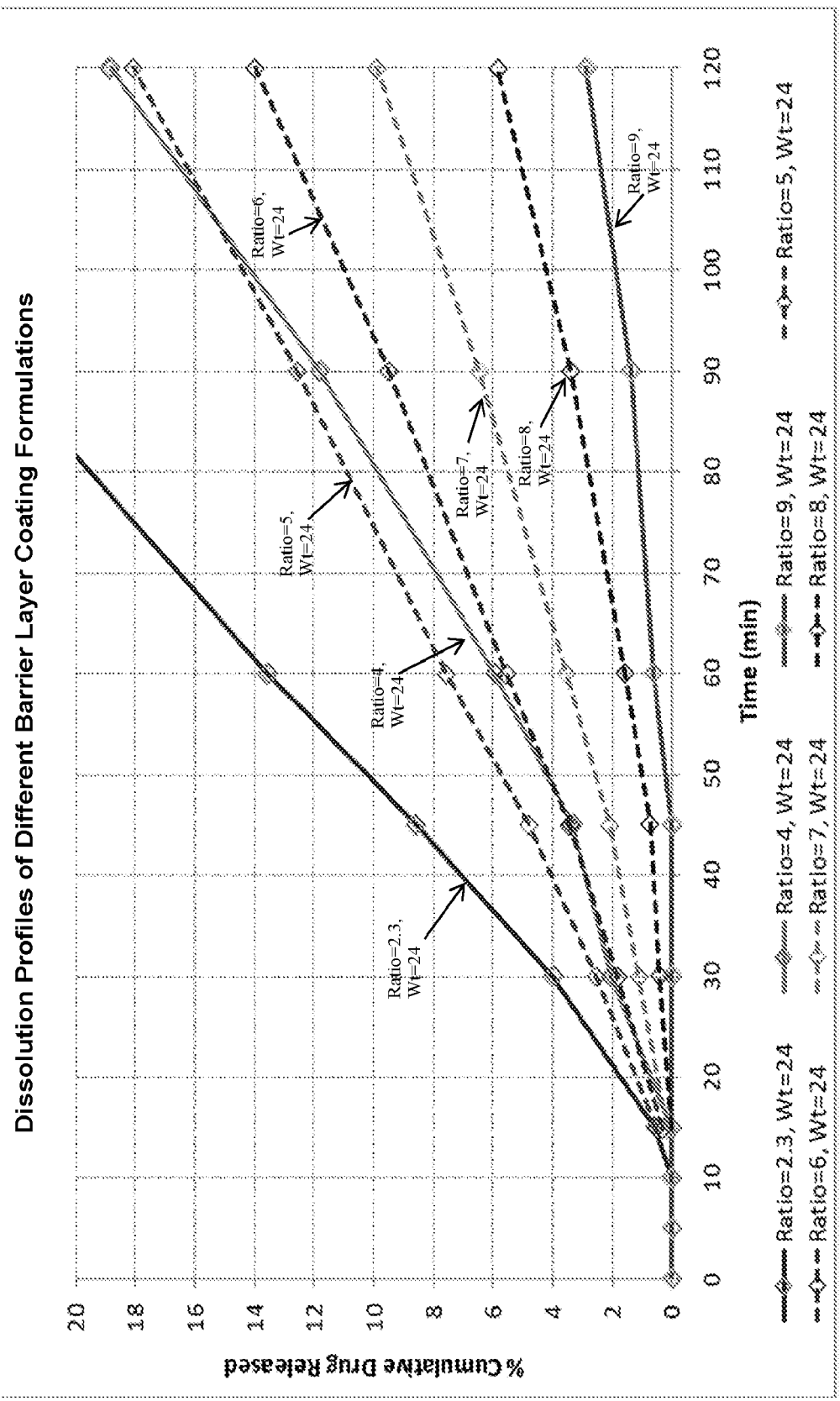
FIG. 16 provides a graph showing the dissolution profiles of different barrier layer coating formulations including empirical and predicted % cumulative drug release values at a targeted weight gain for the barrier layer of 24 mg.
Figure 17:
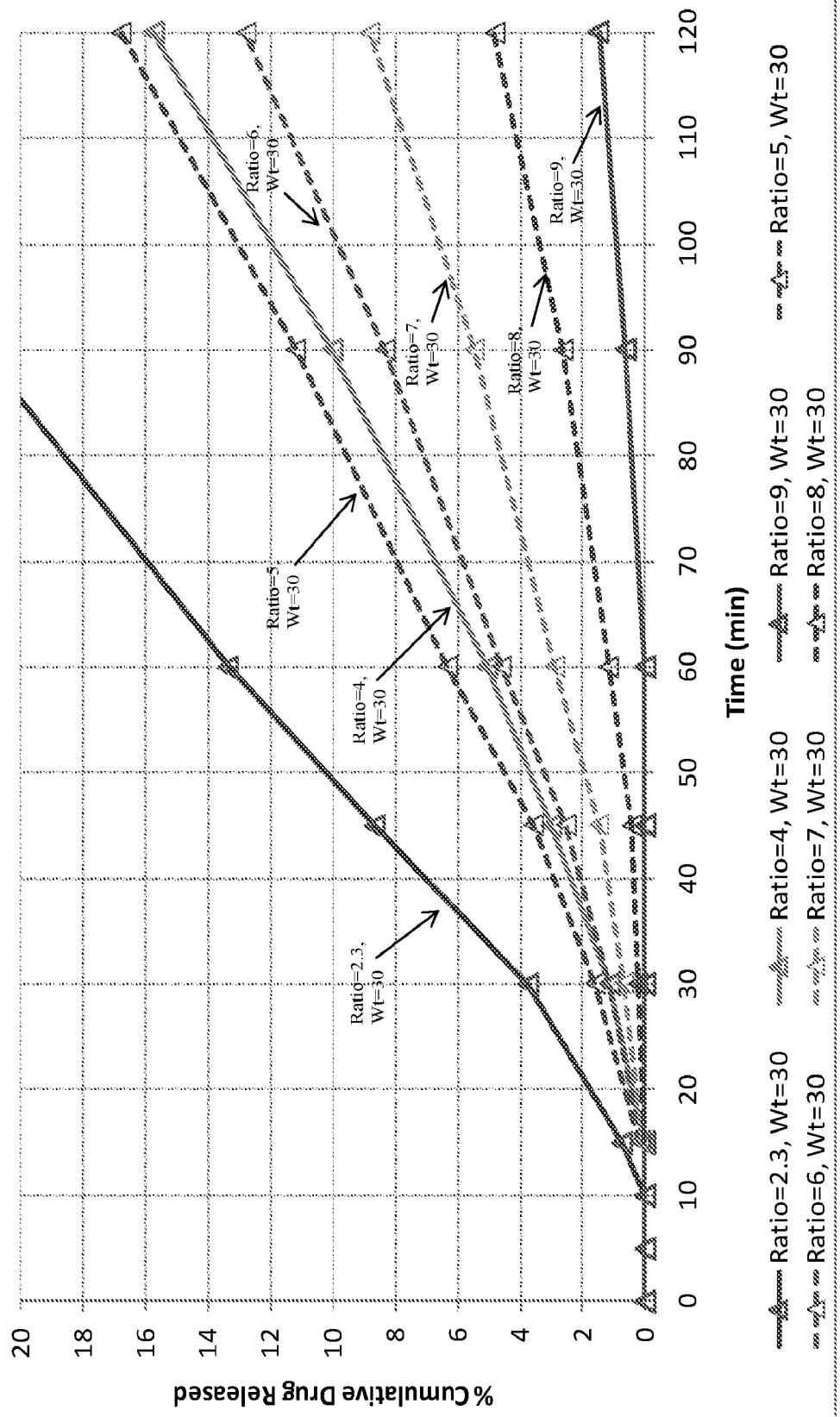
FIG. 17 provides a graph showing the dissolution profiles of different barrier layer coating formulations including empirical and predicted % cumulative drug release values at a targeted weight gain for the barrier layer of 30 mg.
Figure 18:
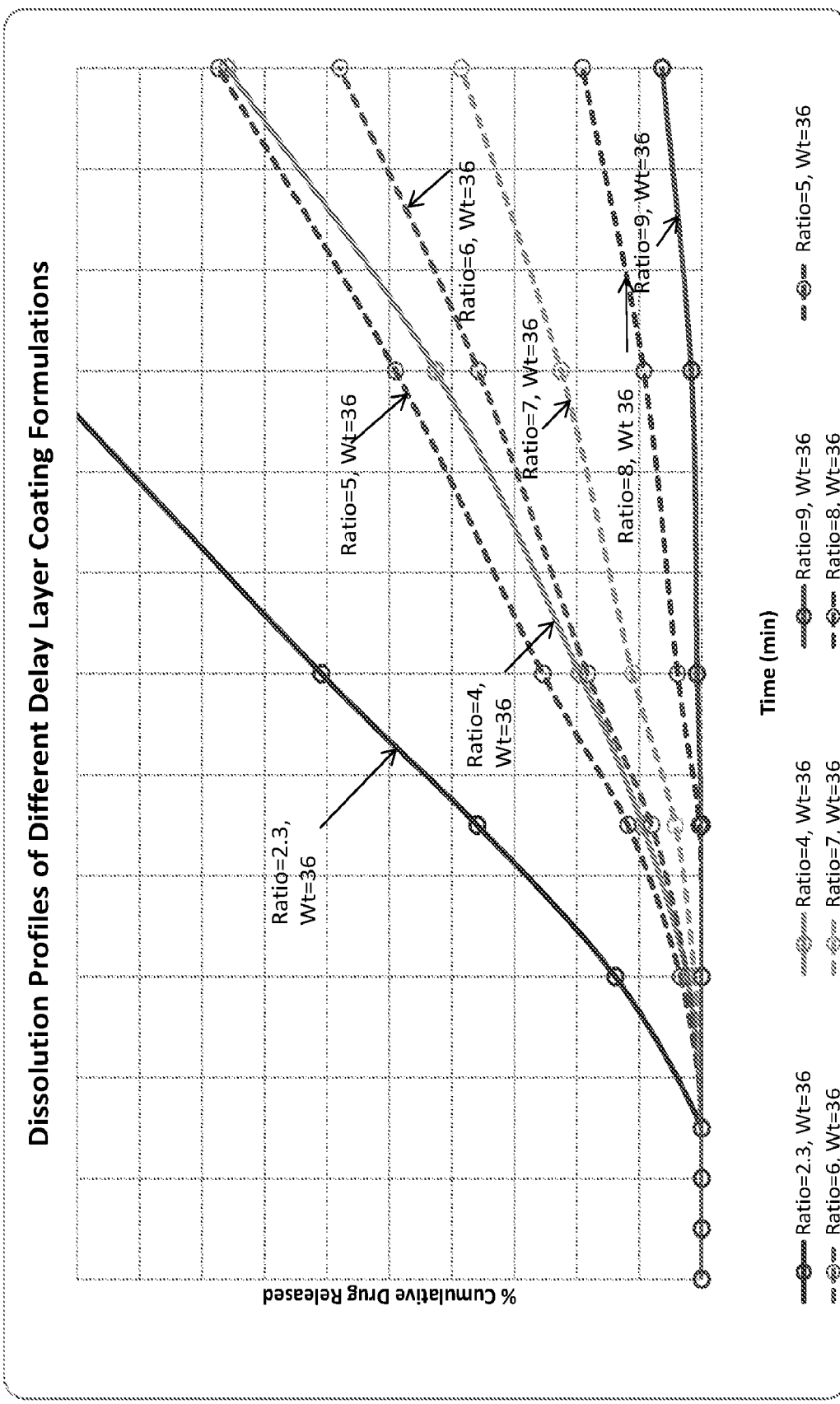
FIG. 18 provides a graph showing the dissolution profiles of different barrier layer coating formulations including empirical and predicted % cumulative drug release values at a targeted weight gain for the barrier layer of 36 mg.

A statistical analysis was performed and an experimental model was established. The dissolution data for additional formulations were predicted based on the model and are presented in Table 37. The actual dissolution profiles for barrier layer composition (a)-(i) along with the predicted dissolution profiles for P1-P12 are shown in FIGS. 16-18.

TABLE 37

| | | | Predicted Values | | | | | |
|---|---|---|---|---|---|---|---|---|
| | Acryl-EZE/ Opdry AMB | Coating wt | 15 min | 30 min | 45 min | 60 min | 90 min | 120 min |
| P1 | 5 | 24 | 0.5 | 2.5 | 4.8 | 7.6 | 12.6 | 18.1 |
| P2 | 5 | 30 | 0.2 | 1.6 | 3.6 | 6.3 | 11.2 | 16.8 |
| P3 | 5 | 36 | −0.1 | 0.7 | 2.4 | 5.1 | 9.8 | 15.5 |
| P4 | 6 | 24 | 0.3 | 1.8 | 3.4 | 5.6 | 9.5 | 14.0 |
| P5 | 6 | 30 | 0.1 | 1.1 | 2.5 | 4.6 | 8.3 | 12.8 |
| P6 | 6 | 36 | −0.1 | 0.5 | 1.6 | 3.6 | 7.2 | 11.6 |
| P7 | 7 | 24 | 0.2 | 1.1 | 2.1 | 3.6 | 6.5 | 9.9 |
| P8 | 7 | 30 | 0.1 | 0.7 | 1.5 | 2.9 | 5.5 | 8.8 |
| P9 | 7 | 36 | 0.0 | 0.2 | 0.8 | 2.2 | 4.5 | 7.7 |
| P10 | 8 | 24 | 0.0 | 0.4 | 0.7 | 1.6 | 3.4 | 5.8 |
| P11 | 8 | 30 | 0.0 | 0.2 | 0.4 | 1.2 | 2.6 | 4.8 |
| P12 | 8 | 36 | 0.0 | 0.0 | 0.1 | 0.8 | 1.9 | 3.8 |

Example 9 (Prophetic): Modified Drug Composition Formulations

Based on the in-vivo data of Example 6, Treatment C (Formulation 3) had a higher AUC than Treatment B (Formulation 2) as shown in Table 38. These two formulations differ only in the drug composition of the formulations. Treatment B (Formulation 2) has a relatively slow release drug composition while Treatment C (Formulation 3) has a relatively fast release drug composition. Without intending to be bound by any particular theory, some drug may have been retained in the matrix of Treatment B (Formulation 2)'s drug composition and not released in time in the stomach. Therefore, it may be desirable to have formulations with a faster release drug composition. Table 39 shows the potential ER formulations.

TABLE 38

| | Treatment A (44 mg) | Treatment B (44 mg) | Treatment C (44 mg) | Treatment D (44 mg) | Treatment E (36 mg) |
|---|---|---|---|---|---|
| Cmax (ng/mL) | 10.89 (0.96) | 8.86 (0.8) | 10.98 (0.93) | 11.38 (1.02) | 8.09 (0.64) |
| Tmax* (hr) | 3.0 [2.0-5.0] | 4.0 [3.0-8.0] | 4.5 [3.0-5.0] | 4.5 [3.0-6.0] | 7.0 [1.5-8.0] |
| AUC24 (ng*hr/mL) | 79.17 (7.5) | 76.36 (6.12) | 86.76 (5.53) | 87.54 (6.93) | 85.51 (5.73) |
| AUClast (ng*hr/mL) | 83.25 (8.16) | 81.25 (6.11) | 89.95 (6.6) | 91.6 (7.61) | 85.51 (5.73) |
| AUCinf (ng*hr/mL) | 89.89 (7.67) | 85.31 (6.03) | 93.57 (6.89) | 95.20 (7.51) | 87.86 (5.83) |
| F (%) | 84.23 (4.11) | 80.18 (3.44) | 87.45 (3.46) | 88.50 (3.38) | 100 |

TABLE 39

| | Formulation Composition (% w/w) | | | | | | | | | |
|---|---|---|---|---|---|---|---|---|---|---|
| Formulation ID | MPH | SAIB | Triacetin (TA) | IPM | CAB | Cab-O-Sil | Gelucire 44/14 | Fill Wt (mg) | Total | SAIB/TA |
| Formulation 5 | 20.00 | 37.86 | 29.12 | 6.40 | 4.80 | 0.80 | 1.00 | 180.00 | 99.98 | 1.30 |
| Formulation 6 | 20.00 | 37.25 | 28.75 | 6.40 | 4.80 | 0.80 | 2.00 | 180.00 | 100.00 | 1.30 |
| Formulation 7 | 20.00 | 33.50 | 33.50 | 6.40 | 4.80 | 0.80 | 1.00 | 180.00 | 100.00 | 1.00 |
| Formulation 8 | 20.00 | 33.00 | 33.00 | 6.40 | 4.80 | 0.80 | 2.00 | 180.00 | 100.00 | 1.00 |
| Formulation 9 | 20.00 | 35.50 | 31.00 | 6.40 | 4.80 | 0.80 | 1.50 | 180.00 | 100.00 | 1.15 |

Example 10: Clinical Study to Evaluate Safety and Efficacy of Controlled Release Methylphenidate HCL Dosage Form Based on the PK results provided in the study described in Example 6, controlled release methylphenidate HCl formulations, Formulation 4 (44 mg methylphenidate HCl) and variants of Formulation 4 having a total methylphenidate HCl loading of 22 mg (Formulations 10) or 33 mg (Formulation 11), were tested for efficacy in children and adolescents with ADHD as described below.

Materials and Methods

Formulations:

The composition of Formulation 4 and its preparation are described in Example 3. Formulations 10 (22 mg MPH) and Formulation 11 (33 mg MPH) were prepared as described in Example 3 for Formulation 4, with the exception of the utilization of different fill and coating weights and the use of different Opadry® II film coatings as indicated below. The components of the drug composition and the layers coated on the capsules for Formulations 10 and 11 are shown in the following tables. Amounts are % w/w unless otherwise noted.

TABLE 40

Formulation 10 Drug Composition

| | MPH | SAIB | Triacetin | IPM | CAB | Cab-O-Sil | Gelucire 44/14 | BHT | Fill Wt (mg) | Capsule Size |
|---|---|---|---|---|---|---|---|---|---|---|
| Drug Composition | 20.00% | 37.86% | 29.12% | 6.40% | 4.80% | 0.80% | 1.00% | 0.02% | 90 | 4 (HPMC) |

TABLE 41

Formulation 10 - First, Second, and Third Layers

| | Coating Layers | MPH | Pharmacoat 606 HPMC E3 (2910) | Acryl-EZE White (93O18509) | Opadry AMB White (80W68912) | Opadry II Yellow (85F12398) | Coating Wt (mg) |
|---|---|---|---|---|---|---|---|
| Layers | (I): Barrier Layer | | | 70% | 30% | | 24 |
| | (II): Drug Layer | 33.33% | 66.67% | | | | 12 |
| | (III): Film Coating Layer | | | | | 100% | 7 |

TABLE 42

Formulation 11 Drug Composition

| | MPH | SAIB | Triacetin | IPM | CAB | Cab-O-Sil® | Gelucire® 44/14 | BHT | Fill Wt (mg) | Capsule Size |
|---|---|---|---|---|---|---|---|---|---|---|
| Drug Composition | 20.00% | 37.86% | 29.12% | 6.40% | 4.80% | 0.80% | 1.00% | 0.02% | 135 | 4 (HPMC) |

TABLE 43

Formulation 11 - First, Second, and Third Layers

| Layers | | MPH | Pharmacoat 606 HPMC E3 (2910) | Acryl-EZE White (93O18509) | Opadry AMB White (80W68912) | Opadry II Gray (85F17644) | Coating Wt (mg) |
|---|---|---|---|---|---|---|---|
| Layers | (I): Barrier Layer | | | 70% | 30% | | 24 |
| | (II): Drug Layer | 33.33% | 66.67% | | | | 18 |
| | (III): Film Coating Layer | | | | | 100% | 7 |

Study Procedures:

A Phase III, multi-center, randomized, double-blind, placebo controlled, two-way crossover study was designed and conducted as set forth below to observe the efficacy of controlled release methylphenidate HCl in children and adolescents with ADHD age 6 to 18 years old.

The study was comprised of four main phases: a screening period lasting about 14 days, an open-label titration period lasting 2 to 4 weeks, a double-blind and placebo controlled two-way cross-over study period of 4 weeks (2 weeks for Period 1 and 2 weeks for Period 2), then a follow-up phase of 2 weeks. Subjects with documented diagnosis of Attention Deficit Hyperactivity Disorder (ADHD) and verified by investigators using the Diagnostic & Statistical Manual for Mental Disorders-Fifth Edition (DSM-5) were screened for eligibility after providing informed consent. Only subjects who had received ADHD treatment for less than 1 year and those who had not received other ADHD treatments within 30 days prior to screening baseline (Day 0) were enrolled. There were 110 subjects enrolled in this study, of which 99 evaluable subjects completed the study. The patients were subjected to the dose titration period to determine the optimal dose for controlled release methylphenidate HCl treatment.

All subjects received 22 mg controlled release methylphenidate HCl for the first week; dose titration was determined by investigators at Visit 3 (Day 7) based on the clinical presentation, safety, and the assessments from parents. For subjects who did not require dose adjustment, 22 mg controlled release methylphenidate HCl was administered for another week before randomization; the cross-over period for these subjects began on Day 15.

When dose titration was deemed necessary, subjects received 33 mg controlled release methylphenidate HCl for 1 week and were re-evaluated on Visit 4 (Day 14). Subjects whose optimal dose was 33 mg received 33 mg controlled release methylphenidate HCl for another week before randomization; the cross-over period for these subjects began on Day 22. When further dose titration was deemed necessary, subjects received 44 mg controlled release methylphenidate HCl for 1 week and were re-evaluated on Visit 5 (Day 21). Subjects whose optimal dose was 44 mg received 44 mg controlled release methylphenidate HCl for another week before randomization; the cross-over period for these subjects began on Day 29.

At the last day of the titration period (Day 14 for 22 mg, Day 21 for 33 mg group, and Day 28 for 44 mg group), subjects were randomly assigned to receive controlled release methylphenidate HCl at their optimal dose or placebo at a 1:1 ratio according to the randomization scheme during each study period (Period 1 and Period 2) at treatment phase; no washout period was included between the two treatment periods.

The primary objective of this study was to determine the Swanson, Nolan, and Pelham-IV (SNAP-IV) teacher form score (Gau, S. S., C. H. Lin, et al. (2009). "Psychometric properties of the Chinese version of the Swanson, Nolan, and Pelham, Version IV Scale-Teacher Form." *J Pediatr Psychol* 34(8): 850-861) of children and adolescents with ADHD who were administered controlled release methylphenidate HCl versus those who were administered placebo.

The intent-to-treat (ITT) population was comprised of all subjects who were randomized, received at least one dose of study treatment, and completed at least one primary efficacy endpoint assessment.

Primary Endpoint: To compare the change from baseline of SNAP-IV teacher form score between children and adolescents with ADHD who were administered controlled release methylphenidate HCl versus those who were administered placebo at Period 1 and Period 2.

Results

Treatment with controlled release methylphenidate HCl showed a statistically significant improvement in ADHD symptom control compared to placebo ($p=0.0044$ for the SNAP-IV teacher form total score change for the intent-to-treat population). No serious adverse events were reported during the trial, and the adverse event profile was consistent with the established safety profile of extended-release methylphenidate products.

Example 11: Stability Study for Controlled Release Methylphenidate HCL Dosage Form A stability study was conducted for Formulations 4, 10 and 11 from the Phase III study.

Materials and Methods

The following apparatus and conditions were utilized to determine drug release from the formulations over time:

TABLE 44

Dissolution Conditions:

| | |
|---|---|
| Dissolution Medium: | 950 mL of 0.1N Hydrochloric acid |
| Apparatus: | USP apparatus II; 50 rpm (with spiral stainless sinker) |
| Temperature: | $37 \pm 0.5°$ C. |
| Amount of sampling: | 1 mL (without replacement) |
| Filter: | 10-μm UHMWPE |
| Sampling Time: | 0.25, 0.5, 1, 1.5, 2, 3, 6, 9, 12, and 24 hours |

An Assay to calculate the content of Methylphenidate HCl as percent of Label Strength (% LS) was conducted as follows:

Five capsules were weighed and transferred into separate volumetric flasks, 10% of the volume of each flask of extraction solution (1 mM Phosphoric Acid) was added to each flask. The capsules were sonicated at 37° C. for 15 minutes or until the capsule shell dissolved and separated from the formulation. 15% of the volume of each flask of acetonitrile was added into each flask and shaken at 300 rpm for 30-45 minutes or until all the formulation was broken into small pieces. The flask contents were then mixed well.

About 40% of the volume of each flask of extraction solution was added into each flask and the sample was placed on the mechanical shaker at 300 rpm for 15-30 minutes. The sample was diluted to volume with extraction solution and mixed well. About 1.5 mL of the solution was centrifuged at 10,000 rpm for 10 minutes or 3500 rpm for at least 30 minutes. The clear supernatant was collected for HPLC analysis. An organic impurity test was also conducted with supernatant collected for HPLC analysis as described above.

Water content was determined using the Karl Fischer Titration Method as set forth in USP <921> Method 1C.

Results

The results of the stability study are provided in FIGS. 19A-21B. These results indicate that the Dissolution profile, % of Label Strength, Organic Impurities, Microbial Count and Water Content were acceptable.

What is claimed is:

1. A dosage form, comprising:
a drug composition in a capsule comprising a first pharmacologically active agent, which is methylphenidate at about 15% to about 25% w/w relative to the total weight of the drug composition, and sucrose acetate isobutyrate; a barrier layer covering at least a portion of an outer surface of the capsule; and a drug layer covering at least a portion of the barrier layer wherein the barrier layer comprises at least one member selected from cellulose acetate phthalate, hydroxypropyl methylcellulose phthalate, hydroxypropyl methylcellulose acetate succinate, polyvinyl acetate phthalate, cellulose acetate trimelitate, methacrylic acid copolymer, shellac, and zein,
wherein the drug layer comprises a second pharmacologically active agent, which is methylphenidate,
wherein the dosage form is configured to have initial release of the first pharmacologically active agent from the dosage form occurs at a time of 5 minutes to 120 minutes when assayed by USP Apparatus II using 750 mL of 0.1 N HCl dissolution medium, a paddle speed of 50 rpm, and a dissolution medium temperature of 37° C.

2. The dosage form of claim 1, wherein sucrose acetate isobutyrate is present at about 30% to about 60% w/w relative to the total weight of the drug composition.

3. The dosage form of claim 1, wherein the drug composition comprises an organic solvent.

4. The dosage form of claim 3, wherein the organic solvent comprises at least one member selected from triacetin, N-methyl-2-pyrrolidone, 2-pyrrolidone, dimethylsulfoxide, ethyl lactate, propylene carbonate, and glycofurol.

5. The dosage form of claim 1, wherein the drug composition comprises a rheology modifier.

6. The dosage form of claim 5, wherein the rheology modifier comprises at least one member selected from a caprylic/capric triglyceride, isopropyl myristate, ethyl oleate, triethyl citrate, dimethyl phthalate, labrafil, labrasol, a polyglycolized glyceride, and benzyl benzoate.

7. The dosage form of claim 1, wherein the drug composition comprises a network former.

8. The dosage form claim 7, wherein the network former comprises at least one member selected from a cellulose acetate butyrate, a carbohydrate polymer, an organic acid of a carbohydrate polymer, a hydrogel, a cellulose acetate phthalate, an ethyl cellulose, a triblock copolymer, an acrylic polymer, hydroxyl propyl methyl cellulose, cellulose triacetate, and poly (methyl methacrylate).

9. The dosage form of claim 1, wherein the drug composition comprises a viscosity enhancing agent.

10. The dosage form of claim 1, wherein the drug composition comprises a polyoxylglyceride.

11. The dosage form of claim 1, wherein the barrier layer comprises a methacrylic acid copolymer and a polyvinyl alcohol.

12. The dosage form of claim 1, wherein the dosage form comprises a coating layer covering at least a portion of the drug layer.

* * * * *